US009567584B2

(12) United States Patent
Dale et al.

(10) Patent No.: US 9,567,584 B2
(45) Date of Patent: *Feb. 14, 2017

(54) OLIGONUCLEOTIDE—CONTAINING PHARMACOLOGICAL COMPOSITIONS AND THEIR USE

(71) Applicant: Lakewood-Amedex, Inc., Sarasota, FL (US)

(72) Inventors: Roderic M.K. Dale, Wilsonville, OR (US); Amy Arrow, Bethel, ME (US); Teresa Thompson, West Linn, OR (US)

(73) Assignee: Lakewood Amedex, Inc., Sarasota, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/534,901

(22) Filed: Nov. 6, 2014

(65) Prior Publication Data
US 2015/0232857 A1 Aug. 20, 2015

Related U.S. Application Data

(63) Continuation of application No. 11/673,486, filed on Feb. 9, 2007, now Pat. No. 8,916,529, which is a continuation of application No. 10/191,997, filed on Jul. 10, 2002, now abandoned.

(60) Provisional application No. 60/303,820, filed on Jul. 10, 2001.

(51) Int. Cl.
C12N 15/113 (2010.01)
A61K 8/60 (2006.01)
A61Q 19/00 (2006.01)

(52) U.S. Cl.
CPC ........... C12N 15/1137 (2013.01); A61K 8/606 (2013.01); A61Q 19/00 (2013.01); C12N 15/113 (2013.01); C12N 15/1136 (2013.01); C12N 15/1138 (2013.01); A61K 2800/74 (2013.01); C12N 2310/11 (2013.01); C12N 2320/35 (2013.01)

(58) Field of Classification Search
None
See application file for complete search history.

(56) References Cited

U.S. PATENT DOCUMENTS

| | | | |
|---|---|---|---|
| 2,003,214 A | 5/1935 | Edward | |
| 2,003,216 A | 5/1935 | Nadig | |
| 3,008,347 A | 11/1961 | Arrow et al. | |
| 3,018,078 A | 1/1962 | Holdren | |
| 4,012,135 A | 3/1977 | Komine | |
| 4,897,355 A | 1/1990 | Eppstein et al. | |
| 5,002,581 A | 3/1991 | Paxson et al. | |
| 5,010,734 A | 4/1991 | Ho | |
| 5,011,861 A | 4/1991 | Coull et al. | |
| 5,217,866 A | 6/1993 | Summerton et al. | |
| 5,256,649 A | 10/1993 | Le Fur et al. | |
| 5,474,796 A | 12/1995 | Brennan | |
| 5,514,788 A | 5/1996 | Bennett et al. | |
| 5,576,208 A | 11/1996 | Monia et al. | |
| 5,591,840 A | 1/1997 | Narayanan et al. | |
| 5,603,915 A | 2/1997 | Nelson et al. | |
| 5,652,131 A | 7/1997 | Beavo et al. | |
| 5,734,039 A | 3/1998 | Calabretta et al. | |
| 5,776,905 A | 7/1998 | Gibbons et al. | |
| 5,801,154 A | 9/1998 | Baracchini et al. | |
| 5,821,234 A | 10/1998 | Dzau | |
| 5,830,140 A | 11/1998 | Dillinger et al. | |
| 5,834,443 A | 11/1998 | Masiello | |
| 5,849,902 A | 12/1998 | Arrow et al. | |
| 5,948,768 A | 9/1999 | McMichael et al. | |
| 5,951,455 A | 9/1999 | Cowsert | |
| 5,989,912 A | 11/1999 | Arrow et al. | |
| 5,998,203 A | 12/1999 | Matulic-Adamic et al. | |
| 6,008,048 A | 12/1999 | Monia et al. | |
| 6,015,886 A | 1/2000 | Dale et al. | |
| 6,037,346 A | 3/2000 | Doherty, Jr. et al. | |
| 6,069,008 A * | 5/2000 | Bennett ................ | C12N 15/113 435/366 |
| 6,087,112 A | 7/2000 | Dale | |
| 6,136,603 A * | 10/2000 | Dean ................... | C12N 15/1136 435/366 |
| 6,211,162 B1 | 4/2001 | Dale et al. | |
| 6,211,349 B1 | 4/2001 | Dale et al. | |
| 6,344,323 B1 | 2/2002 | Seifert | |
| 6,395,736 B1 | 5/2002 | Parks et al. | |
| 6,403,597 B1 | 6/2002 | Wilson et al. | |
| 6,440,723 B1 | 8/2002 | Dale | |
| 6,562,569 B1 | 5/2003 | Dale | |
| 6,582,908 B2 | 6/2003 | Fodor et al. | |
| 6,627,215 B1 | 9/2003 | Dale et al. | |

(Continued)

FOREIGN PATENT DOCUMENTS

JP 2000-245488 A 9/2000
JP 4999255 B2 8/2012

(Continued)

OTHER PUBLICATIONS

Agrawal et al. "Absorption, Tissue Distribution and In Vivo Stability in Rats of a Hybrid Antisense Oligonucleotide Following Oral Administration." Biochem. Pharmacol. 50.4(1995):571-576.
Agrawal et al. "Antisense Therapeutics." Curr. Opin. Chem. Biol. 2.4(1998):519-528.
Agrawal et al. "Antisense Therapeutics: Is it as Simple as Simple as Complementary Base Recognition." Mol. Med. Today. 6.2(2000):72-81.
Agrawal et al. "Modified Oligonucleotides as Therapeutic and Diagnostic Agents." Curr. Opin. Biotechnol. 6.1(1995):12-19.
Altschul et al. "Gapped BLAST and PSI-BLAST: A New Generation of Protein Database Search Programs." Nucleic Acid Res. 5.17(1997):3389-3402.
Altschul et al. "Issues in Searching Molecular Sequence Databases." Nat. Genet. 6(1994):119-129.

(Continued)

Primary Examiner — Tracy Vivlemore
(74) Attorney, Agent, or Firm — Ice Miller LLP

(57) ABSTRACT

The present invention relates to methods and compositions containing oligonucleotides suitable for administration to humans and other mammals.

12 Claims, No Drawings

(56) References Cited

U.S. PATENT DOCUMENTS

| | | |
|---|---|---|
| 6,656,717 B1 | 12/2003 | Xin et al. |
| 6,844,151 B1 | 1/2005 | Dale |
| 2002/0003214 A1 | 1/2002 | Morrissey, Jr. et al. |
| 2002/0032164 A1 | 3/2002 | Dale et al. |
| 2002/0142980 A1 | 10/2002 | Thompson et al. |
| 2003/0045490 A1 | 3/2003 | Dale et al. |
| 2003/0083477 A1 | 5/2003 | Arrow et al. |
| 2003/0180789 A1 | 9/2003 | Dale |
| 2003/0207834 A1 | 11/2003 | Dale et al. |
| 2004/0121352 A1 | 6/2004 | Dale |
| 2005/0025815 A1 | 2/2005 | Dale et al. |
| 2005/0107344 A1 | 5/2005 | Dale et al. |
| 2005/0118618 A1 | 6/2005 | Dale |
| 2008/0161257 A1 | 7/2008 | Dale et al. |
| 2008/0167257 A1 | 7/2008 | Dale et al. |
| 2008/0234214 A1 | 9/2008 | Dale et al. |

FOREIGN PATENT DOCUMENTS

| | | |
|---|---|---|
| WO | WO-9014074 A1 | 11/1990 |
| WO | WO-9116024 A1 | 10/1991 |
| WO | WO-9117424 A1 | 11/1991 |
| WO | WO-9203568 A1 | 3/1992 |
| WO | WO-9415619 A1 | 7/1994 |
| WO | WO-9428144 A1 | 12/1994 |
| WO | WO-9510938 A1 | 4/1995 |
| WO | WO-9515761 A1 | 6/1995 |
| WO | WO-9747325 A1 | 12/1997 |
| WO | WO-9803533 A1 | 1/1998 |
| WO | WO-9813526 A1 | 4/1998 |
| WO | WO-9849348 A1 | 11/1998 |
| WO | WO-9914346 A2 | 3/1999 |
| WO | 99/37809 A1 | 7/1999 |
| WO | WO-9953101 A1 | 10/1999 |
| WO | WO-0040525 A2 | 7/2000 |
| WO | WO-0040591 A1 | 7/2000 |
| WO | WO-0040592 A1 | 7/2000 |
| WO | WO-0040714 A2 | 7/2000 |
| WO | WO-0057890 A1 | 10/2000 |
| WO | 00/70092 A1 | 11/2000 |
| WO | WO-0070093 A1 | 11/2000 |
| WO | WO-0123620 A2 | 4/2001 |
| WO | WO-0200854 A2 | 1/2002 |
| WO | WO-0232614 A1 | 4/2002 |
| WO | WO-02089581 A1 | 11/2002 |
| WO | WO-03006478 A1 | 1/2003 |

OTHER PUBLICATIONS

Belikova et al. "Synthesis of Rebonucleosides and Diribonucleoside Phosphates Containing 2-Chloro-Ethylamine and Nitrogen Mustard Residues." *Tetrahed. Lett.* 37(1967):3557-3562.

Bennett et al. "Pharmacology of Antisense Therapeutic Agents." *Meth. Mol. Med.* (1996):13-46.

Bost et al. "The Jun Kinase 2 Isoform is Preferentially Required for Epidermal Growth Factor-Induced Transformation of Human A549 Lung Carcinoma Cells." *Mol. Cell. Biol.* 19.3(1999):1938-1949.

Branch. "A Good Antisense Molecule is Hard to Find." *Trends Biochem. Sci.* 23(1998):45-50.

Calculated melting temperature of sequence CCC CCA CCA CTT CCC CTC CT from the Oligonucleotide Properties Calculator at www. basic. northwestern.edu1biotoolsloiigocalc. html.

Chen et al. "In Vivo Expression of Single-Stranded DNA in Mammalian Cells With DNA Enzyme Sequences Targeted to C-raf." *Antisense Nucleic Acid Drug Dev.*I0(2000):415-422.

Cohen et al. "Phosphorothioate Oligodeoxynucleotide Analogues." CRC Press:Boca Raton, FL. (1989):82-92, 97-117.

Dagle et al. "Oligonucleotide-Based Strategies to Reduce Gene Expression." *Differentiation.* 69(2001):75-82.

Dobashi et al. "Simultaneous Suppression of cdc2 and cdk2 Activities Induces Neuronal Differentiation of PC12 Cells."*J. Biol. Chem.* 275.17(Apr. 2000):12572-12580.

Doherty. "Phosphodiesterase 4 Inhibitors as Novel Anti-Inflammatory Agents." *Curr. Opin. Chem. Biol.* 3(1999):466-473.

Egholm et al. "Peptide Nucleic Acids (PNA) Oligonucleotide Analogues With an Achiral Peptide Backbone." *J. Am. Chem. Soc.* 114(1992):1895-I897.

Flanagan et al. "Cellular Penetration and Antisense Activity by a Phenoxazine-Substituted Heptanucleotide." *Nat. Biotechnol.* 17.1(1999):48-52.

Francischi et al. "Anti-Inflammatory and Analgesic Effects of the Phosphodiesterase 4 Inhibitor Rolipram in a Rat Model of Arthritis." *Eur. J. Pharmacol.* 399.2-3(2000):243-249.

Froehler et al. "Phosporamidate Analogues of DNA: Synthesis and Thermal Stability of Heteroduplexes." *Nucleic Acids Res.* 16.11(1988):4831-4839.

Galym et al. "Complex Host Cell Responses to Antisense Suppression of ACHE Gene Expression." *Antisese Nucleic Acid Drug Dev.* 11(2001):51-57.

Ghosh et al. "Evaluation of Some Properties of a Phosphorodithioate Oligodeoxyribonucleotide for Antisense Application." *Nucleic Acids Res.* 21.24(1993):5761-5765.

Green et al. "Antisense Oligonucleotides: An Evolving Technology for the Modulation of Gene Rxpression in Human Disease." *J. Am. Coll. Surg.* 191.1(2000):93-105.

Henikoff et al. "Amino Acid Substitution Matrices From Protein Blocks." *PNAS.* 89(1992):10915-10919.

Higashi et al. "Enhanced Expression of Cyclooxygenase (COX)-2 in Human Skin Epidermal Cancer Cells: Evidence for Growth Suppression by Inhibiting COX-2 Expression." *Int. J. Cancer.* 86(2000):667-671.

Huang et al. "Acyclic Nucleic Acid Analogues: Synthesis and Oligomerization of Gamma, 4-Diamino-2oxo-1(2H)-pyrimidinepentanoic Acid and Delta, 4-Diamino-2-oxo-1(2H)-pyrimidinehexanoic Acid." *J. Org. Chem.* 56(1991):6007-6017.

Hughes et al. "The Cellular Delivery of Antisense Oligonucleotides and Ribozymes." *Drug Disc. Today.* 6.6(2001):303-315.

Jen et al. "Suppression of Gene Expression by Targeted Disruption of Messenger RNA: Available Options and Current Strategies." *Stem Cells.* 18.5(2000):307-319.

Karlin et al. "Methods for Assessing the Statistical Significance of Molecular Sequence Features by Using General Scoring Schemes." *PNAS.* 87(1990):2264-2268.

Khan et al. "In Vivo Inhibition of Cyclooxygenase-2 by a Selective Phosphorothioated Oligonucleotide." *Antisense Nucleic Acid Drug Dev.* 11(2001):199-207.

Kushner et al. "Antisense Cancer Therapy: The State of the Science." *Curr. Oncol. Rep.* 2(2000):23-30.

Lazzeri et al. "Effects of Prostaglandin E2 and cAMP Elevating Drugs in GM-CSF Release by Cultured Human Airway Smooth Muscle Cells." *Am. J. Respir. Cell Mol. Biol.* 24(2001):44-48.

Lesnick et al. "Ologiodeoxynucleotides Containing 2'-0-Modified Adeosine: Synthesis and Effects on Stability of DNA:RNA Duplexes." *Biochem.* 32.30(1993):7832-7838.

Lisziewicz et al. "Specific Inhibition of Human Immunodeficiency Virus Rype 1 Replication by Antisense Oligonucleotides: An in vitro Model for Treatment." *PNAS.* 89(1992):11209-11213.

Ma et al., "Synthetic Oligonucleotides as Therapeutics: The Coming of Age." *Biotechnol. Ann. Rev.* 5(2000):155-196.

Marcus-Sekura et al. "Comparative Inhibition of Chloramphenicol Acetyltransferase Gene Expression by Antisense Oligonucleotide Analogus Having Alkyl Phospotriester, Methylphosphonate and Phosphothioate Linkages." *Nucleic Acids Res.* 15.14(1987):5749-5763.

Mardini et al. "Selective Inhibitors of cyclooxygenase-2: A Growing Class of Anti-Inflammatory Drugs." *Mol. Interv.* 1.1(2001):30-38.

Matthews et al. "Expanded Sequence Dependence of Thermodynamic Parameters Improves Prediction of RNA Secondary Structure." *J. Mol. Biol.* 288(1999):911-940.

Matthews et al. "Predicting Oligonucleotide Affinity to Nucleic Acid Targets." *RNA.* 5(1999):1458-1469.

Mickefield. "Backbone Modification of Nucleic Acids: Synthesis, Structure and Therapeutic Applications." *Curr. Med. Chem.* 8.10(2001):1157-1179.

(56) References Cited

OTHER PUBLICATIONS

Milligan et al. "Current Concepts in Antisense Drug Design." *J. Med. Chem.* 36.14(1993):1923-1937.
Miraglia et al. "Variations in mRNA Contect have no Effect on the Potency of Antisense Oligonucleotides." *Antisense Nucleic Acid Drug Dev.* 10(2000):453-461.
Miyake et al. "Inhibition of Progression to Androgen-Independence by Combined Adjuvant Treatment with Antisense BCL-XL and Antisense BCL-2 Oligonucleotides plus Taxol After Castration in the Shionogi Tumor Model." *Int. J. Cancer.* 86.6(2000):855-862.
National Center for Homeopathy Home Page www.homeopathic.org.
Neurath et al. "Cytokine Gene Transcription by NF-Kappa B Family Members in Patients with Inflammatory Bowel Disease." *Ann. N. Y. Acad. Sci.* 85991998):149-159.
Neurath et al. "Local Administration of Antisense Phosphorothioate Oligonucleotides to the p65 Subunit of NF- Kappa B Abrogates Established Experimental Colitis in Mice." *Nat. Med.* 2.9(1996):998-1004.
Normanno et al. "Growth Inhibition of Human Colon Carcinoma Cells by Combinations of Anti-Epidermal Growth Factor-Related Growth Factor Antisense Oligonucleotides." *Clin. Cancer Res.* 2(1996):601-609.
Némoz et al. "Identification of Cyclic AMP-Phosphodiesterase Variants from the PDE4D Gene Expressed in Human Peripheral Mononuclear Cells." *FEBS Lett.* 384(1996):97-102.
Okamoto et al. "Attempt for Liver-Targeted Delivery of Antisense Oligonucleotides by Cholesterol Modification and Oral Administration." *Heptaol. Res.* 13.3(1999):252-258.
Rubenstein et al. "A Review of Various Antisense Oligonucleotide Therapeutic Approaches for Prostate Cancer." *Prostate J.* 2.4(2000):179-188.
Rudin et al. "Phase I Trial of ISIS 5132, an Antisense Oligonucleotide Inhibitor of c-raf-1, Administered by 24-Hour Weekly Infusion to Patients with Advance Cancer." *Clin. Cancer Res.* 7(2001):1214-1220.
Sambrook et al. "Molecular Cloning: A Laboratory Manual." Cold Spring Harbor Laboratory Press (1989).
Sano. "Genetic Therapy for Chronic Rheumatoid Arthritis." *J. Clin. Exp. Med. (IGAKU NO AYUMI).* 195.7(2000):463-468. (Japanese Original and English Translation).
Seibert et al. "Pharmacological and Biochemical Demonstration of the Role of Cyclooxygenase 2 in Inflammation and Pain." *PNAS.* 91(1994):12013-12017.
Shibahara et al. "Inhibition of Human Immunodeficiency Virus (HIV-1) Replication by Synthetic Oligo-RNA Derivatives." *Nucleic Acids Res.* 17.1(1989):239-252.

Shohami et al. "Antisense Prevention of Neuronal Damages Following a Head Injury in Mice." *J. Mol. Med.* 78(2000):228-236.
Sumitani et al. "Specific Inhibition of Cyclooxygenase-2 Results in Inhibition of Proliferation of Oral Cancer Cell Lines via Suppression of Prostaglandin E2 Production." *J. Oral Pathol. Med.* 30(2001):41-47.
Summerton et al., "Sequence-specific Crosslinking Agents for Nucleic Acids", *Journal of Molecular Biology*, 122:145-162 (1978).
Summerton. "Intracellular Inactivation of Specific Nucleotide Sequences: A General Approach to the Treatment of Viral Diseases and Virally-Mediated Cancers." *J. Theoret. Biol.* 78(1979):77-99.
Taylor et al. "Antisense Oligonucleotides: A Systematic High-Throughput Approach to Target Validation and Gene Function Determination." *Drug Disc. Today.* 4(1999):562-567.
Tortora et al. "Oral Antisense That Targets Protein Kinase A Cooperates With Taxol and Inhibits Tumor Growth, Antiogenesis and Growth Factor Production." *Clin. Cancer Res.* 6.1(2000):2506-2512.
Vlassov et al. "Penetration of Oligonucleotides Into Mouse Organism Through Mucosa and Skin." *Fed. Eur. Biochem. Soc.* 327.3(1993):271-274.
Wang. "Antitumor Activity and Pharmacokineticc of a Mixed-Backbone Antisense Oligonucleotide Targeted to the RIα Subunit of Protein Kinase A After Oral Administration." *PNAS.* 96.24(1999):13989-13994.
Weller et al. "Molecular Modeling of Acyclic Polyamide Oligonucleotide Analogues." *J. Org. Chem.* 56.21(1991):6000-6006.
Yamada et al. "Selective Inhibition of Cyclooxygenase-2 with Antisense Oligodeoxynucleotide Restricts Induction of Rat Adjuvant-Induced Arthritis." *Biochem. Biophys. Res. Commun.* 269(2000):415-421.
Zamecnik et al. "Inhibition of Rous Sarcoma Virus Replication and Cell Transformation by a Specific Oligodeoxynucleotide." *PNAS.* 75.1(1978):280-284.
Zhu et al. "Inhibition of the Expression of Phosphodiesterase 5 by Antisense Inhibits the Growth of Human Colon Carcinoma (HT-29) cells in Culture." *J. Fed. Am. Soc. Exp. Biol.* 15.5(2001):A924.
Zhu et al. "Stable Expression of Phospodiesterase (PDE) 5 Antisense in Human Colon Tumor HT29 Cell is Associated with Delayed G2h4 Cell Cycle Progression." *Proc. Am. Assoc. Cancer Res. Ann. Meeting.* 43(2002):64.
Lin et al., Regulation of human PDE5A2 intronic promoter by cAMP and cGMP: identification of a critical Sp1-binding site. Biochem Biophys Res Commun. Jan. 26, 2001;280(3):693-9.
Yanaka et al., Expression, structure and chromosomal localization of the human cGMP-binding cGMP-specific phosphodiesterase PDE5A gene. Eur J Biochem. Jul. 15, 1998;255(2):391-9.

* cited by examiner

OLIGONUCLEOTIDE—CONTAINING PHARMACOLOGICAL COMPOSITIONS AND THEIR USE

CROSS REFERENCE TO RELATED APPLICATIONS

This application is a continuation of U.S. patent application Ser. No. 11/673,486, filed Feb. 9, 2007, which is a continuation of U.S. patent application Ser. No. 10/191,997, filed Jul. 10, 2002, which claims the benefit of U.S. Provisional Application Ser. No. 60/303,820, filed Jul. 10, 2011, the contents of which are incorporated herein by reference.

FIELD OF THE INVENTION

The present invention relates to compositions containing oligonucleotides, and particularly to oligonucleotide-containing compositions suitable for administration to humans and other mammals.

INCORPORATION BY REFERENCE OF SEQUENCE LISTING

The contents of the text file named "Oligos5019US.txt" which was created on Jul. 31, 2002 and is 235 KB in size, are thereby incorporated by reference in their entirety

BACKGROUND OF THE INVENTION

Oligonucleotides, oligonucleotide analogs and other sequence-specific binding polymers designed to block translation of selected messenger RNA (the sense strand) are commonly called antisense oligonucleotides. Development of such oligonucleotides, for therapeutic applications entails selecting a target genetic sequence unique and critical to the pathogen or pathogenic state one wishes to treat. One then assembles an oligomer of genetic bases (adenine, cytosine, guanine, and thymine or uracil) complementary to that selected sequence. When such an antisense oligonucleotide binds to its targeted disease-causing sequence, it can inactivate that target and thereby alleviate the disease. Antisense oligonucleotides offer the prospect of safe and effective therapeutics for a broad range of intractable diseases. Nonetheless, developing therapeutics that function by a true antisense mechanism presents a number of forbidding challenges. The oligonucleotides should achieve adequate efficacy at a concentration attainable within the cells of the patient. They should inhibit their selected target sequences without concomitant attack on any other sequences in the patient's pool of approximately 200 million bases of unique-sequence RNA. They should be stable in extracellular compartments and within cells. They must be deliverable into the cellular compartments containing their targeted sequences. They should be adequately soluble in aqueous solution. Finally, they should exhibit little or no toxicity at therapeutic concentrations.

First-generation antisense oligonucleotides comprised natural genetic material (Belikova et al. (1967) Tetrahedron Lett. 37, 3557-3562; Zamecnik et al. (1978) Proc. Natl. Acad. Sci. USA 75, 280-284; Summerton (1979) J. Theor. Biol. 78, 77-99) and often contained crosslinking agents for binding their targets irreversibly (Summerton et al. (1978) J. Mol. Biol. 122, 145-162). As the design challenges became more fully appreciated, a number of non-natural antisense structural types were developed in an effort to improve efficacy, stability and delivery. Of particular note are the early non-ionic DNA analogs including phosphotriester-linked DNA and methylphosphonate-linked DNA (Cohen (1989) Oligodeoxynucleotides: Antisense Inhibitors of Gene Expression, CRC Press, pp. 82-92). Other nucleic acid analogs of note include carbamate-linked DNA (Cohen (1989) Ohgodeoxynucleotides: Antisense Inhibitors of Gene Expression, CRC Press, pp. 97-117), phosphoroamidate-linked DNA (Froehler et al. (1988) Nucleic Acids Res. 16, 4831-4839) and 2'-O-methyl RNA (Shibahara et al. (1989) Nucleic Acids Res. 17, 239-252). These second generation oligonucleotides include oligonucleotides containing acyclic backbone moieties, including nylon (Weller et al. (1991) J. Org. Chem. 56, 6000-6006; Huang et al. (1991) J. Org. Chem. 56, 6007-6018), the exceptionally high-affinity peptide nucleic acids (PNA) (Egholm et al. (1992) J. Am. Chem. Soc. 114, 1895-1897) and related types (U.S. Pat. No. 5,217,866).

One approach to improving the potency of antisense oligonucleotides is to enhance the affinity or the efficiency with which the antisense oligonucleotides interact with their targets and induce RNase degradation of their target gene transcripts. The doses at which effects have been observed generally range from 10 to 30 mg/kg i.v. (Miraglia et al. (2000) Antisense Nuc. Acid Drug Devel. 10, 453-461). Some clinical studies, however, have not demonstrated antisense activity at doses up to 30 mg/kg i.v. (Rudin et al. (2001) Clin. Cancer Res. 7, 1214-1220; Kushner et al. (2000) Curr. Oncol. Reports 2, 23-30), indicating that results vary based on the structure of the oligonucleotide administered. Typical dose-response curves for antisense oligonucleotides both in vivo and in vitro, often reveal that less than a factor of ten often separates the concentration producing antisense activity from the concentration producing no activity (Branch (1998) Trends Biochem. Sci. 23, 45-50). Since the ratio of antisense to non-antisense effects drops sharply outside a restricted concentration range, it remains challenging to identify common structural features for any antisense oligonucleotide that will enhance affinity and efficiency of the oligonucleotide for its target. Furthermore, no studies to date have identified common structural features of antisense oligonucleotides that would make them suitable for oral administration, thus necessitating intravenous administration (Chen et al. (2000) Antisense Nuc. Acid. Drug Develop. 10, 415-422). Identification of common structural modifications of antisense oligonucleotides that facilitate oral or topical administration would therefore also be advantageous.

Although each of these newer structural types provides one or more significant advantages over the first-generation oligonucleotides, none yet appear to provide the full combination of properties needed in antisense therapeutics for successful therapeutic applications.

SUMMARY OF THE INVENTION

The invention encompasses a composition suitable for administration in a mammal comprising a modified oligonucleotide of about seven to seventy-five nucleotides containing seven or more contiguous ribose groups linked by achiral 5' to 3' internucleoside phosphate linkages, wherein the modified oligonucleotide is complementary to a region of a gene associated with a pathological disorder. In some embodiments, the mammal is a human and the oligonucleotide is a ribonucleotide or deoxyribonucleotide. The modified oligonucleotide can be complementary to a region of the gene selected from the group consisting of the 5' UTR region, translational start site, the 3' UTR, and translational termination site.

In some embodiments, the gene is a gene selected from Table 1 and the pathological disorder is selected from the group consisting of abnormal appetite, hypertension, hypercholesteroremia, hyperlipidemia, erectile dysfunction, eczema, depression, anxiety, stress, inflammatory bowel syndrome, ulcerative colitis, Crohn's disease, renal stones, gall stones, constipation, migraine headache, seizure, multiple sclerosis, polymyositis, fiboromyalgia, Parkinson's disease, ALS, chronic pain, pre-menstrual syndrome, sinusitis, colds, trauma, carpal tunnel syndrome, chronic fatigue syndrome, rosacea, arthritis, psoriasis, prostatitis, inflammation, heartburn, infection, poison ivy, colon cancer, malignant melanoma and malignant nasal polyps. In preferred embodiments, the modified oligonucleotide is selected from the group consisting of SEQ ID NO: 1-81.

In some embodiments, the modified oligonucleotide is present in the composition at a concentration effective to reduce the expression of the gene when administered. When the composition is administered, the modified oligonucleotide is administered at a dose of less than 100 µg/kg, preferably less than 50 µg/kg, more preferably less than 5.0 µg/kg, even more preferably less than 0.50 µg/kg, yet even more preferably less than 0.0501. µg/kg, and most preferably less than 0.0050 µg/kg. Furthermore, the modified oligonucleotide present in the composition may be suitable for oral administration.

The modified oligonucleotides present in the compositions of the invention preferably have a Tm of about 75-115° C. at a concentration of 1 mM and a length of 10 to 26 bases, or a Tm of 40° C. to 85° C. at a concentration of 1 pM and a length of 10 to 26 bases. In one embodiment, the ribose group has a modified 2' substituent selected from the group consisting of hydrogen, methoxy, propoxy, methoxy-ethoxy, flourine, chlorine, bromine and iodine. In another embodiment, the modified oligonucleotide is 3' or 5' end-blocked.

The compositions of the invention may be formulated as pharmaceutical compositions, nutritional or dietary supplement compositions, or as cosmetic compositions. In some embodiments, the compositions of the invention comprise two or more different modified oligonucleotides, while in other embodiments, three or more different modified oligonucleotides.

The invention also encompasses a method of treating a patient with a pathological disorder comprising administering one or more of the aforementioned modified oligonucleotides of the invention, wherein the modified oligonucleotides are about seven to seventy-five nucleotides, contain seven or more contiguous ribose groups linked by achiral 5' to 3' internucleoside phosphate linkages. Preferably, the modified oligonucleotide is complementary to a region of a gene associated with the pathological disorder. More preferably, the gene is selected from Table 1 and the aforementioned pathological disorders are selected from the group consisting of abnormal appetite, hypertension, hypercholesteroremia, hyperlipidemia, erectile dysfunction, eczema, depression, anxiety, stress, inflammatory bowel syndrome, ulcerative colitis, Crohn's disease, renal stones, gall stones, constipation, migraine headache, seizure, multiple sclerosis, polymyositis, fibromyalgia, Parkinson's disease, ALS, chronic pain, pre-menstrual syndrome, sinusitis, colds, trauma, carpal tunnel syndrome, chronic fatigue syndrome, rosacea, arthritis, psoriasis, prostatitis, inflammation, heart burn, infection, poison ivy, colon cancer, malignant melanoma and malignant nasal polyps.

As mentioned above, the invention includes a nutritional supplement comprising a modified oligonucleotide of about seven to seventy-file nucleotides containing seven or more contiguous ribose groups linked by achiral 5' to 3' internucleoside phosphate linkages. The invention also includes a method of supplementing the diet of an individual comprising administering this nutritional supplement, wherein administration of the nutritional supplement improves the health of the individual.

The invention further includes a cosmetic composition comprising a modified oligonucleotide of about seven to seventy-file nucleotides containing seven or more contiguous ribose groups linked by achiral 5' to 3' internucleoside phosphate linkages, wherein the modified oligonucleotide is complementary to a region of a gene associated with a skin disorder. The invention also includes a method of improving the appearance of the skin in an individual with a skin disorder comprising administering this cosmetic composition.

DETAILED DESCRIPTION

The present invention relates to compositions that comprise oligonucleotide molecules, and the use of such compositions to treat the symptoms of diseases/conditions such as acroparaesthsia, allergic (psoric) conditions, allergic reactions, alopecia, amnesia, anaphrodisia, angina, arthritis, asthenopia, biliary sycosis, burns, cancerous conditions, such as colon cancer, malignant melanoma and malignant nasal polyps, carpal tunnel syndrome, colds, conjunctivitis, Crohn's disease, depression, depressive psychosis, dysthyroidism, epilepsy, erectile dysfunction, excessive appetite (i.e., appetite control and suppression, promotion of healthy weight loss while naturally satisfying the appetite), gingivitis, heart burn (i.e., relief of occasional heartburn or occasional acid indigestion), hemorrhage, hypertension (i.e., helps maintain cardiovascular function, and a healthy heart and circulatory system), high cholesterol (i.e., helps to maintain cholesterol levels that are already within the normal range), hyperthyroidism, infections, inflammatory disease, lack of willpower, laryngitis, leucopenia, liver disorders, mental disorders (i.e., reduces stress, frustration, muscle tension, anxiety, and occasional simple nervous tension; enhances resistance to stress), myopia, neurosis, neurological disorders such as multiple sclerosis and ALS, obesity, pain (i.e., relief of minor or temporary aches and pains), pancreatic disorders, poison ivy, premature senescence, pre-menstrual syndrome (i.e., treatment of common symptoms associated with the menstrual cycle such as edema, breast tenderness, headaches, skin problems, cramps and mild mood changes), prostatitis, psoriasis, rosacea, seborrhea, sinusitis, and trauma.

The Oligonucleotide

Generally

A double-stranded DNA molecule encoding a gene has both a sense and an antisense strand. The transcription of RNA uses the antisense strand to make an exact sequence copy of the sense strand (with the minor changes of employing uridine for thymidine, and an RNA backbone in lieu of a DNA backbone). Thus, the RNA formed in transcription has the same nucleotide sequence as the sense strand of the gene. The RNA transcript is processed in the cell to become niRNA, which may subsequently be used as a template to make protein.

The term "oligonucleotides" as used herein, refers to a molecule comprised of nucleotides (i.e., ribonucleotides, deoxyribonucleotides, or both). The term includes monomers and polymers of ribonucleotides and deoxyribonucleotides, or mixtures thereof, with the nucleotides being connected together via, for example 5' to 3' linkages, 5' to 2' linkages, etc. The nucleotides used in the oligonucleotides may be naturally occurring or may be synthetically produced analogues that are capable of forming base-pair relationships with naturally occurring base pairs. Examples of non-naturally occurring bases that are capable of forming base-pairing relationships include, but are not limited to, aza and deaza pyrimidine analogues, aza and deaza purine analogues, and other heterocyclic base analogues, wherein one or more of the carbon and nitrogen atoms of the purine and pyrimidine rings have been substituted by heteroatoms, e.g., oxygen, sulfur, selenium, phosphorus, etc.

The oligonucleotides of the present invention are at least five contiguous nucleotides in length. For example, the oligonucleotide can be five to seventy-five nucleotides in length. The oligonucleotide can also be at least ten sequential nucleotides and alternatively, at least fifteen sequential nucleotides in length. In one embodiment, the oligonucleotide is twelve to twenty-six nucleotides in length. The oligonucleotide sequence can be derived from any of the genes listed in Table I (SEQ ID NO: 82-132). Examples of suitable antisense oligonucleotide sequences for the compositions of the present invention are described in Table 1 below.

TABLE 1

Representation antisense oligonucleotides

| Oligo Name(s) | Gene Target (Accession #) | Nucleic Acid Sequence | SEQ ID |
|---|---|---|---|
| Asm | PDE-4 phosphodiesterase 4 (U50158) (SEQ ID NO: 82) | CGTGTCAGGAGAAC | 1 |
| Ace1, Ace12 | angiotensin I converting enzyme (J04144.1) (SEQ ID NO: 83) | CATGACGCGGTGCG | 2 |
| Acid-2 | ATP4A H+/K+ ATPase alpha (NM_000704) (SEQ ID NO: 84) | GGCAGTCGTCCCTCTA | 3 |
| Acid B2 | ATP4B H+/K+ ATPase beta (NM_000705) (SEQ ID NO: 85) | AACGTTTCACTTCTCA | 4 |
| cd18-1 | Cd-18 (M15395) (SEQ ID NO: 86) | TTGCTACCAGTCT | 5 |
| COX2 CX2 | cyclooxygenase 2 (M90100) (SEQ ID NO: 87) | TCTACAGTTCAGTCGA | 6 |
| Mg44 | HMGCoA reductase 3-hydroxy-3-methylglutaryl-coenzyme A reductase (NM_000859) (SEQ ID NO: 88) | TGACAACATTGTAGCTAC, AGCTACAGAATCCTTGGA, GTCGGGCTATTCAGGC | 7 |
| P65-2M 65 | NficappaB p65 (NM 021975) (SEQ ID NO: 89) | GAACAGTTCGTCCATG | 10 |
| IL-501 | IL-5 (NM_000879) (SEQ ID NO: 90) | CCTCATGGCTCTGAA | 11 |
| LO5 | lipoxygenase 5 (J03571) (SEQ ID NO: 91) | GGAGGGCATGGCGCGG | 12 |
| MPB-19 | SRD5A2 steroid 5-alpha-reductase-2 (M74047) (SEQ ID NO: 92) | CCTGCATCGCGCCGTG | 13 |

TABLE 1 -continued

Representation antisense oligonucleotides

| Oligo Name(s) | Gene Target (Accession #) | Nucleic Acid Sequence | SEQ ID |
|---|---|---|---|
| NEP-1 CALLA | neutral endopeptidase (NM 000902) (SEQ ID NO: 93) | GACTTGCCCATCACCT | 14 |
| NPY-1 | Neuropeptide Y (K01911) (SEQ ID NO: 94) | ACCTAGCATGGTGGCT | 15 |
| D5 PDE5.1 | phosphodiesterase 5 (SEG AB001615) (SEQ ID NO: 95) | CGCTCCATGGTTGGC | 16 |
| D7 | phosphodiesterase 7A (L12052) (SEQ ID NO: 96) | CTTCCATTGAATACGC | 17 |
| Per | Perilipin (AB005293) (SEQ ID NO: 97) | ACTGCCATCCTCGCTC | 18 |
| TTP | tripeptidyl peptidase II | CGGTGGCCATGGACGC | 19 |
| TTPII | (M73047) (SEQ ID NO: 98) | AAGTTCATGGTTTCGGA | 20 |
| MTP | Microsomal trigylceride protein (X59657) (SEQ ID NO: 99) | GAATCATATTTGACCAGCA | 21 |
| HisR1 | Histamine receptor 1 (D14436) (SEQ ID NO: 100) | GGCTCATTGGCGCAAG AGAGCCTCCCTTAGGA | 22 23 |
| CRP | C-reactive protein (M11880) (SEQ ID NO: 101) | CATGGTCACGTCCTGC | 24 |
| CETP | Cholesteryl ester transfer protein (XM_008050) (SEQ ID NO: 102) | ATGGTTATCAGGCAGTGG CATGGTTATCAGGCAGTGG CTGAAGAATTGACCAC | 25 26 27 |
| ICAM | ICAM-1 (J03132) (SEQ ID NO: 103) | CATAGCGAGGCTGAGG | 28 |
| TNF-α | Tumor necrosis factor-alpha (X02910) (SEQ ID NO: 104) | GTGCTCATGGTGTCC | 29 |
| BMP-4 | Bone morphogenic protein (U43842) (SEQ ID NO: 105) | CGACCATCAGCATTC | 30 |
| BAR-1, BB1 | beta adrenergic receptor-1 (NM_000684) (SEQ ID NO: 106) | GCCCATGCCGAGCTGC | 31 |
| IL-6 | Interleukin-6 (X04430) (SEQ ID NO: 107) | AGGAGTTCATACTCTGG | 32 |
| FAAH, FA2H | fatty acid amid hydrolase (U82535) (SEQ ID NO: 108) | GCACCATGATCCCTTC | 33 |

TABLE 1-continued

Representation antisense oligonucleotides

| Oligo Name(s) | Gene Target (Accession #) | Nucleic Acid Sequence | SEQ ID |
|---|---|---|---|
| ACAT-1 | sterol-O-acyl-transferase (XM_031119) (SEQ ID NO: 109) | CTTCACCCACCATTGT | 34 |
| IBAT | ileal sodium dependent bile acid transporter (NM_000452) (SEQ ID NO: 110) | CATTCATTGCTGGGTCTG | 35 |
| HMGIC | High mobility group phosphor-protein isoform C (U28749) (SEQ ID NO: 111) | CGTGCGCTCATCCTG<br>AACGTTGCGCCCCTA | 36<br>37 |
| Ghre | Ghrelin (NM_016362) (SEQ ID NO: 112) | TGCAGACAGGTGGGCC<br>GCATGGCCTCAGCTGGG<br>TGGGCGATCACTTGTC | 38<br>39<br>40 |
| AAT1R | angiotensin II receptor (S77410) (SEQ ID NO: 113) | CATTTTGATCACCTGGGT<br>CGAACATGTCACTCAA | 41<br>42 |
| VEGF | vascular endothelial growth factor (XM_166457) (SEQ ID NO: 114) | AAGTTCATGGTTTCGGA,<br>TCACCG CCTCGG CTTGT | 43<br>44 |
| FA S | fatty acid synthase (U29344) (SEQ ID NO: 115) | CCTCCTCCATGGCTG<br>GCCTAGCCCTCCCGC | 45<br>46 |
| AmP | amyloid P (NM_001639) (SEQ ID NO: 116) | GCAGCGGCTTGTTCAT<br>GAGTCAAGACCTCAG | 47<br>48 |
| PanLip | pancreatic lipase (NM_000936) (SEQ ID NO: 117) | GTGGCAGCATCGTGGC<br>CCTAACACGGTGTGAG | 49<br>50 |
| ACC2 | Acetyl-CoA carboxylase (U89344) (SEQ ID NO: 118) | GAAGCAAGACCATTCAG<br>TCAGGTGGAGGCCGGGC | 51<br>52 |
| PKARIIbeta | cAMP dependent protein kinase subunit RH-beta (M31158) (SEQ ID NO: 119) | TGCTCATCCTGCCTCC<br>GCTTCATGCAGTGGGT | 53<br>54 |
| VR1R | vanilloid receptor subtype 1 (XM_008512) (SEQ ID NO: 120) | TCTTCATCCTTGCTGG<br>CTCACTTCTCCCCGGA | 55<br>56 |
| ADAMTS | disintegrin-like and metalloprotease with thrombospodin type 1 motif (NM_005099) (SEQ ID NO: 121) | GGGACATGGCACTGGT<br>TTATTTCCTGCCCGCC | 57<br>58 |
| NPY-Y5R | neuropeptide Y5 receptor (U94320) (SEQ ID NO: 122) | TGTGGCAGGTCAGTTG<br>ATCCATATTATAGTCT<br>TATTACATATGAAGAC | 59<br>60 |
| GNTV | mannosyl (alpha-1,6) glycopro tein beta- | AGCCATTGCTCTCTGG<br>TGCTATAGGCAGTCTT | 62<br>63 |

TABLE 1 -continued

Representation antisense oligonucleotides

| Oligo Name(s) | Gene Target (Accession #) | Nucleic Acid Sequence | SEQ ID |
|---|---|---|---|
| | 1,6 N-acetyl glucosaminyl transferase (NM_002410) (SEQ ID NO: 123) | | |
| FCRG3 | FC-gamma receptor III-1 (X16863) (SEQ ID NO: 124) | TGCCACATGATGCCAC GTTGAGCTTCAAATGT | 64 65 |
| CD4OL | tumor necrosis factor (ligand) superfamily, member 5 (XM_042961) (SEQ ID NO: 125) | TCGATCATGCTUTGTT GGTGACACTGTTCAG | 66 67 |
| ETS-1 | erythorbl astos is virus oncogene homolog 1 (J04101) (SEQ ID NO: 126) | ACGGCCGCCTICATGG GCCATCACTCGTCGGC | 68 69 |
| ADAMTS-5 | dis inte grin-like metalloprotease with throbospondin type 1, motif 5 (XM_047802) (SEQ ID NO: 127) | CCGAGCAGCATAGTGC TCATAACCACAGGCTA | 70 71 |
| PTP-1B | protein tyrosine phosphatase, non-receptor type 1 (NM_002827) (SEQ ID NO: 128) | CATGACGGGCCAGGGC GGGTCAGGCTATGTGT | 72 73 |
| MMP-1 | matrix metalloproteinase 1 (NM_002421) (SEQ ID NO: 129) | GCATACTGGCCTTTGTC TCAATTTTTCCTGCAGT | 74 75 |
| Cat | Catalase (NM_001752) (SEQ ID NO: 130) | GCCATAGCGTGCGGTT CCCGGCCTCACAGATT | 76 77 |
| MMP-17 | matrix metalloproteinase 17 (NM_016155) (SEQ ID NO: 131) | CATGGCGCTCACATGGG TGTCATAGCGTCAGGGC | 78 79 |
| OPG | Osteoprotegerin (U94332) (SEQ ID NO: 132) | TCATTGTGGTCCCCGG TCCAGTTATAAGCAGC | 80 81 |
| Nu-3 | | 3'5'-dibutyl-dipho spho-thymidine | |

In one embodiment, the oligonucleotide composition of the present invention comprises at least about two oligonucleotides of differing sequence. In another embodiment, the oligonucleotide composition of the present invention comprises at least about three, four, five, six, seven, eight, nine, or ten oligonucleotides of differing sequences. Although Table 1 depicts the sequences as oligonucleotides containing only deoxyribonucleotide residues, it is to be understood that the present invention also includes the embodiments wherein the oligonucleotides are composed of ribonucleotide residues (e.g., by substituting uridine for thymidine, and ribosyl substituents for deoxyribosyl substituents). Moreover, it is to be understood that the present invention also includes the embodiments in which the oligonucleotides are composed of only deoxyribonucleotide residues, of only ribonucleotide residues, or of mixtures of deoxyribonucleotide and ribonucleotide residues.

The oligonucleotides in the present invention display greater than or equal to 80 percent sequence identity to a nucleotide sequence selected from the group of SEQ ID NO: 1-81 (see Table 1). Also preferred, the oligonucleotides display greater than or equal to 85 percent sequence identity to a nucleotide sequence selected from the group of SEQ ID NO: 1-81. Still preferred, the oligonucleotides display 90 percent sequence identity and still more preferred, the oligonucleotides display 95 percent sequence identity. Most preferably, the oligonucleotides of the present invention are selected such that their nucleotide sequence is complementary to the sense strand of a gene.

The degree of similarity between two sequences can be determined using methods well known to the art (e.g., computer programs including Fasta (Oxford Molecular Group Inc.) and BLAST (www.ncbi.nlm.nih.gov) (Altschul et al. (1997) Nucleic Acid Res. 25, 3389-3402). These methods can be employed to take into account gaps in the sequences due to deletions or insertions. Homology or sequence identity at the nucleotide or amino acid sequence level determined by BLAST (Basic Local Alignment Search Tool) analysis uses the algorithm employed by the programs blastp, blastn, blastx, tblastn and tblastx (Altschul et al. (1997) Nucleic Acids Res. 25, 3389-3402 and Karlin et al. (1990) Proc. Natl. Acad. Sci. USA 87, 2264-2268, both fully incorporated by reference) which are tailored for sequence similarity searching. The approach used by the BLAST program is to first consider similar segments, with gaps (non-contiguous) and without gaps (contiguous), between a query sequence and a database sequence, then to evaluate the statistical significance of all matches that are identified and finally to summarize only those matches which satisfy a preselected threshold of significance.

For a discussion of basic issues in similarity searching of sequence databases, see Altschul et al. (1994) Nature Genetics 6, 119-129 which is fully incorporated by reference. The search parameters for histogram, descriptions, alignments, expect (i.e., the statistical significance threshold for reporting matches against database sequences), cutoff, matrix and filter (low complexity) are at the default settings. The default scoring matrix used by blastp, blastx, tblastn, and tblastx is the BLOSUM62 matrix (Henikoff et al. (1992) Proc. Natl. Acad. Sci. USA 89, 10915-10919, fully incorporated by reference), recommended for query sequences over 85 nucleotides or amino acids in length.

For blastn, the scoring matrix is set by the ratios of M (i.e., the reward score for a pair of matching residues) to N (i.e., the penalty score for mismatching residues), wherein the default values for M and N are +5 and −4, respectively. Four blastn parameters were adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings were Q=9; R=2; wink=1; and gapw=32. A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

In a related vein, the oligonucleotides described herein have a Guanine: Cytosine (GC content) greater than 35 percent. The GC content is preferably greater than 40 percent and most preferably, greater than 45 percent.

The Modified Oligonucleotide

The oligonucleotides that may be employed in accordance with the present invention may be modified. An oligonucleotide that comprises at least one modification has one or more chemical modifications at the molecular level of the natural molecular structures of all or any of the nucleic acid bases, sugar moieties, internucleoside phosphate linkages, as well as molecules having added substituents, such as diamines, cholesteryl or other lipophilic groups, or a combination of modifications at these sites. For example, oligonucleotides can be end-blocked, protonated, exhibit substantial acid resistance, substantial nuclease resistance, and contain achiral internucleoside phosphate linkages and modified ribose or deoxyribose substituents.

The term "end-blocked" as used herein refers to a nucleic acid with a chemical modification at the molecular level that prevents the degradation of selected nucleotides, e.g., by exonuclease action. This chemical modification is positioned such that it protects the integral portion of the nucleic acid, for example the portion of an RNA or DNA that is chemically similar to the gene involved in the physiological condition. An end block may be a 3' end block, a 5' end block, or both. For example, a 3' end block may be at the 3'-most position of the molecule, or it may be internal to the 3' ends, provided it is 3' of the integral sequences of the nucleic acid.

The term "protonated compound" refers to a molecule of the invention that, when dissolved in water having a pH of 7 causes the pH of the solution to fall. Generally, compounds are protonated by adding protons to the reactive sites on the molecule, although other modifications of the molecule are possible, and are intended to be encompassed by this term. Such protonation can be accomplished, for example by incubating the compound in the presence of a strong acid, most preferably one with a volatile conjugate base. The term "protonation" and "acidification" as used interchangeably herein refers to the process by which protons (or positively charged hydrogen ions) are added to proton acceptor sites on a compound of the invention. The proton acceptor sites include the substituted or unsubstituted phosphates of the central group, as well as any additional proton acceptor sites on either the central group or the end blocking groups. As the pH of the solution is decreased, the number of these acceptor sites which are protonated increases, resulting in a more highly protonated compound.

Many nucleic acid backbones are not stable at low pH (e.g., pH 1-3) and experience depurination, although a number of backbones are relatively stable at pH 4-5. One aspect of the present invention reflects the recognition that certain modifications, including 2'-halide, 2'-O-alkyl, 3'-O-alkyl, and 2'-O-alkyl-n(O-alkyl) nucleic acid molecules are stable at the desired pH of 2 to 1. These modifications enhance the ability of the oligonucleotides of the pharmacological compositions of the present invention to affect a condition in vivo. Thus, the composition of the present invention may include nucleic acid molecules that are substantially acid resistant. The compositions of the present invention may also include nucleic acid molecules that are nuclease resistant. This includes nucleic acid molecules completely derivatized by 2'-O-methylphosphodiesters, 2'-O-alkyl, 2'-O-alkyl-n(O-alkyl), 2'-fluoro, 2'-deoxy-erythropentofuranosyl, chimeric linkages, and any other backbone modifications, as well as other modifications, which render the nucleic acid molecules substantially resistant to endogenous nuclease activity. Additional suitable methods of rendering nucleic acid molecules nuclease resistant include, but are not limited to, covalently modifying the purine or pyrimidine bases that comprise the nucleic acid. For example, bases may be methylated, hydroxymethylated, or otherwise substituted (e.g., glycosylated) such that the nucleic acid molecules comprising the modified bases are rendered substantially nuclease resistant. Nuclease resistance also aids the oligonucleotides of the compositions of the present invention in retaining their effect in vivo.

Preferably, the oligonucleotides of the of the present invention remain relatively unchanged chemically upon administration to a subject and retain their activity in acidic conditions (pH less than 6.0) or in the presence of an endonuclease or exonuclease (e.g., in an in vivo setting).

The term "substantially acid resistant" as used herein refers to nucleic acid molecules that are resistant to acid degradation as compared to unmodified nucleic acid molecules. Typically, the relative acid resistance of a nucleic acid will be measured by comparing the percent degradation of a resistant nucleic acid with the percent degradation of its unmodified counterpart (i.e., a corresponding nucleic acid of the same length and sequence having a "normal" backbone and bases). A nucleic acid that is acid resistant is preferably at least one and a half times more resistant to acid degradation, more preferably at least two times more resistant, even more preferably at least five times more resistant, and most preferably at least ten times more resistant than their unmodified counterpart.

Although certain acid resistant nucleic acid molecules exhibit marked acid stability and endonuclease resistance, they are sensitive to 3' exonucleases. In order to enhance the exonuclease resistance of 2'-O-alkyl substituted nucleic acid molecules, the 3' or 5' and 3' ends of the nucleic acid are preferably attached to a chemical moiety that provides an exonuclease blocking function. For example, one or more phosphorothioate nucleotides can be placed at either end of the RNA or DNA. Additionally, one or more inverted bases can be placed on either end of the RNA or DNA, or one or more alkyl or alcohol (e.g., butanol-substituted) nucleotides or chemical groups can be placed on one or both ends. Accordingly, a preferred embodiment of the present invention is a nucleic acid comprising a nucleic acid having the following structure: A-B-C, wherein "B" is a 2'-O-alkyl or 2'-O-alkyl-n(O-alkyl) substituted RNA between about 1 and about 98 bases in length, and "A" and "C" are respective 5' and 3' end blocking groups (e.g., one or more phosphorothioate nucleotides (but typically fewer than six), inverted base linkages, or alkyl, alkenyl, alkynyl, O-alkyl, and O-alkyl-n(O-alkyl) groups or substituted nucleotides). A partial list of blocking groups includes inverted bases, dideoxynucleotides, methylphosphates, alkyl groups, aryl groups, cordycepin, cytosine arabanoside, 2'-methoxy, ethoxy nucleotides, phosphoramidates, a peptide linkage, dinitrophenyl group, 2'- or 3'43-methyl bases with phosphorothioate linkages, 3'-O-methyl bases, fluorescein, cholesterol, biotin, acridine, rhodamine, psoralen, glyceryl, methyl phosphonates, butanol, butyl, hexanol, and 3'-O-alkyls. An enzyme-resistant butanol preferably has the structure OH—$CH_2CH_2CH_2CH_2$ (4-hydroxybutyl), which is also referred to as a C4 spacer.

The term "substantially nuclease resistant" refers to nucleic acid molecules that are resistant to nuclease degradation, as compared to naturally occurring or unmodified nucleic acid molecules. Modified oligonucleotides of the invention are at least 1.25 times more resistant to nuclease degradation than an unmodified nucleic acid having the same sequence and number of nucleotides, more preferably at least 2 times more resistant, even more preferably at least 5 times more resistant, and most preferably at least 10 times more resistant than their unmodified counterpart. Such substantially nuclease resistant nucleic acid molecules include, but are not limited to, nucleic acid molecules with modified backbones such as ethylphosphotriesters, 2'-O-methylphosphorothioates, 2'-O-methyl-p-ethoxy ribonucleotides, 2'-O-alkyls, 2'-O-alkyl-n(O-alkyl), 2'-fluoros, 2'-deoxy-erythropentofuranosyls, 2'-O-methyl ribonucleosides, 3'-O-methylribonucleotides, inverted bases (e.g., inverted T's), or chimeric versions of these backbones.

The modified oligonucleotide includes RNA or DNA comprising modifications to the sugar moieties such as 2'-substituted or 3'-substituted ribonucleotides, or deoxyribonucleotide monomers, any of which are connected together via internucleoside linkages. Modified RNA or DNA may also be comprised of PNA or morpholino modified backbones where specificity of the sequence is maintained.

The ribose groups and the internucleoside linkages link the bases in a nucleic acid and are referred to as the nucleic acid backbone. A modified backbone includes modifications to the chemical linkage between nucleotides, as well as other modifications that may be used to enhance stability and affinity, such as modifications to the sugar structure. For example, an L-anomer of deoxyribose may be used, where the base is inverted with respect to the natural D-anomer. In one embodiment, the 2'-OH of the sugar group may be altered to 2'-halogen, 2'-O-alkyl or 2'-O-alkyl-n(O-alkyl), which provides resistance to degradation without compromising affinity. Other suitable modified backbones include the following types of internucleotide linkages: 2'-O-methyl-phosphodiesters, 2'-O-alkyl, 2'-O-ethyl, 2'-O-propyl, 2'-O-butyl, 2'-O-alkyl-n(O-alkyl), 2'-methoxyethoxy, 2'-fluoro, 2'-deoxy-erythropentofuranosyl, 3'-O-methyl, p-isopropyl oligonucleotides, 2'-O($CH_2CH_2O$), $CH_3$, and/or butyne linkages. An oligonucleotide may have combinations of such modified backbones, may be completely modified, or may comprise all or some linkages being phosphodiester linkages.

Preferred internucleoside linkages on the modified oligonucleotide are achiral. The term "achiral" as used herein, refers to a molecule that is superimposable with its mirror image, whereas the term "chiral" refers to a molecule that is not superimposable with its mirror image. Oligonucleotides containing achiral 5' to 3' internucleoside phosphate linkages have internucleotide linkages which are achiral (i.e., no stereochemistry). The achiral oligonucleotides preferably contain at least about three to eight contiguous achiral internucleoside linkages, more preferably, nine to ten contiguous achiral internucleoside linkages, even more preferably, eleven to twelve contiguous achiral internucleoside linkages, and most preferably, is completely comprised of achiral internucleoside linkages through the entire contiguous sequence. In another embodiment, the achiral internucleoside linkages are interspersed with chiral internucleoside linkages (e.g., two contiguous achiral linkages followed by one chiral linkage followed by two contiguous achiral linkages; three contiguous achiral linkages followed by one chiral linkage; four contiguous achiral lingages followed by two achiral linkages, etc.). Examples of achiral internucleoside linkages include, but are not limited to, phosphodiester and diphosphorothioate linkages. Achiral RNA and DNA linkages in the backbone are routinely generated during automated synthesis of oligonucleotides if the final structure is a symmetrical molecule (i.e., a phosphate with the same atom attached to both sides). The internucleoside phosphate linkages can be phosphodiester, or 3' to 3',5' to 2' or 5' to 5' linkages, and combinations of such similar linkages (to produce mixed backbone modified RNA or DNA). The modifications can be internal (single or repeated) or at the end(s) of the RNA or DNA molecule. These modifications can include additions to the nucleic acid molecule, such as cholesteryl, diamine compounds with varying numbers of carbon residues between amino groups and terminal ribose, and deoxyribose or phosphate modifications which cleave or cross-link to the opposite chains or to associated enzymes or other proteins. Electrophilic groups such as ribose-dialdehyde could covalently link with an epsilon amino group of the lysyl-residue of such a protein. A nucleophilic group such as n-ethylmaleimide tethered to an RNA or DNA could covalently attach to the 5' end of an mRNA or to another electrophilic site.

Suitable oligonucleotides for the present invention can be determined by evaluating the Delta G or Gibbs Free energy of oligonucleotide binding to the complementary RNA strand at 37° C. and the Tm. The Gibbs Free energy and Tm are measured from the part of the target gene that corresponds to the RNA oligonucleotide that is added. These values can be calculated using the program found on ftp://ma.chem.rochester.edu and are described in Matthews et al. (1999) J. Mol. Biol. 288, 911-940 and Matthews et al. (1999) RNA 5, 1458-1469. Accordingly, a composition comprising an oligonucleotide, (i) wherein said oligonucleotide is at least 10 nucleotides in length, (ii) the Gibbs Free energy of the binding of said oligonucleotide/RNA target duplex at 37° C. is −15 kCal, (iii) said oligonucleotide is complementary to a region within the target gene selected from the group consisting of 5' UTR, translational start site and translational termination site and (iv) wherein said target gene is a gene as listed in Table 1. The Gibbs free energy is measured between that part of the target gene that corresponds to the oligonucleotide, that part typically being the 5'UTR, translational start site or the translational termination site.

In a preferred embodiment, the Gibbs Free energy of the binding of said oligonucleotide/RNA target duplex at 37° C. is <−20 kCal. Also preferred, the Gibbs Free energy is <−25 kCal. For 12-14 mer oligonucleotides, the Gibbs Free energy is preferably <−15 kCal, for 15-17 mer oligonucleotides, the Gibbs Free energy is preferably <−20 kCal, for 18-20 mer oligonucleotides, the Gibbs Free energy is preferably <−25 kCal, for 21-23 mer oligonucleotides, the Gibbs Free energy is <−30 kCal, and for 24-26 mer oligonucleotides, the Gibbs Free energy is <35 kCal.

Further described in the present invention is a composition comprising an oligonucleotide, (i) wherein said oligonucleotide is at least 10 nucleotides in length, (ii) the Tm of said oligonucleotide to a target gene is about 65-90° C., (iii) said oligonucleotide is complementary to a region within the target gene selected from the group consisting of 5' UTR, translational start site an termination site, and (iv) wherein said target gene is selected from a gene as listed in Table 1. Preferably, the oligonucleotide has a Tm of about 75-90° C. Still preferred, the oligonucleotide has a Tm of about 85-90° C. Still preferred, the Tm of said oligonucleotide to a target gene at 1M monovalent cation concentration is about 65-90° C. The Gibbs free energy is measured between that part of the target gene that corresponds to the oligonucleotide, that part typically being the 5' UTR, translational start site or the translational termination site.

Nutritional Supplements

As used herein, the term "nutritional supplement" refers to a composition that is intended to supplement the diet. A nutritional supplement includes any dietary substance used in mammals to supplement the diet by increasing total dietary intake; or a concentrate, metabolite, constituent, extract, etc. Nutritional supplement includes any product that is intended for ingestion in tablet, capsule, powder, soft-gel, gel-cap, or liquid form. As used herein, the term "nutritional supplement" is used synomously with the term "dietary supplement" and "nutraceutical" throughout the specification.

The present invention provides a composition which is useful as a nutritional supplement to maintain or improve the an individual's health. Preferred indications for dietary supplements include, but are not limited to, maintenance of cardiovascular function and a healthy circulatory system, maintenance of cholesterol levels that are already within the normal range, reduction of stress and frustration, relief of occasional simple nervous tension, relief of nervousness due to common everyday overwork and fatigue, alleviation of restlessness, reduction in nervous irritability, relief from anxiety, relief of muscle tension, enhancement of resistance to stress, promotion of emotional balance and a positive outlook, relief of sour stomach or upset stomach, relief of occasional heartburn or occasional acid indigestion, appetite suppression, promotion of healthy weight loss while naturally satisfying the appetite, appetite control, relief of minor or temporary aches and pains, treatment of common symptoms associated with the menstrual cycle, treatment of mild mood changes, cramps, and edema associated with the menstrual cycle, maintenance of a normal, healthy attitude during pre-menstrual syndrome, diminish the normal symptoms of pre-menstrual syndrome and maintenance of hormonal balance and alleviation of minor pre-menstrual syndrome symptoms such as cramping, breast tenderness, minor mood changes, headaches, bloating and skin problems.

The nutritional supplement composition of the present invention include compositions with a single oligonucleotide and/or a combination of about two or more oligonucleotides. The use of the nutritional supplement compositions of the present invention can be used to treat any of the aforementioned indications. These agents may be combined in an oral dosage with other well known nutritional supplements and/or non-flavonoid antioxidants (e.g., selenium, vitamin E (tocopherol, particularly alpha-tocopherol), vitamin C (ascorbic acid) and coenzyme Q10). Dietary fiber supplements may also be used in the composition.

Other additives may be incorporated in the nutritional supplement of the present invention. Such additives include minerals, (e.g., boron, etc. and trace metals such as zinc, magnesium, manganese, chromium, molybdenum, copper, iron, calcium, and potassium; and other micronutrients such as thiamine, riboflavin, niacin, pantothenic acid, pyridoxine, choline, biotin, inositol, para-aminobenzoic acid, vitamin D, vitamin K, vitamin A). In another embodiment of the invention a dietary fiber supplement such as oat bran or other natural fiber source may also be added to the composition.

Typically the nutritional supplement will further include a pharmaceutically acceptable carrier such as lactose, glucose, sucrose, corn starch, potato starch, cellulose acetate, ethyl cellulose, etc. Diluents and other additives such as one or more pharmaceutically acceptable binding agents, fillers, supports, thickening agents, taste-improving agents, coloring agents, preservatives, stabilizers, regulators, emulsifiers or mixtures thereof may be used depending on the form of the composition employed.

In addition to providing the aforementioned compositions, the invention also includes a method for orally administering the nutritional supplement composition in dosages effective to aid in the maintenance and improvement of an individual's health. The supplement is preferably administered orally. Suitable forms for the nutritional supplement composition for oral administration include tablets, capsules, lozenges, syrups, granules, solutions and suspensions which contain unit doses of the supplement for administration once or several times a day. The nutritional supplement composition of the invention will typically be administered orally as a liquid, tablet or a capsule. Tablets, gel tabs, capsules, liquid and sustained release formulations can be formulated and prepared according to manufacturing techniques well known in the pharmaceutical industry and in a variety of dosage forms.

In one embodiment, the nutritional supplement is a sports drink comprising one or more modified antisense oligonucleotides capable of hybridizing to one or more of the genes listed in Table 1. In a preferred embodiment, the sport drink comprises the modified oligonucleotides Asm (SEQ ID NO: 1), Pde5 (SEQ ID NO: 16), FAAH (SEQ ID NO: 23), CX2 (SEQ ID NO: 6), CRP (SEQ ID NO: 24), LO5 (SEQ ID NO: 12), P65 (SEQ ID NO: 10), CD18 (SEQ ID NO: 5).

Therapeutic Oligonucleotide Compositions

In a related vein, the present invention includes a pharmaceutical composition comprising at least about one oligonucleotide, wherein said oligonucleotide comprises (i) at least about ten contiguous nucleotides in length, (ii) at least about three to eight contiguous achiral internucleoside linkages, (iii) further comprising a pharmaceutically suitable excipient. In alternative embodiments, other oligonucleotides, described herein, are used in the inventive compositions. In some embodiments, the therapeutic composition can be a pharmaceutical or homeopathic composition.

As used herein, the term "pharmaceutical composition" refers to a therapeutic composition that is used to treat a particular disease or pathological disorder that is suitable for parenteral, oral or topical administration in humans.

The compositions containing the modified oligonucleotides of the invention in an admixture with a pharmaceutically acceptable carrier can be prepared according to known techniques. The carrier may take a wide variety of forms depending on the form of preparation desired for administration, e.g., intravenous, oral, topical, aerosol (for topical or inhalation therapy), suppository, parenteral, or spinal injection. The excipient may contain any number of carriers. In the case of homeopathic pharmaceuticals the carriers would preferably be homeopathic carriers, e.g., homeopathic agents that may increase the efficacy of the homeopathic composition or help to alleviate symptoms associated with a physiological condition. In addition, the composition may contain stabilizers, preservatives, and other ingredients, preferably in amounts from about 0.5 to 2.0 percent by weight, provided they do not adversely affect the ability of the pharmacological composition to treat the physiological condition. It is well within the skill of one in the art to determine an appropriate mode of administration and to select an appropriate delivery system.

Administration of the composition will introduce the modified oligonucleotides to the individual in a diluted amount. Exemplary ranges of dosage for oral or topical administration are between about 0.001 mg and 10 mg per day, and preferably between about 0.010 mg and 1.0 mg per day of oligonucleotide in the composition. When orally administered, it is preferred that one dosage unit be administered one to four times per day until relief is achieved or until the symptoms disappear or are satisfactorily attenuated. Normally, a patient is instructed to orally take two to three dosage units per day. The dosage unit may be placed under the tongue of the patient or simply swallowed for such oral administration.

The pharmaceutical compositions of the present invention may be formulated for administration to humans and animals in liquid form, or in tablets, pills, granules, powders, or in ointments, creams, injectables, or suppositories. Ointments and creams are impregnated with a low liquid potency or, sometimes, mother tinctures and are generally prescribed as specific remedies. Liquid compositions may be supplied in amber glass dropper bottles to protect them from light.

In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs, and solutions); or carriers' such as starches, sugars, diluents, granulating agents, lubricants, binders, disintegrating agents and the like in the case of oral solid preparations (such as, for example, powders, capsules and tablets). For homeopathic preparations for example, RNA can be dissolved in a liquid 1 part by weight to produce a ten volumes of liquid attenuation labeled 1×. To produce lower dilutions 1 ml of the 1× attenuation is used (mixed thoroughly) with 9 ml of diluent to produce 2×. This process is repeated until the desired attenuation is achieved.

For administration by injection, preparations may comprise an aqueous solution of a water soluble, or solubilized, and pharmacologically acceptable form of the nucleic acid in an appropriate liquid, e.g., water or saline solution. Injectable suspensions may also be prepared using appropriate liquid carriers, suspending agents, agents for adjusting the isotonicity, preserving agents, and the like. Actual methods for preparing administrable pharmacological compositions and adjustments necessary for administration to subjects will be known or apparent to those skilled in the art.

For topical administration, the carrier may take a wide variety of forms depending on the preparation, which may be a cream, dressing, gel, lotion, ointment, or liquid. A surfactant can be included in the composition to provide deeper penetration of the ingredients. Although natural surfactants are preferred, others such as isopropyl myristate can be used. In one embodiment, the composition is a cosmetic composition for topical administration to the skin. As used herein, the term "cosmetic composition" refers to a composition that is applied topically to the skin to improve the appearance of the skin.

Aerosols are prepared by dissolving or suspending the nucleic acid in a propellant such as ethyl alcohol or in propellant and solvent phases. The pharmaceutical compositions for topical or aerosol form will generally contain from about 0.001 percent by weight (of the nucleic acid) to about 40 percent by weight, preferably about 0.02 percent to about 10 percent by weight, and more preferably about 0.05 percent to about 5 percent by weight depending on the particular form employed. Suppositories are prepared by mixing the nucleic acid with a lipid vehicle such as theobroma oil, cacao butter, glycerin, gelatin, or polyoxyethylene glycols.

The compositions of the invention may also include plant or herbal extracts. For example, topical compositions may include Paraguay tea, Kola and Guarana which provide a source of methylxanthines, saponius, tannins and glycosides which have been shown to reduce swelling and redness. The extract of Paraguay tea is known as "Mate extract" and is described in the International Cosmetic Ingredient Dictionary, 5th Edition. Mate extract is commercially available in combination with extracts of Kola and Guarana that is sold by Cosmetic Ingredient Resources (Stamford, Conn.) under the "QUENCHT" trademark. Suitable herbs which can be used also include *Symphytum officinale, Moschus moscheferous, Pripalia geniculata, Plantago asiatica, Causticum, Helianthemum canadense, Ornithogaluin umbellatum, Clematis crispa, Impatiens pallida, Prunus cerasus, arnica*, etc.

The nucleic acid molecule(s) may be combined with a lipid, cationic lipid, or anionic lipid and the active agent delivered via a nucleic acid/lipid emulsion, or a liposomal suspension. The use of cationic, anionic, and/or neutral lipid compositions or liposomes is generally described in International Publications WO90/14074, WO91/16024, WO91/17424, and U.S. Pat. No. 4,897,355, all herein incorporated by reference. By assembling nucleic acid molecules into lipid-associated structures, the nucleic acid molecules may exhibit an increased half-life in vivo. Examples of suitable anionic lipids for use with RNA or DNA include, but are not limited to, cardiolipin, dimyristoyl, dipalmitoyl, or dioleoyl phosphatidyl choline or phosphatidyl glycerol, palmitoyloleoyl phosphatidyl choline or phosphatidyl glycerol, phosphatidic acid, lysophosphatidic acid, phosphatidyl serine, phosphatidyl inositol, and anionic forms of cholesterol.

Making an Oligonucleotide Composition

The invention includes a method for making an oligonucleotide composition comprising (i) selecting an oligonucleotide that is adjacent to or overlaps a target region of a gene, (ii) determining the Gibbs Free energy value associated with said oligonucleotide in reference to said target gene, (iii) assessing Tm in reference to said target gene, and (iv) performing a sequence database search to determine if said oligonucleotide overlaps the 5' UTR, the translational start sequence, or the translational termination site of an mRNA of a gene different from the target gene.

The oligonucleotide of the present invention can be directed to a translational start site, a 5' UTR or a termination site. Preferably, the oligonucleotide is adjacent to or overlaps the translational start site of the gene by at least about one base. Still preferred, the oligonucleotide overlaps the translational start site by at least about two bases. Still more preferred, the oligonucleotide overlaps the translational start site by at least about three bases.

It is generally preferable to design an RNA or DNA that has the same or similar base sequence as the portion of the complement of a gene that encodes the 5' end of an RNA. However, a nucleic acid may also have, for example, a same or similar base sequence as other regions of the gene, such as the region encoding a translation start site or the 3' untranslated region. In another example, a nucleic acid may be designed to reflect the region around a splice donor or splice acceptor site, either with or without the intervening intron. Of particular interest are nucleic acid molecules whose sequences comprise all or a fragment of the sequence of the complement of a gene that is over-expressed in individuals exhibiting the disease or condition. The identification of overexpression of a gene can be through molecular means, e.g., detection of expression in affected tissue using conventional molecular techniques (e.g., Sambrook et al. (1989) Molecular Cloning: A Laboratory Manual, Cold Spring Harbor Laboratory Press). Overexpression of a gene may also be detected using array technology, or inferred from the results of protein assays, such as ELISA.

Making a Homeopathic Oligonucleotide Composition

A method of making a homeopathic composition comprising (i) triturating solid RNA in a 1/9 ratio with lactose to produce a 1× solid and (ii) repeating the process until the desired attenuation is achieved, is described in the present invention. In a related vein, a method of making a homeopathic composition comprising (i) dissolving 1 part RNA by weight in liquid to produce ten volumes of liquid attenuation labeled 1× and optionally (ii) mixing 1 ml of the 1× attenuation with 9 ml of diluent to produce a lower concentration, is also addressed.

In another embodiment, the invention includes homeopathic compositions containing modified oligonucleotides. In one embodiment, tablets for homeopathic use are preferably produced as placebo tablets that are then medicated by dripping or spraying liquid potencies onto the tablets in such a manner as to ensure a coefficient of impregnation of almost 100 percent. The placebo tablets are preferably formed by compression. Pills or granules are preferably spherical in shape, of about 4 millimeters diameter and 3 to 5 centigrams in weight. They are preferably prepared (form pure lactose) and medicated in the same manner as tablets. For example, solid RNA can be triturated (i.e., ground up) in a 1/9 ratio with lactose (1 gram of RNA+9 grams of lactose) to produce a 1× solid. The process is repeated (1 gram of that material plus 9 grams of lactose) until the desired attenuation is achieved.

For homeopathic compositions, the excipient may contain any number of carriers, and preferably homeopathic carriers, e.g., homeopathic agents that may increase the efficacy of the homeopathic composition or help to alleviate symptoms associated with a physiological condition. For example, RNA can be dissolved in a liquid 1 part by weight to produce a ten volumes of liquid attenuation labeled 1×. To produce lower dilutions 1 ml of the 1× attenuation is used (mixed thoroughly) with 9 ml of diluent to produce 2×. This process is repeated until the desired attenuation is achieved. A homeopathic carrier solution such as that described in U.S. Pat. No. 5,603,915 may be used for increasing the efficacy of the homeopathic agent. This carrier solution is sequentially subjected to an alternating current electrical treatment and a direct current electrical treatment, after which additional ingredients such as seawater, brain hormones, and biologically active enzymes are added. The electrical treatment of the carrier, along with the addition of homeopathically active substances, can be used to increase the efficacy of the homeopathic composition. Alternatively, an electromagnetic carrier, such as described in U.S. Pat. No. 5,830,140 may be employed.

Methods of Treatment

The invention includes a method of treating a disorder comprising administering an oligonucleotide to a patient in a therapeutically effective amount. As used herein, the term "therapeutically effective" amount is meant to refer to an amount of a pharmacological composition that is non-toxic and is the lowest amount necessary to provide a desired physiological effect. Preferably, the oligonucletide compositions of the present invention are administered at concentrations at or below 100 μg per kg of body weight. Also preferred, the concentration is at or below 10 μg per kg of body weight, still preferred, the concentration is at or below 1 μg per kg of body weight, and still more preferred, the concentration is at or below 0.1 μg per kg of body weight. Furthermore, for homeopathic use, the oligonucleotide compositions of the present invention can be combined with any homeopathic drug and still elicit a therapeutic effect.

Preferably, the oligonucleotide comprises at least one modification according to the present invention. A preferred modification is the incorporation of at least about three to eight contiguous achiral internucleoside phosphate linkages into the oligonucleotide backbone. More preferably the oligonucleotide incorporates at least nine to ten continuous achiral internucleoside phosphate linkages, even more preferably, eleven to fifteen achiral internucleoside phosphate linkages, and most preferably, the entire oligonucleotide contains achiral internucleoside phosphate linkages. Also preferred, the oligonucleotide is 3' end-blocked, comprises at least 10 contiguous nucleotides greater than or equal to 80 percent identical to a nucleotide sequence selected from SEQ ID NO: 1-81. Also preferred, the oligonucleotide is at least 85 percent identical to a nucleotide sequence selected from the group of SEQ ID NO: 1-81. Still preferred, the oligonucleotide is at least 90 percent identical and more preferred, at least 95 percent identical. Most preferably, the oligonucleotide comprises a sequence from SEQ ID NO: 1-81.

The methods of the present invention can be used to treat disorders including, but not limited to, acroparaesthsia, allergic (psoric) conditions, allergic reactions, alopecia, amnesia, anaphrodisia, angina, arthritis, asthenopia, biliary sycosis, burns, cancerous conditions, such as colon cancer, malignant melanoma and malignant nasal polyps, carpal tunnel syndrome, colds, conjunctivitis, Crohn's disease, depression, depressive psychosis, dysthyroidism, epilepsy, erectile dysfunction, excessive appetite (i.e., appetite control and suppression, promotion of healthy weight loss while naturally satisfying the appetite), gingivitis, heart burn (i.e., relief of occasional heartburn or occasional acid indigestion), hemorrhage, hypertension (i.e., helps maintain cardiovascular function, and a healthy heart and circulatory system), high cholesterol (i.e., helps to maintain cholesterol levels that are already within the normal range), hyperthyroidism, infections, inflammatory disease, lack of willpower, laryngitis, leucopenia, liver disorders, mental disorders (i.e., reduces stress, frustration, muscle tension, anxiety, and occasional simple nervous tension; enhances resistance to stress), myopia, neurosis, neurological disorders such as multiple sclerosis and ALS, obesity, pain (i.e., relief of minor or temporary aches and pains), pancreatic disorders, poison ivy, premature senescence, pre-menstrual syndrome (i.e., treatment of common symptoms associated with the menstrual cycle such as edema, breast tenderness, headaches, skin problems, cramps and mild mood changes), prostatitis, psoriasis, rosacea, seborrhea, sinusitis, and trauma.

Table 2 lists the oligonucleotides, or combinations of oligonucleotides that are preferably employed in remedies for the treatment of various symptoms and conditions. In Table 2, the use of a combination of oligonucleotides is denoted by a "/" (for example, "A/B/C" denotes the combined use of oligonucleotides A, B and C); where two or more different combinations are preferred, each such combination is presented on a separate line. The oligonucleotides are usually used in a 1:1:1 ratio, but this can vary. For example, a combination of 4x, 5x, and 6x solutions may be used, which deviates from 1:1:1.

TABLE 2

| Indication or Condition | Oligonucleotide Combination |
|---|---|
| Arthritis | Asm/X2/P65-2M |
|  | Asm/X2/P65-2M/L05-38 |
| Carpal Tunnel Syndrome | Asm |
|  | Asm/X2/P65-2M |
| Chronic Fatigue/Fibromyalgia | Asm/D5/X2 |
| Colds | Asm |
| Crohn's Disease | X2/P65-2M |
| Depression | Asm/D5 |
| Erectile Dysfunction (ED) | Asm/D5 |
| Heartburn | Acid-2/B2 |
| High Cholesterol | Mg44 |
| Hyperlipidemia | Mg44/Asm/D5 |
| Hypertension | Acel |
|  | Acel/Nep-1 |
| Inflammation | Asm/X2 |
|  | Asm/X2/P65-2M |
|  | Asm/X2/P65-2M/L05-38 |
| Pain | Asm/X2 |
|  | Asm/X2/P65-2M |
| Pre-Menstrual Syndrome (PMS) | Asm/D5/X2 |
| Psoriasis | Asm/D5/P65-2M |

TABLE 2-continued

| Indication or Condition | Oligonucleotide Combination |
|---|---|
| Rosacea | Asm |
|  | Asm/D5 |
| Prostatitis | MBP |
| Stress | Asm/D5 |
| Trauma | Asm |
|  | Asm/X2/P65-2M |
| Ulcerative colitis | X2/P65-2M/L05-38 |
| Weight Management | TIP |

The compositions of the present invention are formulated to contain a "nutritionally effective" or "allopathically effective" or "homeopathically effective" amount of one or more nucleic acid molecules. As used herein, the term "nutritionally effective" amount is meant to refer to an amount of a oligonucleotide composition that is non-toxic and greater than the minimum amount necessary to maintain a desired physiological effect. As used herein, the term "allopathically effective" amount is meant to refer to an amount of a oligonucleotide composition that is non-toxic and greater than the minimum amount necessary to produce a desired physiological effect.

As used herein, the term "homeopathically effective" amount is meant to refer to an amount of a oligonucleotide composition that is non-toxic and is the lowest amount necessary to provide a desired physiological effect. A homeopathic effect, in accordance with the present invention, is achieved by a dose of modified nucleic acid that will be effective in treating (i.e., relieving, ameliorating, or preventing) symptoms of a particular condition or disease. Such treatment may be prophylactic in nature (i.e., completely or partially preventing the future occurrence of a symptom) and/or it may be therapeutic in nature (i.e., providing a partial or complete cessation or amelioration of a symptom). The method of treating of the present invention covers any treatment of symptoms of a disorder in a mammal, particularly a human, and includes:

(a) preventing symptoms of a disorder from occurring in a subject that may be predisposed to a condition but has not yet been diagnosed as having it;

(b) inhibiting symptoms of a disorder (i.e., arresting its development); or (c) relieving symptoms of a disorder (i.e., ameliorating and/or causing regression of the condition); and/or (d) maintaining homeostasis (i.e., the normal balance of RNA or DNA in a subject).

One of ordinary skill will appreciate that, from a medical practitioner's or patient's perspective, virtually any alleviation or prevention of an undesirable symptom would be desirable. Homeopathic compositions typically employ substantially less nucleic acid than is employed in allopathic compositions. Exemplary dosages to be employed in accordance with the present invention, are described in Table 3 below.

| Homeopathic RNA/DNA Concentration | |
|---|---|
| Dilution/Potency | µ/kg |
| 2x | 50 |
| 3x | 5 |
| 4x | 0.5 |
| 5x | 0.05 |
| 6x | 0.005 |

When used in the therapeutic treatment of disease, an appropriate dosage of one or more therapeutic compositions of the invention may be determined by any of several well-established methodologies. Additionally, dosages may also be altered depending upon factors such as the severity of infection, and the size or species of the host.

Preferably, animals are treated using compositions of the present invention having agents with compositions containing nucleic acid molecules having a sequence appropriate for the particular animal. Targeted species include, but are not limited to birds, fish, and mammals (especially pigs, goats, sheep, cows, dogs, horses, cats, and most preferably, humans).

Having now generally described the invention, the same will be more readily understood through reference to the following examples, which are provided by way of illustration, and are not intended to be limiting of the present invention, unless specified. The effectiveness of the RNA oligonucleotide compositions according to the preferred embodiments of the present invention is demonstrated in the Examples below.

Example 1

Individuals with cancers were typically administered a composition containing oligonucleotides complementary to cyclo-oxygenase 2 and $NF_KB$ p65 at concentrations of 3 to 30 $A_{260}$/RNA/ml (1.0-10 µg/kg). Some individuals were additionally administered oligonucleotides complementary to lipoxygenase 5. After approximately one to two months of therapy, the effect of the composition was then evaluated on individuals who completed the study (see Table 4). Treatment efficacy was evaluated by each patient and confirmed by the treating physician. A scaled score of 1 to 10 was used to evaluate treatment efficacy over a period of one to two months where a score=10 represented no improvement and a score=1 represented total alleviation of symptoms.

Example 2

Individuals with excessive appetite were orally administered an oligonucleotide composition containing RNA oligonucleotides complementary to the tripeptidyl gene. RNA oligonucleotide concentrations were typically 0.3 to 3.0 $A_{260}$/RNA/inland given in dosages (0.1-1.0 µg/kg of 0.5 ml twice daily). The effect of the composition was then evaluated after approximately one to two months of therapy (see Table 5). Treatment efficacy was evaluated by each patient and confirmed by the treating physician. A scaled score of 1 to 10 was used to evaluate treatment efficacy where a score=10 represented a voracious appetite and a score=1 represented the absence of hunger and the ability to lose weight.

Example 3

Individuals diagnosed with arthritis were orally administered oligonucleotide compositions with RNA oligonucleotides complementary to phosphodiesterase 4 and $NF_KB$ p65. Some people were additionally given compositions further containing RNA oligonucleotides complementary to other genes. RNA oligonucleotide concentrations were typically between the range of 0.3 to 300 $A_{260}$/RNA/ml and given in dosages (0.1-100 µg/kg) of 0.5 ml twice daily. The effect of the composition was then evaluated after approximately one to two months of therapy (see Table 6). Treatment efficacy was evaluated by each patient and confirmed by the treating physician. A scaled score of 1 to 10 was used to evaluate treatment efficacy where a score=10 represented severe arthritis characterized by inability to freely move affected joints, restricted movement, pain and inflammation and a score—1 represented reduced inflammation, restoration of movement and the absence of pain.

Example 4

Individuals with elevated blood pressure were orally administered oligonucleotide compositions with RNA oligonucleotides complementary to CE and/or neutral endopeptidase genes. Some individuals were additionally given compositions with RNA oligonucleotides complementary to other genes. Concentrations were typically 3.0 to 30 $A_{260}$/RNA/ml and given in dosages (1.0-10 µg/kg) of 0.5 ml twice daily. The effect of the composition was evaluated after approximately one to two months of therapy (see Table 7). Treatment efficacy was determined by measuring changes in blood pressure where a decrease in blood pressure below 160/89 was assessed as a successful treatment because blood pressure above this level has been associated with stroke, heart disease and kidney failure.

Example 5

Individuals with elevated cholesterol were orally administered oligonucleotide compositions containing RNA oligonucleotides complementary to the 3-hydroxy-3-methyl-glutaryl-coenzyme A reductase gene. Some individuals were also given oligonucleotide compositions further containing RNA oligonucleotides complementary to other genes such as phosphodiesterase 4 and phosphodiesterase 5. RNA oligonucleotide concentrations were typically 3.0 to 30 $A_{260}$/RNA/ml and given in dosages (1.0-10 µg/kg) of 0.5 ml twice daily. The effect of the composition on serum cholesterol was evaluated after approximately one to two months of therapy (see Table 8). Treatment efficacy was determined by measuring changes in serum cholesterol where a one-point drop corresponded to a two percent reduction in the probability of heart disease and a twenty-five-point drop corresponded to a fifty percent reduction in the probability of heart disease.

In addition, the effect of compositions containing RNA oligonucleotide with eight or more contiguous achiral internucleoside phosphate linkages on cholesterol levels was also assessed. In a representative individual, oligonucleotide compositions containing achiral RNA oligonucleotides complementary to 3-hydroxy-3-methylglutaryl-coenzyme A reductase, phosphodiesterase 4 and phosphodiesterase 5 were given orally in combination at a concentration of 3.0 $A_{260}$/RNA/ml at dosages of 0.5 ml, twice daily. The achiral RNA oligonucleotides produced a decrease of 46 mg/dL in serum cholesterol. The achiral 2'methoxy-RNA supplements resulted in a 31 mg/dL decrease in serum cholesterol levels. Chiral RNA or DNA did not effect cholesterol levels.

Example 6

Individuals with emotional distress were orally administered an oligonucleotide composition containing RNA oligonucleotides complementary to the phosphodiesterase 4 and phosphodiesterase 5 genes. RNA oligonucleotide concentrations were typically 0.3 to 3.0 $A_{260}$/RNA/ml and were given in dosages (0.1-1.0 µg/kg) of 0.5 ml two to six times per day. The effect of the composition was evaluated after approximately one to two months of therapy (see Table 9).

A scaled score of 1 to 10 was used to evaluate treatment efficacy where a score=10 represented a severely depressed patient with suicidal tendencies and a score=1 represented a emotionally stable patient.

Example 7

Individuals with various gastrointestinal disorders were orally administered oligonucleotide compositions with RNA oligonucleotides complementary to the phosphodiesterase 4 and/or cyclooxygenase 2 genes. Some individuals were given compositions additionally containing RNA oligonucleotides complementary to other genes such as phosphodiesterase 5 and $NF_KB$ p65. Oligonucleotide concentrations were typically 0.3 to 3.0 $A_{260}$/RNA/ml and given in 0.5 ml dosages (0.1-1.0 μg/kg) twice per day. The effect of the composition was evaluated after approximately one to two months of therapy (see Table 10). A scaled score of 1 to 10 was used to evaluate treatment efficacy where a score=10 represented a patient with above normal bowel movement frequency and the presence of blood in the feces and a score=1 represented a patient with normal frequency of bowel movements and the absence of blood in the feces.

Example 8

Individuals with various types of inflammation were orally or topically (as indicated) administered oligonucleotide compositions containing oligonucleotides complementary to the phosphodiesterase 4 or interleukin 5 genes. Some individuals were given compositions additionally containing RNA oligonucleotides complementary to other genes such as cyclooxygenase 2 and $NF_KB$ p65. RNA oligonucleotide concentrations were typically 0.03 to 300 $A_{260}$/RNA/ml given in doses (0.01-100 μg/kg) of 0.5 ml twice per day. The effect of the composition was then evaluated (see Table 11). A scaled score of 1 to 10 was used to evaluate treatment efficacy after approximately one to two months of therapy, where a score=10 represented presence of debilitating inflammation with severe pain and a score=1 represented the absence of inflammation and pain.

Example 9

Individuals suffering from migraine headaches were orally administered oligonucleotide compositions containing RNA oligonucleotides complementary to the phosphodiesterase 4, phosphodiesterase 5, cyclooxygenase 2 and 3-hydroxy-3-methylglutaryl-coenzyme A reductase genes. Oligonucleotide concentrations were typically 3.0 to 30 $A_{260}$/RNA/ml taken in dosages (1.0-10 μg/kg) of 0.5 ml two to four times per day. The effect of the composition was evaluated after approximately one to two months of therapy (see Table 12). A scaled score of 1 to 10 was used to evaluate treatment efficacy where a score=10 represented severe debilitating headache pain including facial pain accompanied by nausea and sensitivity to light and a score=1 represented the absence of these conditions.

Example 10

Individuals with various neurological disorders were orally administered oligonucleotide compositions containing RNA oligonucleotides complementary to the phosphodiesterase 4, cyClooxygenase 2 and p65 genes. Some individuals were given compositions containing additional RNA oligonucleotides complementary to other genes such as lipoxygenase 5. Oligonucleotide concentrations were typically 3.0 to 30 $A_{260}$/RNA/ml taken in dosages (1-10 μg/kg) of 0.5 ml two to four times per day. The effect of the compositions was evaluated after approximately one to two months of therapy (see Table 13). A scaled score of 1 to 10 was used to evaluate treatment efficacy where a score=10 represented a patient with a debilitating form of the indicated neurological disorder (i.e., amyotrophic lateral sclerosis, multiple sclerosis, Alzheimer's disease, Parkinson's disease) and a score=1 represented a patient with no symptoms or mild symptoms associated with the indicated neurological disorder.

Example 11

Individuals suffering from various types of pain were orally administered oligonucleotide compositions containing RNA oligonucleotides complementary to phosphodiesterase 4 and/or cyclooxygenase 2. Some individuals were given compositions containing additional RNA oligonucleotides complementary to other genes such as phosphodiesterase 5 and p65. Oligonucleotide concentrations were typically 0.3 to 3.0 $A_{260}$/RNA/ml and taken in dosages (0.1-10 μg/kg) of 0.5 ml two to four times a day. The effect of the composition was evaluated after approximately one to two months of therapy (see Table 14). A scaled score of 1 to 10 was used to evaluate treatment efficacy where a score=10 represented a patient with severe pain requiring treatment with a subscription analgesic and a score=1 represented a patient with the absence of pain.

Example 12

Female individuals diagnosed with pre-menstrual syndrome were orally administered oligonucleotide compositions containing RNA oligonucleotides complementary to the phosphodiesterase 4 gene. Some individuals were given compositions containing additional RNA oligonucleotides complementary to other genes such as phosphodiesterase 5 and cyclooxygenase 2. RNA oligonucleotide concentrations were typically 0.03 to 3.0 $A_{260}$/RNA/ml taken in doses (0.01, 1.0 μg/kg) of 0.5 ml two to four times per day. The effect of the composition was evaluated after approximately one to two months of therapy (see Table 15). A scaled score of 1 to 10 was used to evaluate treatment efficacy where a score=10 represented a patient with cramps, bloating, irritability, nausea and vomiting and a score=1 represented a patient with the absence of these conditions.

Example 13

Male individuals diagnosed with prostatitis were orally administered oligonucleotide compositions containing RNA oligonucleotides complementary to the steroid 5-alpha-reductase-2 gene. Some individuals were given compositions containing additional RNA oligonucleotides complementary to other genes such as phosphodiesterase 4 and p65 (Super 8+composition=Asm, X2, D5, P65, cd-18, IL-5, LO5 and ICAM). Oligonucleotide concentrations were typically 3.0 $A_{260}$/RNA/ml taken in doses (1.0 μg/kg) of 0.5 ml two to four times per day. The effect of the composition was evaluated after approximately one to two months of therapy (see Table 16). A scaled score of 1 to 10 was used to evaluate treatment efficacy where a score=10 represented a patient with urgent need to urinate three to five times per night and a score=1 represented a patient who slept through the night without urinating.

Example 14

Individuals suffering from cold and sinusitis symptoms were administered (intranasal) oligonucleotide compositions containing RNA oligonucleotides complementary to phosphodiesterase 4 and a DNA monomer, Nu 3. Some individuals were given compositions containing additional RNA oligonucleotides complementary to other gene targets such as cyclooxygenase 2 and NF$_K$B p65. RNA and DNA concentrations were typically 0.3 to 30 A$_{260}$/RNA/ml (0.1-10 µg/kg). Treatment efficacy was evaluated after approximately one to two months of therapy (see Table 17). A scaled score of 1 to 10 was used to evaluate treatment efficacy where a score=10 represented a patient with sneezing, stuffy nose and watery eyes and a score=1 represented a patient with the absence of these conditions.

Example 15

Individuals with various types of trauma were orally or topically (as indicated) administered oligonucleotide compositions containing RNA oligonucleotides complementary to phosphodiesterase 4. Some individuals were given compositions containing additional RNA oligonucleotides complementary to other genes such as cyclooxygenase 2 and NF$_K$B p65. Oligonucleotide concentrations ranged from 0.3 to 3.0 A$_{260}$/RNA/ml and taken in 0.5 ml doses (0.1-1.0 µg/kg) two to four times per day. The effect of the composition was evaluated after approximately one to two months of therapy (see Table 18). A scaled score of 1 to 10 was used to evaluate treatment efficacy where a score=10 represented a patient with severe inflammation and pain associated with the indicated trauma and a score=1 represented a patient with no inflammation or pain.

Example 16

Individuals diagnosed with carpal tunnel syndrome were orally administered oligonucleotide compositions containing RNA oligonucleotides complementary to the phosphodiesterase 4 gene. Some individuals were given compositions containing additional RNA oligonucleotides complementary to other genes such as cyclooxygenase 2, NF$_K$B p65 and other gene targets. Oligonucleotide concentrations were typically 0.03 to 300 A$_{260}$/RNA/ml taken in doses (0.01-100 µg/kg) of 0.5 ml two to four times per day. The effect of the composition was evaluated after approximately one to two months of therapy (see Table 19). A scaled score of 1 to 10 was used to evaluate treatment efficacy where a score=10 represented a patient with pain; tingling and numbness in the wrist area necessitating the use of a wrist brace and a score=1 represented a patient with the absence of these conditions and who did not require the assistance of a wrist brace.

Example 17

Individuals diagnosed with chronic fatigue syndrome or fibromyalgia were orally administered oligonucleotide compositions containing RNA oligonucleotides complementary to the phosphodiesterase 4 gene. Some individuals were given compositions containing additional RNA oligonucleotides complementary to other genes such as cyclooxygenase 2 and p65. Oligonucleotide concentrations were typically 3.0 to 30 A$_{260}$/RNA/ml taken in doses (1.0-10 µg/kg) of 0.5 ml two to four times per day. The effect of the composition was evaluated after approximately one to two months of therapy (see Table 20). A scaled score of 1 to 10 was used to evaluate treatment efficacy where a score=10 represented a patient who complained of being chronically exhaustion accompanied by minor aches and pain and a score=1 represented a patient who did not complain of any such symptom.

Example 18

Individuals suffering from eczema and atopic dermatitis were orally or topically (as indicated) administered oligonucleotide compositions containing RNA oligonucleotides complementary to the phosphodiesterase 4 gene. Some individuals were given compositions containing additional RNA oligonucleotides complementary to other genes such as cyclooxygenase 2 and p65 and other gene targets. Oligonucleotide concentrations were typically 0.3 to 3.0 A$_{260}$/RNA/ml taken in doses (0.1-1.0 µg/kg) of 0.5 ml two to four times per day. The effect of the composition was evaluated after approximately one to two months of therapy (see Table 21). A scaled score of 1 to 10 was used to evaluate treatment efficacy where a score=10 represented patient with itching, inflamed skin and minor bleeding, and a score=-I represented a patient with normal skin.

Example 19

Male individuals suffering from erectile dysfunction were orally administered compositions containing RNA oligonucleotides complementary to the phosphodiesterase 4 gene. Some individuals were given compositions containing additional RNA oligonucleotides complementary to other genes such as phosphodiesterase-5. Oligonucleotide concentrations were typically 3.0 to 3.0 A$_{260}$/RNA/ml taken in doses (1.0-10 µg/kg) of 0.5 ml two to four times per day. The effect of the composition was evaluated after approximately one to two months of therapy (see Table 22). A scaled score of 1 to 10 was used to evaluate treatment efficacy where a score=10 represented a patient who could not obtain or maintain an erection and a score=1 represented a patient who was able to obtain and maintain an erection.

Example 20

Individuals suffering from acid reflux were orally administered compositions containing RNA oligonucleotides complementary to the ATP4A gene. Some individuals were given compositions containing additional RNA oligonucleotides complementary to other genes such as ATP4B. Oligonucleotide concentrations were typically 3.0 to 30 A$_{260}$/RNA/ml taken in doses (1.0-10 µg/kg) of 0.5 ml two to four times per day. The effect of the composition was evaluated after approximately one to two months of therapy (see Table 23). A scaled score of 1 to 10 was used to evaluate treatment efficacy where a score=10 represented a patient with heartburn requiring treatment with excessive amounts of antacid medication and a score=1 represented a patient with no heartburn.

Example 21

Individuals suffering from poison ivy were orally or topically (as indicated) administered compositions containing RNA oligonucleotides complementary to the phosphodiesterase 4 gene. Oligonucleotide concentrations were typically 0.3 to 300 A$_{260}$/RNA/ml taken in doses 0.1-100 µg/kg) of 0.5 ml two to four times per day. The effect of the composition was evaluated after approximately one to two months of therapy (see Table 24). A scaled score of 1 to 10 was used to evaluate treatment efficacy where a score=10 represented a patient with poison ivy covering up to ninety-five percent of the entire body with dermal discharge and secondary inflammation restricting eye openings and a score=1 represented a patient without these symptoms.

Example 22

Individuals with psoriasis were orally or topically administered compositions containing RNA oligonucleotides complementary to the phosphodiesterase 4 gene. Some individuals were given compositions containing additional RNA oligonucleotides complementary to other genes such as phosphodiesterase-5 and p65. Oligonucleotide concentrations were typically 0.3 to 300 $A_{260}$/RNA/ml taken in doses of 0.5 ml (0.1-100 μg/kg) two to four times per day. The effect of the composition was evaluated after approximately one to two months of therapy (see Table 25). A scaled score of 1 to 10 was used to evaluate treatment efficacy where a score=10 represented a patient with thick silvery-colored scaly patches of skin with dermal discharge and bleeding and a score=1 represented a patient with normal skin.

Example 23

Ten individuals with rosacea were orally or topically administered compositions containing RNA oligonucleotides complementary to the phosphodiesterase 4 gene. Some individuals were given compositions containing additional RNA oligonucleotides complementary to other genes such as cyclooxygenase 2 and p65. Oligonucleotide concentrations were typically 0.3 to 300 $A_{260}$/RNA/ml taken in doses (0.1-100 μg/kg) of 0.5 ml two to four times per day. The effect of the composition was evaluated after approximately one to two months of therapy (see Table 26). A scaled score of 1 to 10 was used to evaluate treatment efficacy where a score=10 represented a patient with red, inflamed facial skin with pimples (e.g., acne) and a score=1 represented a patient normal skin.

TABLE 4

Cancer Therapy

| | sex | age | condition | oligonucleotides | Severity before | Severity after |
|---|---|---|---|---|---|---|
| 1 | m | 38 | Skin cancer | X2/65 | 7-8 | 1-2 |
| 2 | m | 72 | Skin cancer | X2/65/L05-38 | 7-8 | stable |
| 3 | f | 52 | Malignant nasal polyps | X2/65/L05-38/Mg44 | 10 | 1 |
| 4 | f | 47 | Malignant melanoma | X2/65/L05-38/Mg44 | 10 | stable |
| 5 | f | 56 | Breast cancer | X2/65/L05-38 | 10 | stable |

TABLE 5

Appetite Control

| | sex | age | condition | oligonucleotide | Efficacy |
|---|---|---|---|---|---|
| 1 | f | 37 | appetite control | Ttp | 7 |
| 2 | f | 52 | appetite control | Ttp | 10 |
| 3 | f | 65 | appetite control | Ttp | 5 |
| 4 | f | 46 | appetite control | Ttp | 8 |
| 5 | f | 44 | appetite control | Ttp | 7 |

TABLE 5-continued

Appetite Control

| | sex | age | condition | oligonucleotide | Efficacy |
|---|---|---|---|---|---|
| 6 | f | 63 | appetite control | Ttp | 8 |
| 7 | f | 48 | appetite control | Ttp | 6 |
| 8 | f | 59 | appetite control | Ttp | 7 |
| 9 | m | 40 | appetite control | Ttp | |
| 10 | f | 40 | appetite control | Ttp | 8 |
| 11 | f | 54 | appetite control | Ttp | 8 |
| 12 | f | 52 | appetite control | Ttp | 7 |
| 13 | f | 58 | appetite control | Ttp | 7 |
| 14 | f | 41 | Appetite control | Ttp | 8 |
| 15 | f | 39 | Appetite control | Ttp | 8 |
| 16 | f | 54 | Appetite control | Ttp | 7 |

TABLE 6

Arthritis Treatment

| | sex | age | condition | oligonucleotide | Severity before | Severity after |
|---|---|---|---|---|---|---|
| 1 | m | 50 | Arthritis (back) | Asm/X2/65 | 5 | 1 |
| 2 | f | 60 | Arthritis (general) | Asm/X2/65 | 6 | 1 |
| 3 | f | 63 | Rheumatoid Arthritis | Asm/X2/65/L05-38/CRP | 10 | 5 |
| 4 | f | 66 | Arthritis (general) | Asm/X2/65/1D5 | 7 | 1 |
| 5 | m | 50 | Arthritis (hands) | Asm/65 | 10 | 2 |
| 6 | f | 28 | Arthritis (knee) | Asm/X2/65 | 7 | 1-2 |
| 7 | f | 74 | Arthritis (knee) | Asm/X2/65 | 8 | 2-3 |
| 8 | f | 82 | Arthritis (general) | Asm/X2/65/L05-38 | 8 | 2 |
| 9 | m | 65 | Arthritis (back/hand) | Asm/X2/65 | 6 | 2 |
| 10 | f | 63 | Arthritis (knee) | Asm/X2/65/L05-38/CRP | 10 | 3-4 |
| 11 | f | 55 | Arthritis (back/hands) | Asm/X2/65 | 7 | 1 |
| 12 | m | 48 | Arthritis (general) | Asm/X2/65 | 6 | 1 |
| 13 | m | 46 | Arthritis (general) | Asm/X2/65 | 5 | 1 |
| 14 | f | 90 | Arthritis (hand) | Asm/X2/65 | 9-10 | 1 |
| 15 | m | 53 | Arthritis (fingers) | Asm/X2/65 | 8 | 1 |
| 16 | f | 28 | Arthritis (neck) | Asm/X2/65 | 7-8 | 1 |
| 17 | f | 49 | Arthritis (hands) | 65 | 5-6 | 1 |
| 18 | f | 51 | Arthritis (shoulder) | Asm/X2/65 | 5 | 1 |
| 19 | m | 77 | Arthritis (knee) | Asm/X2/65/L05-38/CRP/D5 | 10 | 3-4 |
| 20 | m | 52 | Arthritis (knee) | Asm/X2/65/L05-38/D7/CRP | 7 | 3-4 |
| 21 | f | 53 | Arthritis (back) | Asm/X2/65/L05-38/CRP | 7 | 4 |
| 22 | f | 64 | Arthritis (thumbs) | Asm/X2/65/L05-38/CRP | 7 | 3 |
| 23 | f | 47 | Arthritis (general) | Asm/X2/65 | 8-9 | 2 |
| 24 | f | 74 | Arthritis (general) | Asm/X2/65/L05-38/Mg44 | 10 | 1 |
| 25 | m | 65 | Arthritis (back) | Asm/X2/65 | 9 | 2-3 |
| 26 | f | 61 | Arthritis (knees) | Asm/X2/65 | 8-9 | 2 |

TABLE 7

Blood Pressure

| | sex | age | Condition | oligonucleotides | Blood Pressure before | Blood Pressure after |
|---|---|---|---|---|---|---|
| 1 | f | 74 | Untreated hypertension | CE/NEP-1/Asm/D5 | 190/100 | 165/75 |
| 2 | f | 56 | Untreated hypertension | CE/NEP-1/Asm/D5 | 190/100 | 160/80 |
| 3 | f | 62 | Hypertension despite treatment with Zestril. | CE/NEP-1/Asm/D5 | 200/90 | 170/75 |

TABLE 7-continued

Blood Pressure

|   | sex | age | Condition | oligonucleotides | Blood Pressure before | Blood Pressure after |
|---|-----|-----|-----------|------------------|-----------------------|----------------------|
| 4 | f | 63 | Hypertension despite treatment with Atenolol & Furosemide | CE/NEP-1/Asm/D5 | 170/70 | 150/70 |
| 5 | m | 65 | Hypertension despite treatment with Atenolol & Prinivil | CE/NEP-1/Asm/D5 | 190/98 | 150/80 |
| 6 | f | 55 | Untreated Hypertension | CE | 190/100 | 160/100 |
| 7 | m | 76 | Hypertension | NEP-1 | 170/69 | 158/74 |
| 8 | m | 36 | Untreated Hypertension | NEP-1 | 214/144 | 160/80 |

TABLE 8

Elevated Cholesterol

|   | sex | age | Condition | oligonucleotides | Cholesterol Level before | Cholesterol Level after |
|---|-----|-----|-----------|------------------|--------------------------|-------------------------|
| 1 | f |  | Hyperlipidemia | Mg44/Asm/D5 | 244 | 125 |
| 2 | f |  | Hyperlipidemia | Mg44/Asm/D5 | 220 | <150 |
| 3 | m |  | Hyperlipidemia | Mg44 | 265 | 177 |
| 4 | f |  | Hyperlipidemia | Mg44 | 212 | 205 |
| 5 | m |  | Hyperlipidemia | Mg44/Asm/D5 | 207 | 168 |
| 6 | f |  | Hyperlipidemia | Mg44/Asm/D5 | 229 | 163 |
| 7 | f |  | Hyperlipidemia | Mg44/Asm/D5 | 300 | 184 |
| 8 | m |  | Hyperlipidemia (shifted from Zocor) | Mg44/Asm/D5/MTP | 213 | <150 |
| 9 | m |  | Hyperlipidemia (shifted from Zocor) | Mg44/Asm/D5 | <150 | <150 |
| 10 | m |  | Hyperlipidemia | Mg44/Asm/D5 | 201 | 164 |

TABLE 9

Emotional Distress

|   | sex | age | condition | oligonucleotides | Severity before | Severity after |
|---|-----|-----|-----------|------------------|-----------------|----------------|
| 1 | f | 39 | Stress | Asm/D5 | 9 | 1-2 |
| 2 | f | 46 | Stress | Asm/D5 | 8 | 2 |
| 3 | f | 52 | Depression | Asm/D5 | 10 | 1-2 |
| 4 | f | 29 | Stress/depression | Asm/D5 | 10 | 3 |
| 5 | m | 56 | Severe depression | Asm/D5 | 10 | 2 |
| 6 | f | 47 | Spousal abuse | Asm/D5 | 8-9 | 1-2 |
| 7 | f | 57 | stress | Asm/D5 | 10 | 1-2 |
| 8 | f | 40 | stress | Asm/D5 | 9 | 3 |
| 9 | f | 52 | Severe depression | Asm/D5 | 10 | 1 |
| 10 | f | 26 | stress | Asm/D5 | 8-9 | 1 |
| 11 | f | 36 | stress | Asm/D5 | 4-5 | 1 |
| 12 | f | 62 | Severe depression | Asm/D5 | 10 | 1 |
| 13 | m | 31 | stress | Asm/D5 | 8-9 | 1 |
| 14 | f | 52 | Stress/anxiety | Asm/D5 | 9-10 | 2-3 |
| 15 | f | 56 | Mild stress | Asm/D5 | 6 | 1 |
| 16 | f | 51 | mood swings | Asm/D5 | 7 | 1 |
| 17 | m | 47 | High stress | Asm/D5 | 10 | 2-3 |
| 18 | f | 56 | Spousal abuse | Asm/D5 | 10 | 5 |
| 19 | f | 56 | Stress | Asm/D5 | 7 | 2 |
| 20 | f | 63 | Depression | Asm/D5 | 10 | 1-2 |
| 21 | m | 51 | SAD | Asm/D5 | 10 | 1-2 |
| 22 | f | 35 | Suicidal | Asm/D5 | 10 | 1-2 |
| 23 | f | 38 | Severe depression | Asm/D5 | 10 | 1-3 |
| 24 | f | 63 | Severe depression | Asm/D5 | 10 | 1-2 |
| 25 | f | 45 | Depression | Asm/D5 | 8-9 | 1-2 |
| 26 | f | 31 | depression | Asm/D5 | 8 | 1-2 |
| 27 | f | 34 | stress | Asm/D5 | 9 | 2 |
| 28 | m | 63 | anxiety | Asm/D5 | 9 | 1 |
| 29 | m | 32 | Stress/anxiety | Asm/D5 | 10 | 1 |
| 30 | f | 60 | Severe depression | Asm/D5 | 10 | 1-2 |
| 31 | f | 25 | OCD/stress | Asm/D5 | 10 | 3 |
| 32 | m | 41 | agoraphobic | Asm/D5 | 10 | 3-4 |
| 33 | f | 42 | Severe anxiety | Asm/D5 | 10 | 1 |
| 34 | f | 36 | depression | Asm/D5 | 9-10 | 1-2 |
| 35 | m | 59 | Spousal abuse | Asm/D5 | 10 | 2 |
| 36 | f | 52 | Depression | Asm/D5 | 8 | 2 |
| 37 | f | 31 | stress | Asm/D5 | 9 | 1 |
| 38 | f | 63 | stress | Asm/D5 | 8 | 1 |
| 39 | m | 55 | Anxiety/stress | Asm/D5 | 7 | 4 |
| 40 | m | 45 | stress | Asm/D5 | 4 | 1 |
| 41 | f | 42 | stress | Asm/D5 | 10 | 1 |
| 42 | f | 38 | Severe depression | Asni/D5 | 10 | 1-2 |
| 43 | m | 50 | Mild stress | Asm/D5 | 4 | 1 |
| 44 | f | 33 | Mild stress | Asm/D5 | 5 | 1 |
| 45 | f | 42 | depression | Asm/D5 | 8 | 1 |
| 46 | f | 65 | depression | Asrn/D5 | 9 | 2-3 |
| 47 | f | 63 | Stress/anxiety | Asm/D5 | 10 | 2-3 |
| 48 | f | 44 | Stress/anxiety | Asm/D5 | 9-10 | 1-2 |
| 49 | f | 34 | stress | Am-I/DS | 9 | 2 |
| 50 | f | 50 | Mild stress | Asm/D5 | 7 | 1 |
| 51 | m | 65 | depression | Asm/D5 | 9-10 | 1-2 |
| 52 | f | 38 | stress | Asm/D5 | 8 | 1 |
| 53 | f | 32 | Stress/anxiety | Asm/D5 | 9 | 2-3 |
| 54 | f | 40 | stress | Asm/D5 | 8-9 | 1-2 |
| 55 | f | 54 | stress | Asm/D5 | 7-8 | 1 |
| 56 | f | 33 | anxiety | Asm/D5 | 8 | 1 |
| 57 | f | 54 | Stress/depression | Asm/D5 | 9 | 2-3 |
| 58 | f | 41 | stress | Asm/D5 | 10 | 1-2 |
| 59 | m | 15 | Panic attacks | Asm/D5 | 10 | 1 |
| 60 | f | 44 | stress | Asm/D5 | 6 | 1 |
| 61 | f | 41 | stress | Asm/D5 | 9 | 1 |
| 62 | m | 40 | stress | Asm/D5 | 7-8 | 1-2 |
| 63 | f | 13 | Mood swings | Asm/D5 | 8-9 | 1-2 |
| 64 | f | 15 | Mood swings | Asm/D5 | 7-8 | 1 |
| 65 | f | 22 | stress | Asm/D5 | 10 | 1 |
| 66 | f | 51 | anxiety | Asm/D5 | 9 | 1 |
| 67 | m | 54 | Depression | Asm/D5 | 8 | 2 |
| 68 | f | 54 | depression | Asm/D5 | 8-9 | 3 |
| 69 | f | 51 | depression | Asm/D5 | 10 | 1-2 |
| 70 | f | 51 | stress | Asm/D5 | 5 | 1 |
| 71 | f | 56 | stress | Asm/D5 | 10 | 1-2 |
| 72 | f | 58 | depression | Asm/D5 | 8 | 2 |
| 73 | f | 39 | Mild stress | Asm/D5 | 5 | 1 |
| 74 | m | 24 | anxiety | Asm/D5 | 6 | 1 |
| 75 | in | 29 | stress | Asm/D5 | 8 | 4 |
| 76 | f | 43 | anxiety | Asm/D5 | 5 | 1 |
| 77 | m | 21 | Panic attacks | Asm/D5 | 10 | 1 |
| 78 | m | 66 | stress | Asm/D5 | 7-8 | 1-2 |
| 79 | f | 45 | Stress/anxiety | Asm/D5 | 7 | 1 |
| 80 | f | 74 | stress | Asm/D5 | 8-9 | 2 |
| 81 | f | 50 | Mild anxiety | Asm/D5 | 4 | 1 |
| 82 | f | 18 | Severe depression | Asm/D5 | 10 | 1 |
| 83 | f | 53 | stress | Asm/D5 | 9 | 3 |
| 84 | f | 32 | stress | Asm/D5 | 7 | 3 |
| 85 | f | 25 | stress | Asm/D5 | 8 | 1-2 |
| 86 | m | 47 | Severe depression | Asm/D5 | 9 | 1-2 |
| 87 | f | 38 | stress | Asm/D5 | 7 | 2 |
| 88 | m | 52 | stress | Asm/D5 | 5 | 1 |
| 89 | f | 14 | Panic attacks | Asm/D5 | 10 | 1-2 |
| 90 | m | 65 | anxiety | Asm/D5 | 8 | 1 |
| 91 | f | 39 | stress | Asm/D5 | 9 | 2 |
| 92 | m | 11 | stress | Asm/D5 | 7 | 1-2 |
| 93 | f | 31 | Severe depression | Asm/D5 | 10 | 3 |
| 94 | m | 67 | depression | Asm/D5 | 7 | 3 |
| 95 | f | 58 | stress | Asm/D5 | 7 | 2 |

TABLE 9-continued

Emotional Distress

| | sex | age | condition | oligonucleotides | Severity before | Severity after |
|---|---|---|---|---|---|---|
| 96 | m | 67 | stress | Asrn/D5 | 9 | 2 |
| 97 | m | 12 | ADD | Asm/D5 | 8 | 1 |
| 98 | f | 58 | stress. | Asm/D5 | 9-10 | 2-3 |
| 99 | f | 30 | stress | Asm/D5 | 7 | 1 |
| 100 | m | 45 | stress | Asm/D5 | 6 | 1 |
| 101 | m | 13 | ADD | Asm/D5 | 9-10 | 2-3 |

TABLE 10

Gastrointestinal Disorders

| | sex | age | condition | oligonucleotides | Elimination/day b/f | Elimination/day after | Severity b/f | Severity after |
|---|---|---|---|---|---|---|---|---|
| 1 | f | 46 | IBS | Asm/X2/65 | 11 | 2 | 10 | 3 |
| 2 | m | 40 | Ulcerative colitis | Asm/X2/65 | 5 | 2 | 7 | 1 |
| 3 | f | 40 | IBS | Asm/X2/65 | 20 | 1-2 | 10 | 1 |
| 4 | f | 38 | Ulcerative colitis | Asm/X2/65 | 10-20 | 1 | 10 | 3 |
| 5 | f | 31 | Crohn's | X2/65 | 22 | 1 | 10 | 1 |
| 6 | f | 34 | Crohn's | X2/65 | 8-10 | 1-2 | 7 | 2 |
| 7 | f | 33 | IBS | Asm/X2/65 | 20 | 1-2 | 8 | 1 |
| 8 | m | 50 | IBS | Asm/X2/65 | 5 | 1-2 | 5 | 1 |
| 9 | f | 22 | Chronic constipation | Asm/X2/65 | 0 | 1-2 | 10 | 2 |
| 10 | f | 26 | Crohn's | X2/65 | 19-20 | 1 | 10 | I |
| 11 | f | 57 | Ulcerative colitis | Asm/X2/65 | 5-6 | 1 | 6 | 2 |
| 12 | f | 42 | IBS | Asm/X2/65 | 12 | 1 | 9 | 1 |
| 14 | f | 8 | IBS | Asm/65 (testing + X22) | 8 | 3-4 | 10 | 3 |
| 16 | f | 47 | IBS | Asm/X2/65 | 8 | 1-2 | 9 | 1 |
| 17 | f | 55 | IBS | Asm/X2/65 | 10 | 1 | 10 | 1 |
| 18 | m | 67 | IBS | Asm/X2/65 | 6-7 | 1-2 | 6 | 1 |
| 19 | f | 36 | IBS | Asm/X2/65 | 4 | 1 | 7-8 | 1 |
| 20 | m | 31 | Gall bladder | Asm/D5/Mg44 | nd | nd | 10 | 1 |
| 21 | m | 56 | Kidney stones | Mg44 | nd | nd | 10 | 1 |
| 22 | f | 37 | Gall bladder attack | Astri/X2/65/Mg4 | nd | nd | 4 | 1 |
| 23 | f | 57 | Gall bladder attack | Asm/D5/Mg44 | nd | nd | 7-8 | 1 |
| 25 | f | 54 | IBS | Super 8 | 5 | 1-2 | 5 | 1 |
| 26 | f | 7 | IBS | Super 8 | nd | nd | 8 | 2 |
| 27 | f | 38 | Ulcerative colitis | Super 8 | 3 | 1-2 | 4-5 | 1 |

TABLE 11

Inflammation

| | sex | age | condition | oligonucleotides | Severity before | Severity after |
|---|---|---|---|---|---|---|
| 1 | f | 39 | Post surgical | Asm/X2/65/cd18-1 | 10 | 4 |
| 2 | f | 64 | Post surgical | Asm | 10 | 2 |
| 3 | m | 55 | Asthma/emphysema | Asm/X2/65 | 9 | 7 |
| 4 | f | 33 | asthma | Asm/X2/65 | 10 | 1-2 |
| 5 | f | 40 | asthma | Asm | 10 | 1 |
| 6 | f | 40 | Bee sting | Asm | 10 | 1 |

TABLE 11-continued

Inflammation

| | sex | age | condition | oligonucleotides | Severity before | Severity after |
|---|---|---|---|---|---|---|
| 7 | m | 5 | Bee sting | Asm/topical | 10 | 1 |
| 8 | f | 44 | Black fly bite | IL-501 | 10 | 1 |
| 9 | f | 8 | Black fly bite | IL-501 | 10 | 1 |
| 10 | f | 6 | Black fly bite | IL-501 | 10 | 1 |
| 11 | f | 63 | Hair implants | Asm | 10 | 1 |
| 12 | m | 66 | gout | Asm | 8 | 2 |
| 13 | m | 51 | gout | Asm | 10 | 1 |
| 14 | m | 45 | gout | Asm | 10 | 1 |
| 15 | f | 56 | Polymyalgia rheumatica | Asm/X2/65/D7/CRP | 10 | 3 |
| 16 | f | 31 | Multiple sclerosis | Asm/X2/65 | 9-10 | 2 |
| 17 | f | 67 | polymyositis | Asm/X2/65/D7/CRP | 8-9 | 3-4 |
| 18 | m | 32 | Swollen joints | Asm | 9 | 1-2 |
| 19 | m | 65 | Inner ear inflammation | Asm | 7 | 1 |
| 20 | m | 26 | hemorrhoids | Asm | 10 | 5 |
| 21 | f | 41 | hemorrhoids | Asm | 10 | 1 |
| 22 | f | 75 | shingles | Asm/D7 | 10 | 3 |
| 23 | m | 48 | Sore muscles | Asm | 7 | 1 |
| 24 | f | 36 | Varicose veins | Asm | 7 | 7 |
| 25 | f | 74 | Swollen ankle | Asm/X2/65 | 10 | 2 |
| 26 | f | 41 | Swollen ankle | Asm | 10 | 1 |
| 27 | f | 63 | Swollen knee | Asm/X2/65/cd18-1 | 10 | 2 |
| 28 | f | 45 | Ganglion cyst | Asm/X2/65 | 7 | 1 |
| 29 | f | 73 | sciatica | Asm | 10 | 1 |
| 30 | m | 25 | sciatica | Asm | 10 | 1 |
| 31 | m | 54 | sciatica | Asm/X2/65 | 10 | 6 |
| 32 | m | 47 | sciatica | Asm/X2/65 | 10 | 1 |
| 33 | f | 44 | sciatica | Asm | 10 | 1 |
| 34 | f | 46 | Itchy ears | Asm | 6 | 1 |
| 35 | m | 59 | cellulitis | Asm/Nu-3 | 10 | 3-4 |
| 36 | f | 22 | Stomach inflammation | Asm/X2/65 | 9 | 2 |
| 37 | f | 44 | Pinched nerve | Asm/X2/65 | 10 | 1 |
| 38 | f | 44 | Pinched nerve | Asm/X2/65 | 10 | 1 |
| 39 | m | 46 | Hockey/tennis elbow | Asm/X2/65 | 9 | 1 |
| 40 | m | 40 | Hockey/tenms elbow | Asm/X2/65 | 10 | 1 |
| 41 | m | 16 | Pitcher's arm | Asm | 10 | 1 |
| 42 | f | 58 | Heel spur | Asm | 7 | 1 |
| 43 | f | 46 | Multiple sclerosis | Asm/X2/65 | 8 | 2 |
| 44 | f | 63 | hemorrhoids | Asm/Nu-3 | 10 | 3 |
| 45 | m | 64 | bursitis | Asm/X2/65/L05-38 | 9 | 1-2 |
| 46 | f | 25 | Interstitial cystitis | Asm/X2/65/L05-38 | 10 | 2 |
| 47 | m | 67 | Inflamed hands | Asm/D5/X2/65/IL-501 | 10 | 5 |
| 48 | f | 30 | Morning sickness | Asm/D5 | 10 | 7 |
| 49 | f | 12 | Inflamed tonsils | Asm | 10 | 1-2 |
| 50 | f | 33 | Inflamed cat scratch | Asm/topical | 6 | 1 |
| 51 | f | 38 | Allergies | Asm | 10 | 3 |
| 52 | f | 42 | Insect bite | IL-501/topical | 9 | 1 |
| 53 | f | 10 | Severe wasp bites | Asm/topical | 10 | 1 |
| 54 | f | 45 | Black fly bites | IL-501/topical | 9 | 1 |
| 55 | f | 62 | Wasp bite | Asm | 8 | 1 |
| 56 | f | 7 | Ear piercing | Asm | 8 | 1 |
| 57 | f | 9 | Ear piercing | Asm | 8 | 1 |
| 58 | m | 37 | Pinched nerve | Asm/X2/65 | 9-10 | 1 |
| 59 | f | 7 | "goose egg" on forehead | Asm/topical | 8 | 1 |
| 60 | m | 12 | Knee injury | Asm/topical | 6 | 1 |
| 61 | f | 43 | sciatica | Asm/topical | 9-10 | 1 |
| 62 | f | 45 | Pulled muscle (knee) | Asm/topical | 6 | 1 |
| 63 | f | 43 | Degenerative hip | Asm/topical | 5 | 1-2 |
| 64 | m | 65 | Chronic cough | D7 | 10 | 4 |
| 65 | m | 38 | Extreme autoimmune graft rejection/ sinusitis/Erosive Peptic Esophagitis | Asm/X2/65/D7/L05-38fICAM/cd-18-1/IL6/HisR1 | 10 | 3 |

TABLE 11-continued

Inflammation

| | sex | age | condition | oligonucleotides | Severity before | Severity after |
|---|---|---|---|---|---|---|
| 66 | f | 10 | Seasonal allergies | Asm | 7-8 | 1 |
| 67 | f | 42 | Interstitial cystitis | Asm/X2/65 | 9 | 1 |
| 68 | f | 34 | Chronic allergies | Asm/X2/65/D5 | 8 | 2 |
| 69 | f | 44 | Seasonal allergies/cough | IL-501 | 6 | 1 |
| 70 | f | 61 | Seasonal allergies/cough | IL-501 | 6 | 1 |

TABLE 12

Migraines

| | sex | age | Condition | oligonucleotides | Severity before | Severity after |
|---|---|---|---|---|---|---|
| 1 | f | 42 | migraine | Asm/D5/X2/Mg44 | 10 | 1 |
| 2 | f | 51 | migraine | Asm/D5/X2/Mg44 | 9 | 1-2 |
| 3 | f | 28 | migraine | Asm/D5/X2/Mg44 | 10 | 1 |
| 4 | f | 36 | migraine | Asm/D5/X2/Mg44 | 10 | 2 |
| 5 | f | 46 | migraine | Asm/D5/X2/Mg44 | 10 | 1 |
| 6 | f | 51 | migraine | Asm/D5/X2/Mg44 | 9 | 1 |
| 7 | f | 39 | migraine | Asm/D5/X2/Mg44 | 8 | 1 |
| 8 | f | 30 | migraine | Asm/D5/X2/M144 | 9 | 1 |
| 9 | f | 58 | Migraine | Asm/D5/X2/Mg44 | 9 | 1 |
| 10 | f | 57 | Migraine | Asm/D5/X2/Mg44 | 10 | 1 |
| 11 | f | 21 | migraine | Asm/D5/X2/Mg44 | 9 | 2-3 |

TABLE 13

Neurological Disorders

| | sex | age | Condition | oligonucleotides | Severity before | Severity after |
|---|---|---|---|---|---|---|
| 1 | f | 56 | polymyalgia | Asm/X2/65/D7/CRP | 10 | 3 |
| 2 | f | 31 | multiple sclerosis | Asm/X2/65 | 9-10 | 2 |
| 3 | f | 67 | polymyositis | Asm/X2/65/D7/CRP | 8-9 | 3-4 |
| 4 | f | 46 | multiple sclerosis | Asm/X2/65 | 8 | 2 |

TABLE 14

Pain

| | sex | age | Condition | oligonucleotides | Severity before | Severity after |
|---|---|---|---|---|---|---|
| 1 | f | 74 | Back | Asm/X2/65/L05-38/Mg44 | 10 | 5 |
| 2 | m | 54 | back | Asm/X2/65 | 9 | 2 |
| 3 | f | 37 | shoulder | Asm/X2 | 6-7 | 1 |
| 4 | f | 41 | ankle | X2 | 5 | 1 |
| 5 | f | 61 | knee | X2 | 8 | 3 |
| 6 | f | 41 | ovarian | Asm/X2 | 8-9 | 3 |
| 7 | f | 61 | headache | Asm/X2 | 8 | 1 |
| 8 | f | 54 | headache | Asm/X2/65 | 8 | 5 |
| 9 | m | 26 | headache | Asm/X2 | 9 | 1 |
| 10 | f | 65 | headache | Asm/X2/65 | 8 | 1 |
| 11 | f | 36 | headache | Asm/X2 | 7 | 1 |
| 12 | f | 39 | headache | Asm/X2/D5 | 6 | 1 |
| 13 | f | 62 | headache | Asm/X2/D5 | 10 | 1-2 |
| 14 | f | 46 | knee | Asm/X2/D5 | 6 | 2 |
| 15 | f | 31 | knee | Asm/X2/65 | 7 | 1 |
| 16 | f | 62 | knee | Asm/X2/65 | 7 | 2 |

TABLE 14-continued

Pain

| | sex | age | Condition | oligonucleotides | Severity before | Severity after |
|---|---|---|---|---|---|---|
| 17 | f | 61 | knee | Asm/X2 | 8 | 3 |
| 18 | f | 37 | knee | Asm/X2 | 9 | 1-2 |
| 19 | f | 39 | Surgical pain | Asm/X2/65 | 10 | 4 |
| 20 | m | 56 | Cancer pain | X2 | 10 | 6 |
| 21 | m | 30 | stitches | Asm/X2 | 10 | 1-2 |
| 22 | m | 20 | Tooth extraction | Asm/X2 | 10 | 1 |
| 23 | f | 53 | Tooth extraction | Asm/X2 | 9 | 1-2 |
| 24 | f | 30 | Tooth extraction | Asm/X2 | 10 | 1 |
| 25 | f | 45 | Tooth extraction | Asm/X2 | 8 | 1-2 |
| 26 | f | 74 | Rib soreness | Asm/X2/L05-38/Mg44 | 10 | 1 |
| 27 | f | 48 | shoulder | Asm/X2/65 | 8 | 1 |
| 28 | f | 43 | headache | X2 | 8-9 | 1-2 |
| 29 | m | 38 | headache | X2 | 7 | 1-2 |
| 30 | m | 76 | Tooth extraction | Asm/X2/65 | 8, | 1 |
| 31 | m | 23 | Wisdom tooth pain | Asm/X2/65 | 9 | 2-3 |
| 32 | f | 42 | headaches | Asm/D5/X2 | 7 | 1 |
| 33 | f | 47 | Neck pain | Super 8 | 7 | 1 |
| 34 | f | 31 | Headaches | Asm/D5/X2 | 10 | 3 |
| 35 | f | 59 | Teeth pain | Super 8 | 6 | 1 |
| 36 | f | 31 | Knee pain | Super 8 | 6 | 1 |
| 37 | m | 10 | Ankle pain | Asm/65 | 5 | 1 |
| 38 | f | 13 | Tooth extraction | Asm/X2/65 | 7 | 1 |
| 39 | m | 65 | thyroidectomy | Super 8 | 10 | 1 |
| 40 | f | 46 | Surgical pain | Super 8 | 9 | 1 |

TABLE 15

Premenstrual Syndrome

| | sex | age | Condition | oligonucleotides | Severity before | Severity after |
|---|---|---|---|---|---|---|
| 1 | f | 41 | PMS | Asm/D5/X2 | 10 | 1-2 |
| 2 | f | 34 | PMS | Asm/D5/X2 | 10 | 1 |
| 3 | f | 37 | PMS | Asm/D5/X2 | 10 | 1 |
| 4 | f | 53 | PMS | Asm | 10 | 1 |
| 5 | f | 13 | PMS | Asm/D5/X2 | 10 | 1 |
| 6 | f | 15 | PMS | Asm/D5/X2 | 10 | 1 |
| 7 | f | 47 | PMS | Asm/D5/X2 | 10 | 9 |
| 8 | f | 44 | PMS | Asm | 10 | 1 |
| 9 | f | 20 | PMS | Asm/D5/X2 | 10 | 1 |

TABLE 16

Prostatitis

| | sex | age | Condition | oligonucleotides | Severity before | Severity after |
|---|---|---|---|---|---|---|
| 1 | m | 63 | BPH | MPB/Asm/X2/65 | 10 | 1 |
| 2 | m | 77 | BPH | Asm/D5/X2 | 3 | 1 |
| 3 | m | 45 | Inflamed prostate | Asm/D5/X2 | 4 | 1 |
| 4 | m | 69 | BPH | MPB/Asm/X2/65 | 7 | 1-2 |

TABLE 17

Sinus

| | sex | age | Condition | oligonucleotides | Severity before | Severity after |
|---|---|---|---|---|---|---|
| 1 | m | 8 | Sinus/cold | Asm/Nu-3 nasal | 5 | 1-2 |
| 2 | f | 60 | Sinus/cold | Asm/Nu-3 nasal | 7 | 2 |

TABLE 17-continued

Sinus

| | sex | age | Condition | oligonucleotides | Severity before | Severity after |
|---|---|---|---|---|---|---|
| 3 | f | 42 | . Sinus/cold | Asm/Nu-3 nasal | 8 | 1 |
| 4 | f | 41 | Sinus/cold | Asm/Nu-3 nasal | 6 | 4 |
| 5 | m | 55 | Sinus/cold | Asm/Nu-3 nasal | 6 | 1 |
| 6 | f | 47 | Sinus/cold | Asm/Nu-3 nasal | 7 | 1-2 |
| 7 | f | 40 | Sinus/cold | Asm/Nu-3 nasal | 5 | 1-2 |
| 8 | f | 35 | Sinus/cold | Asm/Nu-3 nasal | 7 | 1 |
| 9 | f | 12 | Sinus/cold | Asm/Nu-3 nasal | 5 | 1 |
| 10 | f | 34 | Sinus/cold | Asm/Nu-3 nasal | 9 | 1 |
| 11 | m | 17 | Sinus/cold | Asm/Nu-3 nasal | 7 | 2 |
| 12 | m | 15 | Sinus/cold | Asrn/Nu-3 nasal | 6 | 2 |
| 13 | m | 70 | Sinus/cold | Asm/Nu-3 nasal | 5 | 1 |
| 14 | f | 53 | Sinus/cold | Asm/Nu-3/CRP | 7 | 3 |
| 15 | m | 77 | Sinus/cold | Asm/Nu-3 nasal | 8 | 3 |
| 16 | f | 37 | Sinus/cold | Asm/Nu-3 nasal | 8 | 2 |
| 17 | f | 55 | Sinus/cold | Asm/Nu-3 nasal | 9 | 2 |
| 18 | m | 17 | Sinus/cold | Asm/Nu-3 nasal | 7 | 1 |
| 19 | f | 62 | Sinus/cold | Asrn/Nu-3 nasal | 7 | 1 |
| 20 | m | 43 | Sinus/cold | Asm/Nu-3 nasal | 9 | 1 |
| 21 | f | 41 | Sinus/cold | Asm/Nu-3 nasal | 6 | 1 |
| 22 | f | 58 | Sinus/cold | Asm/Nu-3 nasal | 6 | 1 |
| 23 | f | 34 | Sinus/cold | Asm/Nu-3 nasal | 8 | 1 |
| 24 | f | 61 | Sinus/cold | Asm/Nu-3 nasal | 6 | 2 |
| 25 | f | 19 | Sinus/cold | Asm/Nu-3 nasal | 8 | 1 |
| 26 | f | 50 | Sinus/cold | Asm/Nu-3 nasal | 6 | 1 |
| 27 | m | 36 | Sinus/cold | Asm/Nu-3 nasal | 7 | 6 |
| 28 | f | 48 | Sinus/cold | Asm/Nu-3 nasal | 8 | 2 |
| 29 | f | 60 | Sinus/cold | Asm/Nu-3 nasal | 7 | 1 |
| 30 | m | 40 | Sinus/cold | Asm/Nu-3 nasal | 8 | 1 |
| 31 | f | 45 | Sinus/cold | Asm/Nu-3 nasal | 8 | 1 |
| 32 | f | 32 | Sinus/cold | Asm/Nu-3 nasal | 6 | 1 |
| 33 | f | 48 | Sinus/cold | Asm/Nu-3 nasal | 9 | 2-3 |
| 34 | f | 37 | Sinus/cold | Asm/Nu-3 nasal | 7 | 2 |
| 35 | f | 49 | Sinus/cold | Asm/Nu-3 nasal | 7 | 1-2 |
| 36 | m | 30 | Sinus/cold | Asm/Nu-3 nasal | 8-9 | 1 |
| 37 | m | 52 | Sinus/cold | Asm/Nu-3 nasal | 7 | 3 |
| 38 | f | 67 | Sinus/cold | Asm/Nu-3 nasal | 8 | 1 |
| 39 | m | 53 | Sinus/cold | Asm/Nu-3 nasal | 7 | 1 |
| 40 | f | 12 | Sinus/cold | Asm/Nu-3 nasal | 9 | 2-3 |
| 41 | f | 8 | Sinus/cold | Asm/Nu-3 nasal | 5 | 1 |
| 42 | f | 25 | Sinus/cold | Asm/Nu-3 nasal | 7 | 1 |
| 43 | f | 42 | Sinus/cold | Asm/Nu-3 nasal | 9 | 1-2 |
| 44 | f | 54 | Sinus/cold | Asm/Nu-3 nasal | 9 | 2-3 |
| 45 | f | 42 | Sinus/cold | Asm/Nu-3 nasal | 7 | 2 |
| 46 | f | 45 | Sinus/cold | Asm/Nu-3 nasal | 6 | 1 |
| 47 | m | 47 | Sinus/cold | Asm/Nu-3 nasal | 7 | 1 |
| 48 | f | 60 | Sinus/cold | Asm/Nu-3 nasal | 8 | 1 |
| 49 | f | 34 | Sinus/cold | Asm/Nu-3 nasal | 9 | 2 |
| 50 | f | 37 | Sinus/cold | Asm/Nu-3 nasal | 9 | 2-3 |
| 51 | f | 49 | Sinus/cold | Asm/Nu-3 nasal | 7 | 1 |
| 52 | f | 39 | Sinus/cold | Asm/Nu-3 nasal | 9 | 1 |
| 53 | f | 51 | Sinus/cold | Asm/Nu-3 nasal | 10 | 1-2 |

TABLE 18

Trauma

| | sex | age | Condition | oligonucleotides | Severity before | Severity after |
|---|---|---|---|---|---|---|
| 1 | f | 41 | Broke femur | Asm | 10 | 1 |
| 2 | f | 54 | Torn ligament | Asm | 7 | 1 |
| 3 | m | 57 | Compound fracture/leg | Asm/X2/65 | 10 | 4 |
| 4 | f | 72 | Sprained ankle | Asm/X2/65 | 6 | 1 |
| 5 | f | 47 | Root canal | Asm/X2/65 | 7 | 2 |
| 6 | f | 28 | Neck surgery | Asm/X2/65 | 9 | 1 |
| 7 | f | 47 | Torn rotator cup | Asm/X2/65/L05-38 | 7 | 2-3 |
| 8 | f | 28 | Fractured ankle | Asm/X2/65 | 10 | 1 |
| 9 | in | 48 | Hyperextended elbow | Asm/X2/65/D7 | 7 | 2 |
| 10 | m | 19 | Motorcycle back injury | Asm/X2/65 | 9 | 2 |
| 11 | f | 64 | Fractured tibia | Asm/X2/65/L05-38 | 10 | 3 |
| 12 | f | 41 | Cellulitis from impaled object | Asm/X2/65/D7 | 10 | 3-4 |
| 13 | f | 74 | Broken ribs | Asm/X2/65/LO5-38/Mg44 | 10 | 1 |
| 14 | f | 36 | Lumpectomy pain | Asm/topical | 10 | 1 |
| 15 | f | 37 | Torn miniscus | Asm/topical | 10 | 1 |
| 16 | m | 43 | Two broken arms | Asm | 10 | 2-3 |
| 17 | m | 1 | Finger slammed in door | Asm | 9 | 1 |
| 18 | f | 48 | Hysterectomy scar | Asm/topical | 7 | 1 |
| 19 | f | 45 | Broken toe | Asm/topical | 10 | 1-2 |
| 20 | f | 37 | Shoulder injury | Asm/X2 | 6 | 1 |
| 21 | m | 59 | Fluid on knee | Super 8 | 7 | 1 |
| 22 | f | 33 | Broken collarbone | Super 8 | 9 | 2 |
| 23 | m | 12 | Sprained finger | Asm/65 | 8 | 1 |
| 24 | f | 43 | Broken foot | Super 8/Mg44 | 9 | 1 |

TABLE 19

Carpal tunnel

| | sex | age | Condition | oligonucleotides | Severity before | Severity after |
|---|---|---|---|---|---|---|
| 1 | m | 36 | Carpal tunnel | Asm | 9 | 1 |
| 2 | f | 42 | Carpal tunnel | Asm | 10 | 1 |
| 3 | f | 56 | Carpal tunnel | Asm | 9 | 1 |
| 4 | m | 75 | Carpal tunnel | Asm | 8 | 1-2 |
| 5 | m | 55 | Carpal tunnel | Asm/X2/65 | 8 | 1 |
| 6 | m | 21 | Carpal tunnel | Asm | 9 | 2 |
| 7 | in | 56 | Carpal tunnel | Asm/X2/65 | 10 | 1-2 |
| 8 | f | 63 | Carpal tunnel | Asm | 10 | 2-3 |
| 9 | f | 45 | Carpal tunnel | Super 8 | 7 | 2 |

TABLE 20

Chronic Fatigue/Fibromyalgia

| | sex | age | Condition | oligonucleotides | Severity before | Severity after |
|---|---|---|---|---|---|---|
| 1 | f | 62 | CFS | Asm/D5/X2 | 9 | 1 |
| 2 | f | 60 | Fibromyalgia | Asm/D5/X2 | 10 | 1 |
| 3 | f | 56 | CFS | Asm/D5/X2 | 9 | 1 |
| 4 | in | 36 | CFS | Asm/D5/X2 | 8 | 1-2 |
| 5 | m | 69 | CFS | Asm/D5/X2 | 8 | 1 |
| 6 | m | 51 | CFS | Asm/D5/X2 | 9 | 2 |
| 7 | m | 38 | CFS | Asm/D5/X2 | 10 | 1-2 |
| 8 | f | 40 | Fibromyalgia | Asm/D5/X2 | 10 | 2-3 |

TABLE 21

Eczema/atopic Dermatitis

| | sex | age | Condition | oligonucleotides | Severity before | Severity after |
|---|---|---|---|---|---|---|
| 1 | f | 63 | Foot rash | Asm | 8 | 1 |
| 2 | f | 49 | hives | Asm/X2/65/D7 | 10 | 1-2 |
| 3 | f | 13 | Severe leg rashes | Asm | 10 | 3-4 |

TABLE 21-continued

Eczema/atopic Dermatitis

|   | sex | age | Condition | oligonucleotides | Severity before | Severity after |
|---|-----|-----|-----------|------------------|-----------------|----------------|
| 4 | m | 36 | eczema | Asm/X2/65 | 7-8 | 3-4 |
| 5 | f | 41 | Non-specific rash | Asm | 8 | 1 |
| 6 | m | 11 | eczema | Asm | 10 | 1-2 |
| 7 | f | 51 | rash | Asm/X2 | 5 | 1 |
| 8 | m | 48 | rash | Asm | 6-7 | 1-2 |
| 9 | f | 30 | Atopic dermatitis | Asm | 9 | 1 |
| 10 | f | 26 | Face rash | Asm | 7 | 2 |
| 11 | m | 42 | Severe rash | Asm/X2/65/D7 | 10 | 1 |
| 12 | f | 8 | Rash | Asm | 4 | 1 |
| 13 | f | 12 | eczema | Asm | 6 | 1 |
| 14 | m | 67 | Severely inflamed fingers | Asm/X2/65/11,-501 | 103-4 | |
| 15 | f | 52 | rash | Asm | 6 | 1 |
| 16 | f | 42 | Severe hives | Asm/X2/65 | 10 | 1 |
| 17 | f | 14 | Chronic eczema | Asm | 7 | 1 |
| 18 | m | 64 | eczema | Asm/X2/65 | 8 | 1 |
| 19 | f | 63 | Non-specific itching | Asm | 7-8 | 1 |
| 20 | f | 58 | Contact dermatitis | Asm/topical | 8 | 1 |
| 21 | f | 47 | Itchy scar | Asm/topical | 5 | 1 |
| 22 | f | 37 | Severe contact dermatitis | Asm/topical | 7 | 2 |
| 23 | m | 36 | Severe atopic dermatitis | Asm | 10 | 1 |
| 24 | m | 1 | Severe diaper rash | Asm/topical | 10 | 1 |
| 25 | f | 40 | Eczema | Asm | 6 | 1-2 |
| 26 | f | 35 | Itchy/scaly patches on feet | Asm | 7-8 | 1 |
| 27 | m | 17 | Atopic dermatitis | Asm | 7 | 1 |
| 28 | f | 19 | Severe razor burn | Asm/topical | 10 | 1 |
| 29 | m | 24 | Severe razor burn | Asm/topical | 10 | 1 |
| 30 | f | 40 | Inflamed hands | Asm/topical | 7 | 1 |
| 31 | m | 19 | split, cracked cuticles | cd18-1 | 7 | 1 |
| 32 | f | 51 | Split lips | cd18-1 | 5 | 1 |
| 33 | f | 30 | Dry, cracked skin on hands | cd18-1/topical | 8 | 1 |
| 34 | f | 60 | rash | Super 8 | 9 | 1 |
| 35 | f | 38 | Spider bite | Super 8 | 10 | 2-3 |
| 36 | f | 15 | rash | Super 8 | 5 | 1 |

TABLE 22

Erectile Dysfunction

|   | sex | age | Condition | oligonucleotides | Severity before | Severity after |
|---|-----|-----|-----------|------------------|-----------------|----------------|
| 1 | m | 65 | ED/blood pressure med. | D5 | 10 | 1 |
| 2 | m | 69 | ED/blood pressure med. | Asm/D5 | 9 | 2-3 |
| 3 | m | 52 | ED | Asm/D5 | 10 | 1 |

TABLE 23

Heartburn/Acid Reflux

|   | sex | age | Condition | oligonucleotides | Severity before | Severity after |
|---|-----|-----|-----------|------------------|-----------------|----------------|
| 1 | f | 63 | heartburn | Acid-2/Acid B2 | 10 | 1 |
| 2 | f | 49 | heartburn | Acid-2/Acid B2 | 10 | 1 |
| 3 | f | 22 | Heartburn | Acid-2/Acid B2 | 10 | 1 |
| 4 | f | 42 | Heartburn | Acid-2 | 7-8 | 1 |
| 5 | f | 41 | Heartburn | Acid-2/Acid B2 | 9-10 | 1 |
| 6 | f | 70 | Heartburn | Acid-2/Acid B2 | 5 | 1 |
| 7 | f | 47 | heartburn | Acid-2/Acid B2 | 8 | 1 |
| 8 | f | 41 | heartburn | Acid-2/Acid B2 | 10 | 1 |
| 9 | f | 19 | heartburn | Acid-2/Acid B2 | 7 | 1 |
| 10 | m | 77 | heartburn | Acid-2/Acid B2 | 10 | 1 |
| 11 | f | 52 | heartburn | Acid-2/Acid B2 | 10 | 1 |
| 12 | f | 21 | Heartburn | Acid-2/Acid B2 | 10 | 1 |
| 13 | f | 41 | heartburn | Acid-2/Acid B2 | 10 | 1 |
| 14 | f | 46 | heartburn | Acid-2/Acid B2 | 10 | 1 |
| 15 | f | 63 | heartburn | Acid-2/Acid B2 | 10 | 1 |
| 16 | f | 62 | heartburn | Acid-2/Acid B2 | 10 | 1 |

TABLE 24

Poison Ivy

|   | sex | age | Condition | oligonucleotides | Severity before | Severity after |
|---|-----|-----|-----------|------------------|-----------------|----------------|
| 1 | m | 10 | Poison ivy | Asm | 7 | 1 |
| 2 | f | 43 | Poison ivy | Asm | 7 | 1 |
| 3 | f | 63 | Poison ivy | Asm | 10 | 1 |
| 4 | f | 42 | Poison ivy | Asm | 6 | 1 |
| 5 | m | 3 | Poison ivy | Asm | 6 | 1 |
| 6 | m | 47 | Poison ivy | Asm | 10 | 1 |
| 7 | f | 53 | Poison ivy | Asm | 10 | 1 |
| 8 | m | 21 | Poison ivy | Asm/topical | 8-9 | 1 |
| 9 | f | 12 | Poison ivy | Asm/topical | 10 | 1 |
| 10 | f | 56 | Poison ivy | Asm/topical | 9 | 1 |
| 11 | f | 40 | Poison ivy | Asm/topical | 7-8 | 1 |
| 12 | f | 49 | Poison ivy | Asm | 10 | 1 |
| 13 | m | 17 | Poison ivy | Asm | 7 | 1 |
| 14 | f | 65 | Poison ivy | Asm | 5-6 | 1 |

TABLE 25

Psoriasis

|   | sex | age | Condition | oligonucleotideS' | Severity before | Severity after |
|---|-----|-----|-----------|-------------------|-----------------|----------------|
| 1 | m | 59 | stress induced psoriasis | Asm/D5/X2 | 10 | 3 |
| 2 | f | 77 | psoriasis | Asm/D5/65 | 5 | 1 |
| 3 | f | 34 | psoriasis | Asm/D5/65 | 9-10 | 1 |
| 4 | m | 27 | psoriasis | Asm/D5/65 | 7 | 1 |
| 5 | f | 41 | psoriasis | Asm/D5/65 | 7 | 2-3 |
| 6 | f | 19 | psoriasis | Asm/D5/65 | 9 | 1 |
| 7 | f | 6 | psoriasis | Asm | 6 | 1 |
| 8 | f | 75 | psoriasis | Asm | 4 | 1 |
| 9 | m | 47 | Severe psoriasis | Asm | 10 | 2-3 |
| 10 | m | 36 | psoriasis | Asm/D5/65 | 5 | 1 |
| 11 | f | 24 | psoriasis | Asm/D5/65 | 9 | 1 |

TABLE 26

Rosacea

|   | sex | age | Condition | oligonucleotideS' | Severity before | Severity after |
|---|-----|-----|-----------|-------------------|-----------------|----------------|
| 1 | f | 40 | Rosacea | Asm | 6 | 1-2 |
| 2 | f | 38 | Rosacea | Asm | 4 | 1 |
| 3 | f | 58 | Rosacea | Asm | 7 | 1 |
| 4 | f | 40 | Rosacea | Asm | 8 | 1 |

TABLE 26-continued

Rosacea

| sex | age | Condition | oligonucleotideS' | Severity before | after |
|---|---|---|---|---|---|
| 5 | f | 40 | Rosacea | Asm | 8-9 | 1 |
| 6 | f | 36 | Rosacea | Asm | 6 | 3 |
| 7 | f | 48 | Rosacea | Asm/X2/65 | 6-7 | 1 |
| 8 | f | 32 | Rosacea | Asm | 6 | 1 |

TABLE 27

Average of Results

| Condition | # cases | pre-treatment average | post-treatment average |
|---|---|---|---|
| elevated cholesterol | 10 | 230 | 166 |
| hypertension | 8 | 190/96 | 159/79 |
| inflammatory bowel | 12 | 10 toilet trips | 1-2 toilet trips |
| crohn's disease | 3 | 17 toilet trips | 1-2 toilet trips |
| ulcerative colitis | 5 | 8 toilet trips | 1-2 toilet trips |
| acid reflux/heartburn | 16 | 9.2 | 1.0 |
| emotional distress | 127 | 8.2 | 1.4 |
| PMS | 9 | 10.0 | 1.0 |
| inflammation | 70 | 9.0 | 1.7 |
| pain | 40 | 8.8 | 2.0 |
| infection | 78 | 7.1 | 1.6 |
| migraine | 14 | 9.4 | 1.3 |
| neurological disorders | 9 | 9.0 | 3.0 |
| poison ivy | 14 | 8.0 | 1.0 |
| prostatitis | 5 | 6.6 | 1.2 |
| psoriais | 14 | 7.1 | 1.5 |
| rocacea | 10 | 6.3 | 1.1 |
| trauma | 25 | 8.7 | 1.7 |
| sinus/cold | 53 | 7.3 | 1.6 |
| erectile dysfunction | 5 | 9.0 | 1.5 |
| eczema/rash | 36 | 8.5 | 1.4 |
| fibromialgia | 7 | 10.0 | 1.8 |
| chronic fatigue | 9 | 9.5 | 1.2 |
| carpal tunnel syndrome | 9 | 8.9 | 1.3 |
| arthritis | 30 | 7.6 | 2.0 |
| appetite | 16 | 9.5 | 2.3 |

Example 24

For animal studies, animals with different indications were provided with oligonucleotide compositions containing RNA oligonucleotides complementary to the phosphodiesterase 4 or phosphodiesterase 5 genes. Some animals were additionally given compositions containing additional RNA oligonucleotides complementary to other genes such as cyclooxygenase 2 and p65. Oligonucleotide concentrations were typically 0.3 to 300 $A_{260}$/RNA/ml taken in doses (0.1-100 µg/kg) of 0.5 ml two to four times per day. The effect of the composition was then evaluated (see Table 27). Treatment efficacy was evaluated by an attending veterinarian.

TABLE 27

Animal studies

| animal | Condition | oligonucleotides | Severity before | after |
|---|---|---|---|---|
| dog | skin allergy | Asm | 8 | 2 |
| dog | inflammatory bowel disease | Asm, CX2, P65 | 7 | 2 |
| horse | nervous and agitated | Asm, D5 | 8 | 2 |

Example 25

The following is the method for selecting nucleic acid sequences from a known gene sequence for the design of oligonucleotides. Preferred choices are sequences that either are adjacent to, or overlap the start site, followed by sequences that are in the 5' un-translated region, followed by sequences immediately adjacent to or overlapping the termination signal. This method is very effective and when combined with, achiral RNA, it produces oligonucleotides that display therapeutic efficacy consistently.

For example, achiral RNA oligonucleotides (10-30 bases in length), or achiral 2'-methoxy oligonucleotides (10-30 bases in length), or achiral 2'-methoxy oligonucleotides (10-30 bases in length) with (a) 3' or 3' & 5' acid stable end-blocks located in the 5' UTR, or (b) immediately adjacent to or more preferably overlapping at least one of the three bases of the start site and extending either 5' or 3' of the start site, or (c) immediately adjacent to or overlapping one of the three bases of the termination signal and extending 3' or 5' of the termination site that are ten to thirty contiguous bases in length and complementary to a RNA or DNA and that have the following binding characteristics:

(d) AG of the oligonucleotide binding the complementary RNA strand at 37° C.

(i) $(G_{37}°)<-15$ KCal or less (more negative=more stable) for 10 to 14 mer, (ii) $(G_{37}°)<-20$ KCaI or less (more negative=more stable) for 15 to 17 mer, (iii) $(G_{37}°)<-25$ KCal or less (more negative=more stable) for 18 to 20 mer, (iv) $(G_{37}°)<-30$ KCaI or less (more negative=more stable) for 21 to 23 mer, (v) $(G_{37}°)<-35$ KCaI or less (more negative=more stable) for 24 to 30 mer, (e) the AG of any hairpin structure the oligonucleotide could assume is >-3.0, (f) the Tm any hairpin that could form is at least 10° C. lower than the Tm of the oligonucleotide binding to the target RNA or DNA, (g) a melting temperature for the oligonucleotide binding to the target RNA is 45° C. by the percent GC method at 1.0 M salt For composition parameters, the percent G+C of the oligonucleotide to be used is >35 percent and are administered so that each specific RNA is at a concentration (1.0 g/100 ml), or lower in doses not to exceed 100 µg/kg per RNA, or more preferably 10 µg/kg, or more preferably 1 µg/kg, or still more preferably <1 µg/kg. Sequences are then screened to be sure they do not overlap the same regions in other known genes by conducting BLAST searches against the entire GenBank list of human sequences.

Factors contributing to the selective inhibition of gene expression in vivo by the modified oligonucleotides of the invention include the influence of chirality on melting temperature. 2'-0-methyl modified RNA oligonucleotides with achiral linkages resemble backbone linkages that very closely resemble normal unmodified nucleic acids. Typically, oligonucleotides synthesized using phosphoramidite based synthesis of phosphorothioates produces mixed isomers present at each modified phosphorothioate linkage. A measurable result of the presence of these mixed isomers is a decrease in melting temperature of the phosphorothioate oligonucleotide in a primer target duplex as compared to an unmodified oligonucleotide in the same duplex. The melting temperature of a 2'-O-methyl RNA oligonucleotide, however, is not substantially lowered relative to an unmodified oligonucleotide. Thus, the melting temperatures for 2'-O-methyl RNA oligonucleotides closely resemble those for unmodified RNA because the presence of the 2'-O-methyl group does not result in the generation of isomers.

While the invention has been described and illustrated herein by references to various specific materials, procedures and examples, it is understood that the invention is not restricted to the particular combinations of material and procedures selected for that purpose. Numerous variations of such details can be implied as will be appreciated by those skilled in the art. It is intended that the specification and examples be considered as exemplary, only, with the true scope and spirit of the invention being indicated by the following claims. All references, patents and patent applications referred to in this application are herein incorporated by reference in their entirety.

We claim:

1. A composition suitable for oral administration to a mammal suffering from a pathological disorder or disease comprising a first and a second modified oligonucleotide, wherein
   (a) said first and said second modified oligonucleotide each comprise about seven to seventy-five nucleotides containing seven or more contiguous ribose groups linked by achiral 5' to 3' internucleotide phosphate linkages, wherein said ribose groups of said modified oligonucleotides have a 2' modification, and wherein the 5' and/or 3' ends of said modified oligonucleotides are blocked;
   (b) said first modified oligonucleotide is complementary to a region of a first gene associated with said pathological disorder or disease and said second modified oligonucleotide is complementary to a region of a second gene associated with said pathological disorder or disease, wherein the nucleotide sequence of said first modified oligonucleotide comprises SEQ ID NO:1 and the nucleotide sequence of said second modified oligonucleotide comprises SEQ ID NO:6; and
   (c) wherein said pathological disorder or disease comprises inflammation.

2. The composition of claim 1, wherein the mammal is a human.

3. The composition of claim 1, wherein the 2' position of each of said ribose groups comprises a substituent selected from the group consisting of hydrogen, methoxy, propoxy, methoxy-ethoxy, fluorine, chlorine, bromine, and iodine.

4. The composition of claim 1, wherein the composition is a pharmaceutical composition.

5. A method of treating a patient with inflammation comprising administering to said patient the composition of claim 1.

6. The method of claim 5, wherein the composition of claim 1 is orally administered.

7. The method of claim 5, wherein the 2' position of each of said ribose groups comprises a substituent selected from the group consisting of hydrogen, methoxy, propoxy, methoxy-ethoxy, fluorine, chlorine, bromine, and iodine.

8. The method of claim 5, wherein said first and said second modified oligonucleotide are 3' end-blocked.

9. The method of claim 5, wherein said first and said second modified oligonucleotide are 5' end-blocked.

10. The method of claim 5, wherein at least three different modified oligonucleotides are administered.

11. The composition of claim 1, further comprising a third modified oligonucleotide, wherein said third modified oligonucleotide is complementary to a region of a third gene associated with said pathological disorder or disease, and wherein the nucleotide sequence of said third modified oligonucleotide comprises SEQ ID NO:10.

12. The composition of claim 11, further comprising a fourth modified oligonucleotide, wherein said fourth modified oligonucleotide is complementary to a region of a fourth gene associated with said pathological disorder or disease, and wherein the nucleotide sequence of said fourth modified oligonucleotide comprises SEQ ID NO:12.

* * * * *

```
                        SEQUENCE LISTING

<160> NUMBER OF SEQ ID NOS: 132

<210> SEQ ID NO 1
<211> LENGTH: 14
<212> TYPE: DNA
<213> ORGANISM: Artificial sequence
<220> FEATURE:
<223> OTHER INFORMATION: ASM oligonucleotide

<400> SEQUENCE: 1
cgtgtcagga gaac                                                    14

<210> SEQ ID NO 2
<211> LENGTH: 14
<212> TYPE: DNA
<213> ORGANISM: Artificial sequence
<220> FEATURE:
<223> OTHER INFORMATION: Ace1 oligonucleotide

<400> SEQUENCE: 2
catgacgcgg tgcg                                                    14

<210> SEQ ID NO 3
<211> LENGTH: 16
<212> TYPE: DNA
<213> ORGANISM: Artificial sequence
<220> FEATURE:
<223> OTHER INFORMATION: Acid-2 oligonucleotide

<400> SEQUENCE: 3
ggcagtcgtc cctcta                                                  16

<210> SEQ ID NO 4
<211> LENGTH: 16
<212> TYPE: DNA
<213> ORGANISM: Artificial sequence
<220> FEATURE:
<223> OTHER INFORMATION: Acid B2 oligonucleotide

<400> SEQUENCE: 4
aacgtttcac ttctca                                                  16

<210> SEQ ID NO 5
<211> LENGTH: 13
<212> TYPE: DNA
<213> ORGANISM: Artificial sequence
<220> FEATURE:
<223> OTHER INFORMATION: cd18-1 oligonucleotide

<400> SEQUENCE: 5
ttgctaccag tct                                                     13

<210> SEQ ID NO 6
<211> LENGTH: 16
<212> TYPE: DNA
<213> ORGANISM: Artificial sequence
```

```
<220> FEATURE:
<223> OTHER INFORMATION: CX2 (X2) oligonucleotide

<400> SEQUENCE: 6
tctacagttc agtcga                                                    16

<210> SEQ ID NO 7
<211> LENGTH: 18
<212> TYPE: DNA
<213> ORGANISM: Artificial sequence
<220> FEATURE:
<223> OTHER INFORMATION: Mg44 oligonucleotide

<400> SEQUENCE: 7
tgacaacatt gtagctac                                                  18

<210> SEQ ID NO 8
<211> LENGTH: 18
<212> TYPE: DNA
<213> ORGANISM: Artificial sequence
<220> FEATURE:
<223> OTHER INFORMATION: Mg44 oligonucleotide

<400> SEQUENCE: 8
agctacagaa tccttgga                                                  18

<210> SEQ ID NO 9
<211> LENGTH: 16
<212> TYPE: DNA
<213> ORGANISM: Artificial sequence
<220> FEATURE:
<223> OTHER INFORMATION: Mg44 oligonucleotide

<400> SEQUENCE: 9
gtcgggctat tcaggc                                                    16

<210> SEQ ID NO 10
<211> LENGTH: 16
<212> TYPE: DNA
<213> ORGANISM: Artificial sequence
<220> FEATURE:
<223> OTHER INFORMATION: P65-2M (65) oligonucleotide

<400> SEQUENCE: 10
gaacagttcg tccatg                                                    16

<210> SEQ ID NO 11
<211> LENGTH: 15
<212> TYPE: DNA
<213> ORGANISM: Artificial sequence
<220> FEATURE:
<223> OTHER INFORMATION: IL-501 oligonucleotide

<400> SEQUENCE: 11
cctcatggct ctgaa                                                     15

<210> SEQ ID NO 12
<211> LENGTH: 16
<212> TYPE: DNA
<213> ORGANISM: Artificial sequence
<220> FEATURE:
<223> OTHER INFORMATION: LO5-38 oligonucleotide

<400> SEQUENCE: 12
ggagggcatg gcgcgg                                                    16
```

```
<210> SEQ ID NO 13
<211> LENGTH: 16
<212> TYPE: DNA
<213> ORGANISM: Artificial sequence
<220> FEATURE:
<223> OTHER INFORMATION: MPB-19 oligonucleotide

<400> SEQUENCE: 13
cctgcatcgc gccgtg                                                    16

<210> SEQ ID NO 14
<211> LENGTH: 16
<212> TYPE: DNA
<213> ORGANISM: Artificial sequence
<220> FEATURE:
<223> OTHER INFORMATION: NEP-1 (CALLA) oligonucleotide

<400> SEQUENCE: 14
gacttgccca tcacct                                                    16

<210> SEQ ID NO 15
<211> LENGTH: 16
<212> TYPE: DNA
<213> ORGANISM: Artificial sequence
<220> FEATURE:
<223> OTHER INFORMATION: NPY-1 oligonucleotide

<400> SEQUENCE: 15
acctagcatg gtggct                                                    16

<210> SEQ ID NO 16
<211> LENGTH: 15
<212> TYPE: DNA
<213> ORGANISM: Artificial sequence
<220> FEATURE:
<223> OTHER INFORMATION: D5 (PDE5.1) oligonucleotide

<400> SEQUENCE: 16
cgctccatgg ttggc                                                     15

<210> SEQ ID NO 17
<211> LENGTH: 16
<212> TYPE: DNA
<213> ORGANISM: Artificial sequence
<220> FEATURE:
<223> OTHER INFORMATION: D7 oligonucleotide

<400> SEQUENCE: 17
cttccattga atacgc                                                    16

<210> SEQ ID NO 18
<211> LENGTH: 16
<212> TYPE: DNA
<213> ORGANISM: Artificial sequence
<220> FEATURE:
<223> OTHER INFORMATION: Per oligonucleotide

<400> SEQUENCE: 18
actgccatcc tcgctc                                                    16

<210> SEQ ID NO 19
<211> LENGTH: 16
<212> TYPE: DNA
<213> ORGANISM: Artificial sequence
<220> FEATURE:
<223> OTHER INFORMATION: TTP (TTPII) oligonucleotide
```

```
<400> SEQUENCE: 19
cggtggccat ggacgc                                                    16

<210> SEQ ID NO 20
<211> LENGTH: 17
<212> TYPE: DNA
<213> ORGANISM: Artificial sequence
<220> FEATURE:
<223> OTHER INFORMATION: TTPII oligonucleotide

<400> SEQUENCE: 20
aagttcatgg tttcgga                                                   17

<210> SEQ ID NO 21
<211> LENGTH: 19
<212> TYPE: DNA
<213> ORGANISM: Artificial sequence
<220> FEATURE:
<223> OTHER INFORMATION: MTP oligonucleotide

<400> SEQUENCE: 21
gaatcatatt tgaccagca                                                 19

<210> SEQ ID NO 22
<211> LENGTH: 16
<212> TYPE: DNA
<213> ORGANISM: Artificial sequence
<220> FEATURE:
<223> OTHER INFORMATION: HisR1 oligonucleotide

<400> SEQUENCE: 22
ggctcattgg cgcaag                                                    16

<210> SEQ ID NO 23
<211> LENGTH: 16
<212> TYPE: DNA
<213> ORGANISM: Artificial sequence
<220> FEATURE:
<223> OTHER INFORMATION: HisR1 oligonucleotide

<400> SEQUENCE: 23
agagcctccc ttagga                                                    16

<210> SEQ ID NO 24
<211> LENGTH: 16
<212> TYPE: DNA
<213> ORGANISM: Artificial sequence
<220> FEATURE:
<223> OTHER INFORMATION: CRP oligonucleotide

<400> SEQUENCE: 24
catggtcacg tcctgc                                                    16

<210> SEQ ID NO 25
<211> LENGTH: 18
<212> TYPE: DNA
<213> ORGANISM: Artificial sequence
<220> FEATURE:
<223> OTHER INFORMATION: CETP oligonucleotide

<400> SEQUENCE: 25
atggttatca ggcagtgg                                                  18

<210> SEQ ID NO 26
```

```
<211> LENGTH: 19
<212> TYPE: DNA
<213> ORGANISM: Artificial sequence
<220> FEATURE:
<223> OTHER INFORMATION: CETP oligonucleotide

<400> SEQUENCE: 26
catggttatc aggcagtgg                                                   19

<210> SEQ ID NO 27
<211> LENGTH: 16
<212> TYPE: DNA
<213> ORGANISM: Artificial sequence
<220> FEATURE:
<223> OTHER INFORMATION: CETP oligonucleotide

<400> SEQUENCE: 27
ctgaagaatt gaccac                                                      16

<210> SEQ ID NO 28
<211> LENGTH: 16
<212> TYPE: DNA
<213> ORGANISM: Artificial sequence
<220> FEATURE:
<223> OTHER INFORMATION: ICAM oligonucleotide

<400> SEQUENCE: 28
catagcgagg ctgagg                                                      16

<210> SEQ ID NO 29
<211> LENGTH: 15
<212> TYPE: DNA
<213> ORGANISM: Artificial sequence
<220> FEATURE:
<223> OTHER INFORMATION: TNF-alpha oligonucleotide

<400> SEQUENCE: 29
gtgctcatgg tgtcc                                                       15

<210> SEQ ID NO 30
<211> LENGTH: 15
<212> TYPE: DNA
<213> ORGANISM: Artificial sequence
<220> FEATURE:
<223> OTHER INFORMATION: Bone morphgenic protein-4 oligonucleotide

<400> SEQUENCE: 30
cgaccatcag cattc                                                       15

<210> SEQ ID NO 31
<211> LENGTH: 16
<212> TYPE: DNA
<213> ORGANISM: Artificial sequence
<220> FEATURE:
<223> OTHER INFORMATION: Beta adrenergic receptor-1 oligonucleotide

<400> SEQUENCE: 31
gcccatgccg agctgc                                                      16

<210> SEQ ID NO 32
<211> LENGTH: 16
<212> TYPE: DNA
<213> ORGANISM: Artificial sequence
<220> FEATURE:
<223> OTHER INFORMATION: IL-6 oligonucleotide

<400> SEQUENCE: 32
```
aggagttcat agctgg                                                           16

<210> SEQ ID NO 33
<211> LENGTH: 16
<212> TYPE: DNA
<213> ORGANISM: Artificial sequence
<220> FEATURE:
<223> OTHER INFORMATION: FAAH oligonucleotide

<400> SEQUENCE: 33
gcaccatgat cccttc                                                           16

<210> SEQ ID NO 34
<211> LENGTH: 16
<212> TYPE: DNA
<213> ORGANISM: Artificial sequence
<220> FEATURE:
<223> OTHER INFORMATION: ACAT oligonucleotide

<400> SEQUENCE: 34
cttcacccac cattgt                                                           16

<210> SEQ ID NO 35
<211> LENGTH: 18
<212> TYPE: DNA
<213> ORGANISM: Artificial sequence
<220> FEATURE:
<223> OTHER INFORMATION: IBAT oligonucleotide

<400> SEQUENCE: 35
cattcattgc tgggtctg                                                         18

<210> SEQ ID NO 36
<211> LENGTH: 15
<212> TYPE: DNA
<213> ORGANISM: Artificial sequence
<220> FEATURE:
<223> OTHER INFORMATION: HMGIC oligonucleotide

<400> SEQUENCE: 36
cgtgcgctca tcctg                                                            15

<210> SEQ ID NO 37
<211> LENGTH: 16
<212> TYPE: DNA
<213> ORGANISM: Artificial sequence
<220> FEATURE:
<223> OTHER INFORMATION: HMGIC oligonucleotide

<400> SEQUENCE: 37
aacgttgcgc cccta                                                            16

<210> SEQ ID NO 38
<211> LENGTH: 16
<212> TYPE: DNA
<213> ORGANISM: Artificial sequence
<220> FEATURE:
<223> OTHER INFORMATION: Ghre oligonucleotide

<400> SEQUENCE: 38
tgcagacagg tgggcc                                                           16

<210> SEQ ID NO 39
<211> LENGTH: 17
<212> TYPE: DNA

```
<213> ORGANISM: Artificial sequence
<220> FEATURE:
<223> OTHER INFORMATION: Ghre oligonucleotide

<400> SEQUENCE: 39
gcatggcctc agctggg                                                   17

<210> SEQ ID NO 40
<211> LENGTH: 16
<212> TYPE: DNA
<213> ORGANISM: Artificial sequence
<220> FEATURE:
<223> OTHER INFORMATION: Ghre oligonucleotide

<400> SEQUENCE: 40
tgggcgatca cttgtc                                                    16

<210> SEQ ID NO 41
<211> LENGTH: 18
<212> TYPE: DNA
<213> ORGANISM: Artificial sequence
<220> FEATURE:
<223> OTHER INFORMATION: AAT1R oligonucleotide

<400> SEQUENCE: 41
cattttgatc acctgggt                                                  18

<210> SEQ ID NO 42
<211> LENGTH: 16
<212> TYPE: DNA
<213> ORGANISM: Artificial sequence
<220> FEATURE:
<223> OTHER INFORMATION: AAT1R oligonucleotide

<400> SEQUENCE: 42
cgaacatgtc actcaa                                                    16

<210> SEQ ID NO 43
<211> LENGTH: 17
<212> TYPE: DNA
<213> ORGANISM: Artificial sequence
<220> FEATURE:
<223> OTHER INFORMATION: VEGF oligonucleotide

<400> SEQUENCE: 43
aagttcatgg tttcgga                                                   17

<210> SEQ ID NO 44
<211> LENGTH: 17
<212> TYPE: DNA
<213> ORGANISM: Artificial sequence
<220> FEATURE:
<223> OTHER INFORMATION: VEGF oligonucleotide

<400> SEQUENCE: 44
tcaccgcctc ggcttgt                                                   17

<210> SEQ ID NO 45
<211> LENGTH: 15
<212> TYPE: DNA
<213> ORGANISM: Artificial sequence
<220> FEATURE:
<223> OTHER INFORMATION: FAS oligonucleotide

<400> SEQUENCE: 45
cctcctccat ggctg                                                     15
```

```
<210> SEQ ID NO 46
<211> LENGTH: 15
<212> TYPE: DNA
<213> ORGANISM: Artificial sequence
<220> FEATURE:
<223> OTHER INFORMATION: FAS oligonucleotide

<400> SEQUENCE: 46
gcctagccct cccgc                                                   15

<210> SEQ ID NO 47
<211> LENGTH: 16
<212> TYPE: DNA
<213> ORGANISM: Artificial sequence
<220> FEATURE:
<223> OTHER INFORMATION: AmP oligonucleotide

<400> SEQUENCE: 47
gcagcggctt gttcat                                                  16

<210> SEQ ID NO 48
<211> LENGTH: 15
<212> TYPE: DNA
<213> ORGANISM: Artificial sequence
<220> FEATURE:
<223> OTHER INFORMATION: AmP oligonucleotide

<400> SEQUENCE: 48
gagtcaagac ctcag                                                   15

<210> SEQ ID NO 49
<211> LENGTH: 16
<212> TYPE: DNA
<213> ORGANISM: Artificial sequence
<220> FEATURE:
<223> OTHER INFORMATION: PanLip oligonucleotide

<400> SEQUENCE: 49
gtggcagcat cgtggc                                                  16

<210> SEQ ID NO 50
<211> LENGTH: 16
<212> TYPE: DNA
<213> ORGANISM: Artificial sequence
<220> FEATURE:
<223> OTHER INFORMATION: PanLip oligonucleotide

<400> SEQUENCE: 50
cctaacacgg tgtgag                                                  16

<210> SEQ ID NO 51
<211> LENGTH: 17
<212> TYPE: DNA
<213> ORGANISM: Artificial sequence
<220> FEATURE:
<223> OTHER INFORMATION: ACC2 oligonucleotide

<400> SEQUENCE: 51
gaagcaagac cattcag                                                 17

<210> SEQ ID NO 52
<211> LENGTH: 17
<212> TYPE: DNA
<213> ORGANISM: Artificial sequence
<220> FEATURE:
```

```
<223> OTHER INFORMATION: ACC2 oligonucleotide

<400> SEQUENCE: 52
tcaggtggag gccgggc                                                    17

<210> SEQ ID NO 53
<211> LENGTH: 16
<212> TYPE: DNA
<213> ORGANISM: Artificial sequence
<220> FEATURE:
<223> OTHER INFORMATION: PKARIIbeta oligonucleotide

<400> SEQUENCE: 53
tgctcatcct gcctcc                                                     16

<210> SEQ ID NO 54
<211> LENGTH: 16
<212> TYPE: DNA
<213> ORGANISM: Artificial sequence
<220> FEATURE:
<223> OTHER INFORMATION: PKARIIbeta oligonucleotide

<400> SEQUENCE: 54
gcttcatgca gtgggt                                                     16

<210> SEQ ID NO 55
<211> LENGTH: 16
<212> TYPE: DNA
<213> ORGANISM: Artificial sequence
<220> FEATURE:
<223> OTHER INFORMATION: VR1R oligonucleotide

<400> SEQUENCE: 55
tcttcatcct tgctgg                                                     16

<210> SEQ ID NO 56
<211> LENGTH: 16
<212> TYPE: DNA
<213> ORGANISM: Artificial sequence
<220> FEATURE:
<223> OTHER INFORMATION: VR1R oligonucleotide

<400> SEQUENCE: 56
ctcacttctc cccgga                                                     16

<210> SEQ ID NO 57
<211> LENGTH: 16
<212> TYPE: DNA
<213> ORGANISM: Artificial sequence
<220> FEATURE:
<223> OTHER INFORMATION: ADAMTS oligonucleotide

<400> SEQUENCE: 57
gggacatggc actggt                                                     16

<210> SEQ ID NO 58
<211> LENGTH: 16
<212> TYPE: DNA
<213> ORGANISM: Artificial sequence
<220> FEATURE:
<223> OTHER INFORMATION: ADAMTS oligonucleotide

<400> SEQUENCE: 58
ttatttcctg cccgcc                                                     16
```

```
<210> SEQ ID NO 59
<211> LENGTH: 16
<212> TYPE: DNA
<213> ORGANISM: Artificial sequence
<220> FEATURE:
<223> OTHER INFORMATION: NPY-Y5R oligonucleotide

<400> SEQUENCE: 59
tgtggcaggt cagttg                                                      16

<210> SEQ ID NO 60
<211> LENGTH: 16
<212> TYPE: DNA
<213> ORGANISM: Artificial sequence
<220> FEATURE:
<223> OTHER INFORMATION: NPY-Y5R oligonucleotide

<400> SEQUENCE: 60
atccatatta tagtct                                                      16

<210> SEQ ID NO 61
<211> LENGTH: 16
<212> TYPE: DNA
<213> ORGANISM: Artificial sequence
<220> FEATURE:
<223> OTHER INFORMATION: NPY-Y5R oligonucleotide

<400> SEQUENCE: 61
tattacatat gaagac                                                      16

<210> SEQ ID NO 62
<211> LENGTH: 16
<212> TYPE: DNA
<213> ORGANISM: Artificial sequence
<220> FEATURE:
<223> OTHER INFORMATION: GNTV oligonucleotide

<400> SEQUENCE: 62
agccattgct ctctgg                                                      16

<210> SEQ ID NO 63
<211> LENGTH: 16
<212> TYPE: DNA
<213> ORGANISM: Artificial sequence
<220> FEATURE:
<223> OTHER INFORMATION: GNTV oligonucleotide

<400> SEQUENCE: 63
tgctataggc agtctt                                                      16

<210> SEQ ID NO 64
<211> LENGTH: 16
<212> TYPE: DNA
<213> ORGANISM: Artificial sequence
<220> FEATURE:
<223> OTHER INFORMATION: FCRG3 oligonucleotide

<400> SEQUENCE: 64
tgccacatga tgccac                                                      16

<210> SEQ ID NO 65
<211> LENGTH: 16
<212> TYPE: DNA
<213> ORGANISM: Artificial sequence
<220> FEATURE:
<223> OTHER INFORMATION: FCRG3 oligonucleotide
```

```
<400> SEQUENCE: 65
gttgagcttc aaatgt                                                    16

<210> SEQ ID NO 66
<211> LENGTH: 16
<212> TYPE: DNA
<213> ORGANISM: Artificial sequence
<220> FEATURE:
<223> OTHER INFORMATION: CD40L oligonucleotide

<400> SEQUENCE: 66
tcgatcatgc tgtgtt                                                    16

<210> SEQ ID NO 67
<211> LENGTH: 16
<212> TYPE: DNA
<213> ORGANISM: Artificial sequence
<220> FEATURE:
<223> OTHER INFORMATION: CD40L oligonucleotide

<400> SEQUENCE: 67
aggtgacact gttcag                                                    16

<210> SEQ ID NO 68
<211> LENGTH: 16
<212> TYPE: DNA
<213> ORGANISM: Artificial sequence
<220> FEATURE:
<223> OTHER INFORMATION: ETS-1 oligonucleotide

<400> SEQUENCE: 68
acggccgcct tcatgg                                                    16

<210> SEQ ID NO 69
<211> LENGTH: 16
<212> TYPE: DNA
<213> ORGANISM: Artificial sequence
<220> FEATURE:
<223> OTHER INFORMATION: ETS-1 oligonucleotide

<400> SEQUENCE: 69
gccatcactc gtcggc                                                    16

<210> SEQ ID NO 70
<211> LENGTH: 16
<212> TYPE: DNA
<213> ORGANISM: Artificial sequence
<220> FEATURE:
<223> OTHER INFORMATION: ADAMTS-5 oligonucleotide

<400> SEQUENCE: 70
ccgagcagca tagtgc                                                    16

<210> SEQ ID NO 71
<211> LENGTH: 16
<212> TYPE: DNA
<213> ORGANISM: Artificial sequence
<220> FEATURE:
<223> OTHER INFORMATION: ADAMTS-5 oligonucleotide

<400> SEQUENCE: 71
tcataaccac aggcta                                                    16

<210> SEQ ID NO 72
<211> LENGTH: 16
```

```
<212> TYPE: DNA
<213> ORGANISM: Artificial sequence
<220> FEATURE:
<223> OTHER INFORMATION: PTP-1B oligonucleotide

<400> SEQUENCE: 72
catgacgggc cagggc                                                  16

<210> SEQ ID NO 73
<211> LENGTH: 16
<212> TYPE: DNA
<213> ORGANISM: Artificial sequence
<220> FEATURE:
<223> OTHER INFORMATION: PTP-1B oligonucleotide

<400> SEQUENCE: 73
gggtcaggct atgtgt                                                  16

<210> SEQ ID NO 74
<211> LENGTH: 17
<212> TYPE: DNA
<213> ORGANISM: Artificial sequence
<220> FEATURE:
<223> OTHER INFORMATION: MMP-1 oligonucleotide

<400> SEQUENCE: 74
gcatactggc ctttgtc                                                 17

<210> SEQ ID NO 75
<211> LENGTH: 17
<212> TYPE: DNA
<213> ORGANISM: Artificial sequence
<220> FEATURE:
<223> OTHER INFORMATION: MMP-1 oligonucleotide

<400> SEQUENCE: 75 tcaattttc ctgcagt                                                  17

<210> SEQ ID NO 76
<211> LENGTH: 16
<212> TYPE: DNA
<213> ORGANISM: Artificial sequence
<220> FEATURE:
<223> OTHER INFORMATION: Cat oligonucleotide

<400> SEQUENCE: 76
gccatagcgt gcggtt                                                  16

<210> SEQ ID NO 77
<211> LENGTH: 16
<212> TYPE: DNA
<213> ORGANISM: Artificial sequence
<220> FEATURE:
<223> OTHER INFORMATION: Cat oligonucleotide

<400> SEQUENCE: 77
cccggcctca cagatt                                                  16

<210> SEQ ID NO 78
<211> LENGTH: 17
<212> TYPE: DNA
<213> ORGANISM: Artificial sequence
<220> FEATURE:
<223> OTHER INFORMATION: MMP-17 oligonucleotide

<400> SEQUENCE: 78
```
catggcgctc acatggg    17

<210> SEQ ID NO 79
<211> LENGTH: 17
<212> TYPE: DNA
<213> ORGANISM: Artificial sequence
<220> FEATURE:
<223> OTHER INFORMATION: MMP-17 oligonucleotide

<400> SEQUENCE: 79
tgtcatagcg tcagggc    17

<210> SEQ ID NO 80
<211> LENGTH: 16
<212> TYPE: DNA
<213> ORGANISM: Artificial sequence
<220> FEATURE:
<223> OTHER INFORMATION: OPG oligonucleotide

<400> SEQUENCE: 80
tcattgtggt ccccgg    16

<210> SEQ ID NO 81
<211> LENGTH: 16
<212> TYPE: DNA
<213> ORGANISM: Artificial sequence
<220> FEATURE:
<223> OTHER INFORMATION: OPG oligonucleotide

<400> SEQUENCE: 81
tccagttata agcagc    16

<210> SEQ ID NO 82
<211> LENGTH: 1684
<212> TYPE: DNA
<213> ORGANISM: Homo sapiens
<220> FEATURE:
<221> NAME/KEY: misc_feature
<223> OTHER INFORMATION: Pde4: Acc. No. U50158

<400> SEQUENCE: 82
aatatgaagg agcagccctc atgtgccggc accgggcatc cgagcatggc gggaggaggc    60
ctaccagaaa ctggccagcg agaccctgga ggagctggac tggtgtctgg accagctaga    120
gaccctacag accaggcact ccgtcagtga gatggcctcc aacaagttta aaggatgct    180 taatcgggag ctcacccatc tctctgaaat gagtcggtct ggaaatcaag tgtcagagtt    240
tatatcaaac acattcttag ataagcaaca tgaagtggaa attccttctc caactcagaa    300
ggaaaaggag aaaaagaaaa gaccaatgtc tcagatcagt ggagtcaaga aattgatgca    360
cagctctagt ctgactaatt caagtatccc aaggtttgga gttaaaactg aacaagaaga    420
tgtccttgcc aaggaactag aagatgtgaa caaatggggt cttcatgttt tcagaatagc    480
agagttgtct ggtaaccggc ccttgactgt tatcatgcac accatttttc aggaacggga    540
tttattaaaa acatttaaaa ttccagtaga tactttaatt acatatctta tgactctcga    600
agaccattac catgctgatg tggcctatca caacaatatc catgctgcag atgttgtcca    660
gtctactcat gtgctattat ctacacctgc tttggaggct gtgttacag atttggagat    720 tcttgcagca atttttgcca gtgcaataca tgatgtagat catcctggtg tgtccaatca    780
atttctgatc aatacaaact ctgaacttgc cttgatgtac aatgattcct cagtcttaga    840
gaaccatcat ttggctgtgg gctttaaaatt gcttcaggaa gaaaactgtg acattttcca    900

```
gaatttgacc aaaaaacaaa gacaatctttt aaggaaaatg gtcattgaca tcgtacttgc    960
aacagatatg tcaaaacaca tgaatctact ggctgatttg aagactatgg ttgaaactaa   1020
gaaagtgaca agctctggag ttcttcttct tgataattat tccgatagga ttcaggttct   1080
tcagaatatg gtgcactgtg cagatctgag caacccaaca aagcctctcc agctgtaccg   1140
ccagtggacg gaccggataa tggaggagtt cttccgccaa ggagaccgag agagggaacg   1200
tggcatggag ataagcccca tgtgtgacaa gcacaatgct tccgtggaaa aatcacaggt   1260
gggcttcata gactatattg ttcatcccct ctgggagaca tgggcagacc tcgtccaccc   1320
tgacgcccag gatattttgg acactttgga ggacaatcgt gaatggtacc agagcacaat   1380
ccctcagagc ccctctcctg cacctgatga cccagaggag ggccggcagg gtcaaactga   1440
gaaattccag tttgaactaa ctttagagga agatggtgag tcagacacgg aaaaggacag   1500
tggcagtcaa gtggaagaag acactagctg cagtgactcc aagactcttc gtactcaaga   1560
ctcagagtct actgaaattc cccttgatga acaggttgaa gaggaggcag taggggaaga   1620
agaggaaagc caacctgaag cctgtgtcat agatgatcgt tctcctgaca cgtaacagtg   1680
caaa                                                               1684

<210> SEQ ID NO 83
<211> LENGTH: 4020
<212> TYPE: DNA
<213> ORGANISM: Homo sapiens
<220> FEATURE:
<221> NAME/KEY: misc_feature
<223> OTHER INFORMATION: ACE-1:  Acc. No. J04144.1

<400> SEQUENCE: 83
gccgagcacc gcgcaccgcg tcatgggggc cgcctcgggc cgccgggggc cggggctgct     60
gctgccgctg ccgctgctgt tgctgctgcc gccgcagccc gccctggcgt tggaccccgg    120
gctgcagccc ggcaactttt ctgctgacga ggccggggcg cagctcttcg cgcagagcta    180
caactccagc gccgaacagg tgctgttcca gagcgtggcc gccagctggg cgcacgacac    240
caacatcacc gcggagaatg caaggcgcca ggaggaagca gccctgctca gccaggagtt    300
tgcggaggcc tggggccaga aggccaagga gctgtatgaa ccgatctggc agaacttcac    360
ggacccgcag ctgcgcagga tcatcggagc tgtgcgaacc ctgggctctg ccaacctgcc    420
cctggctaag cggcagcagt acaacgccct gctaagcaac atgagcagga tctactccac    480
cgccaaggtc tgcctcccca acaagactgc cacctgctgg tccctggacc cagatctcac    540
caacatcctg gcttcctcgc gaagctacgc catgctcctg tttgcctggg agggctggca    600
caacgctgcg ggcatcccgc tgaaaccgct gtacgaggat ttcactgccc tcagcaatga    660
agcctacaag caggacggct tcacagacac ggggggctac tggcgctcct ggtacaactc    720
ccccaccttc gaggacgatc tggaacacct ctaccaacag ctagagcccc tctacctgaa    780
cctccatgcc ttcgtccgcc gcgcactgca tcgccgatac ggagacagat acatcaacct    840
caggggaccc atccctgctc atctgctggg agacatgtgg gcccagagct gggaaaacat    900
ctacgacatg gtggtgccttt cccagacaa gcccaacctc gatgtcacca gtactatgct    960
gcagcagggc tggaacgcca cgcacatgtt ccggtggca gaggagttct tcacctcccct   1020 ggagctctcc cccatgcctc ccgagttctg ggaagggtcg atgctggaga agccggccga   1080
cgggcgggaa gtggtgtgcc acgcctcggc ttgggactc tacaacagga aagacttcag   1140
gatcaagcag tgcacacggg tcacgatgga ccagctctcc acagtgcacc atgagatggg   1200
```

-continued

```
ccatatacag tactacctgc agtacaagga tctgcccgtc tccctgcgtc ggggggccaa      1260
ccccggcttc catgaggcca ttggggacgt gctggcgctc tcggtctcca ctcctgaaca      1320
tctgcacaaa atcggcctgc tggaccgtgt caccaatgac acggaaagtg acatcaatta      1380
cttgctaaaa atggcactgg aaaaaattgc cttcctgccc tttggctact ggtggacca      1440 gtggcgctgg ggggtcttta gtgggcgtac cccccttcc cgctacaact tcgactggtg       1500
gtatcttcga accaagtatc aggggatctg tcctcctgtt acccgaaacg aaacccactt      1560
tgatgctgga gctaagtttc atgttccaaa tgtgacacca tacatcaggt actttgtgag      1620
ttttgtcctg cagttccagt tccatgaagc cctgtgcaag gaggcaggct atgagggccc      1680
actgcaccag tgtgacatct accggtccac caaggcaggg gccaagctcc ggaaggtgct      1740
gcaggctggc tcctccaggc cctggcagga ggtgctgaag acatggtcg gcttagatgc        1800 cctggatgcc cagccgctgc tcaagtactt ccagccagtc acccagtggc tgcaggagca      1860
gaaccagcag aacggcgagg tcctgggctg gcccgagtac cagtggcacc cgccgttgcc      1920
tgacaactac ccggagggca tagacctggt gactgatgag gctgaggcca gcaagtttgt      1980
ggaggaatat gaccggacat cccaggtggt gtggaacgag tatgccgagg ccaactggaa      2040
ctacaacacc aacatcacca cagagaccag caagattctg ctgcagaaga acatgcaaat      2100
agccaaccac accctgaagt acggcaccca ggccaggaag tttgatgtga accagttgca      2160
gaacaccact atcaagcgga tcataaagaa ggttcaggac ctagaacggg cagcgctgcc      2220
tgcccaggag ctggaggagt acaacaagat cctgttggat atggaaacca cctacagcgt      2280
ggccactgtg tgccacccga atggcagctg cctgcagctc gagccagatc tgacgaatgt      2340
gatggccaca tcccggaaat atgaagacct gttatgggca tgggagggct ggcgagacaa      2400
ggcggggaga gccatcctcc agttttaccc gaaatacgtg gaactcatca accaggctgc      2460
ccggctcaat ggctatgtag atgcagggga ctcgtggagg tctatgtacg agacaccatc      2520
cctggagcaa gacctggagc ggctcttcca ggagctgcag ccactctacc tcaacctgca      2580
tgcctacgtg cgccgggccc tgcaccgtca ctacggggcc cagcacatca acctggaggg      2640
gcccattcct gctcacctgc tggggaacat gtgggcgcag acctggtcca acatctatga      2700
cttggtggtg cccttcccctt cagccccctc gatggacacc acagaggcta tgctaaagca      2760
gggctggacg cccaggagga tgtttaagga ggctgatgat ttcttcacct ccctgggcgct     2820 gctgcccgtg cctcctgagt tctggaacaa gtcgatgctg gagaagccaa ccgacgggcg      2880
ggaggtggtc tgccacgcct cggcctggga cttctacaac ggcaaggact tccggatcaa      2940
gcagtgcacc accgtgaact tggaggacct ggtggtggcc caccacgaaa tgggccacat      3000
ccagtatttc atgcagtaca aagacttacc tgtggccttg agggagggtg ccaaccccgg      3060
cttccatgag gccattgggg acgtgctagc cctctcagtg tctacgccca agcacctgca      3120
cagtctcaac ctgctgagca gtgagggtgg cagcgacgag catgacatca actttctgat      3180
gaagatggcc cttgacaaga tcgcctttat ccccttcagc tacctcgtcg atcagtggcg      3240
ctggagggta tttgatggaa gcatcaccaa ggagaactat aaccaggagt ggtggagcct      3300
caggctgaag taccagggcc tctgcccccc agtgccccagg actcaaggtg actttgaccc      3360
aggggccaag ttccacattc cttctagcgt gccttacatc aggtactttg tcagcttcat      3420
catccagttc cagttccacg aggcactgtg ccaggcagct ggccacacgg gcccctgca      3480 caagtgtgac atctaccagt ccaaggaggc cgggcagcgc ctggcgaccg ccatgaagct      3540
gggcttcagt aggccgtggc cggaagccat gcagctgatc acgggccagc ccaacatgag      3600
```

```
cgcctcggcc atgttgagct acttcaagcc gctgctggac tggctccgca cggagaacga      3660
gctgcatggg gagaagctgg gctggccgca gtacaactgg acgccgaact ccgctcgctc      3720
agaagggccc ctcccagaca gcggccgcgt cagcttcctg ggcctggacc tggatgcgca      3780
gcaggcccgc gtgggccagt ggctgctgct cttcctggga atcgccctgc tggtagccac      3840
cctgggcctc agccagcggc tcttcagcat ccgccaccgc agcctccacc ggcactccca      3900
cgggccccag ttcggctccg aggtggagct gagacactcc tgaggtgacc cggctgggtc      3960
ggccctgccc aagggcctcc caccagagac tgggatggga acactggtgg gcagctgagg      4020
```

<210> SEQ ID NO 84
<211> LENGTH: 3556
<212> TYPE: DNA
<213> ORGANISM: Homo sapiens
<220> FEATURE:
<221> NAME/KEY: misc_feature
<223> OTHER INFORMATION: Acid2: Acc. No. NM_000704

<400> SEQUENCE: 84

```
tgttgggtgg gagcacaggc accgggcacc atggggaagg ccgagaacta tgagctctac        60 tcggtgagc tgggtcctgg ccctggcggg gacatggctg ccaagatgag caagaagaag       120
aaggcgggtg gcggggtgg caagaggaag gagaagctgg agaacatgaa gaaggagatg       180
gagattaacg accaccagct gtcagtggcg gagctggaac agaaatacca gaccagtgcc       240
accaagggcc tctctgcgag cctggctgct gagctgctgc tgcgggatgg gcccaacgca       300
ctgcggccac cacggggcac cccagagtac gtcaagttcg cgaggcagct ggccggggc       360 ctgcagtgcc tcatgtgggt tgccgccgcc atctgcctca tcgcctttgc catccaggct       420
agtgaggggg acctcaccac cgacgacaat ctgtacctgg caatcgctct cattgctgtg       480
gttgtcgtca ccggctgctt tggctactac caggaattca agagcaccaa catcatcgcc       540
agctttaaga accttgtgcc acagcaagcc actgtcatcc gcgatggaga caaattccag       600
atcaacgctg accaactggt ggtgggcgac ctggtggaga tgaaaggtgg ggacagagtg       660
cccgccgaca tccgcatcct ggcggcccag ggctgcaagg tggacaactc ctcgctgaca       720
ggggagtctg agccacaaac ccgctcaccc gagtgcacgc acgagagccc tctggagacc       780
cgcaacatcg ccttcttctc caccatgtgc cttgagggca ccgcgcaggg cctggtggtg       840
aacacgggcg accgcaccat cattgggcgc atcgcatcgc tggcgtcggg ggtggaaaac       900
gagaagacac ccatcgctat cgagatcgag cattttgtgg acatcatcgc gggcctggcc       960
attctcttcg gtgccacatt ttttattgtg gccatgtgca ttggctacac cttcctgcgg      1020
gccatggtct tcttcatggc catcgtggtg gcctatgtgc tgagggggct gctggccact      1080
gtcacagtct gcctgtccct gacagccaag cgcctggcca gtaagaactg cgtggtcaag      1140
aacctggagg cggtggagac attgggctcc acttcggtga tctgctcgga caagacaggg      1200
actctcactc agaaccgcat gactgtgtcc catctgtggt tgacaaccca catccacaca      1260
gctgacacca cggaagacca gtcagggcag acgtttgacc agtcctcgga gacgtggcgg      1320
gcgctgtgcc gggtgctcac cctgtgcaac cgcgccgcct tcaagtccgg ccaggatgca      1380
gtgcctgtgc ccaagcgcat cgtgattgga gacgcatcgg agacggcgct gctcaagttc      1440
tcggagctga cgctgggcaa cgccatgggc tacgggaccc gcttcccaaa agtctgcgag      1500
ataccctcca actccaccaa caagttccag ctgtccatcc atacgctgga ggacccgcgg      1560
gacccgcgac acttgctggt gatgaagggc gccccgagc gcgtgctgga gcgctgcagc      1620
```

-continued

```
tccatcctta tcaagggcca ggagctgccg ctggacgagc agtggcgcga ggccttccag    1680
accgcctacc tcagcctggg aggcctgggc gaacgcgtgc tcggcttctg ccagctctac    1740
ctgaatgaga aggactaccc gcctggctat gccttcgacg tagaggccat gaactttcca    1800
tctagcggcc tctgctttgc gggacttgta tccatgattg acccaccccg ggccaccgtc    1860
cctgatgctg tgctcaagtg tcgcaccgca ggcatccggg tgatcatggt aacgggtgac    1920
caccccatca ccgccaaggc cattgcagcc agtgtgggca tcatctcgga aggcagcgag    1980
acagtggagg acatcgctgc ccgcctccgt gtgcccgtag accaggttaa tcgcaaggat    2040
gcccgtgcct gtgtgatcaa tggcatgcag ctgaaggaca tggacccatc ggaactggtc    2100
gaggccctgc gcacccaccc cgagatggtg tttgcgcgca ccagccccca gcagaagctg    2160
gtgatcgtgg agagctgcca gcggctgggt gcgattgtgg ccgtcacggg ggatggtgtg    2220
aatgactccc cagctctgaa gaaggcagac atcggagtag ccatgggcat cgctggctca    2280
gatgctgcca aaaatgcagc tgacatgatc ctgctggatg acaactttgc ctccattgtg    2340
acaggcgtgg agcagggtcg actgatcttc gacaacctga agaagtctat tgcctacaca    2400
ttgaccaaga acatcccaga gctgacaccc tacctcatct acatcaccgt cagcgtgccc    2460 ctgccctcg ggtgcatcac catcctcttc atcgaactct gcactgacat tttcccatct    2520
gtgtccctgg catatgaaaa ggccgagagt gacatcatgc acctgcgtcc acgcaaccca    2580
aagcgtgaca gattggtcaa cgagcccctg gctgcctact cctacttcca gattggtgcc    2640
attcagtcct tgctggctt cactgactac ttcacggcaa tggccaggg ggctggttc    2700 ccactgctgt gcgtggggct gcgggcgcag tgggaggacc accacctaca agatctgcag    2760
gacagctacg gccaggagtg gacattcggg cagcgcctgt accagcagta cacctgctac    2820
accgtgttct tcatcagcat tgaggtgtgc cagatcgccg atgtcctcat ccgcaagacg    2880
cgccgtctct ctgccttcca gcaaggcttc ttcaggaata agatcctggt gatcgccatc    2940
gtgttccagg tctgcatcgg ctgcttcctg tgctactgcc ccggcatgcc caacatcttc    3000
aacttcatgc ccattcggtt ccagtggtgg ctggtccccc tgccctacgg catcctcatc    3060
ttcgtctatg atgagatccg gaagcttgga gttcgctgtt gcccagggag ctggtgggac    3120
caggaactct actattagag ggacgactgc cttcaagcat ccctgcaact gccacagcag    3180
gtgggggcag ggcacgtggg accctctgga cagccaccaa gatatctgag caaccaagag    3240
tcccagcccc accagtatct gcttctgtag cccacggcac cccaaacttg gagggacctg    3300
cccactcccc tcccccattc ccaaggttcg cacctcctgg agcagcagcg cctgggcagt    3360
cctctgggct ggcctcggga aagccgccac ctgtggtggc ggtggggctc tgacagggag    3420
tacagctgac cgcttctgga gggtgttct gttcttagga ctccagtcca ggctggacgg    3480
ctgcctgagg gcccttcgtt aaagacacgc ttgtgtcctg ggcgatggta ataaaaccag    3540
ctcatgctga ctgtgc                                                     3556
```

<210> SEQ ID NO 85
<211> LENGTH: 1444
<212> TYPE: DNA
<213> ORGANISM: Homo sapiens
<220> FEATURE:
<221> NAME/KEY: misc_feature
<223> OTHER INFORMATION: AcidB2:  Acc. No. NM_000705

<400> SEQUENCE: 85

```
agtctgggcg tagagggtgc agggagcaga cgggaggatc tcaggccagg gacgatggcg    60
```

```
gctctgcagg agaagaagac gtgtggccag cgcatggagg agttccagcg ttactgctgg      120
aacccggaca cggggcagat gctgggccgc accctgtccc ggtgggtgtg gatcagcctg      180
tactacgtgg ccttctacgt ggtgatgact gggctcttcg ccctgtgcct ctatgtgctg      240
atgcagacag tggacccgta cacaccggac taccaagacc agctacgtc accagggta       300 accttaaggc cggatgttta cggggagaaa ggcctggaaa ttgtctacaa cgtctctgat      360
aacagaacct gggcagacct cacacagact ctccacgcct tcctagcagg ctactctcca      420
gcagcccagg aggacagcat caactgcacc tccgagcagt acttcttcca ggagagtttc      480
cgcgctccca accacaccaa gttctcctgc aagttcacgg cagatatgct gcagaactgc      540
tcaggcctgg cggatcccaa cttcggcttt gaagaaggaa agccatgttt tattattaaa      600
atgaacagga tcgtcaagtt cctccccagc aacggctcgg cccccagagt ggactgcgcc      660
ttcctggacc agccccgcga gctcggccag ccgctgcagg tcaagtacta ccctcccaac      720
ggcaccttca gtctgcacta cttcccttat tacgggaaga agcccagcc ccactacagc       780 aaccccctgg tggcagcgaa gctcctcaac atccccagga acgctgaggt cgccatcgtg      840
tgcaaggtca tggcagagca cgtgaccttc aacaatcccc acgacccgta tgaagggaaa      900
gtggagttca aactcaagat tgagaagtga acgtttgcg caggggtcct gggcacgcct       960
gcggggtcgc tcaaggacac cctcctggtt gggcttacct tgcccgtcag ttccctgcca     1020
aatcatcccc aaagtggttt ggagcaacgg tgttgtcagt gtgcgaactc cagagaagcg     1080
cccacatctg aaggacctgc tcgcgagtat cagttcttcc ttgttgaatt cttacagttt     1140
ttagatggaa tttgctgcta taagaatgtc cagctaccat gggaacgcaa ggcagcaact     1200
ctctaattaa ccaggtcata aaacgattc gtcttctatg tagacatcac tttcttacta      1260
taatttattt ttctacactt caatatgaac tgccccccc acattaatat aaaaactact       1320
aatgcactga tatgaaacac ggcttacact aatgacattc tgaattcttg cttttaaaat     1380
tgcaattcct aagttgtaaa cataaaatat attaaagtta ctcttattgt atgtaaaaaa     1440
aaaa                                                                 1444
```

<210> SEQ ID NO 86
<211> LENGTH: 2776
<212> TYPE: DNA
<213> ORGANISM: Homo sapiens
<220> FEATURE:
<221> NAME/KEY: misc_feature
<223> OTHER INFORMATION: Cd-18: Acc. No. M15395

<400> SEQUENCE: 86

```
cagggcagac tggtagcaaa gcccccacgc ccagccagga gcaccgccgc ggactccagc       60
acaccgaggg acatgctggg cctgcgcccc ccactgctcg cctggtggg gctgctctcc       120 ctcgggtgcg tcctctctca ggagtgcacg aagttcaagg tcagcagctg ccgggaatgc      180
atcgagtcgg ggcccggctg cacctggtgc cagaagctga acttcacagg ccgggggat      240 cctgactcca ttcgctgcga cacccggcca cagctgctca tgagggctg tgcggctgac      300 gacatcatgg accccacaag cctcgctgaa acccaggaag accacaatgg gggccagaag     360
cagctgtccc cacaaaaagt gacgctttac ctgcgaccag gccaggcagc agcgttcaac      420
gtgaccttcc ggcgggccaa gggctacccc atcgacctgt actatctgat ggacctctcc      480
tactccatgc ttgatgacct caggaatgtc aagaagctag gtggcgacct gctccggggcc     540 ctcaacgaga tcaccgagtc cggccgcatt ggcttcgggt ccttcgtgga caagaccgtg      600
```

```
ctgccgttcg tgaacacgca ccctgataag ctgcgaaacc catgccccaa caaggagaaa      660
gagtgccagc ccccgtttgc cttcaggcac gtgctgaagc tgaccaacaa ctccaaccag      720
tttcagaccg aggtcgggaa gcagctgatt ccggaaacc tggatgcacc cgagggtggg      780
ctggacgcca tgatgcaggt cgccgcctgc ccggaggaaa tcggctggcg caacgtcacg      840
cggctgctgg tgtttgccac tgatgacggc ttccatttcg cgggcgacgg aaagctgggc      900
gccatcctga cccccaacga cggccgctgt cacctggagg acaacttgta caagaggagc      960
aacgaattcg actacccatc ggtgggccag ctggcgcaca agctggctga aaacaacatc     1020
cagcccatct tcgcggtgac cagtaggatg gtgaagacct acgagaaact caccgagatc     1080
atccccaagt cagccgtggg ggagctgtct gaggactcca gcaatgtggt ccatctcatt     1140
aagaatgctt acaataaact ctcctccagg gtcttcctgg atcacaacgc cctccccgac     1200
accctgaaag tcacctacga ctccttctgc agcaatggag tgacgcacag gaaccagccc     1260
agaggtgact gtgatggcgt gcagatcaat gtcccgatca ccttccaggt gaaggtcacg     1320
gccacagagt gcatccagga gcagtcgttt gtcatccggg cgctgggctt cacggacata     1380
gtgaccgtgc aggttcttcc ccagtgtgag tgccggtgcc gggaccagag cagagaccgc     1440
agcctctgcc atggcaaggg cttcttggag tgcggcatct gcaggtgtga cactggctac     1500
attgggaaaa actgtgagtg ccagacacag ggccggagca gccaggagct ggaaggaagc     1560
tgccggaagg acaacaactc catcatctgc tcagggctgg gggactgtgt ctgcgggcag     1620
tgcctgtgcc acaccagcga cgtccccggc aagctgatat acgggcagta ctgcgagtgt     1680
gacaccatca actgtgagcg ctacaacggc caggtctgcg gcggcccggg agggggctc      1740 tgcttctgcg ggaagtgccg ctgccacccg ggctttgagg ctcagcgtg ccagtgcgag      1800 aggaccactg agggctgcct gaacccgcgg cgtgttgagt gtagtggtcg tggccggtgc     1860
cgctgcaacg tatgcgagtg ccattcaggc taccagctgc ctctgtgcca ggagtgcccc     1920
ggctgcccct caccctgtgg caagtacatc tcctgcgccg agtgcctgaa gttcgaaaag     1980 ggccccttg gaagaactg cagcgcggcg tgtccgggcc tgcagctgtc gaacaacccc      2040
gtgaagggca ggacctgcaa ggagagggac tcagagggct gctgggtggc ctacacgctg     2100
gagcagcagg acgggatgga ccgctacctc atctatgtgg atgagagccg agagtgtgtg     2160
gcaggcccca catcgccgc catcgtcggg ggcaccgtgg caggcatcgt gctgatcggc     2220
attctcctgc tggtcatctg gaaggctctg atccacctga gcgacctccg ggagtacagg     2280
cgctttgaga aggagaagct caagtcccag tggaacaatg ataatccct tttcaagagc     2340 gccaccacga cggtcatgaa ccccaagttt gctgagagtt aggagcactt ggtgaagaca     2400
aggccgtcag gacccaccat gtctgcccca tcacgcggcc gagacatggc ttggccacag     2460
ctcttgagga tgtcaccaat taaccagaaa tccagttatt ttccgccctc aaaatgacag     2520
ccatggccgg ccgtgcttc tgggggctcg tcgggggac agctccactc tgactggcac      2580
agtctttgca tggagacttg aggagggctt gaggttggtg aggttaggtg cgtgtttcct     2640
gtgcaagtca ggacatcagt ctgattaaag gtggtgccaa tttatttaca tttaaacttg     2700
tcagggtata aatgacatc ccattaatta tattgttaat caatcacgtg tatagaaaaa      2760
aaaataaaac ttcaat                                                     2776
```

<210> SEQ ID NO 87
<211> LENGTH: 3387
<212> TYPE: DNA

<213> ORGANISM: Homo sapiens
<220> FEATURE:
<221> NAME/KEY: misc_feature
<223> OTHER INFORMATION: Cox2: Acc. No. M90100

<400> SEQUENCE: 87

| | |
|---|---|
| gtccaggaac tcctcagcag cgcctccttc agctccacag ccagacgccc tcagacagca | 60 |
| aagcctaccc ccgcgccgcg ccctgcccgc cgctgcgatg ctcgcccgcg ccctgctgct | 120 |
| gtgcgcggtc ctggcgctca gccatacagc aaatccttgc tgttcccacc catgtcaaaa | 180 |
| ccgaggtgta tgtatgagtg tgggatttga ccagtataag tgcgattgta cccggacagg | 240 |
| attctatgga gaaaactgct caacaccgga atttttgaca agaataaaat tatttctgaa | 300 |
| acccactcca aacacagtgc actacatact tacccacttc aagggatttt ggaacgttgt | 360 |
| gaataacatt cccttccttc gaaatgcaat tatgagttat gtgttgacat ccagatcaca | 420 |
| tttgattgac agtccaccaa cttacaatgc tgactatggc tacaaaagct gggaagcctt | 480 |
| ctctaacctc tcctattata ctagagcccct tcctcctgtg cctgatgatt gcccgactcc | 540 |
| cttgggtgtc aaaggtaaaa agcagcttcc tgattcaaat gagattgtgg aaaattgct | 600 |
| tctaagaaga aagttcatcc ctgatcccca gggctcaaac atgatgtttg cattctttgc | 660 |
| ccagcacttc acgcatcagt ttttcaagac agatcataag cgagggccag ctttcaccaa | 720 |
| cgggctgggc catggggtgg acttaaatca tatttacggt gaaactctgg ctagacagcg | 780 |
| taaactgcgc cttttcaagg atggaaaaat gaaatatcag ataattgatg gagagatgta | 840 |
| tcctcccaca gtcaaagata ctcaggcaga gatgatctac cctcctcaag tccctgagca | 900 |
| tctacggttt gctgtggggc aggaggtctt tggtctggtg cctggtctga tgatgtatgc | 960 |
| cacaatctgg ctgagggaac acaacagagt atgcgatgtg cttaaacagg agcatcctga | 1020 |
| atggggtgat gagcagttgt tccagacaag caggctaata ctgataggag agactattaa | 1080 |
| gattgtgatt gaagattatg tgcaacactt gagtggctat cacttcaaac tgaaatttga | 1140 |
| cccagaacta cttttcaaca aacaattcca gtaccaaaat cgtattgctg ctgaatttaa | 1200 |
| caccctctat cactggcatc cccttctgcc tgacaccttt caaattcatg accagaaata | 1260 |
| caactatcaa cagtttatct acaacaactc tatattgctg gaacatggaa ttacccagtt | 1320 |
| tgttgaatca ttcaccaggc aaattgctgg cagggttgct ggtggtagga atgttccacc | 1380 |
| cgcagtacag aaagtatcac aggcttccat tgaccagagc aggcagatga atacccagtc | 1440 |
| ttttaatgag taccgcaaac gctttatgct gaagccctat gaatcatttg aagaacttac | 1500 |
| aggagaaaag gaaatgtctg cagagttgga agcactctat ggtgacatcg atgctgtgga | 1560 |
| gctgtatcct gcccttctgg tagaaaagcc tcggccagat gccatctttg gtgaaaccat | 1620 |
| ggtagaagtt ggagcaccat tctccttgaa aggacttatg ggtaatgtta tatgttctcc | 1680 |
| tgcctactgg aagccaagca cttttggtgg agaagtgggt tttcaaatca tcaacactgc | 1740 |
| ctcaattcag tctctcatct gcaataacgt gaagggctgt ccctttactt cattcagtgt | 1800 |
| tccagatcca gagctcatta aaacagtcac catcaatgca agttcttccc gctccggact | 1860 |
| agatgatatc aatcccacag tactactaaa agaacgttcg actgaactgt agaagtctaa | 1920 |
| tgatcatatt tatttattta tatgaaccat gtctattaat ttaattattt aataatattt | 1980 |
| atattaaact ccttatgtta cttaacatct tctgtaacag aagtcagtac tcctgttgcg | 2040 |
| gagaaaggag tcatacttgt gaagactttt atgtcactac tctaaagatt ttgctgttgc | 2100 |
| tgttaagttt ggaaaacagt ttttattctg ttttataaac cagagagaaa tgagttttga | 2160 |

| | |
|---|---|
| cgtctttta cttgaatttc aacttatatt ataaggacga aagtaaagat gtttgaatac | 2220 |
| ttaaacacta tcacaagatg ccaaaatgct gaaagttttt acactgtcga tgtttccaat | 2280 |
| gcatcttcca tgatgcatta gaagtaacta atgtttgaaa ttttaaagta cttttgggta | 2340 |
| tttttctgtc atcaaacaaa acaggtatca gtgcattatt aaatgaatat ttaaattaga | 2400 |
| cattaccagt aatttcatgt ctactttta aaatcagcaa tgaaacaata atttgaaatt | 2460 |
| tctaaattca tagggtagaa tcacctgtaa aagcttgttt gatttcttaa agttattaaa | 2520 |
| cttgtacata taccaaaaag aagctgtctt ggatttaaat ctgtaaaatc agatgaaatt | 2580 |
| ttactacaat tgcttgttaa atatttat aagtgatgtt ccttttcac caagagtata | 2640 |
| aaccttttta gtgtgactgt taaaacttcc ttttaaatca aaatgccaaa tttattaagg | 2700 |
| tggtggagcc actgcagtgt tatctcaaaa taagaatatc ctgttgagat attccagaat | 2760 |
| ctgtttatat ggctggtaac atgtaaaaac cccataaccc cgccaaaagg ggtcctaccc | 2820 |
| ttgaacataa agcaataacc aaaggagaaa agcccaaatt attggttcca aatttagggt | 2880 |
| ttaaacttt tgaagcaaac tttttttag ccttgtgcac tgcagacctg gtactcagat | 2940 |
| tttgctatga ggttaatgaa gtaccaagct gtgcttgaat aacgatatgt tttctcagat | 3000 |
| tttctgttgt acagtttaat ttagcagtcc atatcacatt gcaaaagtag caatgacctc | 3060 |
| ataaaatacc tcttcaaaat gcttaaattc atttcacaca ttaattttat ctcagtcttg | 3120 |
| aagccaattc agtaggtgca ttggaatcaa gcctggctac ctgcatgctg ttccttttct | 3180 |
| tttcttcttt tagccatttt gctaagagac acagtcttct caaacacttc gtttctccta | 3240 |
| ttttgtttta ctagttttaa gatcagagtt cactttcttt ggactctgcc tatattttct | 3300 |
| tacctgaact tttgcaagtt ttcaggtaaa cctcagctca ggactgctat ttagctcctc | 3360 |
| ttaagaagat taaaaaaaaa aaaaaag | 3387 |

<210> SEQ ID NO 88
<211> LENGTH: 4471
<212> TYPE: DNA
<213> ORGANISM: Homo sapiens
<220> FEATURE:
<221> NAME/KEY: misc_feature
<223> OTHER INFORMATION: HMG Co-A:  Acc. No. NM_000859

<400> SEQUENCE: 88

| | |
|---|---|
| ttcggtggcc tctagtgaga tctggaggat ccaaggattc tgtagctaca atgttgtcaa | 60 |
| gacttttcg aatgcatggc ctctttgtgg cctcccatcc ctgggaagtc atagtgggga | 120 |
| cagtgacact gaccatctgc atgatgtcca tgaacatgtt tactggtaac aataagatct | 180 |
| gtggttggaa ttatgaatgt ccaaagtttg aagaggatgt tttgagcagt gacattataa | 240 |
| ttctgacaat aacacgatgc atagccatcc tgtatattta cttccagttc cagaatttac | 300 |
| gtcaacttgg atcaaaatat attttgggta ttgctggcct tttcacaatt ttctcaagtt | 360 |
| ttgtattcag tacagttgtc attcacttct tagacaaaga attgacaggc ttgaatgaag | 420 |
| ctttgccctt tttcctactt tgattgacc tttccagagc aagcacatta gcaaagtttg | 480 |
| ccctcagttc caactcacag gatgaagtaa gggaaaatat tgctcgtgga atggcaattt | 540 |
| taggtcctac gtttaccctc gatgctcttg ttgaatgtct tgtgattgga gttggtacca | 600 |
| tgtcagggt acgtcagctt gaaattatgt gctgctttgg ctgcatgtca gttcttgcca | 660 |
| actactcgt gttcatgact ttcttcccag cttgtgtgtc cttggtatta gagctttctc | 720 |
| gggaaagccg cgagggtcgt ccaatttggc agctcagcca ttttgcccga gttttagaag | 780 |

| | |
|---|---|
| aagaagaaaa taagccgaat cctgtaactc agagggtcaa gatgattatg tctctaggct | 840 |
| tggttcttgt tcatgctcac agtcgctgga tagctgatcc ttctcctcaa aacagtacag | 900 |
| cagatacttc taaggtttca ttaggactgg atgaaaatgt gtccaagaga attgaaccaa | 960 |
| gtgtttccct ctggcagttt tatctctcta aaatgatcag catggatatt gaacaagtta | 1020 |
| ttaccctaag tttagctctc cttctggctg tcaagtacat cttctttgaa caaacagaga | 1080 |
| cagaatctac actctcatta aaaaacccta tcacatctcc tgtagtgaca caaagaaag | 1140 |
| tcccagacaa ttgttgtaga cgtgaaccta tgctggtcag aaataaccag aaatgtgatt | 1200 |
| cagtagagga agagacaggg ataaaccgag aaagaaaagt tgaggttata aaacccttag | 1260 |
| tggctgaaac agataccccca aacagagcta catttgtggt tggtaactcc tccttactcg | 1320 |
| atacttcatc agtactggtg acacaggaac ctgaaattga acttcccagg gaacctcggc | 1380 |
| ctaatgaaga atgtctacag atacttggga atgcagagaa aggtgcaaaa ttccttagtg | 1440 |
| atgctgagat catccagtta gtcaatgcta agcatatccc agcctacaag ttggaaactc | 1500 |
| tgatggaaac tcatgagcgt ggtgtatcta ttcgccgaca gttactttcc aagaagcttt | 1560 |
| cagaaccttc ttctctccag tacctacctt acagggatta taattactcc ttggtgatgg | 1620 |
| gagcttgttg tgagaatgtt attggatata tgcccatccc tgttggagtg gcaggacccc | 1680 |
| tttgcttaga tgaaaagaa tttcaggttc aatggcaac aacagaaggt tgtcttgtgg | 1740 |
| ccagcaccaa tagaggctgc agagcaatag gtcttggtgg aggtgccagc agccgagtcc | 1800 |
| ttgcagatgg gatgactcgt ggcccagttg tgcgtcttcc acgtgcttgt gactctgcag | 1860 |
| aagtgaaagc ctggctcgaa acatctgaag ggttcgcagt gataaaggag gcatttgaca | 1920 |
| gcactagcag atttgcacgt ctacagaaac ttcatacaag tatagctgga cgcaaccttt | 1980 |
| atatccgttt ccagtccagg tcaggggatg ccatggggat gaacatgatt tcaaagggta | 2040 |
| cagagaaagc actttcaaaa cttcacgagt atttccctga aatgcagatt ctagccgtta | 2100 |
| gtggtaacta ttgtactgac aagaaaacctg ctgctataaa ttggatagag ggaagaggaa | 2160 |
| aatctgttgt ttgtgaagct gtcattccag ccaaggttgt cagagaagta ttaaagacta | 2220 |
| ccacagaggc tatgattgag gtcaacatta acaagaattt agtgggctct gccatggctg | 2280 |
| ggagcatagg aggctacaac gcccatgcag caaacattgt caccgccatc tacattgcct | 2340 |
| gtggacagga tgcagcacag aatgttggta gttcaaactg tattacttta atggaagcaa | 2400 |
| gtggtcccac aaatgaagat ttatatatca gctgcaccat gccatctata gagataggaa | 2460 |
| cggtgggtgg tgggaccaac ctactacctc agcaagcctg tttgcagatg ctaggtgttc | 2520 |
| aaggagcatg caaagataat cctggggaaa atgcccggca gcttgcccga attgtgtgtg | 2580 |
| ggaccgtaat ggctgggaa ttgtcactta tggcagcatt ggcagcagga catcttgtca | 2640 |
| aaagtcacat gattcacaac aggtcgaaga tcaatttaca agacctccaa ggagcttgca | 2700 |
| ccaagaagac agcctgaata gcccgacagt tctgaactgg aacatgggca ttgggttcta | 2760 |
| aaggactaac ataaaatctg tgaattaaaa aagctcaatg cattgtcttg tggaggatga | 2820 |
| ataaatgtga tcactgagac agccacttgg ttttttggctc tttcagagag gtctcaggtt | 2880 |
| ctttccatgc agactcctca gatctgaaca cagtttagtg ctttacatgc tgtgctcttt | 2940 |
| gaagagattt caacaagaat attgtatgtt aaagcatcag agatggtaat ctacagctca | 3000 |
| cctctgaaag caaatataag ctgggaaaaa agttttgatg aaattcttga agttcatggt | 3060 |
| gatcagtgca attgaccttc tccctcactc ctgccagttg aaaatggatt tttaaattat | 3120 |
| actgtagctg atgaaactcc tgattttgta gttaatttat taagtctggg atgtagaact | 3180 |

```
tcaagaagta agagctaagt tctaagttca tgtttgtaaa ttaatacttc atttggtgct      3240
ggtctatttt gattttgggg ggtaatcagc attattcttc agaagggggac ctgttttctt    3300 caagggaaga aacactctta ttcccaaact acagaataat gtgttaaaca tgctaaatag     3360
ttctatcagg aaaacaaatc actgtattta tctccgcagg ctatttgttc agagaggcct    3420
tttgtttaaa tataaatgtt taaatataaa tgtttgtctg gattggctat aacatgtctt   3480
tcagcattag gcttttaaga aacacagggt tttgtattct ttactaaaga tatcagagct   3540
cttaatgttg cttagatgag ggtgactgtc aagtacaagc aagactggga ccttagaaat   3600
cattgtagaa acacagtttt gaaagatttt taccatgtct ctaagccaac tttaattgct   3660
taaaagacat ttttatttag ttgaaaaatc tagtttttt tgtaaactgt accaaatctg   3720
tatatgttgt aataaaactt atgctagttt attggaagtg ttcaagaaat aaaaatcaac   3780
ttgtgtactg ataaaatact ctagcctggg ccagagaaga taatgttctt taatgttgtc   3840
aggaaaccct ggcttgcttg ccgagcctaa tgaaagggaa agtcagcttt cagagccagt   3900
gaaggagcca cgtgaatggc cctagaactg tgcctagttc ctgtggccag gaggttggtg   3960
actgaaacat tcacacaggg ctcttggatg gacccacgaa cgctcttagc tttctcaggg   4020
ggtcagcaga gttattgaat cttaattttt tttaatgtac aagttttgta taaataataa   4080
agaactcctt attttgtatt acatctaatg cttaagtgtt gctcttggaa agctgatgat   4140
gtctcttgta gagatgactc tgaaaaacat tccaggaaac catggcagca tggagagcct   4200
cttagtgatt gtgtctgcat tgttattgtg gaagatttac cttttctgtt gtacgtaaag   4260
cttaaattac ttttgttgtg acttttagc cagtgacttt ttctgagctt ttcatggaag   4320
tggcagtgaa aaatatgttg agtgttcaaa aaagtgactg taattaatat cttgctggat   4380 taatgtttg tacaattact aaaattgtata cattttgtta tagaatactt ttttctagtt   4440
tcagtaaata atgaaaagga agttaatacc a                                   4471
```

<210> SEQ ID NO 89
<211> LENGTH: 2444
<212> TYPE: DNA
<213> ORGANISM: Homo sapiens
<220> FEATURE:
<221> NAME/KEY: misc_feature
<223> OTHER INFORMATION: NM_021975

<400> SEQUENCE: 89

```
ggcacgaggc ggggccgggt cgcagctggg cccgcggcat ggacgaactg ttccccctca     60
tcttcccggc agagcagccc aagcagcggg gcatgcgctt ccgctacaag tgcgaggggc   120
gctccgcggg cagcatccca ggcgagagga gcacagatac caccaagacc cacccccacca  180 tcaagatcaa tggctacaca ggaccaggga cagtgcgcat ctccctggtc accaaggacc   240
ctcctcaccg gcctcacccc cacgagcttg taggaaagga ctgccgggat ggcttctatg    300
aggctgagct ctgcccggac cgctgcatcc acagtttcca gaacctggga atccagtgtg   360
tgaagaagcg ggacctggag caggctatca gtcagcgcat ccagaccaac aacaacccct   420
tccaagttcc tatagaagag cagcgtgggg actacgacct gaatgctgtg cggctctgct   480
tccaggtgac agtgcgggac ccatcaggca ggcccctccg cctgccgcct gtccttttctc   540 atcccatctt tgacaatcgt gcccccaaca ctgccgagct caagatctgc cgagtgaacc   600
gaaactctgg cagctgcctc ggtggggatg agatcttcct actgtgtgac aaggtgcaga   660
aagaggacat tgaggtgtat ttcacgggac caggctggga ggcccgaggc tcctttttcgc   720
```

```
aagctgatgt gcaccgacaa gtggccattg tgttccggac ccctccctac gcagacccca      780
gcctgcaggc tcctgtgcgt gtctccatgc agctgcggcg gccttccgac cgggagctca      840
gtgagcccat ggaattccag tacctgccag atacagacga tcgtcaccgg attgaggaga      900
aacgtaaaag gacatatgag accttcaaga gcatcatgaa gaagagtcct ttcagcggac      960
ccaccgaccc ccggcctcca cctcgacgca ttgctgtgcc ttcccgcagc tcagcttctg     1020
tccccaagcc agcaccccag ccctatccct ttacgtcatc cctgagcacc atcaactatg     1080
atgagtttcc caccatggtg tttccttctg ggcagatcag ccaggcctcg gccttggccc     1140
cggcccctcc ccaagtcctg ccccaggctc agcccctgc ccctgctcca gccatggtat      1200
cagctctggc ccaggcccca gccctgtcc cagtcctagc ccaggccct cctcaggctg       1260 tggccccacc tgcccccaag cccacccagg ctggggaagg aacgctgtca gaggccctgc     1320
tgcagctgca gtttgatgat gaagacctgg gggccttgct tggcaacagc acagacccag     1380
ctgtgttcac agacctggca tccgtcgaca actccgagtt tcagcagctg ctgaaccagg     1440
gcatacctgt ggcccccac acaactgagc ccatgctgat ggagtaccct gaggctataa      1500
ctcgcctagt gacagcccag aggccccccg acccagctcc tgctccactg ggggccccgg     1560
ggctccccaa tggcctcctt tcaggagatg aagacttctc ctccattgcg gacatggact     1620
tctcagccct gctgagtcag atcagctcct aaggggtga cgcctgccct ccccagagca     1680
ctggttgcag gggattgaag ccctccaaaa gcacttacgg attctggtgg ggtgtgttcc     1740
aactgccccc aactttgtgg atgtcttcct tggaggggg agccatattt tattcttta      1800 ttgtcagtat ctgtatctct ctctcttttt ggaggtgctt aagcagaagc attaacttct     1860
ctggaaaggg gggagctggg gaaactcaaa cttttcccct gtcctgatgg tcagctccct    1920
tctctgtagg gaactgtggg gtcccccatc cccatcctcc agcttctggt actctcctag     1980
agacagaagc aggctggagg taaggccttt gagcccacaa agccttatca agtgtcttcc     2040
atcatggatt cattacagct taatcaaaat aacgcccag ataccagccc ctgtatggca      2100
ctggcattgt ccctgtgcct aacaccagcg tttgagggc tgccttcctg ccctacagag      2160
gtctctgccg gctctttcct tgctcaacca tggctgaagg aaacagtgca acagcactgg    2220
ctctctccag gatccagaag gggttttggtc tggacttcct tgctctcccc tcttctcaag    2280
tgccttaata gtagggtaag ttgttaagag tgggggagag caggctggca gctctccagt     2340
caggaggcat agttttagt gaacaatcaa agcacttgga ctcttgctct ttctactctg     2400
aactaataaa gctgttgcca agctggacgg cacgagctcg tgcc                      2444

<210> SEQ ID NO 90
<211> LENGTH: 816
<212> TYPE: DNA
<213> ORGANISM: Homo sapiens

<400> SEQUENCE: 90
atgcactttc tttgccaaag gcaaacgcag aacgtttcag agccatgagg atgcttctgc       60
atttgagttt gctagctctt ggagctgcct acgtgtatgc catccccaca gaaattccca      120
caagtgcatt ggtgaaagag accttggcac tgctttctac tcatcgaact ctgctgatag      180
ccaatgagac tctgaggatt cctgttcctg tacataaaaa tcaccaactg tgcactgaag      240
aaatctttca gggaataggc acactggaga gtcaaactgt gcaaggggt actgtggaaa      300 gactattcaa aaacttgtcc ttaataaaga aatacattga cggccaaaaa aaaaagtgtg      360
```

| | |
|---|---|
| gagaagaaag acggagagta aaccaattcc tagactacct gcaagagttt cttggtgtaa | 420 |
| tgaacaccga gtggataata gaaagttgag actaaactgg tttgttgcag ccaaagattt | 480 |
| tggaggagaa ggacatttta ctgcagtgag aatgagggcc aagaaagagt caggccttaa | 540 |
| ttttcaatat aatttaactt cagagggaaa gtaaatattt caggcatact gacactttgc | 600 |
| cagaaagcat aaaattctta aaatatattt cagatatcag aatcattgaa gtattttcct | 660 |
| ccaggcaaaa ttgatatact tttttcttat ttaacttaac attctgtaaa atgtctgtta | 720 |
| acttaatagt atttatgaaa tggttaagaa tttggtaaat tagtatttat ttaatgttat | 780 |
| gttgtgttct aataaaacaa aaatagacaa ctgttc | 816 |

<210> SEQ ID NO 91
<211> LENGTH: 2484
<212> TYPE: DNA
<213> ORGANISM: Homo sapiens
<220> FEATURE:
<221> NAME/KEY: misc_feature
<223> OTHER INFORMATION: L05: Acc. No. J03571

<400> SEQUENCE: 91

| | |
|---|---|
| gggcccggcg ctcgctgctc ccgcggcccg cgccatgccc tcctacacgg tcaccgtggc | 60 |
| cactggcagc cagtggttcg ccggcactga cgactacatc tacctcagcc tcgtgggctc | 120 |
| ggcgggctgc agcgagaagc acctgctgga caagcccttc tacaacgact cgagcgtgg | 180 |
| cgcggtggat tcatacgacg tgactgtgga cgaggaactg ggcgagatcc agctggtcag | 240 |
| aatcgagaag cgcaagtact ggctgaatga cgactggtac ctgaagtaca tcacgctgaa | 300 |
| gacgccccac ggggactaca tcgagttccc ctgctaccgc tggatcaccg gcgatgtcga | 360 |
| ggttgtcctg agggatggac gcgcaaagtt ggcccgagat gaccaaaatt acattctcaa | 420 |
| gcaacaccga cgtaaagaac tggaaacacg gcaaaaacaa tatcgatgga tggagtggaa | 480 |
| ccctggcttc cccttgagca tcgatgccaa atgccacaag gatttacccc gtgatatcca | 540 |
| gtttgatagt gaaaaaggag tggactttgt tctgaattac tccaaagcga tggagaacct | 600 |
| gttcatcaac cgcttcatgc acatgttcca gtcttcttgg aatgacttcg ccgactttga | 660 |
| gaaaatcttt gtcaagatca gcaacactat ttctgagcgg gtcatgaatc actggcagga | 720 |
| agacctgatg tttggctacc agttcctgaa tggctgcaac cctgtgttga tccggcgctg | 780 |
| cacagagctg cccgagaagc tcccggtgac cacggagatg gtagagtgca gcctggagcg | 840 |
| gcagctcagc ttggagcagg aggtccagca agggaacatt ttcatcgtgg actttgagct | 900 |
| gctggatggc atcgatgcca acaaaacaga ccccctgcaca ctccagttcc tggccgctcc | 960 |
| catctgcttg ctgtataaga acctggccaa caagattgtc cccattgcca tccagctcaa | 1020 |
| ccaaatcccg ggagatgaga accctatttt cctcccttcg gatgcaaaat acgactggct | 1080 |
| tttggccaaa atctgggtgc gttccagtga cttccacgtc caccagacca tcacccacct | 1140 |
| tctgcgaaca catctggtgt ctgaggtttt tggcattgca atgtaccgcc agctgcctgc | 1200 |
| tgtgcacccc attttcaagc tgctggtggc acacgtgaga ttcaccattg caatcaacac | 1260 |
| caaggcccgt gagcagctca tctgcgagtg tggcctcttt gacaaggcca acgccacagg | 1320 |
| gggcggtggg cacgtgcaga tggtgcagag ggccatgaag gacctgacct atgcctccct | 1380 |
| gtgctttccc gaggccatca aggcccgggg catggagagc aaagaagaca tccctactta | 1440 |
| cttctaccgg gacgacgggc tcctggtgtg gaagccatc aggacgttca cggccgaggt | 1500 |
| ggtagacatc tactacgagg gcgaccaggt ggtggaggag gacccggagc tgcaggactt | 1560 |

```
cgtgaacgat gtctacgtgt acggcatgcg gggccgcaag tcctcaggct tccccaagtc   1620
ggtcaagagc cgggagcagc tgtcggagta cctgaccgtg gtgatcttca ccgcctccgc   1680
ccagcacgcc gcggtcaact tcggccagta cgactggtgc tcctggatcc ccaatgcgcc   1740
cccaaccatg cgagcccgc caccgactgc caagggcgtg gtgaccattg agcagatcgt   1800
ggacacgctg cccgaccgcg gccgctcctg ctggcatctg ggtgcagtgt gggcgctgag   1860
ccagttccag gaaaacgagc tgttcctggg catgtaccca gaagagcatt ttatcgagaa   1920
gcctgtgaag gaagccatgg cccgattccg caagaacctc gaggccattg tcagcgtgat   1980
tgctgagcgc aacaagaaga agcagctgcc atattactac ttgtcccag accggattcc   2040 gaacagtgtg gccatctgag cacactgcca gtctcactgt gggaaggcca gctgcccag   2100 ccagatggac tccagcctgc ctggcaggtg tctggccagg cctcttggca gtcacatctc   2160
ttcctccgag gccagtacct ttccatttat tctttgatct tcaggaact gcatagattg   2220 atcaaagtgt aaacaccata gggacccatt ctacacagag caggactgca cagcgtcctg   2280
tccacaccca gctcagcatt tccacaccaa gcagcaacag caaatcacga ccactgatag   2340
atgtctattc ttgttggaga catgggatga ttatttttctg ttctatttgt gcttagtcca   2400
attccttgca catagtaggt acccaattca attactattg aatgaattaa gaattggttg   2460
ccataaaaat aaatcagttc attt                                          2484
```

<210> SEQ ID NO 92
<211> LENGTH: 2437
<212> TYPE: DNA
<213> ORGANISM: Homo sapiens
<220> FEATURE:
<221> NAME/KEY: misc_feature
<223> OTHER INFORMATION: MPB: Acc. No.: M74047

<400> SEQUENCE: 92

```
gcggccaccg gcgaggaaca cggcgcgatg caggttcagt gccagcagag cccagtgctg     60
gcaggcagcg ccactttggt cgcccttggg gcactggcct tgtacgtcgc gaagccctcc    120
ggctacggga agcacacgga gagcctgaag ccggcggcta cccgcctgcc agcccgcgcc    180
gcctggttcc tgcaggagct gccttccttc gcggtgcccg cggggatcct cgcccggcag    240
cccctctccc tcttcgggcc acctgggacg gtacttctgg gcctcttctg cgtacattac    300
ttccacagga catttgtgta ctcactgctc aatcgaggga ggcccttatcc agctatactc    360 attctcagag gcactgcctt ctgcactgga aatggagtcc ttcaaggcta ctatctgatt    420
tactgtgctg aatacctga tgggtggtac acagacatac ggtttagctt gggtgtcttc    480
ttatttattt tgggaatggg aataaacatt catagtgact atatattgcg ccagctcagg    540
aagcctggaa aaatcagcta caggattcca caaggtggct tgtttacgta tgtttctgga    600
gccaattccc tcggtgagat cattgaatgg atcggctatg ccctggccac ttggtccctc    660
ccagcacttg catttgcatt tttctcactt tgttccttg ggctgcgagc ttttcaccac    720
cataggttct acctcaagat gtttgaggac tacccaaat ctcggaaagc ccttattcca    780 ttcatcttt aaaggaacca aattaaaag gagcagagct cccacaatgc tgatgaaaac    840
tgtcaagctg ctgaaactgt aattttcatg atataatagt catatatata tatatata    900 tatatatata tatatatg tatatatgta atagtaggtc tcctggcgtt ctgccagctg    960
gcctggggat tctgagtggt gtctgcttag agtttactcc tacccttcca gggacccta   1020 tcctgatccc caactgaagc ttcaaaaagc cacttttcca aatggcgaca gttgcttctt   1080
```

| | | | | |
|---|---|---|---|---|
| agctattgct | ctgagaaagt | acaaacttct | cctatgtctt | tcaccgggca atccaagtac | 1140 |
| atgtggcttc | atacccactc | cctgtcaatg | caggacaact | ctgtaatcaa gaattttttg | 1200 |
| acttgaaggc | agtacttata | gaccttatta | aaggtatgca | ttttatacat gtaacagagt | 1260 |
| agcagaaatt | taaactctga | agccacaaag | acccagagca | aacccactcc caaatgaaaa | 1320 |
| ccccagtcat | ggcttccttt | ttcttggtta | attaggaaag | atgagaaatt attaggtaga | 1380 |
| ccttgaatac | aggagccctc | tcctcatagt | gctgaaaaga | tactgatgca ttgacctcat | 1440 |
| ttcaaatttg | tgcagtgtct | tagttgatga | gtgcctctgt | tttccagaag atttcacaat | 1500 |
| ccccggaaaa | ctggtatggc | tattcttgaa | ggccaggttt | taataaccac aaacaaaaag | 1560 |
| gcatgaacct | gggtggctta | tgagagagta | gagaacaaca | tgaccctgga tggctactaa | 1620 |
| gaggatagag | aacagtttta | caatagacat | tgcaaactct | catgtttttg gaaactggtg | 1680 |
| gcaatatcca | aataatgagt | agtgtaaaac | aaagagaatt | aatgatgagg ttacatgctg | 1740 |
| cttgcctcca | ccagatgtcc | acaacaatat | gaagtacagc | agaagcccca agcaactttc | 1800 |
| ctttcctgga | gcttcttcct | tgtagttctc | aggacctgtt | caagaaggtg tctcctaggg | 1860 |
| gcagcctgaa | tgcctccctc | aaaggacctg | caggcagaga | ctgaaaattg cagacagagg | 1920 |
| ggcacgtctg | ggcagaaaac | ctgttttgtt | tggctcagac | atatagtttt tttttttta | 1980 |
| caaagtttca | aaaacttaaa | aatcaggaga | ttccttcata | aaactctagc attctagttt | 2040 |
| catttaaaaa | gttggaggat | ctgaacatac | agagcccaca | tttccacacc agaactggaa | 2100 |
| ctacgtagct | agtaagcatt | tgagtttgca | aactcttgtg | aagggtcac cccagcatga | 2160 |
| gtgctgagat | atggactctc | taaggaaggg | gccgaacgct | tgtaattgga atacatggaa | 2220 |
| atatttgtct | tctcaggcct | atgtttgcgg | aatgcattgt | caatatttag caaactgttt | 2280 |
| tgacaaatga | gcaccagtgg | tactaagcac | agaaactcac | tatataagtc acataggaaa | 2340 |
| cttgaaaggt | ctgaggatga | tgtagattac | tgaaaaatac | aaattgcaat catataaata | 2400 |
| agtgtttttg | ttgttcatta | aatacccttta | aatcatg | | 2437 |

<210> SEQ ID NO 93
<211> LENGTH: 5595
<212> TYPE: DNA
<213> ORGANISM: Homo sapiens
<220> FEATURE:
<221> NAME/KEY: misc_feature
<223> OTHER INFORMATION: NEP=CALLA:  Acc. No. NM_000902

<400> SEQUENCE: 93

| | | | | |
|---|---|---|---|---|
| gcggagatgt | gcaagtggcg | aagcttgacc | gagagcaggc | tggagcagcc gcccaactcc | 60 |
| tggcgcggga | tctgctgagg | ggtcacggat | tttaggtgat | gggcaagtca gaaagtcaga | 120 |
| tggatataac | tgtatatcaac | actccaaagc | caaagaagaa | acagcgatgg actcgactgg | 180 |
| agatcagcct | ctcggtcctt | gtcctgctcc | tcaccatcat | agctgtgaga atgatcgcac | 240 |
| tctatgcaac | ctacgatgat | ggtatttgca | agtcatcaga | ctgcataaaa tcagctgctc | 300 |
| gactgatcca | aaacatggat | gccaccactg | agccttgtag | agacttttc aaatatgctt | 360 |
| gcggaggctg | gttgaaacgt | aatgtcattc | ccgagaccag | ctcccgttac ggcaactttg | 420 |
| acattttaag | agatgaacta | gaagtcgttt | tgaaagatgc | ccttcaagaa cccaaaactg | 480 |
| aagatatagt | agcagtgcag | aaagcaaaag | cattgtacag | gtcttgtata aatgaatctg | 540 |
| ctattgatag | cagaggtgga | gaacctctac | tcaaactgtt | accagacata tatgggtggc | 600 |
| cagtagcaac | agaaaactgg | gagcaaaaat | atggtgcttc | ttggacagct gaaaagcta | 660 |

```
ttgcacaact gaattctaaa tatgggaaaa aagtccttat taatttgttt gttggcactg    720
atgataagaa ttctgtgaat catgtaattc atattgacca acctcgactt ggcctccctt    780
ctagagatta ctatgaatgc actggaatct ataaagaggc ttgtacagca tatgtggatt    840
ttatgatttc tgtggccaga ttgattcgtc aggaagaaag attgcccatc gatgaaaacc    900
agcttgcttt ggaaatgaat aaagttatgg aattggaaaa agaaattgcc aatgctacgg    960
ctaaacctga agatcgaaat gatccaatgc ttctgtataa caagatgaga ttggcccaga   1020
tccaaaataa cttttcacta gagatcaatg ggaagccatt cagctggttg aatttcacaa   1080
atgaaatcat gtcaactgtg aatattagta ttacaaatga ggaagatgtg gttgtttatg   1140
ctccagaata tttaaccaaa cttaagccca ttcttaccaa atattctgcc agagatcttc   1200
aaaatttaat gtcctggaga ttcataatgg atcttgtaag cagcctcagc cgaacctaca   1260
aggagtccag aaatgctttc cgcaaggccc tttatggtac aacctcagaa acagcaactt   1320
ggagacgttg tgcaaactat gtcaatggga atatggaaaa tgctgtgggg aggctttatg   1380
tggaagcagc atttgctgga gagagtaaac atgtggtcga ggatttgatt gcacagatcc   1440
gagaagtttt tattcagact ttagatgacc tcacttggat ggatgccgag acaaaaaaga   1500
gagctgaaga aaaggcctta gcaattaaag aaaggatcgg ctatcctgat gacattgttt   1560
caaatgataa caaactgaat aatgagtacc tcgagttgaa ctacaaagaa gatgaatact   1620
tcgagaacat aattcaaaat ttgaaattca gccaaagtaa acaactgaag aagctccgag   1680
aaaaggtgga caaagatgag tggataagtg gagcagctgt agtcaatgca ttttactctt   1740
caggaagaaa tcagatagtc ttcccagccg gcattctgca gccccccttc tttagtgccc   1800
agcagtccaa ctcattgaac tatgggggca tcggcatggt cataggacac gaaatcaccc   1860
atggcttcga tgacaatggc agaaacttta caaagatgg agacctcgtt gactggtgga   1920
ctcaacagtc tgcaagtaac tttaaggagc aatcccagtg catggtgtat cagtatggaa   1980
acttttcctg ggacctggca ggtggacagc accttaatgg aattaataca ctgggagaaa   2040
acattgctga taatggaggt cttggtcaag catacagagc ctatcagaat tatattaaaa   2100
agaatggcga agaaaaatta cttcctggac ttgacctaaa tcacaaacaa ctattttct    2160 tgaactttgc acaggtgtgg tgtggaacct ataggccaga gtatgcggtt aactccatta   2220
aaacagatgt gcacagtcca ggcaatttca ggattattgg gactttgcag aactctgcag   2280
agttttcaga agcctttcac tgccgcaaga attcatacat gaatccagaa aagaagtgcc   2340
gggtttggtg atcttcaaaa gaagcattgc agccttggc tagacttgcc aacaccacag    2400
aaatggggaa ttctctaatc gaaagaaaat gggccctagg ggtcactgta ctgacttgag   2460
ggtgattaac agagagggca ccatcacaat acagataaca ttaggttgtc ctagaaaggg   2520
tgtggaggga ggaaggggt ctaaggtcta tcaagtcaat catttctcac tgtgtacata    2580
atgcttaatt tctaaagata atattactgt ttatttctgt ttctcatatg gtctaccagt   2640
ttgctgatgt ccctagaaaa caatgcaaaa cctttgaggg agaccaggat ttctaatcaa   2700
aagggaaaag aagatgttga agaatagagt taggcaccag aagaagagta ggtgacacta   2760
tagtttaaaa cacattgcct aactactagt ttttactttt atttgcaaca tttacagtcc   2820
ttcaaaatcc ttccaaagaa ttcttataca cattggggcc ttggagctta catagtttta   2880
aactcatttt tgccatacat cagttattca ttctgtgatc atttatttta agcactctta   2940
aagcaaaaaa tgaatgtcta aaattgtttt ttgttgtacc tgcttgact gatgctgaga    3000 ttcttcaggc ttcctgcaat tttctaagca atttcttgct ctatctctca aaacttggta   3060
```

```
tttttcagag atttatataa atgtaaaaat aataattttt atatttaatt attaactaca   3120
tttatgagta actattatta taggtaatca atgaatattg aagtttcagc ttaaaataaa   3180
cagttgtgaa ccaagatcta taaagcgata tacagatgaa aatttgagac tatttaaact   3240
tataaatcat attgatgaaa agatttaagc acaaacttta gggtaaaaat tgcgattgga   3300
cagttgtcta gagatatata tacttgtggt tttcaaattg gactttcaaa attaaatctg   3360
tccctgagag tgtctctgat aaaagggcaa atctgcacct atgtagctct gcatctcctg   3420
tcttttcagg tttgtcatca gatggaaata ttttgataat aaattgaaat tgtgaactca   3480
ttgctcccta agactgtgac aactgtctaa ctttagaagt gcatttctga atagaaatgg   3540
gaggcctctg atggaccttc tagaattata agtcacaaag agttctggaa aagaactgtt   3600
tactgcttga taggaattca tcttttgagg cttctgttcc tctcttttcc tgttgtattg   3660 actatttcg ttcattactt gattaagatt ttacaaaaga ggagcacttc caaaattctt    3720
attttcccta acaaaagatg aaagcaggga atttctatct aaatgatgag tattagttcc   3780
ctgtctcttg aaaaatgccc atttgccttt aaaaaaaaaa gttacagaaa tactataaca   3840
tatgtacata aattgcataa agcataagta tacagttcaa taaacttaac tttaactgaa   3900
caatggccct gtagccagca cctgtaagaa acagagcagt accagcgctc taaaagcacc   3960
tccttgtcac tttattactc ccagaacaac aactatcctg acttctaata tcattcacta   4020
gctttgcctg gttttgtctt ttatgcagat agaatcaatc agtatgtatt cttttgtgcc   4080
tggcttcttt ctctcagcct tacatttgtg agattcctct gtattgtgct gattgtggat   4140
cttttcattc tcattgcaga ataatgttct attgtgggac ttattacaat ttgttcatcc   4200
tattgttgat gggcacttga gaactttcca ttttggcgct attacaaata gtgcaactat   4260
gaatgtactg catgttacca tcttacttga gcctttaatg gacttatttc ttcaaatcct   4320
tccaaaaatt attataagca ttgaaattat agtttcaagc caactgtgga tacccttacc   4380
ctttcctcct ttatcacaac caccgttaca agtatactta tatttcccta aaatacattt   4440
aaaacttacc taagtgacat tgtagttgg agtaatagga gcttccagct ctaataaaac    4500
agctgtctct aacttatttt atttccatca tgtcagagca ggtgaagagc cagaagtgaa   4560
gagtgactag tacaaattat aaaaagccac tagactcttc actgttagct tttttaaaaca  4620 ttaggctccc atccctatgg aggaacaact ctccagtgcc tggatcccct ctgtctacaa   4680
atataagatt ttctgggcct aaaggataga tcaaagtcaa aaatagcaat gcctccctat   4740
ccctcacaca tccagacatc atgaattta catggtactc ttgttgagtt ctatagagcc    4800
ttctgatgtc tctaaagcac taccgattct ttggagttgt cacatcagat aagacatatc   4860
tctaattcca tccataaatc cagttctact atggctgagt tctggtcaaa gaagaaagt    4920 ttagaagctg agacacaaag ggttgggagc tgatgaaact cacaaatgat ggtaggaaga   4980
agctctcgac aatacccgtt ggcaaggagt ctgcctccat gctgcagtgt tcgagtggat   5040
tgtaggtgca agatggaaag gattgtaggt gcaagctgtc cagagaaaag agtccttgtt   5100
ccagccctat tctgccactc ctgacagggt gaccttgggt atttgcaata ttcctttggg   5160
cctctgcttc tctcacctaa aaaaagagaa ttagattata ttggtggttc tcagcaagag   5220
aaggagtatg tgtccaatgc tgccttccca tgaatctgtc tcccagttat gaatcagtgg   5280
gcaggataaa ctgaaaactc ccatttaagt gtctgaatcg agtgagacaa aattttagtc   5340
caaataacaa gtaccaaagt tttatcaagt ttgggtctgt gctgctgtta ctgttaacca   5400
```

```
tttaagtggg gcaaaacctt gctaattttc tcaaaagcat ttatcattct tgttgccaca      5460
gctggagctc tcaaactaaa agacatttgt tattttggaa agaagaaaga ctctattctc      5520
aaagtttcct aatcagaaat ttttatcagt ttccagtctc aaaaatacaa aataaaaaca      5580
aacgttttta atact                                                      5595
```

<210> SEQ ID NO 94
<211> LENGTH: 551
<212> TYPE: DNA
<213> ORGANISM: Homo sapiens
<220> FEATURE:
<221> NAME/KEY: misc_feature
<223> OTHER INFORMATION: NPY: Acc. No. K01911

<400> SEQUENCE: 94

```
accccatccg ctggctctca cccctcggag acgctcgccc gacagcatag tacttgccgc        60
ccagccacgc ccgcgcgcca gccaccatgc taggtaacaa gcgactgggg ctgtccggac       120
tgaccctcgc cctgtccctg ctcgtgtgcc tgggtgcgct ggccgaggcg tacccctcca       180
agccggacaa cccgggcgag gacgcaccag cggaggacat ggccagatac tactcggcgc       240
tgcgacacta catcaacctc atcaccaggc agagatatgg aaaacgatcc agcccagaga       300
cactgatttc agacctcttg atgagagaaa gcacagaaaa tgttcccaga actcggcttg       360
aagaccctgc aatgtggtga tgggaaatga gacttgctct ctggcctttt cctattttca       420
gcccatattt catcgtgtaa aacgagaatc cacccatcct accaatgcat gcagccactg       480
tgctgaattc tgcaatgttt cctttgtca tcattgtata tatgtgtgtt taaataaagt       540
atcatgcatt c                                                          551
```

<210> SEQ ID NO 95
<211> LENGTH: 4382
<212> TYPE: DNA
<213> ORGANISM: Homo sapiens
<220> FEATURE:
<221> NAME/KEY: misc_feature
<223> OTHER INFORMATION: SEG_AB00161S

<400> SEQUENCE: 95

```
aagcttgctg aatcacctct taattcttgt agttgctttg tgcattcctt tgggtattcc        60
tcatagatac tcatgtctgc aaatggagaa tgtttacttt tcatttttta tgccttatat       120
ttcttttttg tgtttttgct tgttgcatt tgtttttct atttgtatga ccaaaatctt       180
tagcagtaca ggtaggtaac aaccaaataa tgtagaaccc cataagccac gttacagagt       240
ttgaatttta ttttagcaca gtgggaatac attgaaggtc tttagttaag ctgttgctca       300
tgagcaacaa atgagcaatg acatatatgt atgtatatac acatatatat cattgatttt       360
atatatatat atatatatat atatatatat atatatatat atatatctat cttagtccac       420
ttgtgttgca ataacaaaat accacagact gggtcattta caaaaattaa atatatatat       480
acatatacac acatatatat atcatacata tacacataca tacatcattg ctcatttgtt       540
tgttataaat agcattaaca gcattttttca agttatatcc tgggagtgtt tatgatttac       600
ttattcttca actaattcca taacaagatt tgaggtgctt agaacaattc atgccaagtt       660
aaaacaaaat aattgggcaa attgggataa agaataaaat ggagttgaaa aacaagaggc       720
ccaggtaatg tcagttcaaa atatgcttac ctttaactac tttaaattta caggaggtat       780
agttacacat tttggctgaa tctcccagag actagaactg tttgagacac ttctgttccc       840
caatcccttg tgatatgttt ctcaggtaat aggccttcac agtaactccc aaactatcat       900
```

```
atataccaca cagacttgag attcactatt gagagaatct atgtactgtt tttctttttt    960
tttctttttt gttatagagc cgggggtctt acactgtcac tgaggctgaa gtgcaatggc   1020
acgatcatgg ctcactgcag ccttgacctc ctgggctcaa tcctcttgcc tcagcctctc   1080
gaataactag gattacaggt gtgttccccc atgcctggct aattttttaaa aattttgtgt   1140
agagatgggg tcatgccatg tggcccaggc tggttcaaac tcctgagctc aagtatcctt   1200
ctacctctcc ctcccaaagt tctgagatta caggaatgag ccactgtgcc cagcctatag   1260
attgttttc ttgaagcaat ttttcagaaa ccttcctggt ttctgataat ttaacccttt   1320
caggttagga gagaaaaatg aacattttga tattacccac tgtcttagtc catttgtgtt   1380
gctgtaataa aatatcacag actgggatat ttataaacaa tagaaattaa tttctctcag   1440
ttctggaggc tggaaactcc aaaatcaaag tgccagcaga tttggcaact ggtgagggct   1500
gctctttgct tacaaaatgg caccttgttg ctgcatcctc agcaagggtc agtgctgtgt   1560
cttcacatag tggaaagaat agaaggggcc aactgtctcc tttgggcctt tttttaaaaa   1620
ggcactaatg cattcacaaa ggcagagccc taatggtcta atcaccactt aaaggcacct   1680
cctcttaata ctgttgaatt agggattaag tttcaacatg aattttggag ggaatacaaa   1740
cattgaaatg attatacgtg tttatttaat caagtatcca acaaaagcaa ataattcaag   1800
ccccaaattc actgcatctt tagtagataa gcagagtttt aaattacgat tgatctcctg   1860
ttaggaggaa tgcatggatt tccacaagaa aaaactgtac tgaggagaaa cttccacag   1920
taatgtgcca cttttcagtc aacgacagac cacatatatg agtcccataa gataatacta   1980
tattttact gtaccttttc tatgtttaga tatgtttaga cacacaaata tcattgcatt    2040
acaattgcct acagtattca gtacagtaat atgctgtata gatttgtggt ctaggagcaa   2100
tagcctaagt gtgtagtagg ctgagccatc tattttgtgt tagtacactg tgatgttcag   2160
agaaggatga aattgcctaa ggatacattt ctcagaatgt atcctgttgt tcggtgacgc   2220
atgactgtat tccatgagca ctataatcac tatcatagta acacattagg agagaattct   2280
catttctaaa tccaatataa tttatcaccc attagttcat actctactgc tttgattgct   2340
tttctttggt tgtggctacc tgcatacagc agtaaagttt cagaaaaact gaagtcgcaa   2400
aaggtcaatt actcaatgaa ggaaagataa accattgcat tgggggacta gaagatactt   2460
ttaaaagttc tcagattatc aatttaatga tgtgtttcta tgtagtgaat aatgccttaa   2520
attcttgcca agagtattta gaaggaagtt gtcagaagta tatcagctaa ctcattttt   2580
tttatatcac tgctaatggt gtcattcaca cattgtgcaa cccataattc cagatttaat   2640
tctaccaaaa aatataggtc attgcaaaat gccatattaa aactgccaat gcatgacagg   2700
aagatgggga tgcagacaaa gcaaaggatg acaccaattc cttttttaaa gaagcaagat   2760
agggattgga caaaaaggct gagccatttt taatggatac ttttgaggga gtgttaattc   2820
caatttaatt aaaatgatgc attaatttaa aattgggata actggttgcc ctcgactgca   2880
cctgggttgc gccagtgctc tcggattaac ctaattgtac agaggtgccc ttgttttcta   2940
acttcatgca caaagcattg gaaattattt gtttgctttt tcttttccaa gtaaatcttt   3000
ttccagttat gcaaagggga agtttgaggc aatggttaaa ggcacttaag ttataattat   3060
tgctgttatc attaacatta agcacgggta tggctttgtt gcaagttacc cacctacacc   3120
tgcaaatctc tcttgctagc acacgcccca gctctctcca cccgcagtgg tccgtggctg   3180
gaccgcttta agtcactgag cgggctgggc tctgaaggag gtcggtcccg ctcctcccag   3240
```

-continued

| | |
|---|---|
| acccaagcgt agggctaggg aaaagctagg cgggaaggtc attgcactcc caggccccag | 3300 |
| gaaaagggcc cagggtctca tcatctctta ctttcgggca aaacttccca catcgcgacc | 3360 |
| ttccctccct ggggcactct gagaacacac ccagtcacct agcgcgctcc ccagaagtcg | 3420 |
| gcttggcaca cagcgcaccc cagcggccgc gcggcctcct tccagccgcc gccacttggc | 3480 |
| ttccggagag ctcgccgggc gctgccgccg ccgccgccgc cgccgccgcc tcctgggaac | 3540 |
| caggggactg aagagcctgc gagagcggaa cactgccgga ccccgggtgg ggggcgcag | 3600 |
| cagctgcgcc tggccccgcc caccacacct gggcgcccgt agaaccgcgc ggggcggggc | 3660 |
| ggggcaggag gctggcctgg cgctccggcc gctttgtcga aagccggccc gactggagca | 3720 |
| ggacgaaggg ggagggtctc gaggccgagt cctgttcttc tgagggacgg accccagctg | 3780 |
| gggtggaaaa gcagtaccag agagcctccg aggcgcgcgg tgccaaccat ggagcgggcc | 3840 |
| ggccccagct tcgggcagca gcgacagcag cagcagcccc agcagcagaa gcagcagcag | 3900 |
| agggatcagg actcggtcga agcatggctg gacgatcact gggactttac cttctcatac | 3960 |
| tttgttagaa aagccaccag gtaagaagag gacccacgga agacccgggg ctgatttctc | 4020 |
| tccctgttg aattgtgccc ttcgttcacc cctgttccca ggccctttgc ttttgaagta | 4080 |
| ggtcctcggt cctgttacga ggtagaaacc tcaactctaa gcgagcacag tcgaaaaact | 4140 |
| caagtgtcgg atttgataca acttgctcac aaagttcaaa tacaaaaatg tacttggttc | 4200 |
| aaatacaaaa atgtacttgc cgacctccca ccctcacccc cgcccctctt ggtattcccc | 4260 |
| gggaacatga ttattttcat acatccgtgc tcacgggcct tcccctagcc cctctctagc | 4320 |
| cctctggttc cccaaaatcc aatcagcaaa acccaaacag tttctgagcc ccttccctgc | 4380 |
| ag | 4382 |

<210> SEQ ID NO 96
<211> LENGTH: 3979
<212> TYPE: DNA
<213> ORGANISM: Homo sapiens
<220> FEATURE:
<221> NAME/KEY: misc_feature
<223> OTHER INFORMATION: Pde7a1: Acc. No. L12052

<400> SEQUENCE: 96

| | |
|---|---|
| ggcggccgcg gcagggcggg cgccgcgcgg aggcagggcg ggcgtattca atggaagtgt | 60 |
| gttaccagct gccggtactg cccctggaca ggccggtccc ccagcacgtc ctcagccgcc | 120 |
| gaggagccat cagcttcagc tccagctccg ctctcttcgg ctgccccaat ccccggcagc | 180 |
| tctctcagag gcgtggagct atttcctatg acagttctga tcagactgca ttatacattc | 240 |
| gtatgctagg agatgtacgt gtaaggagcc gagcaggatt tgaatcagaa agaagaggtt | 300 |
| ctcacccata tattgatttt cgtatttcc actctcaatc tgaaattgaa gtgtctgtct | 360 |
| ctgcaaggaa tatcagaagg ctactaagtt tccagcgata tcttagatct tcacgctttt | 420 |
| ttcgtggtac tgcggtttca aattcccctaa acattttaga tgatgattat aatgacaag | 480 |
| ccaagtgtat gctggaaaaa gttggaaatt ggaattttga tatctttcta tttgatagac | 540 |
| taacaaatgg aaatagtcta gtaagcttaa cctttcattt atttagtctt catggattaa | 600 |
| ttgagtactt ccatttagat atgatgaaac ttcgtagatt tttagttatg attcaagaag | 660 |
| attaccacag tcaaaatcct taccataacg cagtccacgc tgcggatgtt actcaggcca | 720 |
| tgcactgtta cttaaaggaa cctaagcttg ccaattctgt aactccttgg gatatccttg | 780 |
| tgagcttaat tgcagctgcc actcatgatc tggatcatcc aggtgttaat caacctttcc | 840 |

```
ttattaaaac taaccattac ttggcaactt tatacaagaa tacctcagta ctggaaaatc    900
accactggag atctgcagtg ggcttattga gagaatcagg cttattctca catctgccat    960
tagaaagcag gcaacaaatg gagacacaga taggtgctct gatactagcc acagacatca   1020
gtcgccagaa tgagtatctg tctttgttta ggtcccattt ggatagaggt gatttatgcc   1080
tagaagacac cagacacaga catttggttt tacagatggc tttgaaatgt gctgatattt   1140
gtaacccatg tcggacgtgg gaattaagca agcagtggag tgaaaaagta acggaggaat   1200
tcttccatca aggagatata gaaaaaaaat atcatttggg tgtgagtcca ctttgcgatc   1260
gtcacactga atctattgcc aacatccaga ttggttttat gacttaccta gtggagcctt   1320
tatttacaga atgggccagg ttttccaata caaggctatc ccagacaatg cttggacacg   1380
tggggctgaa taaagccagc tggaagggac tgcagagaga acagtcgagc agtgaggaca   1440
ctgatgctgc atttgagttg aactcacagt tattacctca ggaaaatcgg ttatcataac   1500
ccccagaacc agtgggacaa actgcctcct ggaggttttt agaaatgtga atgggtct     1560
tgaggtgaga gaacttaact cttgactgcc aaggtttcca agtgagtgat gccagccagc   1620
attatttatt tccaagattt cctctgttgg atcatttgaa cccacttgtt aattgcaaga   1680
cccgaacata cagcaatatg aatttggctt tcatgtgaaa ccttgaatat aaagcccagc   1740
aggagagaat ccgaaaggag taacaaagga agttttgata tgtgccacga cttttcaaa   1800
gcatctaatc ttcaaaacgt caaacttgaa ttgttcagca acaatctctt ggaatttaac   1860
cagtctgatg caacaatgtg tatcttgtac cttccactaa gttctctctg agaaaatgga   1920
aatgtgaagt gcccagcctc tgctgcctct ggcaagacaa tgtttacaaa tcaactctga   1980
aaatattggt tctaaattgc cttggagcat gattgtgaag gaaccactca aacaaattta   2040
aagatcaaac tttagactgc agctctttcc ccctggtttg cctttttctt ctttggatgc   2100
caccaaagcc tcccatttgc tatagtttta tttcatgcac tggaaactga gcatttatcg   2160
tagagtaccg ccaagctttc actccagtgc cgttttggcaa tgcaattttt tttagcaatt   2220
agtttttaat ttggggtggg aggggaagaa caccaatgtc ctagctgtat tatgattctg   2280
cactcaagac attgcatgtt gttttcacta ctgtacactt gacctgcaca tgcgagaaaa   2340
aggtggaatg tttaaaacac cataatcagc tcaggtattt gccaatctga aataaaagtg   2400
ggatgggaga gcgtgtcctt cagatcaagg gtactaaagt ccctttcgct gcagtgagtg   2460
agaggtatgt tgtgtgtgaa tgtacggatg tgtgtttggt gatgtttgtg catgtgtgac   2520
gtgcatgtta tgtttctcca tgtgggcaaa gatttgaaag taagctttta tttattattt   2580
tagaatgtga cataatgagc agccacactc ggggagggg aaggttggta ggtaagctgt   2640
aacagattgc tccagttgcc ttaaactatg cacatagcta agtgaccaaa cttcttgttt   2700
tgatttgaaa aaagtgcatt gttttcttgt ccctcccttt gatgaaacgt taccctttga   2760
cgggcctttt gatgtgaaca gatgttttct aggacaaact ataaggacta attttaaact   2820
tcaaacattc cactttgta atttgtttta aattgtttta tgtatagtaa gcacaactgt    2880
aatctagttt taagagaaac cggtgctttc ttttagttca tttgtatttc ccttgttact   2940
gtaaaagact gttattaat tgtttacagt tgttgcaac agccatttc ttgggagaaa    3000
gcttgagtgt aaagccattt gtaaaggct ttgccatact catttaata tgtgcctgtt    3060
gctgttaact tttgatgaat aaaaaccat cttttcatga aacttctctc tatacaaatt   3120
gaaatacata atgctttctg gttcttcttc aaaccaaaac ttgtcaaatt catagacaag   3180
ataacagtaa aactgatgaa agtgttccat tgttggtata ccaggaacaa ggttatagag   3240
```

```
atgaaacttc aaagcttcac tcttcagtaa gctataagcc atctctgtaa gattgattcc   3300
aactattgca taagaatacc ctaatttttgg atgatttgaa cgggaaagaa tctgatgagc   3360
ttcactagtg taattttcac tgaaatacac aagattgatt aacccaagta tgcccatgcc   3420
tctgaagtct gtcttgggat catcaccctg aaaaccaatt tcagcccact gcttggagat   3480
tctagcgttt aacttcttcg tgggcattag aagattccaa agcttcatga gtagctcttc   3540
atgctgtagg ttatcagaat catatggcct tttcctcaca ctttctacat ccaaatacag   3600
ctgtttataa ccagttatct gcagtaagca catcttcatg catattttaa aactggcatc   3660
cttctcaggg ttaatattct tttccttcat aatatcatct acatatttgt ccacttcact   3720
ctgaacaaca tgtgtcgcct tctgtaaaac cttattcttg gagtatgtca aggaattttc   3780
tatcctgtgt gtcctttgtg cacctacata ggtatcaaat attcgctgca attcacactt   3840
cccagtcatc tgtcgtaata gccatttcat ccaaaatcga aaaagtgcc catagaagaa   3900
ctcccacaaa gaaataaaca ttttttttttc ctcacaggag cggaagaact aggggggagca   3960
ggagctgcaa tgcggccgc                                                 3979
```

<210> SEQ ID NO 97
<211> LENGTH: 2904
<212> TYPE: DNA
<213> ORGANISM: Homo sapiens
<220> FEATURE:
<221> NAME/KEY: misc_feature
<223> OTHER INFORMATION: Per-1: Acc. No. AB005293

<400> SEQUENCE: 97

```
ggcacgagct ctgtgagact gaggtggcgg tcagccggag tgagtgttgg ggtcctgggg     60
cacctgcctt acatggcttg tttatgaaca ttaaagggaa gaagttgaag cttgaggagc    120
gaggatggca gtcaacaaag gcctcaccttt gctggatgga gacctccctg agcaggagaa    180
tgtgctgcag cgggtcctgc agctgccggt ggtgagtggc acctgcgaat gcttccagaa    240
gacctacacc agcactaagg aagcccaccc cctggtggcc tctgtgtgca atgcctatga    300
gaagggcgtg cagagcgcca gtagcttggc tgcctggagc atggagccgg tggtccgcag    360
gctgtccacc cagttcacag ctgccaatga gctggcctgc cgaggcttgg accacctgga    420
ggaaaagatc cccgccctcc agtaccccc tgaaaagatt gcttctgagc tgaaggacac    480
catctccacc cgcctccgca gtgccagaaa cagcatcagc gttcccatcg cgagcacttc    540
agacaaggtc ctgggggccg ctttggccgg gtgcgagctt gcctgggggg tggcagaga    600
cactgcggaa tttgctgcca acactcgagc tggccgactg gcttctggag gggccgactt    660
ggccttgggc agcattgaga aggtggtgga gtacctcctc cctgcagaca aggaagagtc    720
agccctgct cctggacacc agcaagccca gaagtctccc aaggccaagc caagcctctt    780
gagcagggtt ggggctctga ccaacacccct ctctcgatac accgtgcaga ccatggcccg    840
ggccctggag cagggccaca ccgtggccat gtggatccca ggcgtggtgc ccctgagcag    900
cctggcccag tggggtgcct cagtggccat gcaggcggtg tcccggcgga ggagcgaagt    960
gcgggtaccc tggctgcaca gcctcgcagc cgcccaggag gaggatcatg aggaccagac   1020
agacacggag ggagaggaca cggaggagga ggaagaattg gagactgagg agaacaagtt   1080
cagtgaggta gcagccctgc caggccctcg aggcctcctg gtggtgtgg cacatacccct   1140
gcagaagacc ctccagacca ccatctcggc tgtgacatgg gcacctgcag ctgtgctggg   1200
catggcaggg agggtgctgc acctcacacc agccccgct gtctcctcaa ccaaggggag   1260
```

-continued

```
ggccatgtcc ctatcagatg ccctgaaggg cgttactgac aacgtggtgg acacagtggt    1320
gcattacgtg ccgctcccca ggctgtcgct gatgggaccc gagagcgaat tccgggacat    1380
cgacaaccca ccagccgagg tcgagcgccg ggaggcggag cgcagagcgt ctggggcgcc    1440
gtccgccggc ccggagcccg ccccgcgtct cgcacagccc cgccgcagcc tgcgcagcgc    1500
gcagagcccc ggcgcgcccc ccggcccggg cctggaggac gaagtcgcca cgcccgcagc    1560
gccgcgcccg ggcttcccgg ccgtgccccg cgagaagcca agcgcaggg tcagcgacag     1620 cttcttccgg cccagcgtca tggagcccat cgtgggccgc acgcattaca gccagctgcg    1680
caagaagagc tgagtcgccg caccagccgc gcgccccgg gccggcgggt ttctctaaca     1740
aataaacaga acccgcactg cccaggcgag cgttgccact ttcaaagtgg tcccctgggg    1800
agctcagcct catcctgatg atgctgccaa ggcgcacttt ttattttat tttatttta      1860 tttttttttt agcatccttt tggggcttca ctctcagagc cagtttttaa gggacaccag    1920
agccgcagcc tgctctgatt ctatggcttg gttgttacta taagagtaat tgcctaactt    1980 gattttcat ctctttaacc aaacttgtgg ccaaaagata tttgaccgtt tccaaaattc     2040
agattctgcc tctgcggata atatttgcc acgaatgagt aactcctgtc accactctga     2100
aggtccagac agaaggtttt gacacattct tagcactgaa ctcctctgtg atctaggatg    2160
atctgttccc cctctgatga acatcctctg atgatcaagg ctcccagcag gctactttga    2220
agggaacaat cagatgcaaa agctcttggg tgttatttta aaatactagt gtcactttct    2280
gagtacccgc cgcttcacag gctgagtcca ggcctgtgtg cttgtagag ccagctgctt     2340 gctcacagcc acatttccat ttgcatcatt actgccttca cctgcatagt cactcttttg    2400
atgctgggga accaaaatgg tgatgatata tagactttat gtatagccac agttcatccc    2460
caaccctagt cttcgaaatg ttaatatttg ataaatctag aaaatgcatt catacaatta    2520
cagaattcaa atattgcaaa aggatgtgtg tctttctccc cgagctcccc tgttcccctt    2580
cattgaaaac caccacggtg ccatctcttg tgtatgcagg gctatgcacc tgcaggcacg    2640
tgtgtatgca ctccccgctt tgtgtttacac aagctgtggg gtgttacgca tgcctgcttt   2700
tttcacttaa taatacagct tggagagatt tttgtatcac attataaatc ccactcgctc    2760 ttttttgatgg ccacataata actactgcat aatatggata cgccttattt gatttaacta   2820
gttccctaat gatggacttt taagttgttt cctttttttt tcttttttgc tactgcaaac    2880
gatgctataa taaatgtcct tatc                                           2904
```

<210> SEQ ID NO 98
<211> LENGTH: 4626
<212> TYPE: DNA
<213> ORGANISM: Homo sapiens
<220> FEATURE:
<221> NAME/KEY: misc_feature
<223> OTHER INFORMATION: TPP II: Acc. No. M73047

<400> SEQUENCE: 98

```
gaattcccct ccatcctgcg tccatggcca ccgctgcgac tgaggagccc ttccctttc      60 acggtctcct gccgaagaag gagaccgag ccgcctcctt cctctgccgc tacccggagt     120
atgatgggcg gggggtgctc atcgcagtcc tggacacggg ggtcgacccg ggggctccgg    180
gcatgcaggt tacaactgat ggaaaaccaa aaatcgttga tatcattgat acaacaggaa    240
gtggcgatgt gaatactgct acagaagtag agccaaagga tggtgagatt gttggccttt    300
caggaagagt gcttaagatt cctgcaagct ggacaaatcc ctcaggcaaa tatcatattg    360
```

```
gcataaaaaa tggctatgac ttctatccta aggcactcaa ggaaaggata cagaaagaac      420
ggaaggaaaa aatctgggac cctgttcaca gagtggccct tgcagaagcc tgtagaaaac      480
aggaagaatt tgatgttgcc aacaacggct cttctcaagc aaataaacta atcaaggagg      540
aacttcaaag tcaagtggaa ttgctaaatt cttttgagaa gaaatacagc gatcctggcc      600
ctgtatatga ctgcttggta tggcatgatg gcgaagtctg gagagcctgc attgattcta      660
atgaagatgg ggacttgagt aaatctaccg tgttgagaaa ctacaaagaa gcccaagaat      720
atggctcttt tggcacagct gagatgttga attactccgt taatatatac gatgatagaa      780
acctgctctc cattgtgacc agtggaggag ctcatgggac acatgtagct agtatagctg      840
ctggacactt tccagaagaa cctgaacgga atggggtagc tcctggtgct caaattcttt      900
ccatcaagat tggtgataca agactaagca caatggaaac aggcacaggc ctcataagag      960
ctatgataga agttataaat cataagtgtg atcttgtcaa ctacagttac ggagaagcaa     1020
ctcactggcc aaaattctgg gagaatttgt aagtaattaa tgaagcagta tggaagcata     1080
atataattta tgtttcaagt gctggaaata atggtccatg cctgtctaca gttggttgtc     1140
caggtggaac tacatcaagt gtgataggtg ttggtgctta tgtttctcct gatatgatgg     1200
ttgctgagta ttcactgaga gagaaattac ctgcaaatca atatacttgg tcttctagag     1260
gacctagtgc tgacggggcc cttggtgtga gtatcagtgc gccaggagga gccattgctt     1320
ctgttcctaa ctggacactg agagggacgc agctgatgaa tggaacatct atgtcttccc     1380
ccaatgcatg tggaggcatt gccctgatcc tttcaggtct gaaagctaat aacattgact     1440
acacagttca ttcagtcaga agagctctag aaaacactgc agtgaaggct gacaatatag     1500
aagtatttgc tcaaggacat ggtattattc aggttgataa agcctatgac tacctcgttc     1560
agaatacatc atttgctaat aaaattaggtt ttactgttac tgttggaaat aaccgtggca     1620
tctacctccg agatcctgtt caggtggctg caccttcaga tcatggcgtt ggcattgaac     1680
ctgtatttcc ggagaacaca gaaaaactctg aaaaaatatc ccttcagctt catttagctc     1740
tgacttcaaa ttcatcttgg gttcagtgtc ccagccattt ggaactcatg aatcaatgta     1800
gacacataaa catacgtgtg gatcccaggg gcttaagaga aggattgcat tatacagagg     1860
tatgtggcta tgatatagca tcccctaacg caggtccgct cttcagagtt ccgatcactg     1920
cagttatagc agcaaaagta aatgaatcat cacattatga tctagccttt acagatgtac     1980 acttttaaacc tggtcaaatt cgaaggcatt ttattgaggt tcctgagggt gcaacatggg     2040
ctgaagtgac agtgtgttcg tgttcttctg aggtgtcagc aaagtttgtt ctacatgcag     2100
tccagcttgt gaagcaaaga gcatatcgaa gccatgaatt ctataagttt tgttctcttc     2160
cagagaaagg aacactgact gaagcttttc ctgtcctagg tggaaaagca attgaatttt     2220
gcattgctcg ttggtgggca agtctcagtg atgtcaacat tgattatacc atttcttcc       2280 atgggatagt gtgtactgct cctcagttaa acattcatgc atcggaagga atcaaccgct     2340
ttgatgttca gtcctccttg aaatacgaag atctggctcc ctgcataact ttgaagaact     2400
gggtccaaac actgcgccca gtgagtgcaa aaacaaaacc tttaggatca agagatgttt     2460
tgccaaataa ccgtcaactt tatgagatgg tcctgacata taactttcat caacccaaga     2520
gtggggaagt aactccaagc tgcccactac tttgtgaact attatatgaa tctgaatttg     2580
acagccaact gtggattatt tttgaccaga acaaaagaca gatgggttca ggcgatgcct     2640
atccacatca gtattctttg aaactggaga aaggagatta acaattcga ctacagattc     2700
```

-continued

| | |
|---|---|
| gccatgagca aatcagtgat ttggaacgcc ttaaagacct tccatttatt gtttctcata | 2760 |
| gattgtctaa taccttgagc ttagatattc atgaaaatca tagttttgca cttctaggga | 2820 |
| agaagaaatc aagcaatttg acattaccac ccaaatataa ccagccattc tttgttactt | 2880 |
| ccttacctga tgataaaata cctaaagggg caggacctgg atgctatctt gcaggatcct | 2940 |
| taacattgtc aaagactgaa ctaggaaaga aagctgatgt aatccctgtt cattactact | 3000 |
| taatacctcc accaacaaag actaagaatg cagcaaaga taaggaaaaa gattcagaaa | 3060 |
| aagagaaaga tttaaaagaa gagtttactg aagcattacg agatcttaaa attcagtgga | 3120 |
| tgacaaagct ggattctagt gacatttata acgaattgaa agaaacatat cctaattatc | 3180 |
| ttcctctgta cgttgcacga cttcatcaat tggatgctga aaaggaacga atgaaaagac | 3240 |
| ttaatgaaat tgttgatgcg gcaaatgctg ttatttctca tatagatcaa acagccctag | 3300 |
| cagtttatat tgcaatgaag actgatccca ggcctgatgc agctactata aaaaatgaca | 3360 |
| tggacaaaca aaaatccacc ctcgtagatg ccctttgtag gaaaggttgt gccctggcag | 3420 |
| accatcttct tcacacccag gctcaagacg gagccatttc cactgatgca gaaggaaagg | 3480 |
| aggaggaagg agaaagtcct ttggattctc tggcagaaac attttgggaa actactaaat | 3540 |
| ggactgatct ctttgacaat aaggttttga catttgcata taaacatgca ttagtaaata | 3600 |
| aaatgtatgg gagaggcctt aaatttgcaa ctaaacttgt ggaagaaaaa ccaacaaaag | 3660 |
| aaaactggaa aaattgtatt caactgatga agttacttgg atggacccat tgtgcatctt | 3720 |
| ttactgaaaa ctggctcccc atcatgtatc ctcccgatta ttgcgtattc taaaatagga | 3780 |
| aacaagactt taaattttaa aaaggaagt tttatagtga atgggtataa aaacaaattt | 3840 |
| gtggcatttt tagtctaatg catgttttca tccactatcc agtactgatt attaaaatga | 3900 |
| catgtattta tcagagaatt cactgacgtg tggcttaata catgtaaatc tagacctctg | 3960 |
| acatcatggt gttttcttaa tgcctcacat tgctggcacg gggatgtgcc ctgcctgcca | 4020 |
| gcacctagga cttcgagttg ggttgcagct tatgacatgc atgataggtt ttggaaggta | 4080 |
| acttttaact gcaaacctat aaagtactat ttttttatttt ataaatgaac agggttttaa | 4140 |
| cgtgctcaac tttaattttt ttcaattgta tgaaggcctt aaaaaagcta cattaagcgt | 4200 |
| agctaaaatt atttattgga ctaaaaacta acagaacttc atttccagaa ttttttttt | 4260 |
| tttttttttt ttggcaaatg tttacattca attaagggga aaaagtagaa ccagcacaaa | 4320 |
| tgagtggcag ttgctggagc ataactgctt caataaatct tcatcttggg gtaattacag | 4380 |
| gcaagtcatt ttcacatcct cttgaggttc agagcatcag aatgaactct atgaatacat | 4440 |
| gtgtaagtgc cagacagctg aatctttatc aggtattgta aagatacaca tatgatatgt | 4500 |
| ttattaaaat tgaaataatg taaaacacat gaataaattt gcaaaaccaa gatcacagta | 4560 |
| caccatatgc actctggtac cttaattttt ttttataaat aataaaagtg aatattgaag | 4620 |
| cttctt | 4626 |

<210> SEQ ID NO 99
<211> LENGTH: 3224
<212> TYPE: DNA
<213> ORGANISM: Homo sapiens
<220> FEATURE:
<221> NAME/KEY: misc_feature
<223> OTHER INFORMATION: MTP. Acc. No. X59657

<400> SEQUENCE: 99

| | |
|---|---|
| actccctcac tggctgccat tgaaagagtc cacttctcag tgactcctag ctgggcactg | 60 |

```
gatgcagttg aggattgctg gtcaatatga ttcttcttgc tgtgcttttt ctctgcttca    120
tttcctcata ttcagcttct gttaaaggtc acacaactgg tctctcatta aataatgacc    180
ggctgtacaa gctcacgtac tccactgaag ttcttcttga tcggggcaaa ggaaaactgc    240
aagacagcgt gggctaccgc atttcctcca acgtggatgt ggccttacta tggaggaatc    300
ctgatggtga tgatgaccag ttgatccaaa taacgatgaa ggatgtaaat gttgaaaatg    360
tgaatcagca gagaggagag aagagcatct tcaaaggaaa aagcccatct aaaataatgg    420
gaaaggaaaa cttggaagct ctgcaaagac ctacgctcct tcatctaatc catggaaagg    480
tcaaagagtt ctactcatat caaaatgagg cagtggccat agaaaatatc aagagaggtc    540
tggctagcct atttcagaca cagttaagct ctggaaccac caatgaggta gatatctctg    600
gaaattgtaa agtgacctac caggctcatc aagacaaagt gatcaaaatt aaggccttgg    660
attcatgcaa aatagcgagg tctggattta cgaccccaaa tcaggtcttg ggtgtcagtt    720
caaaagctac atctgtcacc acctataaga tagaagacag ctttgttata gctgtgcttg    780
ctgaagaaac acacaatttt ggactgaatt cctacaaaac cattaagggg aaaatagtat    840
cgaagcagaa attagagctg aagacaaccg aagcaggccc aagattgatg tctggaaagc    900
aggctgcagc cataatcaaa gcagttgatt caaagtacac ggccattccc attgtggggc    960
aggtcttcca gagccactgt aaaggatgtc cttctctctc ggagctctgg cggtccacca   1020
ggaaatacct gcagcctgac aacctttcca aggctgaggc tgtcagaaac ttcctggcct   1080
tcattcagca cctcaggact gcgaagaaag aagagatcct tcaaatacta agatggaaa    1140
ataaggaagt attacctcag ctggtggatg ctgtcacctc tgctcagacc tcagactcat   1200
tagaagccat tttggacttt ttggatttca aaagtgacag cagcattatc ctccaggaga   1260
ggtttctcta tgcctgtgga tttgcttctc atcccaatga agaactcctg agagccctca   1320
ttagtaagtt caaaggttct attggtagca gtgacatcag agaaactgtt atgatcatca   1380
ctgggacact tgtcagaaag ttgtgtcaga atgaaggctg caaactcaaa gcagtagtgg   1440
aagctaagaa gttaatcctg ggaggacttg aaaaagcaga gaaaaagag gacaccagga    1500
tgtatctgct ggctttgaag aatgcccgc ttccagaagg catcccaagt cttctgaagt    1560
atgcagaagc aggagaaggg cccatcagcc acctggctac cactgctctc cagagatatg   1620
atctcccttt cataactgat gaggtgaaga agaccttaaa cagaatatac caccaaaacc   1680
gtaaagttca tgaaaagact gtgcgcactg ctgcagctgc tatcattta aataacaatc    1740
catcctacat ggacgtcaag aacatcctgc tgtctattgg ggagcttccc caagaaatga   1800
ataaatacat gctcgccatt gttcaagaca tcctacgttt ggaaatgcct gcaagcaaaa   1860
ttgtccgtcg agttctgaag gaaatggtcg ctcacaatta tgaccgtttc tccaggagtg   1920
gatcttcttc tgcctacact ggctacatag aacgtagtcc ccgttcggca tctacttaca   1980
gcctagacat tctctactcg ggttctggca ttctaaggag aagtaacctg aacatctttc   2040
agtacattgg gaaggctggt cttcacggta gccaggtggt tattgaagcc caaggactgg   2100
aagccttaat cgcagccacc cctgacgagg gggaggagaa ccttgactcc tatgctggta   2160
tgtcagccat cctctttgat gttcagctca gacctgtcac ctttttcaac ggatacagtg   2220
atttgatgtc caaaatgctg tcagcatctg gcgaccctat cagtgtggtg aaaggactta   2280
ttctgctaat agatcattct caggaacttc agttacaatc tggactaaaa gccaatatag   2340
aggtccaggg tggtctagct attgatattt caggtgcaat ggagtttagc ttgtggtatc   2400
gtgagtctaa aacccgagtg aaaaatagg tgactgtggt aataaccact gacatcacag    2460
```

```
tggactcctc ttttgtgaaa gctggcctgg aaaccagtac agaaacagaa gcaggcttgg      2520
agtttatctc cacagtgcag ttttctcagt acccattctt agtttgcatg cagatggaca      2580
aggatgaagc tccattcagg caatttgaga aaaagtacga aaggctgtcc acaggcagag      2640
gttatgtctc tcagaaaaga aaagaaagcg tattagcagg atgtgaattc ccgctccatc      2700
aagagaactc agagatgtgc aaagtggtgt tgcccctca gccggatagt acttccagcg       2760
gatggttttg aaactgacct gtgatatttt acttgaattt gtctccccga aagggacaca      2820
atgtggcatg actaagtact tgctctctga gagcacagcg tttacatatt tacctgtatt      2880
taagattttt gtaaaaagct acaaaaaact gcagtttgat caaatttggg tatatgcagt      2940
atgctaccca cagcgtcatt tgaatcatc atgtgacgct ttcaacaacg ttcttagttt       3000
acttatacct ctctcaaatc tcatttggta cagtcagaat agttattctc taagaggaaa      3060
ctagtgtttg ttaaaaacaa aaataaaaac aaaaccacac aaggagaacc caattttgtt      3120
tcaacaattt ttgatcaatg tatatgaagc tcttgatagg acttccttaa gcatgacggg      3180
aaaaccaaac acgttccta atcaggaaaa aaaaaaaaaa aaaa                        3224

<210> SEQ ID NO 100
<211> LENGTH: 5856
<212> TYPE: DNA
<213> ORGANISM: Homo sapiens
<220> FEATURE:
<221> NAME/KEY: misc_feature
<223> OTHER INFORMATION: HisR: Acc. No. D14436

<400> SEQUENCE: 100
gagctcatca tttttatgg ctgcatagta ttccatggtg tatatgtgcc acattttctt        60
aatccagtct atcattgttg acagttggg ttggttccaa gtctttgcta ctgtgaatag       120
tgcctcaata acatatgtg tgcatgtgtc tttatagcag caagatttat agtcctttgg       180
gtatataccc agtaatggga tggctgggtc aaatggtatt tctagttcta catccctgag      240
gaatcgccac accgacttcc acaatggttg aactagttta cagtcccacc aaaagtgtaa      300
aaatgttcct atttctccac ttcctctcca gcatctgttg tttcctgact ttttaatgat      360
tgctattcta actggtgtga gatggtatct cattgtggtt ttgatttgca tttctctgat      420
ggccagtgat ggtgagcatt ttttcatgtg ttttttggat gcataaatgt cttcttttga      480
gaagtgtctg ttcatgtcct cgcccactt tttgatgggg atgtttttt cttgtaaatt       540 tgtttgagtt cattgtagat tctggatatt agcccttgt cagatgagta ggttgtgaaa       600
attttctccc attttgtagg ttgcctgttc actctgatgg tagtttcttt tgctgtgcag      660
aaaatcttta gttaattag atcccatttg tcaattttgg cttttgttgc cattgttttt       720
ggtgttttag acatgaagtc cttgcccatg cctatgtcct gaatggtaat gcctaggatt      780
tcttctgggg gttttatggt tttaggtcta atgtttaagt cttaatcca tcttgaatta      840 attttgtat aaggtgtaag gaagggatcc agtttcagct ttctacatat ggctagccag      900
ttttcccagc actttttatt aaatagagaa tccttccc attgcttttc tcaggtttgt       960
caaagatcag atagttgtag atatgcaatg ctatttctga gggctctgtt ctgttccatt     1020
gatctatatc tctgttttgg taccagtacc atgctgtttt ggttactgtg gccttgtagt     1080
atagtttgaa gtcaggtagc atgatgcctc cagctttgtt cttttggctt aggattgact     1140
tggcgatgtg ggctcttttt ggttccatat gaactttaaa gtagttttt ccaattctgt      1200 gaagaaagtc attggtagct tgatgggggat ggcattgaat ctatcaatta ccttgggcag    1260
```

```
tatggccatt ttcaagatat tgattcttcc tacccatgag catgaatgt tcttccattt    1320
gtttgtatcc tcttttattt ccttgagcag tggtttgtag ttctcctcga agaggtcctt    1380
cacatccctt gtaagttgga ttcctaggta ttttattctc tttgaagcaa ttgtgaatgg    1440
gagttcactc atgatttggc tctctgtttg tctgttattg gtgtattaga atgcttgtga    1500
tttttgtaca ttgattttgt atcctgagac tttgctgaag ttgcttatca gcttaaggag    1560
attttgggct gagacaatgg ggttttctag atatacaatc atgtcatctg caaacaggga    1620
caatttgact tcctcttttc ctaattgagt accctttatt ccttctcct gcctaattgc     1680
cctggccaga acttccaaca ctatgttgaa taggagtggt gagagagggc atccctgtct    1740
tgtgccagtt ttcaaaggga atgcttgcag ttttgccca ttcagtatga tactggctgt     1800
gggtttgtca tagatagctc ttattatttt gagatacgtc ccatgaatac ctaatttatt    1860
gagagttttt agcatgaagg gttgttgaat tttgtcaaag gccttttctg catctattga    1920
gataatcatg tggttttgt ctttggttct gtttacatgc tggattacat ttattgattt     1980
gcatatattg aaccagcctt gcatcccagg gatgaagtcc acttgatcac ccccaacagc    2040
atacaactcc agtctgatga acatcatgct actaagtggc cactcatcac ccaagtctct    2100
gaccttactt tttctctctt ttctcccagg gagtgagcca taactggcgg ctgctcttgc    2160
gccaatgagc ctccccaatt cctcctgcct cttagaagac aagatgtgtg agggcaacaa    2220
gaccactatg ccagccccc agctgatgcc cctggtggtg gtcctgagca ctatctgctt     2280
ggtcacagta gggctcaacc tgctggtgct gtatgccgta cggagtgagc ggaagctcca    2340
cactgtgggg aacctgtaca tcgtcagcct ctcggtggcg gacttgatcg tgggtgccgt    2400
cgtcatgcct atgaacatcc tctacctgct catgtccaag tggtcactgg gccgtcctct    2460
ctgcctcttt tggctttcca tggactatgt ggccagcaca gcgtccattt tcagtgtctt    2520
catcctgtgc attgatcgct accgctctgt ccagcagccc ctcaggtacc ttaagtatcg    2580
taccaagacc cgagcctcgg ccaccattct gggggcctgg tttctctctt ttctgtgggt    2640
tattcccatt ctaggctgga atcacttcat gcagcagacc tcggtgcgcc gagaggacaa    2700
gtgtgagaca gacttctatg atgtcacctg gttcaaggtc atgactgcca tcatcaactt    2760
ctacctgccc accttgctca tgctctggtt ctatgccaag atctacaagg ccgtacgaca    2820
acactgccag caccggggagc tcatcaatag gtccctccct tccttctcag aaattaagct    2880
gaggccagag aaccccaagg gggatgccaa gaaaccaggg aaggagtctc cctgggaggt    2940
tctgaaaagg aagccaaaag atgctggtgg tggatctgtc ttgaagtcac catcccaaac    3000
ccccaaggag atgaaatccc cagttgtctt cagccaagag gatgatagag aagtagacaa    3060
actctactgc tttccacttg atattgtgca catgcaggct gcggcagagg ggagtagcag    3120
ggactatgta gccgtcaacc ggagccatgg ccagctcaag acagatgagc agggcctgaa    3180
cacacatggg gccagcgaga tcagagga tcagatgtta ggtgatagcc aatccttctc       3240
tcgaacggac tcagatacca ccacagagac agcaccaggc aaaggcaaat tgaggagtgg    3300
gtctaacaca ggcctggatt acatcaagtt tacttggaag aggctccgct cgcattcaag    3360
acagtatgta tctgggttgc acatgaaccg cgaaaggaag gccgcaaac agtttgggttt    3420
tatcatggca gccttcatcc tctgctggat cccttatttc atcttcttca tggtcattgc    3480
cttctgcaag aactgttgca atgaacattt gcacatgttc accatctggc tgggctacat    3540
caactccaca ctgaacccc tcatctaccc cttgtgcaat gagaacttca agaagacatt    3600
```

```
caagagaatt ctgcatattc gctcctaagg gaggctctga ggggatgcaa caaaatgatc    3660
cttatgatgt ccaacaagga aatagaggac gaaggcctgt gtgttgccag gcaggcacct    3720
gggctttctg gaatccaaac cacagtctta ggggcttggt agtttggaaa gttcttaggc    3780
accatagaag aacagcagat ggcggtgatc agcagagaga ttgaactttg aggaggaagc    3840
agaatctttg caagaaagtc agacctgttt cttgtaactg ggttcaaaaa gaaaaaaata    3900
ataaaaataa aagagagaga gaatcagacc tgggtggaac tctcctgctc ctcaggaact    3960
atgggagcct cagactcatt gtaattcaag cttttccgagt caagtgattg acaactgaag    4020
agacacgtgg ctagggttcc actgagaatt gaaaaggac tcttgagccc tcctggaatg    4080
gagctgtata actgtgcaga gactttatcc atgccaatag ttgctgtccc cttccagggg    4140
tcaccttgag aggcatgaca gctgttccac aggggctatc ccttctcaga aaacttctct    4200
tctgagcctc tttaacagct ttctccagaa ccagtgtctg aaccaccctg gaaattctgc    4260
cttattattt cttactcaaa catgtttaga gtggatagaa aattatgcag cttgcacacc    4320
catcatcttt aaccccaaat ttcctttggc tattaaaaaa gtggtggcaa aaggcatcct    4380
caaaagaaag agaatgaaa tatttttgaa tggttgcacg ttaaaaatta aagaaggaa    4440
tgggggcaga atgccatatt tttgagggct gtactaggtt tatctcattt aagccccaca    4500
acaccccaca ggagggtaat tttctaactc tagtttgcag aggagcaaat tgaggttcag    4560
caaggtgaga gaggtaccca aggtcacata gctagttatg tgagaaagtt agagtacaga    4620
tcctctgggg tttcagctta ttgtagcata ttttctccga aaggcaaaaa tgtgcccttt    4680
tggccgggca tggtagctca agcctataat cccagcatgt tgagaggctg aggtgggcag    4740
atcatttgag gccaggagtt caagaccagt ctggccaata tggagaaacc ttgtctctac    4800
taaaaacaca aaaattatct gggcatggtg gggcatgcct gtagtcccac ttacttggga    4860
ggccgaggca cgagaatcgc ttgaacccgg gaggtggagg ttgccgtgag ccaagatcac    4920
gccactgcac tccagcctgg gcaacagagc aagactctgt ctcaaaaaaa aaaatacaat    4980
attttaacaa tgtgccctct taagtgtgca cagatacaca tacacggtat tcccaagagt    5040
ggtggcagct caaaatgata tgtttgagta gacgaacagc tgacatggag ttcccgtgca    5100
cctacggaag gggacgcttt gaaggaacca agtgcatttt tatctgtgag ttctgttgtg    5160
tttgtcaaaa agtcattgta atcttttcata gccatacctg gtaagcaaaa actagtaaag    5220
acataggaac atgtagttt acttggtgtt tatgttgcaa tctggttgtg atttatattt    5280
taaagcttgg tgctaaacca caatatgtat agcacatgga gtgcctgtac aagctgatgt    5340
tttgtatttt gtgttcctct ttgcatgatc tgtcaaagtg agatattttt acctgcctaa    5400
aatatgatgt ttaaaagcat actctatgtg atttatttat ttctacctt ctgagtctct    5460
tggactaaga agatgttttg aaatgtacca tcaaatgtta acagagtttg atatgggctt    5520
tctctttggt ttctcatcac atttgtaaat gtcttttcaa aaggatttac ttttgtaaa    5580
aagcttcatt ctcactctgc tttgcatccc ccaaacttct tgttcaaaac ggggggagtt    5640
taggagactt taatcccggt ttcagaagct gcagctggtc tgtttccagg tcagaaacca    5700
ttgttcagaa gacctccctg tgagagagtt gctcctcagg gtccctcagg accaaagaac    5760
actcgaaaag agcacttcac acagacaagt ggctaagtgt ccattattta ccttgaacaa    5820
tcaaggcaac tagtggagag aactgattgt gagctc                              5856
```

<210> SEQ ID NO 101
<211> LENGTH: 2438

```
<212> TYPE: DNA
<213> ORGANISM: Homo sapiens
<220> FEATURE:
<221> NAME/KEY: misc_feature
<223> OTHER INFORMATION: CRP:  Acc. No. M11880

<400> SEQUENCE: 101
aataaataac tcacattgat ttctctggtc tgaaataatt ttgcttcccc tcttcccgaa        60
gctctgacac ctgccccaac aagcaatgtt ggaaaattat ttacatagtg gcgcaaactc       120
ccttactgct ttggatataa atccaggcag gaggaggtag ctctaaggca agagatctag       180
gacttctagc ccctgaactt tcagccgaat acatcttttc caaggagtg aattcaggcc        240
cttgtatcac tggcagcagg acgtgaccat ggagaagctg ttgtgtttct tggtcttgac       300
cagcctctct catgcttttg gccagacagg taagggccac cccaggctat gggagagttt       360
tgatctgagg tatggggtg gggtctaaga ctgcatgaac agtctcaaaa aaaaaaaaaa        420
aagactgtat gaacagaaca gtggagcatc cttcatggtg tgtgtgtgtg tgtgtgtgtg       480
tgtgtgtggt gtgtaactgg agaagggtc agtctgtttc tcaatcttaa attctatacg        540
taagtgaggg gatagatctg tgtgatctga gaaacctctc acatttgctt gttttctgg        600
ctcacagaca tgtcgaggaa ggcttttgtg tttcccaaag agtcggatac ttcctatgta       660
tccctcaaag caccgttaac gaagcctctc aaagccttca ctgtgtgcct ccacttctac       720
acggaactgt cctcgacccg tgggtacagt attttctcgt atgccaccaa gagacaagac       780
aatgagattc tcatattttg gtctaaggat ataggataca gttttacagt gggtgggtct       840
gaaatattat tcgaggttcc tgaagtcaca gtagctccag tacacatttg tacaagctgg       900
gagtccgcct cagggatcgt ggagttctgg gtagatggga agcccaggg gaggaagagt         960
ctgaagaagg gatacactgt gggggcagaa gcaagcatca tcttggggca ggagcaggat      1020
tccttcggtg ggaactttga aggaagccag tccctagtgg gagacattgg aaatgtgaac      1080
atgtgggact ttgtgctgtc accagatgag attaacacca tctatcttgg cgggcccttc      1140
agtcctaatg tcctgaactg gcgggcactg aagtatgaag tgcaaggcga agtgttcacc      1200
aaacccagc tgtggccctg aggcccagct gtgggtcctg aaggtacctc ccggtttttt       1260
acaccgcatg ggccccacgt ctctgtctct ggtacctccc gcttttttac actgcatggt      1320
tcccacgtct ctgtctctgg gccttttgttc ccctatatgc attgaggcct gctccaccct     1380
cctcagcgcc tgagaatgga ggtaaagtgt ctggtctggg agctcgttaa ctatgctggg      1440
aaatggtcca aaagaatcag aatttgaggt gttttgtttt cattttatt tcaagttgga      1500
cagatcttgg agataatttc ttacctcaca tagatgagaa aactaacacc cagaaaggag      1560
aaatgatgtt ataaaaaact cataaggcaa gagctgagaa ggaagcgctg atcttctatt      1620
taattcccca cccatgaccc ccagaaagca ggagcattgc ccacattcac agggctcttc      1680
agtatcagaa tcaggacact ggccaggtgt ctggtttggg tccagagtgc tcatcatcat      1740
gtcatagaac tgctgggccc aggtctcctg aaatgggaag cccagcaata ccacgcagtc      1800
cctccacttt ctcaaagcac actggaaagg ccattagaat tgccccagca gagcagatct      1860
gcttttttc cagagcaaaa tgaagcacta ggtataaata tgttgttact gccaagaact        1920
taaatgactg gttttgtttt gcttgcagtg ctttcttaat tttatggctc ttctgggaaa      1980
ctcctcccct tttccacacg aaccttgtgg ggctgtgaat tctttcttca tccccgcatt      2040
cccaatatac ccaggccaca agagtggacg tgaaccacag ggtgtcctgt cagaggagcc      2100
catctcccat ctccccagct ccctatctgg aggatagttg gataggtacg tgttcctagc      2160
```

-continued

| aggaccaact acagtcttcc caaggattga gttatggact ttgggagtga gacatcttct | 2220 |
| tgctgctgga tttccaagct gagaggacgt gaacctggga ccaccagtag ccatcttgtt | 2280 |
| tgccacatgg agagagactg tgaggacaga agccaaactg gaagtggagg agccaaggga | 2340 |
| ttgacaaaca acagagcctt gaccacgtgg agtctctgaa tcagccttgt ctggaaccag | 2400 |
| atctacacct ggactgccca ggtctataag ccaataaa | 2438 |

```
<210> SEQ ID NO 102
<211> LENGTH: 1457
<212> TYPE: DNA
<213> ORGANISM: Homo sapiens
<220> FEATURE:
<221> NAME/KEY: misc_feature
<223> OTHER INFORMATION: CETP:  Acc. No. XM_008050

<400> SEQUENCE: 102
```

| cctggccctg ctgggcaatg cccatgcctg ctccaaaggc acctcgcacg aggcaggcat | 60 |
| cgtgtgccgc atcaccaagc tgccctcct ggtgttgaac cacgagactg ccaaggtgat | 120 |
| ccagaccgcc ttccagcgag ccagctaccc agatatcacg ggcgagaagg ccatgatgct | 180 |
| ccttggccaa gtcaagtatg ggttgcacaa catccagatc agccacttgt ccatcgccag | 240 |
| cagccaggtg gagctggtgg aagccaagtc cattgatgtc tccattcaga acgtgtctgt | 300 |
| ggtcttcaag gggaccctga gtatggcta caccactgcc tggtggctgg gtattgatca | 360 |
| gtccattgac ttcgagatcg actctgccat tgacctccag atcaacacac agctgacctg | 420 |
| tgactctggt agagtgcgga ccgatgcccc tgactgctac ctgtctttcc ataagctgct | 480 |
| cctgcatctc caaggggagc gagagcctgg gtggatcaag cagctgttca caaatttcat | 540 |
| ctccttcacc ctgaagctgg tcctgaaggg acagatctgc aaagagatca acgtcatctc | 600 |
| taacatcatg gccgattttg tccagacaag ggctgccagc atcctttcag atggagacat | 660 |
| tgggggtggac atttccctga caggtgatcc cgtcatcaca gcctcctacc tggagtccca | 720 |
| tcacaaggca gtgctggaga cctggggctt caacaccaac caggaaatct tccaagaggt | 780 |
| tgtcggcggc ttccccagcc aggcccaagt caccgtccac tgcctcaaga tgcccaagat | 840 |
| ctcctgccaa aacaagggag tcgtggtcaa ttcttcagtg atggtgaaat tcctctttcc | 900 |
| acgcccagac cagcaacatt ctgtagctta cacatttgaa gaggatatcg tgactaccgt | 960 |
| ccaggcctcc tattctaaga aaaagctctt cttaagcctc ttggatttcc agattacacc | 1020 |
| aaagactgtt tccaacttga ctgagagcag ctccgagtcc gtccgagct tcctgcagtc | 1080 |
| aatgatcacc gctgtgggca tccctgaggt catgtctcgg ctcgaggtag tgtttacagc | 1140 |
| cctcatgaac agcaaaggcg tgagcctctt cgacatcatc aaccctgaga ttatcactcg | 1200 |
| agatggcttc ctgctgctgc agatggactt tggcttccct gagcacctgc tggtggattt | 1260 |
| cctccagagc ttgagctaga agtctccaag gaggtcggga tggggcttgt agcagaaggc | 1320 |
| aagcaccagg ctcacagctg gaaccctggt gtctcctcca gcgtggtgga agttgggtta | 1380 |
| ggagtacgga gatggagatt ggctcccaac tcctccctat cctaaaggcc cactggcatt | 1440 |
| aaagtgctgt atccaag | 1457 |

```
<210> SEQ ID NO 103
<211> LENGTH: 2986
<212> TYPE: DNA
<213> ORGANISM: Homo sapiens
<220> FEATURE:
<221> NAME/KEY: misc_feature
```

<223> OTHER INFORMATION: ICAM: Acc. No. J03132

<400> SEQUENCE: 103

```
gcgccccagt cgacgctgag ctcctctgct actcagagtt gcaacctcag cctcgctatg      60
gctcccagca gccccccggcc cgcgctgccc gcactcctgg tcctgctcgg ggctctgttc     120
ccaggacctg gcaatgccca gacatctgtg tccccctcaa aagtcatcct gccccgggga     180
ggctccgtgc tggtgacatg cagcacctcc tgtgaccagc caagttgtt gggcatagag      240
accccgttgc ctaaaaagga gttgctcctg cctgggaaca accggaaggt gtatgaactg     300
agcaatgtgc aagaagatag ccaaccaatg tgctattcaa actgccctga tgggcagtca     360
acagctaaaa ccttcctcac cgtgtactgg actccagaac gggtggaact ggcaccccct     420
cctcttggc agccagtggg caagaacctt accctacgct gccaggtgga gggtgggga      480
ccccgggcca acctcaccgt ggtgctgctc cgtggggaga aggagctgaa acgggagcca     540
gctgtggggg agcccgctga ggtcacgacc acgtgctgg tgaggagaga tcaccatgga      600
gccaatttct cgtgccgcac tgaactggac ctgcggcccc aagggctgga gctgtttgag      660
aacacctcgg cccctacca gctccagacc tttgtcctgc agcgactcc cccacaactt      720
gtcagccccc gggtcctaga ggtggacacg caggggaccg tggtctgttc cctggacggg     780
ctgttcccag tctcggaggc ccaggtccac ctggcactgg gggaccagag gttgaacccc     840
acagtcacct atggcaacga ctccttctcg gccaaggcct cagtcagtgt gaccgcagag     900
gacgagggca cccagcggct gacgtgtgca gtaatactgg ggaaccagag ccaggagaca     960
ctgcagacag tgaccatcta cagctttccg gcgcccaacg tgattctgac gaagccagag    1020
gtctcagaag ggaccgaggt gacagtgaag tgtgaggccc accctagagc caaggtgacg    1080
ctgaatgggt tccagccca gccactgggc ccgaggccc agctcctgct gaaggccacc    1140
ccagaggaca acgggcgcag cttctcctgc tctgcaaccc tggaggtggc cggccagctt    1200
atacacaaga accagacccg ggagcttcgt gtcctgtatg ccccgact ggacgagagg    1260
gattgtccgg gaaactggac gtggccagaa aattcccagc agactccaat gtgccaggct    1320
tgggggaacc cattgcccga gctcaagtgt ctaaaggatg gcactttccc actgcccatc    1380
ggggaatcag tgactgtcac tcgagatctt gagggcacct acctctgtcg ggccaggagc    1440
actcaagggg aggtcacccg cgaggtgacc gtgaatgtgc tctccccccg gtatgagatt    1500
gtcatcatca ctgtggtagc agccgcagtc ataatgggca ctgcaggcct cagcacgtac    1560
ctctataacc gccagcggaa gatcaagaaa tacagactac aacaggccca aaaagggacc    1620
cccatgaaac cgaacacaca agccacgcct ccctgaacct atcccgggac agggcctctt    1680
cctcggcctt cccatattgg tggcagtggt gccacactga acagagtgga agacatatgc    1740
catgcagcta cacctaccgg ccctgggacg ccggaggaca gggcattgtc ctcagtcaga    1800
tacaacagca tttggggcca tggtacctgc acacctaaaa cactaggcca cgcatctgat    1860
ctgtagtcac atgactaagc caagaggaag gagcaagact caagacatga ttgatggatg    1920
ttaaagtcta gcctgatgag aggggaagtg gtggggagag catagcccca ccatgaggac    1980
atacaactgg gaaatactga aacttgctgc ctattgggta tgctgaggcc cacagactta    2040
cagaagaagt ggccctccat agacatgtgt agcatcaaaa cacaaaggcc cacacttcct    2100
gacggatgcc agcttgggca ctgctgtcta ctgaccccaa cccttgatga tatgtattta    2160
ttcatttgtt attttaccag ctatttattg agtgtctttt atgtaggcta aatgaacata    2220
ggtctctggc ctcacggagc tcccagtcca tgtcacattc aaggtcacca ggtacagttg    2280
```

```
tacaggttgt acactgcagg agagtgcctg gcaaaaagat caaatggggc tgggacttct    2340
cattggccaa cctgcctttc cccagaagga gtgattttc tatcggcaca aaagcactat    2400
atggactggt aatggttcac aggttcagag attacccagt gaggccttat tcctcccttc    2460
cccccaaaac tgacaccttt gttagccacc tccccaccca catacatttc tgccagtgtt    2520
cacaatgaca ctcagcggtc atgtctggac atgagtgccc agggaatatg cccaagctat    2580
gccttgtcct cttgtcctgt ttgcatttca ctgggagctt gcactattgc agctccagtt    2640
tcctgcagtg atcagggtcc tgcaagcagt ggggaagggg gccaaggtat tggaggactc    2700
cctcccagct ttggaagggt catccgcgtg tgtgtgtgtg tgtatgtgta gacaagctct    2760
cgctctgtca cccaggctgg agtgcagtgg tgcaatcatg gttcactgca gtcttgacct    2820
tttgggctca agtgatcctc ccacctcagc ctcctgagta gctgggacca taggctcaca    2880
acaccacacc tggcaaattt gatttttttt tttttttca gagacggggt ctcgcaacat    2940
tgcccagact tcctttgtgt tagttaataa agctttctca actgcc                  2986
```

<210> SEQ ID NO 104
<211> LENGTH: 3634
<212> TYPE: DNA
<213> ORGANISM: Homo sapiens
<220> FEATURE:
<221> NAME/KEY: misc_feature
<223> OTHER INFORMATION: X02910

<400> SEQUENCE: 104

```
gaattccggg tgatttcact cccggctgtc caggcttgtc ctgctacccc acccagcctt      60
tcctgaggcc tcaagcctgc caccaagccc ccagctcctt ctcccgcag gacccaaaca     120
caggcctcag gactcaacac agcttttccc tccaacccgt tttctctccc tcaacggact     180
cagctttctg aagcccctcc cagttctagt tctatctttt tcctgcatcc tgtctggaag    240
ttagaaggaa acagaccaca gacctggtcc ccaaaagaaa tggaggcaat aggttttgag    300
gggcatgggg acggggttca gcctccaggg tcctacacac aaatcagtca gtggcccaga    360
agaccccct cggaatcgga gcagggagga tggggagtgt gagggtatc cttgatgctt     420
gtgtgtcccc aactttccaa atccccgccc ccgcgatgga gaagaaaccg agacagaagg    480
tgcagggccc actaccgctt cctccagatg agctcatggg tttctccacc aaggaagttt    540
tccgctggtt gaatgattct ttccccgccc tcctctcgcc ccagggacat ataaaggcag    600
ttgttggcac acccagccag cagacgctcc ctcagcaagg acagcagagg accagctaag    660
agggagagaa gcaactacag accccccctg aaaacaaccc tcagacgcca catcccctga    720
caagctgcca gcaggttct cttcctctca catactgacc cacggcttca ccctctctcc    780
cctggaaagg acaccatgag cactgaaagc atgatccggg acgtggagct ggccgaggag    840
gcgctcccca agaagacagg ggggcccag ggctccaggc ggtgcttgtt cctcagcctc    900
ttctcccttcc tgatcgtggc aggcgccacc acgctcttct gcctgctgca ctttggagtg    960
atcggcccc agagggaaga ggtgagtgcc tggccagcct tcatccactc tcccacccaa    1020
ggggaaatga gagacgcaag agaggagag agatgggatg ggtgaaagat gtgcgctgat    1080
agggagggat gagagagaaa aaacatggaa gaaagacggg gatgcagaaa gagatgtggc    1140
aagagatggg gaagagagag agagaaagat ggagagacag gatgtctggc acatggaagg    1200
tgctcactaa gtgtgtatgg agtgaatgaa tgaatgaatg aatgaacaag cagatatata    1260
aataagatat ggagacagat gtggggtgtg agaagagaga tgggggaaga aacaagtgat    1320
```

```
atgaataaag atggtgagac agaaagagcg ggaaatatga cagctaagga gagagatggg   1380
ggagataagg agagaagaag atagggtgtc tggcacacag aagacactca gggaaagagc   1440
tgttgaatgc tggaaggtga atacacagat gaatggagag agaaaaccag acacctcagg   1500
gctaagagcg caggccagac aggcagccag ctgttcctcc tttaagggtg actccctcga   1560
tgttaaccat tctccttctc cccaacagtt ccccagggac ctctctctaa tcagccctct   1620
ggcccaggca gtcagtaagt gtctccaaac ctctttccta attctgggtt tgggtttggg   1680
ggtagggtta gtaccggtat ggaagcagtg ggggaaattt aaagttttgg tcttggggga   1740
ggatggatgg aggtgaaagt aggggggtat tttctaggaa gtttaagggt ctcagctttt   1800
tcttttctct ctcctcttca ggatcatctt ctcgaacccc gagtgacaag cctgtagccc   1860
atgttgtagg taagagctct gaggatgtgt cttggaactt ggagggctag gatttgggga   1920
ttgaagcccg gctgatggta ggcagaactt ggagacaatg tgagaaggac tcgctgagct   1980
caagggaagg gtgaggaac agcacaggcc ttagtgggat actcagaacg tcatggccag   2040
gtgggatgtg ggatgacaga cagagaggac aggaaccgga tgtggggtgg cagagctcg   2100 agggccagga tgtggagagt gaaccgacat ggccacactg actctcctct ccctctctcc   2160
ctccctccag caaaccctca agctgagggg cagctccagt ggctgaaccg ccgggccaat   2220
gccctcctgg ccaatggcgt ggagctgaga gataaccagc tggtggtgcc atcagagggc   2280
ctgtacctca tctactccca ggtcctcttc aagggccaag gctgcccctc cacccatgtg   2340
ctcctcaccc acaccatcag ccgcatcgcc gtctcctacc agaccaaggt caacctcctc   2400
tctgccatca agagcccctg ccagagggag accccagagg gggctgaggc caagccctgg   2460
tatgagccca tctatctggg aggggtcttc cagctggaga agggtgaccg actcagcgct   2520
gagatcaatc ggcccgacta tctcgacttt gccgagtctg ggcaggtcta ctttgggatc   2580
attgccctgt gaggaggacg aacatccaac cttcccaaac gcctcccctg ccccaatccc   2640
tttattaccc cctccttcag acaccctcaa cctcttctgg ctcaaaaaga gaattggggg   2700
cttagggtcg gaacccaagc ttagaacttt aagcaacaag accaccactt cgaaacctgg   2760
gattcaggaa tgtgtggcct gcacagtgaa gtgctggcaa ccactaagaa ttcaaactgg   2820
ggcctccaga actcactggg gcctacagct ttgatccctg acatctggaa tctggagacc   2880
agggagcctt tggttctggc cagaatgctg caggacttga gaagacctca cctagaaatt   2940
gacacaagtg gaccttaggc cttcctctct ccagatgttt ccagacttcc ttgagacacg   3000
gagcccagcc ctccccatgg agccagctcc ctctatttat gtttgcactt gtgattattt   3060
attatttatt tattatttat ttatttacag atgaatgtat ttatttggga gaccggggta   3120
tcctggggga cccaatgtag gagctgcctt ggctcagaca tgttttccgt gaaaacggag   3180
ctgaacaata ggctgttccc atgtagcccc ctggcctctg tgccttcttt tgattatgtt   3240
ttttaaaata tttatctgat taagttgtct aaacaatgct gatttggtga ccaactgtca   3300
ctcattgctg agcctctgct ccccagggga gttgtgtctg taatcgccct actattcagt   3360
ggcgagaaat aaagttttgct tagaaaagaa acatggtctc cttcttggaa ttaattctgc   3420
atctgcctct tcttgtgggt gggaagaagc tccctaagtc ctctctccac aggctttaag   3480
atccctcgga cccagtccca tccttagact cctagggccc tggagaccct acataaacaa   3540
agcccaacag aatattcccc atcccccagg aaacaagagc ctgaacctaa ttacctctcc   3600
ctcagggcat gggaatttcc aactctggga attc                              3634
```

<210> SEQ ID NO 105
<211> LENGTH: 11233
<212> TYPE: DNA
<213> ORGANISM: Homo sapiens

<400> SEQUENCE: 105

```
gaattccttc cgtagcttca ccagacacct aattggccaa gaaggtttga agacctgatg        60
tggttcttaa ttggggatgg ggaattaagg gctactgtat ctataggatt atcttttcac       120
ttgcatagac ctatttggtg tgttcagggc atagtgatac tataattgcc atatttaaca       180
gtttataaag ttcaagccca gcatattctt tgcctgttta atgatgtctt ggtatcagcc       240
ttttaatggt acttatcagc atagaaaatg gaaacaaaat aacttttaaa acagtagctc       300
tcaagcttta gtgtgctcag aatgaccaga gaaccttgtg aaatatacag atttctgggt       360
ccagatctgg ggcaggacca ggaagtctgc atttcatctg caccccccacc ctactctgag       420 gcttatagtc ctgagaacat gctttgaaaa aggctgtccc aagggctcgc agacaggcta       480
ttgaccagct actctttctt gatgttctcc aggaaaaacc caacaaagga atgcctttca       540
ttgagtagta gcagcatagg agcaatagtt gctcctgaat tatggtgggt ttccccctctt      600 catcaatgtg ctttaagggt acagtttcat ttggtctatc taccatgttc tataaaaaca       660
tgaaaattca caggtaagtt tgagatacag aaaataacta aactgattct tctcacgaac       720
tctgatcact aggctgtggt tgatttagct ctctaaccaa caagtaattt gttctttggc       780
atgagtaagg ggggaaaagg aggagtgggt aaaagcagct gataacagat ggcttgcgcc       840
catctaaaat gtggggagag aaataaagct gtcccaagag aactaaagct gagttctctc       900
gtcatatatc tgaagattca tatcaggggt ctaaacatgg tatgtcgggt agcttaattg       960
gaaactcctg gactgtgagt gtcacagact catggatggg ccaatcagtg gccactttag      1020
tgtctgggct gcagcaaaat gagacaatag ctgtcattca caaacctttg gaattaaaaa      1080
aaccccgaaa tgacattggt gctttaaagt aaaataaagt cctgcctttta agtccagcat     1140 atcactgttg tttctgagtt taaatattaa gaaccacatt tcgttaatga ttaaaacaac      1200
agtgattgat ttaggggctc agtgagcatt taatctgtcc tgacttcagg taccatgcta      1260
aaggagcaca atgcctgatg ctgcaggaga acattaggt aactatttaa tggagtttta       1320
attttctgtt attattttta ataattaatt gtgattttga ctatttggaa gctacaggta      1380
tattttgtcc tccttttggg gtggtgttat tgccctgccc tgttttaatc agtggttctt      1440
agagaaagtg aactcaggag tgacttaaaa tgaaggaaga cggactttgg ctaaaattac      1500
aattaaataa tcaaatcatt ttcaaatata aagggagcat gcagatgatc tggcccaatc      1560
ctttcattct gcagatgaga aaactgagac tcataggaat gaaaagactt gcccaaagcc      1620
atacagcttg tttctgttgt ttggtgcatt aggccaaaag acctaggcct aatagatgga      1680
aaagatggca ggatgtcttg gccttgctct gacagttgct tctctgatct cagatatttc      1740 ccacccttg taatctgtgt tccacacagg aagtagttct tgtttttta aatatcgaagg      1800 tgtataaacg taaagttttt atagatgagc cacccagggc caatatctgt ttaagtaaag      1860
acctaaatgc tttgcagaga cagtaaagtg tcatgtctgt cccagggaaa gaaatccagg      1920
acaggaaatg ctcagtcttc cagcactcct ctggctacct ggagctcagg ctatgagcct      1980
caacccctcc ctgaagcatt agctctggag cagaggctgt gatttacttc agagatctgg     2040
gcaagtccct ttaacctggt agtccttcct ttccttgttt gtaaaacaga gagatgaggc      2100
tgatagctcc ctcacagctc catcagaggc agtgtgtgaa attagttcct gtttgggaag      2160
```

```
gtttaaaagc caccacattc cacctccctg ctaatatgat tactaaaatg tttttatatg   2220
aaagggccaa ttcctcatct cccctcttcc tttaaaaaca gaccaagggg catcttttct   2280
tgtctccctg tggcctaaaa ggttactgct tctgtggtta tctccttgga aagacagagt   2340
gtcaggactc ttaggtacac caaaaatgaa caaaaaaatc aacaacaacc ataacaccaa   2400
caaaaataac tgctgtgtcg gttcttaaga cggcttctga gctagaaaca gattttttcta  2460 actgtaaaaa acgtggcccc agcctgtctg caggccacct ctgtctttag gccttggggg   2520
gaggagggaa gtgagctcat ttactggggt ctacctcagg gtcatcacca aggtgttcta   2580
caaaacgcac tttaagaatg ttttggaagg aaattcacct tttaacagcc caagaggtat   2640
ctctctctgg cacacagttc tgcacacagc ctgtttctca acgtttggaa atcttttaac   2700
agtttatgga aggccacctt ttaaaccgat ccaacagctc ctttctccat aacctgattt   2760
tagaggtgtt tcattatctc taattactca gggtaaatgg tgattactca gtgttttaat   2820
catcagtttg ggcagcagtt acactaaact cagggaagcc cagactccca tgggtatttt   2880
tggaaggtac ggcgactagt cggtgcatgc tttctagtac ctccgcacgt ggtccccagg   2940
tgagccccag ccgcttccca gagctggagg cagcggcgtc ccagctccga cggcagctgc   3000
ggactcgggc gctgcctggg cttccgggac ccgggcctgc taggcgaggt cgggcggctg   3060
gaggggagga tgtgggcggg gctcccatcc ccagaaaggg aggcgagcga gggaggaggg   3120
aaggagggag gggccgccgg ggaagaggag gaggaaggaa agaaagaaag cgagggaggg   3180
aaagaggagg aaggaagatg cgagaaggca gaggaggagg gagggaggga aggagcgcgg   3240
agcccggccc ggaagctagg tgagtgtggc atccgagctg agggacgcga gcctgagacg   3300
ccgctgctgc tccggctgag tatctagctt gtctccccga tgggattccc gtccaagcta   3360
tctcgagcct gcagcgccac agtccccggc cctcgcccag gttcactgca accgttcaga   3420
ggtccccagg agctgctgct ggcgagcccg ctactgcagg gacctatggt gagcaaggct   3480
acctggtgag gggagacagg cagaggggt ctaggagcct ccttgggggg aagaagctgg    3540
tcacaggctg tgaccgaggc aaaaggtggc ctaattattt tccaatagtg gtgctggagg   3600
tggggatgct ggcgctgaaa gacctttaaa tatcggctac tgcccctgcc caggccttct   3660
ctgtccagca gtccctggga gattctcacc tttgggaagt gcggggcagg agagcagaaa   3720
caagagaagc ccttggtagg ggggtcgttg gaaaaactg tggggtcttg ggctgaacgc    3780
gttgcccacg ggctggaggt tgcgatcccc ggacggaaag cgcgggagga ggaaggagag   3840
aaccggctct gaggtccaga gagagtgagg gggcagagcg acggcgagat ggggagagaa   3900
cacctagctg gagcaggttc tgcggtagag agcgcagtcc tgctggcctc tggagagtgc   3960
gcgccgctac ggaggctgcg tcgaggggag tgtcacccaa tctggccccc agctggcggg   4020
gcgccctgag agcttgcgaa ctgcagttgc aggacgcgcc ttctccacga gctatttcg    4080 tcgacttgcg gaacccaagg aacctcgcct ctatcatttc acggtgtagg gtccctagag   4140
acgacagcca agatcccagg ggctcccagg acgcttgttc ctgcggtgtc gtgtcctatg   4200
gggagttcct ggcgggacga aaggcggacg cgcggctctt cctggccctc caggcccgga   4260
accgacggga aaggttcccg tgattcccga gtccctgcag gcttcttcca gcgggagttg   4320 gtccggggc cttagaggcc tccaagcact gctttggagg atggtttcca aggatcgcgg   4380
tttgtgagtt gaaggctttg tgagaggtta accccaaa agatacatac ttggtaaact     4440
gaggctacct gtaaacacat ttcggcatta ggagaagatt cgagtaggga agtgaaggac   4500
```

```
aaccaccccg agttacattc cttcccccca ataaaaagct ctggggatga aagttcttt    4560
ggctttatc ttttcgattt aaaaatttga gaagaaaaat gtgactagag atgaatcctg    4620
gtgaatccga aattgaaaca caactccccc ttcccttcc tatcctctcg gttttagaac    4680
cgcgctctcc cgcccagga gattccttgg ggccgagggt tttccgggga acccgggcgc    4740
ccgccccttc tactgtccct ttgccccgcg ggcacagctt gcctccgtct gctttctcta    4800
cttctggacc tctcctcgcc gggcttttta aagggcttct cgtctcaaa acaaaacaaa    4860
aaaacccttt gctcttccca acctttcgc agcccgcccc agcggtggcg cgggaccagc    4920
aaaggcgaaa gccgcgcggc tcttgccggg cgcggacggt cgcgcagggg cgcccgcggc    4980
ctccgcaccc ggacctgagg tgttggtcga ctccgggcat ccacggtcgg gagggagggc    5040
tgagctgttc gatcctttac ttttcttcct caaagtctac ctgccaatgc ccctaagaag    5100
aaaaccaagt atgtgcgtgg agagtggggc ggcaggcaac ccgagttctt gagctccgga    5160
gcgacccaaa gcagcaactg gaacagcct caggaaaggg aggtcgggtg gagtgggctt    5220
tggggcagga gtcatggggc ccgggccccg ggacgacct ggcgctcccg gccctgctga    5280
acgctgagtt gcgcctagtc gggttttcga agaggccctt gcgcagagcg acccacgcgc    5340
gcggcagcat cttcgattag tcaggacatc ccagtaactg cttgaactgt aggtaggtaa    5400
aattcttgaa ggagtatttg ctgcgtgcga ctctgctgct ggtgcaacgg aggaagggg    5460
tgggggaagg aagtggcggg ggaaggagtg tggtggtggg ttaaaaaata agggaagccg    5520
aggcgagaga gacgcagacg cagaggtcga gcgcaggccg aaagctgttc accgttttct    5580
cgactccggg gaacatggtg ggatttcctt tctgcgccgg gtcgggagtt gtaaaacctc    5640
ggccacatta agatctgaaa actgtgatgc gtcctttctg cagagacgcc tctttctgaa    5700
tctgcccgga gcttcgagcc ccggcgtctg tccctcagcc tggcatggct tcttcggggg    5760
tctgctttgc atggggagag gggccacgca gcggcggact aggtttgggg attctcggta    5820
atggacccgg agcaatgact aacagccgct ccctctcact ttcccacagc gatcaccctc    5880
taacaccctc cctcccattc ccggcccgc gcgtgacaag gtcggctgct ttcagccggg    5940
agctagatcg gtgccccggc tcttcggagc cttagcaggc gttcgccaag gggtgactgg    6000
ctgtcattgg gagcaatatt tggccttgag gagaccctgg ggaggaagtg gcggggagct    6060
cgtgtttgct tgtgtgtgtg tggggggggg ggtgtgtgta cacgcgcgtg ggcagggtcc    6120
ctctgcgctt tccttttaa gtgcctctcg gtggtgaggc ttgggcggg tgagactttc    6180
ccgacctcgc tcccggcccc acttaagccg ggttcgagct gggagacgca gtcccttcag    6240
tgcgccccaa atcctctggc ttcaggtggc ccggcgcggg ggcccagcac gacgcaccgc    6300
gccgagaacc gggttctccg tgcgctgcgc cagtagccct gggagcgcgg cggccgcggg    6360
gcaccggccg agggctctgc cgagcgccgc cgggagctcc tcccggaccg ctgaggctcg    6420
ggcggcgggc gcggaggttg gcctcgcctg gaggggcggg cccgcgaggg gcgggggct    6480
gtggaggagg ggagggcgcg caggcccttt cgccgcctgc cgcgggaggg gcctcggcgc    6540
tcacgtgact ccgagggct ggaagaaaaa cagagcctgt ctgcggtgga gtctcattat    6600
attcaaatat tccttttagg agccattccg tagtgccatc ccgagcaacg cactgctgca    6660
gcttccctga gccttttccag caagtttgtt caagattggc tgtcaagaat catggactgt    6720
tattatatgc cttgttttct gtcagtgagt agacacctct tccttccccc tctccggaat    6780
tcactctgcc ctcaccaccc ctgctcgccg gctgtccctt ccgtcggacc tcctttacaa    6840
tatccacact ctgctccctg gcagcactgt cgctcccttc ttggcccggc agccggggcg    6900
```

```
ctggaagcgt acgggttcct tttaaagtgc tgctagcgcg cactcgccct ctcagcgttg    6960
caagaaaggg gagcgcgagg gagctaaaga gatgaaagcc cggggttgta ccttgagggc    7020
taaccactcc cttcccctat ccaacttgtc tgggagagcc cccagtgtct ccgtggcgcg    7080
ttcccactct cttgtcaaaa ctcacagagg tctctccgga atcgtctctc accccttccc    7140
tggggatgag cgggcacgat caggcacttt tggctgaata tttcaaactc atcggccaca    7200
ataaaataag ccctcaagcc acccggttag ctcccagacc accttctcgg cttctggacc    7260
ctgtcgccct ctgtcttcgc ccagcccctg cctctcactt tccctccctc tggctctgaa    7320
ccaactggaa gttgtgaaag ttgggctctg agggtgagg aaaagggaga gaagctgaag    7380
gtctaaagtg gagagcaatg ccatttaat tctccctccc ccaccccttt tcaccccctc    7440
aatgttaact gtttatcctt caagaagcca cgctgagatc atggcccaga tagcagttag    7500
gacaaaaaaa gattaacagg atggaggcta tctgatttgg ggttatttga ctgtaaacaa    7560
gttagaccaa gtaattacag ggcaattctt actttcaggc cgtgcatggc tgcagctggt    7620
gggtgggcgg gtggtgtgag ggagaagaca caaacttgat cttctgacc tgctttccat    7680 cttgcccctc catttctagc cctaaatgca tatgcagaca catctctatt tctccctatt    7740
tattggtgtt tgtttattct ttaaccttcc actcccctcc ccctcccag agacaccatg    7800 attcctggta accgaatgct gatggtcgtt ttattatgcc aagtcctgct aggaggcgcg    7860
agccatgcta gtttgatacc tgagacgggg aagaaaaaag tcgccgagat tcagggccac    7920
gcgggaggac gccgctcagg gcagagccat gagctcctgc gggacttcga ggcgacactt    7980
ctgcagatgt ttgggctgcg ccgccgcccg cagcctagca agagtgccgt cattccggac    8040
tacatgcggg atctttaccg gcttcagtct ggggaggagg aggaagagca gatccacagc    8100
actggtcttg agtatcctga gcgcccggcc agccgggcca acaccgtgag gagcttccac    8160
cacgaaggtc agtctcttcc cccagtctgc gtgggggagg gctggtggga ctggctagag    8220
gggcagtgaa agccctgggg aagaagagtt cgggttacat caaaccccag tccaggaggc    8280
tgaggaacag agctgcttac ctccaagaat ttgcagagct gccgccgaac ttatttttg    8340 gagacagagg gggaggtgtt caggggaagg ggaatgacag cactcagacg tgggctagcc    8400
ccagcggtgt gttttgcta tatcaaagcc ttttctgcta ggttttctgc ccgtttttt    8460 caaagcacct actgaattta atattacagc tgtgtgtttg tcgggtttat tcaatagggg    8520
ccttgtaatc cgatctgaat gtttcctagc ggatgtttct tttccaaagt aaatctgagt    8580
tattaatcca ccagcatcat tactgtgttg gaatttattt tcccctctgt aacatgatca    8640
acaaggcatg ctctgtgttt ccaagatcgc tggggaaatg tttagtaaca tactcaatag    8700
tggaagaggg agagggtggt tgtctccatg tttcctcctg cctgtgctct gttgcccct    8760 cttttctttt acaaccactt gtaaagaaaa ctgtggacac aaagccaagg tgggggttt    8820 aaaagaggag tctgattgtg gtgccataga ggagttgaca catagaaatt attagacata    8880
tcaaggaggc tggatatagt ttctgtcttt ggtgcttgag aaatgctagc tacatttgc    8940 tggtttgtta gctgccccac ttatctgctc cttcaaatta aggggtatgc ttattttccc    9000
ccagtaggtt tcccctgcat aagcagaatt caccattcat tgcccaaccc tgagctatct    9060
cttgactctt ccatctttga aaaagttca tatgcttttt cttttcccct tccttcctaa    9120
ctgtgcctag aacatctgga gaacatccca gggaccagtg aaaactctgc ttttcgtttc    9180
ctctttaacc tcagcagcat ccctgagaac gaggcgatct cctctgcaga gcttcggctc    9240
```

```
ttccgggagc aggtggacca gggccctgat tgggaaaggg gcttccaccg tataaacatt    9300
tatgaggtta tgaagccccc agcagaagtg gtgcctgggc acctcatcac acgactactg    9360
gacacgagac tggtccacca caatgtgaca cggtgggaaa cttttgatgt gagccctgcg    9420
gtccttcgct ggacccggga gaagcagcca aactatgggc tagccattga ggtgactcac    9480
ctccatcaga ctcggaccca ccagggccag catgtcagga ttagccgatc gttacctcaa    9540
gggagtggga attgggccca gctccggccc ctcctggtca cctttggcca tgatggccgg    9600
ggccatgcct tgacccgacg ccggagggcc aagcgtagcc ctaagcatca ctcacagcgg    9660
gccaggaaga agaataagaa ctgccggcgc cactcgctct atgtggactt cagcgatgtg    9720
ggctggaatg actggattgt ggccccacca ggctaccagg ccttctactg ccatgggac     9780
tgccccttc cactggctga ccacctcaac tcaaccaacc atgccattgt gcagaccctg     9840
gtcaattctg tcaattccag tatccccaaa gcctgttgtg tgcccactga actgagtgcc    9900
atctccatgc tgtacctgga tgagtatgat aaggtggtac tgaaaaatta tcaggagatg    9960
gtagtagagg gatgtgggtg ccgctgagat caggcagtcc ttgaggatag acagatatac    10020
acaccacaca cacacaccac atacaccaca cacacgtt cccatccact cacccacaca     10080
ctacacagac tgcttcctta tagctggact tttatttaaa aaaaaaaaa aaaaaatgga    10140
aaaaatccct aaacattcac cttgacctta tttatgactt tacgtgcaaa tgttttgacc    10200
atattgatca tatattttga caaaatatat ttataactac gtattaaaag aaaaaaataa    10260
aatgagtcat tattttaaag gtaaatcatg attttttttt ctccttaatc ctttctcttt    10320
tccttcgggc tcatctcttt tgaatgaggc ttttttctgt tcaggtgagt tggaggctgg    10380
atggaagtca aaaggtggta cctggaggtg gttaagttgt agggacagga agtaaactgt    10440
tggcagagag agatggtaat tgccagcatg aattgttttc tatttctatt taatgttaac    10500
aaggatgcag tatcctctcc catctggatg acacatgcct tggagaaaca ctgggatgaa    10560
aggagtgtag gtcagattaa agacttcatt tcaggccccct tgtacatctt ctgtttcact    10620
cacctgttga ggtgtatcac agctgagcgt gatgaggtct caaccctaga aaaatgatac    10680
ccacctctgc tttcatgata cctcagggta tctccagtta ttacaggtac caatgtgata    10740
tttccaaatc aaaactaatt tgtacactaa catcataatg tgtgtgtgaa ggcatgtttt    10800
taaacttatt ttttttttct ccaggtagga ctcttttgtt ttttcttttg tcttttttt    10860
tttgaaacaa gttctctctt tgttgcccca ggctggtctt gaactcctgg gctcaagcaa    10920
tcttctcatt tcggcctctt tgggattaca ggcatgcact gctattttgt cttttttttt    10980
ttttttgtaac aaataatgta ccctaccttc aaaaagtttg atgactactg ttttaatatg    11040
ccacttgata gaatttccca ttgtttcttg acttttttccc ttgtcctctt ttcccaatgt    11100
gaaggccttc atcaagttta ggatcccaac agattgggct gggtgggggt tgacaatggg    11160
gtcagatact aaagggtcag aatttctaag caggcactgt gaaggtgtcc cactattata    11220
cagaaatctc gag                                                       11233
```

<210> SEQ ID NO 106
<211> LENGTH: 1723
<212> TYPE: DNA
<213> ORGANISM: Homo sapiens
<220> FEATURE:
<221> NAME/KEY: misc_feature
<223> OTHER INFORMATION: BB1=BAR1 Acc. No. NM_000684

<400> SEQUENCE: 106

```
tgctacccgc gcccgggctt ctggggtgtt ccccaaccac ggcccagccc tgccacaccc    60
cccgcccccg gcctccgcag ctcggcatgg gcgcggggt gctcgtcctg ggcgcctccg    120
agcccggtaa cctgtcgtcg gccgcaccgc tccccgacgg cgcggccacc gcggcgcggc    180
tgctggtgcc cgcgtcgccg cccgcctcgt tgctgcctcc cgccagcgaa agccccgagc    240
cgctgtctca gcagtggaca gcgggcatgg gtctgctgat ggcgctcatc gtgctgctca    300
tcgtggcggg caatgtgctg gtgatcgtgg ccatcgccaa gacgccgcgg ctgcagacgc    360
tcaccaacct cttcatcatg tccctggcca gcgccgacct ggtcatgggg ctgctggtgg    420
tgccgttcgg ggccaccatc gtggtgtggg gccgctggga gtacggctcc ttcttctgcg    480
agctgtggac ctcagtggac gtgctgtgcg tgacggccag catcgagacc ctgtgtgtca    540
ttgccctgga ccgctacctc gccatcacct cgcccttccg ctaccagagc ctgctgacgc    600
gcgcgcgggc gcggggcctc gtgtgcaccg tgtgggccat ctcggccctg gtgtccttcc    660
tgcccatcct catgcactgg tggcgggcgg agagcgacga ggcgcgccgc tgctacaacg    720
accccaagtg ctgcgacttc gtcaccaacc gggcctacgc catcgcctcg tccgtagtct    780
ccttctacgt gcccctgtgc atcatggcct tcgtgtacct gcgggtgttc cgcgaggccc    840
agaagcaggt gaagaagatc gacagctgcg agcgccgttt cctcggcggc ccagcgcggc    900
cgccctcgcc ctcgccctcg cccgtccccg cgcccgcgcc gccgcccgga ccccgcgcc     960 ccgccgccgc cgccgccacc gccccgctgg ccaacgggcg tgcgggtaag cggcggcct   1020 cgcgcctcgt ggccctacgc gagcagaagg cgctcaagac gctgggcatc atcatgggcg   1080
tcttcacgct ctgctggctg cccttcttcc tggcaacgt ggtgaaggcc ttccaccgcg    1140
agctggtgcc cgaccgcctc ttcgtcttct caactggct gggctacgcc aactcggcct    1200
tcaaccccat catctactgc cgcagcccg acttccgcaa ggccttccag ggactgctct    1260
gctgcgcgcg cagggctgcc cgccggcgcc acgcgaccca cggagaccgg ccgcgcgcct   1320
cgggctgtct ggcccggccc ggaccccgc catcgcccgg ggccgcctcg acgacgacg    1380 acgacgatgt cgtcggggcc acgccgcccg cgcgcctgct ggagccctgg gccggctgca   1440
acggcggggc ggcggcggac agcgactcga gcctggacga gccgtgccgc cccggcttcg   1500
cctcggaatc caaggtgtag ggccggcgc ggggcgcgga ctccgggcac ggcttcccag    1560
gggaacgagg agatctgtgt ttacttaaga ccgatagcag gtgaactcga agcccacaat   1620
cctcgtctga atcatccgag gcaaagagaa aagccacgga ccgttgcaca aaaaggaaag   1680
tttgggaagg gatgggagag tggcttgctg atgttccttg ttg                    1723
```

<210> SEQ ID NO 107
<211> LENGTH: 1145
<212> TYPE: DNA
<213> ORGANISM: Homo sapiens
<220> FEATURE:
<221> NAME/KEY: misc_feature
<223> OTHER INFORMATION: IL-6: Acc. No. X04430

<400> SEQUENCE: 107

```
aggactggag atgtctgagg ctcattctgc cctcgagccc accgggaacg aaagagaagc     60
tctatctccc ctccaggagc ccagctatga actccttctc cacaagcgcc ttcggtccag    120
ttgccttctc cctggggctg ctcctggtgt tgcctgctgc cttccctgcc ccagtacccc    180
caggagaaga ttccaaagat gtagccgccc cacacagaca gccactcacc tcttcagaac    240
gaattgacaa acaaattcgg tacatcctcg acggcatctc agccctgaga aaggagacat    300
```

| | |
|---|---|
| gtaacaagag taacatgtgt gaaagcagca aagaggcact ggcagaaaac aacctgaacc | 360 |
| ttccaaagat ggctgaaaaa gatggatgct tccaatctgg attcaatgag gagacttgcc | 420 |
| tggtgaaaat catcactggt cttttggagt ttgaggtata cctagagtac ctccagaaca | 480 |
| gatttgagag tagtgaggaa caagccagag ctgtccagat gagtacaaaa gtcctgatcc | 540 |
| agttcctgca gaaaaaggca aagaatctag atgcaataac caccccctgac ccaaccacaa | 600 |
| atgccagcct gctgacgaag ctgcaggcac agaaccagtg gctgcaggac atgacaactc | 660 |
| atctcattct gcgcagcttt aaggagttcc tgcagtccag cctgagggct cttcggcaaa | 720 |
| tgtagcatgg gcacctcaga ttgttgttgt taatgggcat tccttcttct ggtcagaaac | 780 |
| ctgtccactg ggcacagaac ttatgttgtt ctctatggag aactaaaagt atgagcgtta | 840 |
| ggacactatt ttaattattt ttaatttatt aatatttaaa tatgtgaagc tgagttaatt | 900 |
| tatgtaagtc atatttttata tttttaagaa gtaccacttg aaacatttta tgtattagtt | 960 |
| ttgaaataat aatggaaagt ggctatgcag tttgaatatc ctttgtttca gagccagatc | 1020 |
| atttcttgga aagtgtaggc ttacctcaaa taaatggcta actttataca tatttttaaa | 1080 |
| gaaatattta tattgtattt atataatgta taaatggttt ttataccaat aaatggcatt | 1140 |
| ttaaa | 1145 |

<210> SEQ ID NO 108
<211> LENGTH: 2063
<212> TYPE: DNA
<213> ORGANISM: Homo sapiens
<220> FEATURE:
<221> NAME/KEY: misc_feature
<223> OTHER INFORMATION: U82535

<400> SEQUENCE: 108

| | |
|---|---|
| tgccgggcgg taggcagcag caggctgaag ggatcatggt gcagtacgag ctgtgggccg | 60 |
| cgctgcctgg cgcctccggg gtcgccctgg cctgctgctt cgtggcgcg gccgtggccc | 120 |
| tgcgctggtc cgggcgccgg acggcgcggg gcgcggtggt ccgggcgcga cagaagcagc | 180 |
| gagcgggcct ggagaacatg gacagggcgg cgcagcgctt ccggctccag aacccagacc | 240 |
| tggactcaga ggcgctgcta gccctgcccc tgcctcagct ggtgcagaag ttacacagta | 300 |
| gagagctggc ccctgaggcc gtgctcttca cctatgtggg aaaggcctgg gaagtgaaca | 360 |
| aagggaccaa ctgtgtgacc tcctatctgg ctgactgtga gactcagctg tctcaggccc | 420 |
| caaggcaggg cctgctctat ggcgtccctg tgagcctcaa ggagtgcttc acctacaagg | 480 |
| gccaggactc cacgctgggc ttgagcctga atgaaggggt gccggcgag tgcgacagcg | 540 |
| tagtggtgca tgtgctgaag ctgcagggtg ccgtgccctt cgtgcacacc aatgttccac | 600 |
| agtccatgtt cagctatgac tgcagtaacc ccctcttttgg ccagaccgtg aacccatgga | 660 |
| agtcctccaa aagcccaggg ggctcctcag ggggtgaagg ggccctcatc gggtctggag | 720 |
| gctccccccct gggcttaggc actgatatcg gaggcagcat ccgcttcccc tcctccttct | 780 |
| gcggcatctg cggcctcaag cccacaggga accgcctcag caagagtggc ctgaagggct | 840 |
| gtgtctatgg acaggaggca gtgcgtctct ccgtgggccc catggccgg gacgtggaga | 900 |
| gcctggcact gtgcctgcga gccctgctgt gcgaggacat gttccgcttg gaccccactg | 960 |
| tgcctcccctt gcccttcaga gaagaggtct acaccagctc tcagcccctg cgtgtgggt | 1020 |
| actatgagac tgcaactat accatgccct cccggccat gaggcgggcc gtgctggaga | 1080 |
| ccaaacagag ccttgaggct gcggggcaca cgctggttcc cttcttgcca agcaacatac | 1140 |

| | |
|---|---|
| cccatgctct ggagaccctg tcaacaggtg ggctcttcag tgatggtggc cacaccttcc | 1200 |
| tacagaactt caaaggtgat ttcgtggacc cctgcctggg ggacctggtc tcaattctga | 1260 |
| agcttcccca atggcttaaa ggactgctgg ccttcctggt gaagcctctg ctgccaaggc | 1320 |
| tgtcagcttt cctcagcaac atgaagtctc gttcggctgg aaaactctgg gaactgcagc | 1380 |
| acgagatcga ggtgtaccgc aaaaccgtga ttgcccagtg gagggcgctg gacctggatg | 1440 |
| tggtgctgac ccccatgctg gcccctgctc tggacttgaa tgccccaggc agggccacag | 1500 |
| gggccgtcag ctacactatg ctgtacaact gcctggactt ccctgcaggg gtggtgcctg | 1560 |
| tcaccacggt gactgctgag gacgaggccc agatggaaca ttacaggggc tactttgggg | 1620 |
| atatctggga caagatgctg cagaagggca tgaagaagag tgtggggctg ccggtggccg | 1680 |
| tgcagtgtgt ggctctgccc tggcaagaag agttgtgtct gcggttcatg cgggaggtgg | 1740 |
| agcgactgat gacccctgaa aagcagtcat cctgatgggct ctggctccag aggacctgag | 1800 |
| actcacactc tctgcagccc agcctagtca gggcacagct gccctgctgc cacagcaagg | 1860 |
| aaatgtcctg catgggcag aggcttccgt gtcctctccc ccaaccccct gcaagaagcg | 1920 |
| ccgactccct gagtctggac ctccatccct gctctggtcc cctctcttcg tcctgatccc | 1980 |
| tccaccccca tgtggcagcc catgggtatg acataggcca aggcccaact aacagtcaag | 2040 |
| aaacaaaaaa aaaaaaaaaa aaa | 2063 |

```
<210> SEQ ID NO 109
<211> LENGTH: 2729
<212> TYPE: DNA
<213> ORGANISM: Homo sapiens
<220> FEATURE:
<221> NAME/KEY: misc_feature
<223> OTHER INFORMATION: ACAT-1: Acc. No. XM_031119

<400> SEQUENCE: 109
```

| | |
|---|---|
| agcttagcag gcgacgttgc gggccctggg cgccaggaga gcttcccgga gtcgaccttc | 60 |
| ctgctggctg ctctgtgacc gcttcccggc tctgccctct tggccgaagt gcccgctgcc | 120 |
| gggcgcgggc ctcagacaat acaatggtgg gtgaagagaa gatgtctcta agaaaccggc | 180 |
| tgtcaaagtc cagggaaaat cctgaggaag atgaagacca gagaaaccct gcaaaggagt | 240 |
| ccctagagac acctagtaat ggtcgaattg acataaaaca gttgatagca aagaagataa | 300 |
| agttgacagc agaggcagag gaattgaagc cattttttat gaaggaagtt ggcagtcact | 360 |
| ttgatgattt tgtgaccaat ctcattgaaa agtcagcatc attagataat ggtgggtgcg | 420 |
| ctctcacaac cttttctgtt cttgaaggag agaaaaacaa ccatagagcg aaggatttga | 480 |
| gagcacctcc agaacaagga aagattttta ttgcaaggcg ctctctctta gatgaactgc | 540 |
| ttgaagtgga ccacatcaga acaatatatc acatgtttat tgccctcctc attctcttta | 600 |
| tcctcagcac acttgtagta gattacattg atgaaggaag ctggtgctt gagttcagcc | 660 |
| tcctgtctta tgcttttggc aaatttccta ccgttgtttg gacctggtgg atcatgttcc | 720 |
| tgtctacatt ttcagttccc tattttctgt ttcaacattg ggccactggc tatagcaaga | 780 |
| gttctcatcc gctgatccgt tctctcttcc atggctttct tttcatgatc ttccagattg | 840 |
| gagttctagg ttttggacca acatatgttg tgttagcata tacactgcca ccagcttccc | 900 |
| ggttcatcat tatattcgag cagattcgtt ttgtaatgaa ggcccactca tttgtcagag | 960 |
| agaacgtgcc tcgggtacta aattcagcta aggagaaatc aagcactgtt ccaataccta | 1020 |
| cagtcaacca gtatttgtac ttcttatttg ctcctacct tatctaccgt gacagctatc | 1080 |

-continued

| | |
|---|---|
| ccaggaatcc cactgtaaga tggggttatg tcgctatgaa gtttgcacag gtctttggtt | 1140 |
| gcttttcta tgtgtactac atctttgaaa ggctttgtgc cccttgttt cggaatatca | 1200 |
| aacaggagcc cttcagcgct cgtgttctgg tcctatgtgt atttaactcc atcttgccag | 1260 |
| gtgtgctgat tctcttcctt actttttttg ccttttgca ctgctggctc aatgcctttg | 1320 |
| ctgagatgtt acgctttggt gacaggatgt tctataagga ttggtggaac tccacgtcat | 1380 |
| actccaacta ttatagaacc tggaatgtgg tggtccatga ctggctatat tactatgctt | 1440 |
| acaaggactt tctctggttt ttctccaaga gattcaaatc tgctgccatg ttagctgtct | 1500 |
| ttgctgtatc tgctgtagta cacgaatatg ccttggctgt ttgcttgagc ttttctatc | 1560 |
| ccgtgctctt cgtgctcttc atgttctttg gaatggcttt caacttcatt gtcaatgata | 1620 |
| gtcggaaaaa gccgatttgg aatgttctga tgtggacttc tcttttcttg ggcaatggag | 1680 |
| tcttactctg ctttattct caagaatggt atgcacgtca gcactgtcct ctgaaaaatc | 1740 |
| ccacattttt ggattatgtc cggccacgtt cctggacttg tcgttacgtg ttttagaagc | 1800 |
| ttggactttg tttcctcctt gtcactgaag attgggtagc tccctgattt ggagccagct | 1860 |
| gtttccagtt gttactgaag ttatctgtgt tatttggacc actccaggct ttacagatga | 1920 |
| ctcactccat tcctaggtca cttgaagcca aactgttgga agttcactgg agtcttgtac | 1980 |
| acttaagcag agcagaactt tttttgtggg gctgggtggg gggagaagac cgactaacag | 2040 |
| ctgaagtaat gacagattgt tgctgggtca tatcagcttt atcccttggt aattatatct | 2100 |
| gttttgtttc ttgactctgt ccaatcagag aataaacatc atagtttctt ggccactgaa | 2160 |
| ttagccaaaa cacttaggaa gaaatcactt aaatacctct ggcttagaaa tttttcatg | 2220 |
| cacactgttg gaatgtatgc taattgaaca tgcaattggg gaagaaaaaa tgtagaatga | 2280 |
| tttttgctat ttctagtaga aagaaaatgt ctgtttttcca aagataatgt tatacatcct | 2340 |
| attttgtaat ttttttgaaa aaagttcaat gttcagtttt ccttagtttt taccttgttt | 2400 |
| tctctatagg tcatgatttc tgtgaagcaa aaagatgcct tttaccatga attcttgagt | 2460 |
| ttacatcaat aatattgtat attaagggga tcagaagtag gaaggaaaaa ataagagata | 2520 |
| gcagaggaaa aagaaaaaca tttcctctta aacttctga agtaatttgt aaaaaagatt | 2580 |
| tgtagagtca atcatgtgtt taaattattt tatcacaaac ttaacatgga agatattcct | 2640 |
| ttttaacttt gtggtaactt cttttgaagtt atttagaaat atcctttgga acaattattt | 2700 |
| tattgtctaa taaatattga cttctcttg | 2729 |

<210> SEQ ID NO 110
<211> LENGTH: 3779
<212> TYPE: DNA
<213> ORGANISM: Homo sapiens
<220> FEATURE:
<221> NAME/KEY: misc_feature
<223> OTHER INFORMATION: IBAT:  Acc. No. NM_000452

<400> SEQUENCE: 110

| | |
|---|---|
| ttctattgaa agggaaatgg gagaacaata tgtgttccta tggctcagtc cctataagat | 60 |
| tctgtactat tcagagttga ttttaagtgt cacttaactg aaattatcca acaaaccttc | 120 |
| atggcatgaa acattaacac agctcttttt atatggcatg gttcctatgg ctcaatccct | 180 |
| ataagattct gtactagttc agagttgatt ttaaagtca cttaactgaa attatccaac | 240 |
| aaaccctcga ggacattaaa cattaacgtg gctctttta tatggcatgg ttcattatca | 300 |
| tgccaataaa tgattaatcg taactctctg tcttgaccaa taattttgct ggacttttgt | 360 |

```
gattcacaac gtgctctgtg ttgtaatgct acctcttgaa actgacatcc tagctttatt    420 gtttttatt acttccctaa ggtggctttc aaaagagaca ccaagtgaca tattttagg     480 aggggtttaa aagtttgatg gggtagaagt aaacgttgct taactcaacc agcagcagag    540
ccagggccca gggaccagcg cttctgtgga cttggccttt ccagcagcag acccagcaat    600
gaatgatccg aacagctgtg tggacaatgc aacagtttgc tctggtgcat cctgtgtggt    660
acctgagagc aatttcaata acatcctaag tgtggtccta agtacggtgc tgaccatcct    720
gttggccttg gtgatgttct ccatgggatg caacgtggaa atcaagaaat ttctagggca    780
cataaagcgg ccgtggggca tttgtgttgg cttcctctgt cagtttggaa tcatgcccct    840
cacaggattc atcctgtcgg tggcctttga catcctcccg ctccaggccg tagtggtgct    900
cattatagga tgctgccctg gaggaactgc ctccaatatc ttggcctatt gggtcgatgg    960
cgacatggac ctgagcgtca gcatgaccac atgctccaca ctgcttgccc tcggaatgat   1020
gccgctgtgc ctccttatct ataccaaaat gtgggtcgac tctgggagca tcgtaattcc   1080
ctatgataac ataggtacat ctctggttgc tctcgttgtt cctgtttcca ttggaatgtt   1140
tgttaatcac aaatggcccc aaaaagcaaa gatcatactt aaaattgggt ccatcgcggg   1200
cgccatcctc attgtgctca tagctgtggt tggaggaata ttgtaccaaa gcgcctggat   1260
cattgctccc aaactgtgga ttataggaac aatatttcct gtggcgggtt actccctggg   1320
gtttcttctg gctagaattg ctggtctacc ctggtacagg tgccgaacgg ttgcttttga   1380
aacggggatg cagaacacgc agctatgttc caccatcgtt cagctctcct tcactcctga   1440
ggagctcaat gtcgtattca ccttcccgct catctacagc attttccagc tcgcctttgc   1500
cgcaatattc ttaggatttt atgtggcata caagaaatgt catggaaaaa acaaggcaga   1560
aattccagag agcaaagaaa atggaacgga gccagagtca tcgttttata aggcaaatgg   1620
aggatttcaa cctgacgaaa agtagacatc aagtggacaa acagacgag ttccaaatta   1680 cgttcttaaa ccgtaactat atttaattat ttgttttggt aggacagttg gcagaaaaga   1740
gttaaagtga aaattggaat tcattggaa ttcatgtatt ggtttcagta ccaagtgact   1800
ggtggcccaa ttctttaatg ggacaaatat tgtttcctat atatatgtat atgttttata   1860
tatgtatgta tactcatata gatatattgt cattgaaata ttcccccaaa atattctcag   1920
actaaacctg acatagggaa caccgagaat gaaaacatcg ttaacaccaa aactgaattc   1980
ttatgcagaa tttcctagcc catagatgac aacctgagtt tctgtatgtt aaagtagatg   2040
taatgaatta ttattattac agtggtcacg attttcttca gtgtttatga ttataaaaat   2100
tgacatgaac atctttcact gacattttaa tcattatttt aaaagctttg caacctatat   2160
atttatataa ctttgtaata taacatgggc aaatatctga cttcagtatt tttaaaaagt   2220
tgccttctcc agtggcagtc caaaagcaga atgagagga aattattaca aaatagaatt   2280
caataaccat attggatgca ggctcttaac tcagcaggga tatcgtacat ctattgctct   2340
acctcagggg tccagtgata cccactagat cttccaagga aaaacataat tctttcaaac   2400
ggtgtgtatt tggcaaagag ctcttcaaat ctgggagagg gacttcctca aggttttcct   2460
gtgtgcagtg gatccacata gctaatatga cagctagtca gttgacaggg accacccaca   2520
gtaagcacca tggtcaggga ggtggcagga ggtgcaaaga cagaagtatt gagagaaaca   2580
ccaagactct agtggaggaa ttaattcaat gggagatagt ataaaataca tagaaaacac   2640
aagtaacaga aacctggttg aaatgcttaa ctagagtcaa ttagatgtgc aggagtaagt   2700
agtataagaa gaatcaagtc cgagagtgat caggaaatga gtattaaaca gtatttgaaa   2760
```

```
cagagaacgt gtcccagggc ccaaaagtca gaagggcccc accagccagg aaagttgttt    2820
caatgctgta agtaggtgta gccaagggaa gccaggacta tctgatatac ggtagcaggg    2880
gtttacggct gccaggggaa ataaactcat caagtgttgg actttcaatt ataagatcga    2940
atttaatttc ctttccctca ttctgcagca atcagaatac acaatcttaa ccactcggtc    3000
cttagtggtt ttgttccatt ttgcattggg tattttcact gcctcataga gtctatttca    3060
agtgtttggc tgaaagggct ttttgcattt gcatgttctg agttcagatt ctgctggtgc    3120
acccaagcat tatgggaaca ggaactcaac ttagctcttc cagtagaggg gtgagggatt    3180
ctgcttttca aattcataac attgatcttt ttatgcaaga tttccattta cagttgaata    3240
agtacttcat atttttccat cattagacaa atacaaaatg gactaaataa ttttaagaga    3300
tagtggaggc agcagggggt acagacttcc ttcttagaga gtgtcagaga atatgctccc    3360
aatggtggaa aggaagattt acagtctagc ggctaagtac ctcctacaca tttcccatca    3420
atcagaaaat agacaggtac actaaaggga cctgagaact cctcttgtaa tttcaacaca    3480
cccaaaatca agggcctgga tgccagcagc tgcagcaagc aggttttttcc tccctgttga    3540 gcaagacagg tgaggcaaga taggacttgg ctttcttaca tgatgcggta acttgtgact    3600
tgagtctttt tccctaattt gctagtggga agaaaaatag ctgagctttc taaaatgata    3660
gctctctatt tttaaatgaa tttgaaaagt cgattaaatt atgtattta ttgcctctga    3720 gtatcatatt aaatgaatat tttattttaa aggcttaaat aaatgaaaat gattttgt      3779

<210> SEQ ID NO 111
<211> LENGTH: 4067
<212> TYPE: DNA
<213> ORGANISM: Homo sapiens
<220> FEATURE:
<221> NAME/KEY: misc_feature
<223> OTHER INFORMATION: U28749

<400> SEQUENCE: 111
cttgaatctt ggggcaggaa ctcagaaaac ttccagcccg gcagcgcgc gcttggtgca      60 agactcagga gctagcagcc cgtcccctc cgactctccg gtgccgccgc tgcctgctcc     120
cgccacccta ggaggcgcgg tgccacccac tactctgtcc tctgcctgtg ctccgtgccc    180
gaccctatcc cggcggagtc tccccatcct ccttttgcttt ccgactgccc aaggcacttt    240
caatctcaat ctcttctctc tctctctctc tctctctgtc tctctctctc tctctctctc    300
tctctctctc gcagggtggg gggaagagga ggaggaattc tttccccgcc taacatttca    360
agggacacaa ttcactccaa gtctcttccc tttccaagcc gcttccgaag tgctcccggt    420
gcccgcaact cctgatccca acccgcgaga ggagcctctg cgacctcaaa gcctctcttc    480 cttctcccctc gcttccctcc tcctcttgct acctccacct ccaccgccac ctccacctcc    540
ggcacccacc caccgccgcc gccgccaccg gcagcgcctc ctcctctcct cctcctcctc    600
ccctcttctc tttttggcag ccgctggacg tccggtgttg atggtggcag cggcggcagc    660
ctaagcaaca gcagccctcg cagcccgcca gctcgcgctc gccccgcgg cgtccccagc    720 cctatcacct catctcccga aaggtgctgg gcagctccgg ggcggtcgag gcgaagcggc    780
tgcagcggcg gtagcggcgg cgggaggcag gatgagcgca cgcggtgagg gcgcggggca    840
gccgtccact tcagcccagg gacaacctgc cgccccagcg cctcagaaga gaggacgcgg    900
ccgccccagg aagcagcagc aagaaccaac cggtgagccc tctcctaaga gacccagggg    960
aagacccaaa ggcagcaaaa acaagagtcc ctctaaagca gctcaaaaga aagcagaagc   1020
```

```
cactggagaa aaacggccaa gaggcagacc taggaaatgg ccacaacaag ttgttcagaa    1080
gaagcctgct caggaggaaa ctgaagagac atcctcacaa gagtctgccg aagaggacta    1140
gggggcgcaa cgttcgattt ctacctcagc agcagttgga tcttttgaag ggagaagaca    1200
ctgcagtgac cacttattct gtattgccat ggtctttcca ctttcatctg ggtggggtg     1260 gggtggggtg gggaggggg gggtggggtg gggagaaatc acataaccct aaaaaggact     1320
atattaatca ccttctttgt aatcccttca cagtcccagg tttagtgaaa aactgctgta    1380
aacacagggg acacagctta acaatgcaac ttttaattac tgttttcttt tttcttaacc    1440
tactaatagt ttgttgatct gataagcaag agtgggcggg tgagaaaaac cgaattgggt    1500
ttagtcaatc actgcactgc atgcaaacaa gaaacgtgtc acttgtga cgtcgggcat      1560 tcatatagga agaacgcggt gtgtaacact gtgtacacct caaataccac cccaacccac    1620
tccctgtagt gaatcctctg tttagaacac caaagataag gactagatac tactttctct    1680
ttttcgtata atcttgtaga cacttacttg atgatttta acttttatt tctaaatgag       1740 acgaaatgct gatgtatcct ttcattcagc taacaaacta gaaaaggtta tgttcatttt    1800
tcaaaaaggg aagtaagcaa acaaatattg ccaactcttc tatttatgga tatcacacat    1860
atcagcagga gtaataaatt tactcacagc acttgtttc aggacaacac ttcattttca     1920
ggaaatctac ttcctacaga gccaaaatgc catttagcaa taaataacac ttgtcagcct    1980
cagagcattt aaggaaacta gacaagtaaa attatcctct ttgtaattta atgaaaaggt    2040
acaacagaat aatgcatgat gaactcacct aattatgagg tgggaggagc gaaatctaaa    2100
tttcttttgc tatagttata catcaattta aaaagcaaaa aaaaaaggg ggggcaatc      2160 tctctctgtg tctttctctc tctctctccc tctccctctc tcttttcatg tgtatcagtt    2220
tccatgaaag acctgaatac cacttacctc aaattaagca tatgtgttac ttcaagtaat    2280
acgttttgac ataagatggt tgaccaaggt gcttttcttc ggcttgagtt caccatctct    2340
tcattcaaac tgcactttta gccagagatg caatatatcc ccactactca atactacctc    2400
tgaatgttac aacgaattta cagtctagta cttattacat gctgctatac acaagcaatg    2460
caagaaaaaa acttactggg taggtgattc taatcatctg cagttctttt tgtacactta    2520
attacagtta aagaagcaat ctccttactg tgtttcagca tgactatgta tttttctatg    2580
tttttttaat taaaaatttt taaaatactt gtttcagctt ctctgctaga tttctacatt    2640
aacttgaaaa ttttttaacc aagtcgctcc taggttctta aggataattt tcctcaatca    2700
cactacacat cacacaagat ttgactgtaa tatttaaata ttaccctcca agtctgtacc    2760
tcaaatgaat tctttaagga gatggactaa ttgacttgca aagacctacc tccagacttc    2820
aaaaggaatg aacttgttac ttgcagcatt catttgtttt ttcaatgttt gaaatagttc    2880
aaactgcagc taaccctagt caaaactatt tttgtaaaag acatttgata gaaaggaaca    2940 cgttttttaca tactttttgca aaataagtaa ataataaata aaataaagcc aaccttcaaa   3000
gaacttgaag ctttgtaggt gagatgcaac aagccctgct tttgcataat gcaatcaaaa    3060
atatgtgttt ttaagattag ttgaatataa gaaaatgctt gacaaatatt ttcatgtatt    3120
ttacacaaat gtgattttg taatatgtct caaccagatt tattttaaac gcttcttatg     3180
tagagttttt atgcctttct ctccagtga gtgtgctgac ttttaacat ggtattatca      3240 actgggccag gaggtagttt ctcatgacgg cttttgtcag tatggctttt agtactgaag    3300
ccaaatgaaa ctcaaaacca tctctcttcc agctgcttca gggaggtagt ttcaaaggcc    3360
```

-continued

| | |
|---|---|
| acatacctct ctgagactgg cagatcgctc actgttgtga atcaccaaag gagctatgga | 3420 |
| gagaattaaa actcaacatt actgttaact gtgcgttaaa taagcaaata aacagtggct | 3480 |
| cataaaaata aaagtcgcat tccatatctt tggatgggcc ttttagaaac ctcattggcc | 3540 |
| agctcataaa atggaagcaa ttgctcatgt tggccaaaca tggtgcaccg agtgatttcc | 3600 |
| atctctggta aagttacact tttatttcct gtatgttgta caatcaaaac acactactac | 3660 |
| ctcttaagtc ccagtatacc tcatttttca tactgaaaaa aaaagcttgt ggccaatgga | 3720 |
| acagtaagaa catcataaaa ttttatata tatagtttat ttttgtggga gataaatttt | 3780 |
| ataggactgt tctttgctgt tgttggtcgc agctacataa gactggacat ttaacttttc | 3840 |
| taccatttct gcaagttagg tatgtttgca ggagaaaagt atcaagacgt ttaactgcag | 3900 |
| ttgactttct ccctgttcct ttgagtgtct tctaaccttta ttctttgttc tttatgtaga | 3960 |
| attgctgtct atgattgtac tttgaatcgc ttgcttgttg aaaatatttc tctagtgtat | 4020 |
| tatcactgtc tgttctgcac aataaacata acagcctctg tgatccc | 4067 |

<210> SEQ ID NO 112
<211> LENGTH: 511
<212> TYPE: DNA
<213> ORGANISM: Homo sapiens
<220> FEATURE:
<221> NAME/KEY: misc_feature
<223> OTHER INFORMATION: NM_016362

<400> SEQUENCE: 112

| | |
|---|---|
| gcaggcccac ctgtctgcaa cccagctgag gccatgccct ccccagggac cgtctgcagc | 60 |
| ctcctgctcc tcggcatgct ctggctggac ttggccatgg caggctccag cttcctgagc | 120 |
| cctgaacacc agagagtcca gcagagaaag gagtcgaaga agccaccagc caagctgcag | 180 |
| ccccgagctc tagcaggctg gctccgcccg gaagatggag gtcaagcaga aggggcagag | 240 |
| gatgaactgg aagtccggtt caacgccccc tttgatgttg gaatcaagct gtcaggggtt | 300 |
| cagtaccagc agcacagcca ggccctgggg aagtttcttc aggacatcct ctgggaagag | 360 |
| gccaaagagg ccccagccga caagtgatcg cccacaagcc ttactcacct ctctctaagt | 420 |
| ttagaagcgc tcatctggct tttcgcttgc ttctgcagca actcccacga ctgttgtaca | 480 |
| agctcaggag gcgaataaat gttcaaactg t | 511 |

<210> SEQ ID NO 113
<211> LENGTH: 2268
<212> TYPE: DNA
<213> ORGANISM: Homo sapiens
<220> FEATURE:
<221> NAME/KEY: misc_feature
<223> OTHER INFORMATION: S77410

<400> SEQUENCE: 113

| | |
|---|---|
| accccaggca gcagcgagtg acaggacgtc tggaccggcg cgccgctagc agctctgccg | 60 |
| ggccgcggcg gtgatcgatg gggagcggct ggagcggacc cagcgagtga gggcgcacag | 120 |
| ccgggacgcc gaggcggcgg gcgggagacc cgcaccagcg cagccggccc tcggcgggac | 180 |
| gtgacgcagc gcccggggcg cgggtttgat atttgacaaa ttgatctaaa atggctgggt | 240 |
| ttttatctga ataactcact gatgccatcc cagaaagtcg gcaccaggtg tatttgatat | 300 |
| agtgtttgca acaaattcga cccaggtgat caaaatgatt ctcaactctt ctactgaaga | 360 |
| tggtattaaa agaatccaag atgattgtcc caaagctgga aggcataatt acatatttgt | 420 |
| catgattcct actttataca gtatcatctt tgtggtggga atatttggaa acagcttggt | 480 |

-continued

```
ggtgatagtc atttactttt atatgaagct gaagactgtg gccagtgttt ttcttttgaa      540
tttagcactg gctgacttat gcttttact gactttgcca ctatgggctg tctacacagc       600
tatggaatac cgctggccct ttggcaatta cctatgtaag attgcttcag ccagcgtcag      660
tttcaacctg tacgctagtg tgtttctact cacgtgtctc agcattgatc gatacctggc      720
tattgttcac ccaatgaagt cccgccttcg acgcacaatg cttgtagcca aagtcacctg      780
catcatcatt tggctgctgg caggcttggc cagtttgcca gctataatcc atcgaaatgt      840
attttcatt gagaacacca atattacagt ttgtgctttc cattatgagt cccaaaattc       900
aacccttccg atagggctgg gcctgaccaa aaatatactg ggtttcctgt ttccttttct      960
gatcattctt acaagttata ctcttatttg gaaggcccta agaaggctt atgaaattca      1020
gaagaacaaa ccaagaaatg atgatatttt taagataatt atggcaattg tgcttttctt     1080
tttcttttcc tggattcccc accaaatatt cacttttctg gatgtattga ttcaactagg     1140
catcatacgt gactgtagaa ttgcagatat tgtggacacg gccatgccta tcaccatttg     1200
tatagcttat tttaacaatt gcctgaatcc tctttttat ggctttctgg ggaaaaaatt      1260
taaaagatat tttctccagc ttctaaaata tattcccca aaagccaaat cccactcaaa      1320
cctttcaaca aaaatgagca cgcttcccta ccgcccctca gataatgtaa gctcatccac     1380
caagaagcct gcaccatgtt tgaggttga gtgacatgtt cgaaacctgt ccataaagta      1440
attttgtgaa agaaggagca agagaacatt cctctgcagc acttcactac caaatgagca     1500
ttagctactt ttcagaattg aaggagaaaa tgcattatgt ggactgaacc gacttttcta     1560
aagctctgaa caaaagcttt tctttccttt tgcaacaaga caaagcaaag ccacattttg     1620
cattagacag atgacggctg ctcgaagaac aatgtcagaa actcgatgaa tgtgttgatt     1680
tgagaaattt tactgacaga aatgcaatct ccctagcctg cttttgtcct gttatttttt     1740
atttccacat aaaggtattt agaatatatt aaatcgttag aggagcaaca ggagatgaga     1800
gttccagatt gttctgtcca gtttccaaag ggcagtaaag ttttcgtgcc ggttttcagc     1860
tattagcaac tgtgctacac ttgcacctgg tactgcacat tttgtacaaa gatatgctaa     1920
gcagtagtcg tcaagttgca gatcttttg tgaaattcaa cctgtgtctt ataggtttac      1980
actgccaaaa caatgcccgt aagatggctt atttgtataa tggtgttact aaagtcacat     2040
ataaaagtta aactacttgt aaaggtgctg cactggtccc aagtagtagt gtcctcctag     2100
tatattagtt tgatttaata tctgagaagt gtatatagtt tgtggtaaaa agattatata     2160
tcataaagta tgccttcctg tttaaaaaaa gtatatattc tacacatata tatatatgta     2220
tatctatatc tctaaactgc tgttaattga ttaaaatctg gcaaagtt               2268
```

<210> SEQ ID NO 114
<211> LENGTH: 785
<212> TYPE: DNA
<213> ORGANISM: Homo sapiens
<220> FEATURE:
<221> NAME/KEY: misc_feature
<223> OTHER INFORMATION: XM_166457

<400> SEQUENCE: 114

```
gcgcgagccg cgccggcccc ggtcgggcct ccgaaaccat gaactttctg ctgtcttggg       60
tgcattggag ccttgccttg ctgctctacc tccaccatgc caagtggtcc caggctgcac      120
ccatggcaga aggaggaggg cagaatcatc acgaagtgg gaagttcatg gatgtctatc       180
agcgcagcta ctgccatcca atcgagaccc tggtggacat cttccaggag taccctgatg      240
```

```
agatcgagta catcttcaag ccatcctgtg tgcccctgat gcgatgcggg ggctgctgca    300
atgacgaggg cctggagtgt gtgcccactg aggagtccaa catcaccatg cagattatgc    360
ggatcaaacc tcaccaaggc cagcacatag gagagatgag cttcctacag cacaacaaat    420
gtgaatgcag accaaagaaa gatagagcaa gacaagaaaa aaaatcagtt cgaggaaagg    480 gaaagggca aaacgaaag cgcaagaaat cccggtataa gtcctggagc gtgtacgttg       540
gtgcccgctg ctgtctaatg ccctggagcc tccctggccc ccatccctgt gggccttgct    600
cagagcggag aaagcatttg tttgtacaag atccgcagac gtgtaaatgt tcctgcaaaa    660
acacagactc gcgttgcaag gcgaggcagc ttgagttaaa cgaacgtact tgcagatgtg    720
acaagccgag gcggtgagcc gggcaggagg aaggagcctc cctcagggtt tcgggaacca    780
gatct                                                                785

<210> SEQ ID NO 115
<211> LENGTH: 8460
<212> TYPE: DNA
<213> ORGANISM: Homo sapiens
<220> FEATURE:
<221> NAME/KEY: misc_feature
<223> OTHER INFORMATION: U29344
<220> FEATURE:
<221> NAME/KEY: misc_feature
<222> LOCATION: (1)..(8460)
<223> OTHER INFORMATION: n can be a or c or g or t

<400> SEQUENCE: 115
cggccgtcga cacggcagcg gccccggcct ccctctccgc cgcgcttcag cctcccgctc      60
cgccgcgctc cagcctcgct ctccgccgcc cgcaccgccg cccgcgccct caccagagca    120
gccatggagg aggtggtgat tgccggcatg tccgggaagc tgccagagtc ggagaacttg    180
caggagttct gggacaacct catcggcggt gtggacatgg tcacggacga tgaccgtcgc    240
tggaaggcgg ggctctacgg cctgcccgg cggtccggca agctgaagga cctgtctagg     300
tttgatgcct ccttcttcgg agtccacccc aagcaggcac acacgatgga ccctcagctg    360
cggctgctgc tggaagtcac ctatgaagcc atcgtggacg gaggcatcaa cccagattca    420
ctccgaggaa cacacactgg cgtctgggtg ggcgtgagcg gctctgagac ctcggaggcc    480
ctgagccgag accccgagac actcgtgggc tacagcatgg tgggctgcca gcgagcgatg    540
atggccaacc ggctctcctt cttcttcgac ttcagagggc ccagcatcgc actggacaca    600
gcctgctcct ccagcctgat ggcctgcag aacgcctacc aggccatcca gcgggcag      660 tgccctgccg ccatcgtggg gggcatcaat gtcctgctga gcccaacac ctccgtgcag    720 ttcttgaggc tggggatgct cagccccgag ggcacctgca aggccttcga cacagcgggg    780
aatgggtact gccgctcgga gggtgtggtg gccgtcctgc tgaccaagaa gtccctggcc    840
cggcgggtgt acgccaccat cctgaacgcg gcaccaata cagatggctt caaggagcaa    900
ggcgtgacct ccccctcagg ggatatccag gagcagctca tccgctcgtt gtaccagtcg    960
gccggagtgg cccctgagtc atttgaatac atcgaagccc acggcacagg caccaaggtg   1020 ggcgacccc aggagctgaa tgcatcacc cgagccctgt cgccacccg ccaggagccg      1080 ctgctcatcg gctccaccaa gtccaacatg gggcacccgg agccagcctc ggggctggca   1140
gccccggcca aggtgctgct gtccctggag cacgggctct gggcccccaa cctgcacttc    1200 catagccca accctgagat cccagcgctg ttggatgggc ggctgcaggt ggtggaccag    1260 cccctgccg tccgtggcgg caacgtgggc atcaactcct ttggcttcgg gggctccaac    1320
```

```
gtgcacatca tcctgaggcc caacacgcag ccgcccccg cacccgcccc acatgccacc    1380
ctgccccgtc tgctgcgggc cagcggacgc acccctgagg ccgtgcagaa gctgctggag    1440
cagggcctcc ggcacagcca ggacctggct ttcctgagca tgctgaacga catcgcgctg    1500
tccccgacca ccgccatgcc cttccgtggc tacgctgtgc tgggtggtga gcgcggtggc    1560
ccagaggtgc agcaggtgcc cgctggcgag cgcccgctct ggttcatctg ctctgggatg    1620
ggcacacagt ggcgcgggat ggggctgagc ctcatgcgcc tggaccgctt ccgagattcc    1680
atcctacgct ccgatgaggc tgtgaaccga ttcggcctga aggtgtcaca gctgctgctg    1740
agcacagacg agagcacctt tgatgacatc gtccattcgt ttgtgagcct gactgccatc    1800
cagataggcc tcatagacct gctgagctgc atggggctga ggccagatgg catcgtcggc    1860
cactccctgg gggaggtggc ctgtggctac gccgacggct gcctgtccca ggaggaggcc    1920
gtcctcgctg cctactggag gggacagtgc atcaaagaag cccatctccc gccgggcgcc    1980
atggcagccg tgggcttgtc ctgggaggag tgtaaacagc gctgccccc ggcggtggtg     2040
cccgcctgcc acaactccaa ggacacagtc accatctcgg gacctcaggc cccggtgttt    2100
gagttcgtgg agcagctgag gaaggaggg tgtgtttgcca aggaggtgcg gaccggcggt     2160
atggccttcc actcctactt catggaggcc atcgcacccc cactgctgca ggagctcaag    2220
aaggtgatcc gggagccgaa gccacgttca gcccgctggc tcagcacctc tatccccgag    2280
gcccagtggc acagcagcct ggcacgcacg tcctccgccg agtacaatgt caacaacctg    2340
gtgagccctg tgctgttcca ggaggccctg tggcacgtgc ctgagcacgc ggtggtgctg    2400
gagatcgcgc cccacgccct gctgcaggct gtcctgaagc gtggcctgaa gccgagctgc    2460
accatcatcc ccctgatgaa gaaggatcac agggacaacc tggagttctt cctggccggc    2520
atccggaggc tgcacctctc aggcatcgac gccaacccca atgccttgtt cccacctgtg    2580
gagttcccag ctccccgagg aactcccctc atctccccac tcatcaagtg ggaccacagc    2640
ctggcctggg acgtgccggc cgccgaggac ttccccaacg gttcaggttc ccctcagcc     2700
gccatctaca acatcgacac cagctccgag tctcctgacc actacctggt ggaccacacc    2760
ctcgacggtc gcgtcctctt ccccgccact ggctacctga gcatagtgtg gaagacgctg    2820
gcccgacccc tgggcctggg cgtcgagcag ctgcctgtgg tgtttgagga tgtggtgctg    2880
caccaggcca ccatcctgcc caagactggg acagtgtccc tggaggtacg gctcctggag    2940
gcctcccgtg ccttcgaggt gtcagagaac ggcaacctgg tagtgagtgg aaggtgtac    3000
cagtgggatg accctgaccc caggctcttc gaccaccgg aaagcccac ccccaacccc      3060
acggagcccc tcttcctggc ccaggctgaa gtttacaagg agctgcgtct gcgtggctac    3120
gactacggcc tcatttcca gggcatcctg gaggccagct ggaaggtga ctcggggagg      3180
ctgctgtgga aggataactg ggtgagcttc atggacacca tgctgcagat gtccatcctg    3240
ggctcggcca gcacggcct gtacctgccc accgtgtca ccgccatcca catcgaccct      3300
gccacccaca ggcagaagct gtacacactg caggacaagg cccaagtggc tgacgtggtg    3360
gtgagcaggt ggctgagggt cacagtggcc ggaggcgtcc acatctccgg gctccacact    3420
gagtcggccc cgcggcggca gcaggagcag caggtgccca tcctggagaa gtttttgcttc    3480
acttcccaca cggaggaggg gtgcctgtct gagcgcgctg ccctgcagga ggagctgcaa    3540
ctgtgcaagg ggctggtgca ggcactgcag accaaggtga cccagcaggg gctgaagatg    3600
gtggtgcccg gactggatgg ggcccagatc ccccgggacc cctcacagca ggaactgccc    3660
```

```
cggctgttgt cggctgcctg caggcttcag ctcaacggga acctgcagct ggagctggcg    3720
caggtgctgg cccaggagag gcccaagctg ccagaggacc ctctgctcag cggcctcctg    3780
gactccccgg cactcaaggc ctgcctggac actgccgtgg agaacatgcc cagcctgaag    3840
atgaaggtgg tggaggtgct ggccggccac ggtcacctgt attcccgcat cccaggcctg    3900
ctcagccccc atccctgct gcagctgagc tacacggcca ccgaccgcca ccccaggcc     3960 ctggaggctg cccaggccga gctgcagcag cacgacgttg cccagggcca gtgggatccc    4020
gcagaccctg cccccagcgc cctgggcagc gccgacctcc tggtgtgcaa ctgtgctgtg    4080
gctgccctcg ggacccggc ctcagctctc agcaacatgg tggctgccct gagagaaggg     4140
ggctttctgc tcctgcacac actgctccgg gggcacccct cgggacatgt ggccttcctc    4200
acctccactg agccgcagta tggccagggc atcctgagcc aggacgcgtg ggagagcctc    4260
ttctccaggg tgtccgtgcg cctggtgggc ctgaagaagt ccttctacgg ctccacgctc    4320
ttcctgtgcc gccggccac cccgcaggac agccccatct tcctgccggt ggacgatacc     4380
agcttccgct gggtggagtc tctgaagggc atcctggctg acgaagactc ttcccggcct    4440
gtgtggctga aggccatcaa ctgtgccacc tcgggcgtgg tgggcttggt gaactgtctc    4500
cgccgagagc ccgcggaac gctccggtgt gtgctgctct ccaacctcag cagcacctcc     4560
cacgtcccgg aggtggaccc gggctccgca gaactgcaga aggtgttgca gggagacctg    4620
gtgatgaacg tctaccgcga cggggcctgg ggggcttttcc gccacttcct gctggaggag    4680
gacaagcctg aggagccgac ggcacatgcc tttgtgagca ccctcacccg ggggacctg     4740 tcctccatcc gctgggtctg ctcctcgctg cgccatgccc agcccacctg ccctggcgcc    4800
cagctctgca cggtctacta cgcctcccte aacttccgcg acatcatgct ggccactggc    4860
aagctgtccc ctgatgccat cccagggaag tggacctccc aggacagcct gctaggtatg    4920
gagttctcgg gccgagacgc cagcggcaag cgtgtgatgg gactggtgcc tgccaagggc    4980
ctggccacct ctgtcctgct gtcaccggac ttcctctggg atgtgccttc caactggacg    5040
ctggaggagg cggcctcggt gcctgtcgtc tacagcacgg cctactacgc gctggtggtg    5100
cgtgggcggg tgcgccccgg ggagacgctg ctcatccact cgggctcggg cggcgtgggc    5160
caggccgcca tcgccatcgc cctcagtctg ggctgccgcg tcttcaccac cgtggggtcg    5220
gctgagaagc gggcgtacct ccaggccagg ttccccccagc tcgacagcac cagcttcgcc    5280
aactcccggg acacatcctt cgagcagcat gtgctgtggc acacgggcgg gaagggcgtt    5340
gacctggtct tgaactcctt ggcggaagag aagctgcagg ccagcgtgag gtgcttggct    5400
acgcacggtc gcttcctgga aattggcaaa ttcgaccttt ctcagaacca cccgctcggc    5460
atggctatct tcctgaagaa cgtgacattc acgggtcc tactggatgc gttcttcaac     5520
gagagcagtg ctgactggcg ggaggtgtgg gcgcttgtgc aggccggcat ccgggatggg    5580
gtggtacggc ccctcaagtg cacggtgttc catgggccc aggtggagga cgccttccgc      5640
tacatggccc aagggaagca cattggcaaa gtcgtcgtgc aggtgcttgc ggaggagccg    5700
gaggcagtgc tgaaggggc caaacccaag ctgatgtcgg ccatctccaa gaccttctgc    5760
ccggcccaca gagctacat catcgctggt ggtctgggtg gcttcggcct ggagttggcg      5820
cagtggctga tacagcgtgg ggtgcagaag ctcgtgttga cttctcgctc cgggatccgg    5880
acaggctacc aggccaagca ggtccgccgg tgagggccc agggcgtaca ggtgcaggtg    5940
tccaccagca acatcagctc actggagggg gcccggggcc tcattgccga gcggcgcag    6000 cttgggcccg tgggcggcgt cttcaacctg gccgtggtct tgagagatgg cttgctggag    6060
```

```
aaccagaccc cagagttctt ccaggacgtc tgcaagccca agtacagcgg caccctgaac    6120
ctggacaggg tgacccgaga ggcgtgccct gagctggact actttgtggt cttctcctct    6180
gtgagctgcg ggcgtggcaa tgcgggacag agcaactacg gctttgccaa ttccgccatg    6240
gagcgtatct gtgagaaacg ccggcacgaa ggcctcccag gcctggccgt gcagtggggc    6300
gccatcggcg acgtgggcat tttggtggag acgatgagca ccaacgacac gatcgtcagt    6360
ggcacgctgc cccaggccat ggcgtcctgc ctggaggtgc tggacctctt cctgaaccag    6420
ccccacatgg tcctgagcag ctttgtgctg gctgagaagg ctgcggccta tagggacagg    6480
gacagccagc gggacctggt ggaggccgtg cacacatcc tgggcatccg cgacttggct     6540
gctgtcaacc tggacagctc actggcggac ctgggcctgg actcgctcat gagcgtggag    6600
gtgcgccaga cgctggagcg tgagctcaac ctggtgctgt ccgtgcgcga ggtgcggcaa    6660
ctcacgctcc ggaaactgca ggagctgtcc tcaaaggcgg atgaggccag cgagctggca    6720
tgccccacgc ccaaggagga tggtctggcc cagcagcaga ctcagctgaa cctgcgctcc    6780
ctgctggtga acccggaggg ccccacctg atgcggctca actccgtgca gagctcggag     6840
cggcccctgt tcctggtgca cccaatcgag ggctccacca ccgtgttcca cagcctggcc    6900
tcccggctca gcatccccac ctatggcctg cagtgcaccc gagctgcgcc ccttgacagc    6960
atccacagcc tggctgccta ctacatcgac tgcatcaggc aggtgcagcc cgagggcccc    7020
taccgcgtgg ccggctactc ctacggggcc tgcgtggcct ttgaaatgtg ctcccagctg    7080
caggcccagc agagcccagc ccccacccac aacagcctct tcctgttcga cggctcgccc    7140
acctacgtac tggcctacac ccagagctac cgggcaaagc tgaccccagg ctgtgaggct    7200
gaggctgaga cggaggccat atgcttcttc gtgcagcagt tcacggacat ggagcacaac    7260
agggtgctgg aggcgctgct gccgctgaag ggcctagagg agcgtgtggc agccgccgtg    7320
gacctgatca tcaagagcca ccagggcctg gaccgccagg agctgagctt tgcggcccgg    7380
tccttctact acaagctcgg tgccgctgag cagtacacac ccaaggccaa gtaccatggc    7440
aacgtgatgc tactgcgcgc caagacgggg ggcgcctacg gcgaggacct gggcgcggat    7500
tacaacctct cccaggtatg cgacgggaaa gtatccgtcc acgtcatcga gggtgaccac    7560
cgcacgctgc tggagggcag cggcctggag tccatcatca gcatcatcca cagctccctg    7620
gctgagccac gcgtgagcgt gcgggagggc taggcccgtg cccccgcctg ccaccggagg    7680
tcactccacc atccccaccc cacccccacccc caccccgccc atgcaacggg attgaagggt    7740
cctgccggtg ggaccctgtc cggccagtc ccactgcccc cgaggctgc tagatgtagg      7800 tgttaggcat gtcccaccca cccgccgcct cccacggcac ctcggggaca ccagagctgc    7860
cgacttggag actcctggtc tgtgaagagc cggtggtgcc cgttcccgca ggaactgggc    7920
tgggcctcgt gcgcccgtgg ggtctgcgct tggtctttct gtgcttggat ttgcatattt    7980
attgcattgc tggtagagac ccccaggcct gtccacctg ccaagactcc tcaggcagcg     8040
tgtgggtccc gcactctgcc cccatttccc cgatgtcccc tgcgggcgcg ggcagccacc    8100
caagcctgct ggctgcggcc ccctctcggc caggcattgg ctcagccncgc tgagtggggg   8160 gtcgtgggcc agtccccgag gagctgggcc cctgcacagg cacacagggc ccggccacac    8220
ccagcggccc cccgcacagc cacccgtggg gtgctgccct tatcgcccgg cgccgggcac    8280
caactccatg tttggtgttt gtctgtgttt gttttcaag aaatgattca aattgctgct     8340
tggattttga aatttactgt aactgtcagt gtacacgtct ggaccccgtt tcattttac    8400
```

```
accaatttgg taaaaatgct gctctcagcc tcccacaatt aaaccgcatg tgatctcccc    8460
```

<210> SEQ ID NO 116
<211> LENGTH: 959
<212> TYPE: DNA
<213> ORGANISM: Homo sapiens
<220> FEATURE:
<221> NAME/KEY: misc_feature
<223> OTHER INFORMATION: NM_001639

<400> SEQUENCE: 116

```
gggcatgaat atcagacgct aggggggacag ccactgtgtt gtctgctacc ctcatcctgg     60
tcactgcttc tgctataaca gccctaggcc aggaatatga acaagccgct gctttggatc    120
tctgtcctca ccagcctcct ggaagccttt gctcacacag acctcagtgg aaggtgttt     180
gtatttccta gagaatctgt tactgatcat gtaaacttga tcacaccgct ggagaagcct    240
ctacagaact ttaccttgtg ttttcgagcc tatagtgatc tctctcgtgc ctacagcctc    300
ttctcctaca atacccaagg cagggataat gagctactag tttataaaga aagagttgga    360
gagtatagtc tatacattgg aagacacaaa gttacatcca aagttatcga aaagttcccg    420
gctccagtgc acatctgtgt gagctgggag tcctcatcag gtattgctga attttggatc    480
aatgggacac ctttggtgaa aaagggtctg cgacagggtt actttgtgga agctcagccc    540
aagattgtcc tggggcagga acaggattcc tatgggggca agtttgatag gagccagtcc    600
tttgtgggag agattgggga tttgtacatg tgggactctg tgctgccccc agaaaatatc    660
ctgtctgcct atcagggtac ccctctcct gccaatatcc tggactggca ggctctgaac    720
tatgaaatca gaggatatgt catcatcaaa cccttggtgt gggtctgagg tcttgactca    780
acgagagcac ttgaaaatga aatgactgtc taagagatct ggtcaaagca actggatact    840
agatcttaca tctgcagtct ttcttctttg aatttcctat ctgtatgtct gcctaattaa    900
aaaaatatat attgtattat gctacctgca aaaaaaaaaa aaaaaaaaa aaaaaaaaaa    959
```

<210> SEQ ID NO 117
<211> LENGTH: 1471
<212> TYPE: DNA
<213> ORGANISM: Homo sapiens
<220> FEATURE:
<221> NAME/KEY: misc_feature
<223> OTHER INFORMATION: NM_000936

<400> SEQUENCE: 117

```
ggaactgcca cgatgctgcc actttggact ctttcactgc tgctgggagc agtagcagga     60
aaagaagttt gctacgaaag actcggctgc ttcagtgatg actccccatg gtcaggaatt    120
acggaaagac ccctccatat attgccttgg tctccaaaag atgtcaacac ccgcttcctc    180
ctatatacta atgagaaccc aaacaacttt caagaagttg ccgcagattc atcaagcatc    240
agtggctcca atttcaaaac aaatagaaaa actcgcttta ttattcatgg attcatagac    300
aagggagaag aaaactggct ggccaatgtg tgcaagaatc tgttcaaggt ggaaagtgtg    360
aactgtatct gtgtggactg gaaaggtggc tcccgaactg atacacaca agcctcgcag    420
aacatcagga tcgtgggagc agaagtggca tattttgttg aatttcttca gtcggcgttc    480
ggttactcac cttccaacgt gcatgtcatt ggccacagcc tgggtgccca cgctgctggg    540
gaggctggaa ggagaaccaa tgggaccatt ggacgcatca caggggttgga cccagcagaa    600
ccttgctttc aggggcacacc tgaattagtc cgattggacc ccagcgatgc caaatttgtg    660
gatgtaattc acacggatgg tgccccata gtccccaatt ggggtttgg aatgagccaa    720
```

```
gtcgtgggcc acctagattt ctttccaaat ggaggagtgg aaatgcctgg atgtaaaaag    780
aacattctct ctcagattgt ggacatagac ggaatctggg aagggactcg agactttgcg    840
gcctgtaatc acttaagaag ctacaaatat tacactgata gcatcgtcaa ccctgatggc    900
tttgctggat tccccgtgc ctcttacaac gtcttcactg caaacaagtg tttcccttgt     960
ccaagtggag gctgcccaca gatgggtcac tatgctgata gatatcctgg aaaacaaat   1020 gatgtgggcc agaaatttta tctagacact ggtgatgcca gtaattttgc acgttggagg   1080
tataaggtat ctgtcacact gtctggaaaa aaggttacag acacatact agtttctttg    1140 ttcggaaata aaggaaactc taagcagtat gaaattttca agggcactct caaaccagat   1200
agtactcatt ccaatgaatt tgactcagat gtggatgttg gggacttgca gatggttaaa   1260
tttatttggt ataacaatgt gatcaaccca actttaccta gagtgggagc atccaagatt   1320
atagtggaga caaatgttgg aaaacagttc aacttctgta gtccagaaac cgtcagggag   1380
gaagttctgc tcaccctcac accgtgttag gagactactg ttatttgacc aatgaattga   1440
cttctaataa aatctagtgg tgatgcaaaa a                                   1471

<210> SEQ ID NO 118
<211> LENGTH: 7452
<212> TYPE: DNA
<213> ORGANISM: Homo sapiens
<220> FEATURE:
<221> NAME/KEY: misc_feature
<223> OTHER INFORMATION: U89344

<400> SEQUENCE: 118
atggtcttgc ttctttgtct atcttgtctg attttctcct gtctgacctt ttcctggtta    60
aaaatctggg agaaaatgac ggactccaag ccgatcacca agagtaaatc agaagcaaac   120
ctcatcccga gccaggagcc ctttccagcc tctgataact caggggagac accgcagaga   180 aatgggagg ccacactct gcacaaagac acccagccag gccgagccca gcctcccaca     240
aaggcccaaa gatccggtcg gcggagaaac tccctaccac cctcccgcca gaagccccca   300
agaaaccccc ttcttccag tgacgcagca ccctccccag agcttcaagc caacgggact   360
gggacacaag gtctggaggc cacagatacc aatggcctgt cctcctcagc caggccccag   420
ggcagcaagc tggtcccctc caagaagac aagaagcagg caaacatcaa gaggcagctg   480
atgaccaact tcatcctggg ctcttttgat gactactcct ccgacgagga ctctgttgct   540
ggctcatctc gtgagtctac ccggaagggc agccgggcca gcttgggggc cctgtccctg   600
gaggcttatc tgaccacagg tgaagctgag acccgcgtcc ccactatgag gccgagcatg   660
tcgggactcc acctggtgaa gaggggacgg aacacaaga agctggacct gcacagagac   720
tttaccgtgg cttctcccgc tgagtttgtc acacgctttg gggggatcg ggtcatcgag    780 aaggtgctta ttgccaacaa cgggattgcc gctgtgaagt gcatgcgctc catccgcagg   840
tgggcctatg agatgttccg caacgagcgg gccatccggt tgttcgcat ggtgaccccc    900 gaggacctta aggccaacgc agagtacatc aagatggcgg atcattacgg gcccgcccca   960
ggagggccca taacaacaa ctatgccaac gtggagctga ttgtggacat tgccaagaga   1020
atcccgttgc aggcggtgtg ggctggctgg ggccatgctt tagaaaaccc taaacttccg   1080
gagctgctgt gcaagaatgg agttgctttc ttaggccctc ccaggttgag gccaatggtg   1140
ggtctaggag ataagatcgc ctccaccgtt gtcgcccaga cgctacaggt cccaaccctg   1200
cccaggagtg gaagcgccct gacagtggag tggacagaag atgatctgca gcagggaaaa   1260
```

```
agaatcagtg tcccagaaga tgtttatgac aagggttgcg tgaaagacgt agatgagggc    1320
ttggaggcag cagaaagaat tggttttcca ttgatgatca aagcttctga aggtggcgga    1380
gggaagggaa tccgggaaac tgagagtgcg gaggacttcc cgatccttt cagacaagta    1440 cagagtgaga tcccaggctc gcccatcttt ctcatgaagc tggcccagca cgcccgtcac    1500
ctggaagttc agatcctcgc tgaccagtat gggaatgctg tgtctctgtt tggtcgcgac    1560
tgctccatcc agcggcggca tcagaagatc gttgaggaag caccggccac catcgcgccg    1620
ctggccatat tcgagttcat ggagcagtgt gccattcgcc tggccaagac cgtgggctat    1680
gtgagtgcag ggacagtgga atacctctat agtcaggatg gtagcttcca cttcttggag    1740
ctgaatcctc gcttgcaggt ggaacatccc tgcacagaaa tgattgctga cgttaatctg    1800
ccggccgccc agctacagat cgccatgggt gccccactgc accggctgaa agatatccgg    1860
cttctgtatg gagagtcacc ctggggagac tccccaattt cttttgaaaa ctcagctcat    1920
ctcccctgcc cccgaggcca cgtcattgcc accagaatca ccagcgaaaa cccagacgag    1980
ggttttaagc cgagctccgg gactgtccag gaactgaatt tccggagcag caagaacgtc    2040
tggggttact tcacggtggc cgctactgga ggcctgcacg agtttgcgat tcccagtttt    2100
gggcactgct tctcctgggg agagaaccgg aaagaggcca tttcgaacat ggtggtggct    2160
ttgaaggaac tgtccctccg aggcgacttt aggactaccg tggaatacct cattaacctc    2220
ctggagaccg agagcttcca gaacaactac atcgacaccg ggtggttgga ctacctcatt    2280
gctgagaaag tgcaaaagaa accgaatatc atgcttgggg tggtatgcgg ggcccttgaa    2340
cgtggagatg cgatgttcag aacgtgcatg acagatttct tacactccct ggaaaggggc    2400
caggtcctcc cagcggattc actactgaac ctcgtagatg tggaattaat ttacgagggt    2460
gtaaagtaca ttctaaaggt gacccggcag tctctgacca tgttcgttct catcatgaat    2520
ggctgccaca tcgagattga tgcccaccgg ctgaatgatg gggggctcct gctctcctac    2580
aatgggaaca gctacaccac ctacatgaag gaagaggttg acagttaccg taccatcggc    2640
aataagacgt gtgtttttga aaggagaaac gatcctacag tcctgagatc ccctcgggct    2700
gggaagctga cacagatcac agtggaggat gggggccacg ttgaggctgg gagacgctac    2760
gctgagatgg aggtgatgaa gatgatcatg accctgaacg ttcaggaaag aggccgggtg    2820
aagtacatca agcgtccagg tgcggtgctg aagcaggct gcgtggtggc caggctggag    2880
ctcgatgacc cttctaaagt ccacccggct gaaccgttca caggagaact ccctgcccag    2940
cagaacactg ccgacctcgg aaagaaactg cacagggtct tccacagcgt cctgggaagc    3000
ctcaccaacg tcatgagtgg cttttgtctg ccagagccgt tttttagcat aaagctgaag    3060
gagtgggtgc agaagctcat gatgaccctc cggcacccgt cactgctgct ggacgtgcag    3120
gagatcatga ccagtcgtgc aggccgcatc ccccccctg ttgagaagtc tgtccgcaag    3180
gtgatggccc agtatgccag caacatcacc tcggtgctgt gccagttccc cagccagcag    3240
atagccacca tcctggactg ccatgcagcc accctgcagc ggaaggctga tcgagaggtc    3300
ttcttcatca acacccagag catggtgcag ttggtccaga ggtaccgaag tggaatccgc    3360
ggtcatatga aaacagtggt gatcgatctc ttgagaagat acttgcgtgt tgagaccatt    3420
ttcggcaagg caagagatgc tgatgccaac tccagtggga tggtgggggg cgtgaggagc    3480
ctgagcttta cctctgtgtg ggtggttttg tctccccag cccactacga caagtgtgtg    3540
ataaacctca gggaacagtt caagccagac atgtcccagg tgctggactg catcttctcc    3600
```

```
cacgcacagg tgaccaagaa gaaccagctg gtgatcatgt tgatcgatga gctgtgtggc   3660
ccagacccct tccctgtcgga cgagctgatc tccatcctca acgagctcac tcagctgagc   3720
aaaagcgagc actgcaaagt ggccctcaga gcccggcaga tcctgatcgc ctcccctcc    3780 tacgagctgc ggcataacca ggtggagtcc attttcctgt ctgccattga catgtacggc   3840
caccagttct gccccgagaa cctccagaaa ttaatacttt cggaaacaac catcttcgac   3900
gtcctgaata ctttcttcta tcacgcaaac aaagtcgtgt gcatggcgtc cttggaggtt   3960
tacgtggggg gggcttacat cgcctatgtg ttaaacagcc tgcagcaccg gcagctcccg   4020
gacggcacct gcgtggtaga attccagttc atgctgccgt cctcccaccc aaaccggatg   4080
accgtgccca tcagcatcac caaccctgac ctgctgaggc acacgacaga gctcttcatg   4140
gacagcggct tctccccact gtgccagcgc atgggagcca tggtagcctt caggagattc   4200
gaggacttca ccagaaattt tgatgaagtc atctcttgct tcgccaacgt gccgaaagac   4260
ccccccctct tcagcgaggc ccgcacctcc ctatactccg aggatgactg caagagcctc   4320
agagaagagc ccatccacat tctgaatgtg tccatccagt gtgcggacca cctggaggat   4380
gaggcactgg tgccgatttt acgtacattc gtacagtcca agaaaaatat ccttgtggat   4440
tatggactcc gacgaatccc attcttgatt gcccaagaga agaatttcc caagtttttc    4500 acattcagag caagagatga gtttgcagaa gatcgcattt accgtcactt ggaacctgcc   4560
ctggctttcc agctggaact caaccggatg cgtaacttcg atctgaccgc cgtgccctgt   4620
gccaaccaca agatgcacct ttacctgggt gctgccaagg tggaaggaag gtatgaagtg   4680
acggaccata ggttcttcat ccgtgccatc atcaggcact ctgacctgat cacaaaggaa   4740
gcctccttcg aatacctgca gaacgagggt gagcggctgc tcctggaggc catggacgag   4800
ctggaggtgg cgttcaataa caccaacgtg cgcaccgact gcaaccacat cttcctcaac   4860
ttcgtgccca ctgtcatcat ggaccccaac aagatcgagg agtccgtgcg ctacatggtt   4920
atgcgctacg gcagccggct gtggaaactc cgtgtgctac aggctgaggt caagatcaac   4980
atccgccaga ccaccaccgg cagtgccgtt cccatccgcc tgttcatcac caatgagtcg   5040
ggctactacc tggacatcag cctctacaaa gaagtgactg actccagatc tggaaatatc   5100
atgtttcact ccttcggcaa caagcaaggg ccccagcacg ggatgctgat caatactccc   5160
tacgtcacca aggatctgct ccaggccaag cgattccagg cccagaccct gggaaccacc   5220
tacatctatg acttcccgga aatgttcagg caggctctct ttaaactgtg gggctcccca   5280
gacaagtatc ccaaagacat cctgacatac actgaattag tgttggactc tcagggccag   5340
ctggtggaga tgaaccgact tcctggtgga aatgaggtgg gcatggtggc cttcaaaatg   5400
aggtttaaga cccaggagta cccggaagga cgggatgtga tcgtcatcgg caatgacatc   5460 accttttcgca ttggatcctt tggccctgga gaggaccttc tgtacctgcg ggcatccgag   5520
atggcccggg cagaggcgat tcccaaaatt tacgtggcag ccaacagtgg cgcccgtatt   5580
ggcatggcag aggagatcaa acacatgttc cacgtggctt gggtggaccc agaagacccc   5640
cacaaaggat ttaaatacct gtacctgact ccccaagact acaccagaat cagctccctg   5700
aactccgtcc actgtaaaca catcgaggaa ggaggagagt ccagatacat gatcacggat   5760
atcatcggga aggatgatgg cttgggcgtg gagaatctga ggggctcagg catgattgct   5820
ggggagtcct ctctggctta cgaagagatc gtcaccatta gcttggtgac tgccgagcc    5880 attgggattg gggcctactt ggtgaggctg ggccagcgag tgatccaggt ggagaattcc   5940
cacatcatcc tcacaggagc aagtgctctc aacaaggtcc tgggaagaga ggtctacaca   6000
```

| | | | |
|---|---|---|---|
| tccaacaacc | agctgggtgg | cgttcagatc atgcattaca | atggtgtctc ccacatcacc | 6060 |
| gtgccagatg | actttgaggg | ggtttatacc atcctggagt | ggctgtccta tatgccaaag | 6120 |
| gataatcaca | gccctgtccc | tatcatcaca cccactgacc | ccattgacag agaaattgaa | 6180 |
| ttcctcccat | ccagagctcc | ctacgacccc cggtggatgc | ttgcaggaag gcctcaccca | 6240 |
| actctgaagg | gaacgtggca | gagcggattc tttgaccacg | gcagtttcaa ggaaatcatg | 6300 |
| gcaccctggg | cgcagaccgt | ggtgacagga cgagcaaggc | ttgggggat tcccgtggga | 6360 |
| gtgattgctg | tggagacacg | gactgtggag gtggcagtcc | ctgcagaccc tgccaacctg | 6420 |
| gattctgagg | ccaagataat | tcagcaggca ggacaggtgt | ggttcccaga ctcagcctac | 6480 |
| aaaaccgccc | aggccatcaa | ggacttcaac cgggagaagt | tgcccctgat gatctttgcc | 6540 |
| aactggaggg | ggttctccgg | tggcatgaaa gacatgtatg | accaggtgct gaagtttgga | 6600 |
| gcctacatcg | tggacggcct | tagacaatac aaacagccca | tcctgatcta tatccgccct | 6660 |
| atgcgggagc | tccggggagg | ctcctgggtg gtcatagatg | ccaccatcaa cccgctgtgc | 6720 |
| atagaaatgt | atgcagacaa | agagagcagg ggtggtgttc | tggaaccaga ggggacagtg | 6780 |
| gagattaagt | tccgaaagga | agatctgata aagtccatga | aaggatcga tccagcttac | 6840 |
| aagaagctca | tggaacagct | aggggaacct gatctctccg | acaaggaccg aaaggacctg | 6900 |
| gagggccggc | taaaggctcg | cgaggacctg ctgctcccca | tctaccacca ggtggcggtg | 6960 |
| cagttcgccg | acttccatga | cacacccggc cggatgctgg | agaagggcgt catatctgac | 7020 |
| atcctggagt | ggaagaccgc | acgcaccttc ctgtattggc | gtctgcgccg cctcctcctg | 7080 |
| gaggaccagg | tcaagcagga | gatcctgcag gccagcgggg | agctgagtca cgtgcatatc | 7140 |
| cagtccatgc | tgcgtcgctg | gttcgtggag acggaggggg | ctgtcaaggc ctacttgtgg | 7200 |
| gacaacaacc | aggtggttgt | gcagtggctg gaacagcact | ggcaggcagg ggatggcccg | 7260 |
| cgctccacca | tccgtgagaa | catcacgtac ctgaagcacg | actctgtcct caagaccatc | 7320 |
| cgaggcctgg | ttgaagaaaa | ccccgaggtg gccgtggact | gtgtgatata cctgagccag | 7380 |
| cacatcagcc | cagctgagcg | ggcgcaggtc gttcacctgc | tgtctaccat ggacagcccg | 7440 |
| gcctccacct | ga | | | 7452 |

<210> SEQ ID NO 119
<211> LENGTH: 3259
<212> TYPE: DNA
<213> ORGANISM: Homo sapiens
<220> FEATURE:
<221> NAME/KEY: misc_feature
<223> OTHER INFORMATION: M31158

<400> SEQUENCE: 119

| | | | |
|---|---|---|---|
| gacgcgcgcc | gggagccggc | ggccgggcca | gccggcgccg gggcccagtg cgccgcgctc | 60 |
| gcagccggta | gcgcgccagc | cgtaggcgtc | gctcggcagc cgcggggccc taggcgtgcc | 120 |
| ggggaggggg | cgagggcggc | caggcgcctg | ccgccccgga ggcaggatga gcatcgagat | 180 |
| cccggcggga | ctgacggagc | tgctgcaggg | cttcacggtg gaggtgctga ggcaccagcc | 240 |
| cgcggacctg | ctggagttcg | cgctgcagca | cttcacccgc ctgcagcagg agaacgagcg | 300 |
| caaaggcacc | gcgcgcttcg | ccatgagggg | caggacctgg ggggacctgg cgccgctgc | 360 |
| cggggggcggc | accccccagca | aggggggtcaa | cttcgccgag gagcccatgc agtccgactc | 420 |
| cgaggacggg | gaggaggagg | aggcggcgcc | cgcggacgca ggggcgttca atgctccagt | 480 |
| aataaaccga | ttcacaaggc | gtgcctcagt | atgtgcagaa gcttataatc ctgatgaaga | 540 |

```
agaagatgat gcagagtcca ggattataca tccaaaaact gatgatcaaa gaaataggtt    600
gcaagaggct tgcaaagaca tcctgctgtt taagaatctg gatccggagc agatgtctca    660
agtattagat gccatgtttg aaaaattggt caaagatggg gagcatgtaa ttgatcaagg    720
tgacgatggt gacaactttt atgtaattga tagaggcaca tttgatattt atgtgaaatg    780
tgatggtgtt ggaagatgtg ttggtaacta tgataatcgt gggagtttcg gcgaactggc    840
cttaatgtac aatacaccca gagcagctac aatcactgct acctctcctg gtgctctgtg    900
gggtttggac agggtaacct tcaggagaat aattgtgaaa acaatgccaa aaagagaaa    960 aatgtatgaa agctttattg agtcactgcc attccttaaa tctttggagt tttctgaacg    1020
cctgaaagta gtagatgtga taggcaccaa agtatacaac gatggagaac aaatcattgc    1080
tcagggagat tcggctgatt cttttttcat tgtagaatct ggagaagtga aaattactat    1140
gaaaagaaag ggtaaatcag aagtggaaga gaatggtgca gtagaaatgc ctcgatgctc    1200
gcggggacag tactttggag agcttgccct ggtaactaac aaacctcgag cagcttctgc    1260
ccacgccatt gggactgtca atgtttagc aatggatgtg caagcatttg aaaggcttct    1320
gggaccttgc atggaaatta tgaaaaggaa catcgctacc tatgaagaac agttagttgc    1380
cctgtttgga acgaacatgg atattgttga acccactgca tgaagcaaaa gtatggagca    1440
agacctgtag tgacaaaatt acacagtagt ggttagtcca ctgagaatgt gtttgtgtag    1500
atgccaagca ttttctgtga tttcaggttt tttccttttt ttacatttac aacgtatcaa    1560
taaacagtag tgatttaata gtcaataggc tttaacatca ctttctaaag agtagttcat    1620
aaaaaaatca acatactgat aaaatgactt tgtactccac aaaattatga ctgaaaggtt    1680
tattaaaatg attgtaatat atagaaagta tctgtgttta agaagataat taaaggatgt    1740
tatcataggc tatatgtgtt ttacttattc agactgataa tcatattagt gactatcccc    1800
atgtaagagg gcacttggca attaaacatg ctacacagca tggcatcact ttttttttata    1860 actcattaaa cacagtaaaa ttttaatcat ttttgtttta agttttctta gcttgataag    1920
ttatgtgctg ccttggccta ttggtgaaat ggtataaaat atcatatgca gttttaaaac    1980
tttttatatt tttgcaataa agtacatttt gactttgttg gcataatgtc agtaacatac    2040
atattccagt ggttttatgg acaggcaatt tagtcattat gataataagg aaaacagtgt    2100
tttagatgag agatcattaa tgcattttc cctcatcaag catatatctg ctttttttta    2160
ttttgcaatt ctctgtattc tatgtcttta aaaatttgat cttgacattt aatgtcacaa    2220
agttttgttt tttaaaaag tgatttaaac ttaagatccg acatttttg tattctttaa    2280 gattttacac ctaaaaaatc tctcctatcc caaaataat gtgggatcct tatcagcatg    2340
cccacagttt atttctttgt tcttcactag gcctgcataa tacagtccta tgtagacatc    2400
tgttcccttg ggtttccgtt ctttcttagg atggttgcca acccacaatc tcattgatca    2460
gcagccaata tgggtttgtt tggtttttt aattcttaaa aacatcctct agaggaatag    2520
aaacaaattt ttatgagcat aaccctatat aaagacaaaa tgaatttctg accttaccat    2580
atataccatt aggccttgcc attgctttaa tgtagactca tagttgaaat tagtgcagaa    2640
agaactcaga tgtactagat tttcattgtt cattgatatg ctcagtatgc tgccacataa    2700
gatgaattta attatattca accaaagcaa tatactctta catgatttct aggccccatg    2760
acccagtgtc tagagacatt aattctaacc agttgtttgc ttttaaatga gtgatttcat    2820
tttgggaaac aggtttcaaa tgaatatata tacatgggta aaattactct gtgctagtgt    2880
```

| | |
|---|---:|
| agtcttacta gagaatgttt atggtcccac ttgtatatga aaatgtggtt agaatgttaa | 2940 |
| ttggataatg tatatataag aagttaaagt atgtaaagta taacttcagc cacattttta | 3000 |
| gaacactgtt taacattttt gcaaaacctt cttgtaggaa aagagagctc tctacatgaa | 3060 |
| gatgacttgt tttatatttc agattttatt ttaaaagcca tgtctgttaa acaagaaaaa | 3120 |
| acacaaaaga actccagatt cctggttcat cattctgtat tcttactcac tttttcaagt | 3180 |
| tatctatttt gttgcataaa ctaattgtta actattcatg gaacagcaaa cgcctgttta | 3240 |
| ataaagaact tgaccaag | 3259 |

<210> SEQ ID NO 120
<211> LENGTH: 3261
<212> TYPE: DNA
<213> ORGANISM: Homo sapiens
<220> FEATURE:
<221> NAME/KEY: misc_feature
<223> OTHER INFORMATION: XM_008512

<400> SEQUENCE: 120

| | |
|---|---:|
| gcccgggacc ccacggaggc ggggagacca ctcttctccc acacgagccc agctctccct | 60 |
| tcgagtagca accgccttca agctcacaag cacccgtggg cctggggtgt gcctgcgtct | 120 |
| agctggttgc acactgggcc acagaggatc cagcaaggat gaagaaatgg agcagcacag | 180 |
| acttggggc agctgcggac ccactccaaa aggacacctg cccagacccc ctggatggag | 240 |
| accctaactc caggccacct ccagccaagc cccagctctc cacggccaag agccgcaccc | 300 |
| ggctctttgg gaagggtgac tcggaggagg ctttcccggt ggattgccct cacgaggaag | 360 |
| gtgagctgga ctcctgcccg accatcacag tcagccctgt tatcaccatc cagaggccag | 420 |
| gagacggctc caccggtgcc aggctgctgt cccaggactc tgtcgccgcc agcaccgaga | 480 |
| agaccctcag gctctatgat cgcaggagta tctttgaagc cgttgctcag aataactgcc | 540 |
| aggatctgga gagcctgctg ctcttcctgc agaagagcaa gaagcacctc acagacaacg | 600 |
| agttcaaaga ccctgagaca gggaagacct gtctgctgaa agccatgctc aacctgcatg | 660 |
| acggacagaa caccaccatc cccctgctcc tggagatcgc gcggcaaacg gacagcctga | 720 |
| aggagcttgt caacgccagc tacacggaca gctactacaa gggccagaca gcactgcaca | 780 |
| tcgccatcga gagacgcaac atggccctgg tgaccctcct ggtggagaac ggagcagacg | 840 |
| tccaggctgc ggcccatggg gacttcttta agaaaaccaa agggcggcct ggattctact | 900 |
| tcggtgaact gccctgtcc ctggccgcgt gcaccaacca gctgggcatc gtgaagttcc | 960 |
| tgctgcagaa ctcctggcag acggccgaca tcagcgccag ggactcggtg ggcaacacgg | 1020 |
| tgctgcacgc cctggtggag gtggccgaca cacggccga caacacgaag tttgtgacga | 1080 |
| gcatgtacaa tgagattctg atcctggggg ccaaactgca cccgacgctg aagctggagg | 1140 |
| agctcaccaa caagaaggga atgacgccgc tggctctggc agctgggacc gggaagatcg | 1200 |
| gggtcttggc ctatattctc agcggggaga tccaggagcc cgagtgcagg cacctgtcca | 1260 |
| ggaagttcac cgagtgggcc tacgggcccg tgcactcctc gctgtacgac ctgtcctgca | 1320 |
| tcgacacctg cgagaagaac tcggtgctgg aggtgatcgc ctacagcagc agcgagaccc | 1380 |
| ctaatcgcca cgacatgctc ttggtggagc cgctgaaccg actcctgcag acaagtggg | 1440 |
| acagattcgt caagcgcatc ttctacttca acttcctggt ctactgcctg tacatgatca | 1500 |
| tcttcaccat ggctgcctac tacaggcccg tggatggctt gcctcccttt aagatggaaa | 1560 |
| aaattggaga ctatttccga gttactggag agatcctgtc tgtgttagga ggagtctact | 1620 |

```
tcttttccg agggattcag tatttcctgc agaggcggcc gtcgatgaag accctgtttg    1680
tggacagcta cagtgagatg cttttcttc  tgcagtcact gttcatgctg gccaccgtgg   1740
tgctgtactt cagccacctc aaggagtatg tggcttccat ggtattctcc ctggccttgg   1800
gctggaccaa catgctctac tacacccgcg gtttccagca gatgggcatc tatgccgtca   1860
tgatagagaa gatgatcctg agagacctgt gccgtttcat gtttgtctac atcgtcttct   1920
tgttcgggtt ttccacagcg gtggtgacgc tgattgaaga cgggaagaat gactccctgc   1980
cgtctgagtc cacgtcgcac aggtggcggg ggcctgcctg caggccccc  gatagctcct    2040 acaacagcct gtactccacc tgcctggagc tgttcaagtt caccatcggc atgggcgacc   2100
tggagttcac tgagaactat gacttcaagg ctgtcttcat catcctgctg ctggcctatg   2160
taattctcac ctacatcctc ctgctcaaca tgctcatcgc cctcatgggt gagactgtca   2220
acaagatcgc acaggagagc aagaacatct ggaagctgca gagagccatc accatcctgg   2280
acacggagaa gagcttcctt aagtgcatga ggaaggcctt ccgctcaggc aagctgctgc   2340
aggtggggta cacacctgat ggcaaggacg actaccggtg gtgcttcagg gtggacgagg   2400
tgaactggac cacctggaac accaacgtgg gcatcatcaa cgaagacccg ggcaactgtg   2460
agggcgtcaa gcgcaccctg agcttctccc tgcggtcaag cagagtttca ggcagacact   2520
ggaagaactt tgccctggtc ccccttttaa gagaggcaag tgctcgagat aggcagtctg   2580
ctcagcccga ggaagtttat ctgcgacagt tttcagggtc tctgaagcca gaggacgctg   2640
aggtcttcaa gagtcctgcc gcttccgggg agaagtgagg acgtcacgca gacagcactg   2700
tcaacactgg gccttaggag accccgttgc acgggggc   tgctgaggga acaccagtgc    2760
tctgtcagca gcctggcctg gtctgtgcct gcccagcatg ttcccaaatc tgtgctggac   2820
aagctgtggg aagcgttctt ggaagcatgg ggagtgatgt acatccaacc gtcactgtcc   2880
ccaagtgaat ctcctaacag actttcaggt ttttactcac tttactaaac agtttggatg   2940
gtcagtctct actgggacat gttaggcccc tgttttcttt gatttattc  ttttttttga    3000 gacagaattt cactcttctc acccaggctg gaatgcagtg gcacaatttt ggctccctgc   3060
aacctccgcc tcctggattc cagcaattct cctgcctcgg cttcccaagt agctgggatt   3120
acaggcacgt gccaccatgt ctggctaatt ttttgtattt ttttaataga tatggggttt   3180
cgccatgttg gccaggctgg tctcgaactc ctgacctcag gtgatccgcc cacctcggcc   3240
tcccaaagtg ctgggattac a                                              3261
```

<210> SEQ ID NO 121
<211> LENGTH: 4307
<212> TYPE: DNA
<213> ORGANISM: Homo sapiens
<220> FEATURE:
<221> NAME/KEY: misc_feature
<223> OTHER INFORMATION: NM_005099

<400> SEQUENCE: 121

```
cacagacaca tatgcacgag agagacagag gaggaaagag acagagacaa aggcacagcg     60
gaagaaggca gagacagggc aggcacagaa gcggcccaga cagagtccta cagagggaga    120
ggccagagaa gctgcagaag acacaggcag ggagagacaa agatccagga aaggagggct    180
caggaggaga gtttggagaa gccagacccc tgggcacctc tcccaagccc aaggactaag    240 tttttctccat ttccttaac ggtcctcagc ccttctgaaa actttgcctc tgaccttggc    300
aggagtccaa gccccaggc  tacagagagg agctttccaa agctagggtg tggaggactt    360
```

| | |
|---|---|
| ggtgccctag acggcctcag tccctcccag ctgcagtacc agtgccatgt cccagacagg | 420 |
| ctcgcatccc gggaggggct tggcagggcg ctggctgtgg ggagcccaac cctgcctcct | 480 |
| gctccccatt gtgccgctct cctggctggt gtggctgctt ctgctactgc tggcctctct | 540 |
| cctgccctca gcccggctgg ccagccccct ccccgggag gaggagatcg tgtttccaga | 600 |
| gaagctcaac ggcagcgtcc tgcctggctc gggcacccct gccaggctgt tgtgccgctt | 660 |
| gcaggccttt ggggagacgc tgctactaga gctggagcag gactccggtg tgcaggtcga | 720 |
| ggggctgaca gtgcagtacc tgggccaggc gcctgagctg ctgggtggag cagagcctgg | 780 |
| cacctacctg actggcacca tcaatggaga tccggagtcg gtggcatctc tgcactggga | 840 |
| tgggggagcc ctgttaggcg tgttacaata tcgggggct gaactccacc tccagcccct | 900 |
| ggagggaggc acccctaact ctgctggggg acctggggct cacatcctac gccggaagag | 960 |
| tcctgccagc ggtcaaggtc ccatgtgcaa cgtcaaggct cctcttggaa gccccagccc | 1020 |
| cagaccccga agagccaagc gctttgcttc actgagtaga tttgtggaga cactggtggt | 1080 |
| ggcagatgac aagatggccg cattccacgg tgcgggcta aagcgctacc tgctaacagt | 1140 |
| gatggcagca gcagccaagg ccttcaagca cccaagcatc cgcaatcctg tcagcttggt | 1200 |
| ggtgactcgg ctagtgatcc tggggtcagg cgaggagggg ccccaagtgg ggcccagtgc | 1260 |
| tgcccagacc ctgcgcagct tctgtgcctg gcagcgggc ctcaacaccc ctgaggactc | 1320 |
| ggaccctgac cactttgaca cagccattct gtttacccgt caggacctgt gtggagtctc | 1380 |
| cacttgcgac acgctgggta tggctgatgt gggcaccgtc tgtgacccgg ctcggagctg | 1440 |
| tgccattgtg gaggatgatg ggctccagtc agccttcact gctgctcatg aactgggtca | 1500 |
| tgtcttcaac atgctccatg acaactccaa gccatgcatc agtttgaatg gcctttgag | 1560 |
| cacctctcgc catgtcatgg cccctgtgat ggctcatgtg gatcctgagg agccctggtc | 1620 |
| cccctgcagt gcccgcttca tcactgactt cctggacaat ggctatgggc actgtctctt | 1680 |
| agacaaacca gaggctccat tgcatctgcc tgtgactttc cctggcaagg actatgatgc | 1740 |
| tgaccgccag tgccagctga ccttcgggcc cgactcacgc cattgtccac agctgccgcc | 1800 |
| gccctgtgct gccctctggt gctctggcca cctcaatggc catgccatgt gccagaccaa | 1860 |
| acactcgccc tgggccgatg gcacaccctg cgggcccgca caggcctgca tgggtggtcg | 1920 |
| ctgcctccac atggaccagc tccaggactt caatattcca caggctggtg gctgggtcc | 1980 |
| ttggggacca tggggtgact gctctcggac ctgtgggggt ggtgtccagt tctcctcccg | 2040 |
| agactgcacg aggcctgtcc cccggaatgg tggcaagtac tgtgagggcc gccgtacccg | 2100 |
| cttccgctcc tgcaacactg aggactgccc aactggctca gccctgacct tcgcgagga | 2160 |
| gcagtgtgct gcctacaacc accgcaccga cctcttcaag agcttcccag ggcccatgga | 2220 |
| ctgggttcct cgctacacag gcgtggcccc ccaggaccag tgcaaactca cctgccaggc | 2280 |
| ccgggcactg ggctactact atgtgctgga gccacgggtg gtagatggga cccctgttc | 2340 |
| cccggacagc tcctcggtct gtgtccaggg ccgatgcatc catgctggct gtgatcgcat | 2400 |
| cattggctcc aagaagaagt ttgacaagtg catggtgtgc ggaggggacg gttctggttg | 2460 |
| cagcaagcag tcaggctcct tcaggaaatt caggtacgga tacaacaatg tggtcactat | 2520 |
| ccccgcgggg gccacccaca ttcttgtccg gcagcaggga aaccctggcc accggagcat | 2580 |
| ctacttggcc ctgaagctgc cagatggctc ctatgccctc aatggtgaat acacgctgat | 2640 |
| gccctccccc acagatgtgg tactgcctgg ggcagtcagc ttgcgctaca gcggggccac | 2700 |
| tgcagcctca gagacactgt caggccatgg gccactggcc cagcctttga cactgcaagt | 2760 |

```
cctagtggct ggcaaccccc aggacacacg cctccgatac agcttcttcg tgccccggcc    2820
gaccccttca acgccacgcc ccactcccca ggactggctg caccgaagag cacagattct    2880
ggagatcctt cggcggcgcc cctgggcggg caggaaataa cctcactatc ccggctgccc    2940
tttctgggca ccggggcctc ggacttagct gggagaaaga gagagcttct gttgctgcct    3000
catgctaaga ctcagtgggg aggggctgtg ggcgtgagac ctgcccctcc tctctgccct    3060
aatgcgcagg ctggccctgc cctggtttcc tgccctggga ggcagtgatg ggttagtgga    3120
tggaaggggc tgacagacag ccctccatct aaactgcccc ctctgccctg cgggtcacag    3180
gagggagggg gaaggcaggg agggcctggg ccccagttgt atttatttag tatttattca    3240
cttttattta gcaccaggga aggggacaag gactagggtc ctggggaacc tgacccctga    3300
cccctcatag ccctcaccct ggggctagga aatccaggat ggtggtgata ggtataagtg    3360
gtgtgtgtat gcgtgtgtgt gtgtgtgtga aaatgtgtgt gtgcttatgt atgaggtaca    3420
acctgttctg ctttcctctt cctgaatttt atttttttggg aaaagaaaag tcaagggtag    3480
ggtgggcctt cagggagtga gggattatct tttttttttt ttctttcttt ctttcttttt    3540
tttttttgag acagaatctc gctctgtcgc ccaggctgga gtgcaatggc acaatctcgg    3600
ctcactgcat cctccgcctc ccgggttcaa gtgattctca tgcctcagcc tcctgagtag    3660
ctgggattac aggctcctgc caccacgccc agctaatttt tgttttgttt tgtttggaga    3720
cagagtctcg ctattgtcac cagggctgga atgatttcag ctcactgcaa ccttcgccac    3780
ctgggttcca gcaattctcc tgcctcagcc tcccgagtag ctgagattat aggcacctac    3840
caccacgccc ggctaatttt tgtatttttta gtagagacgg ggtttcacca tgttggccag    3900
gctggtctcg aactcctgac cttaggtgat ccactcgcct tcatctccca aagtgctggg    3960
attacaggcg tgagccaccg tgcctggcca cgcccaacta attttgtat ttttagtaga    4020 gacagggttt caccatgttg gccaggctgc tcttgaactc ctgacctcag gtaatcgacc    4080
tgcctcggcc tcccaaagtg ctgggattac aggtgtgagc caccacgccc ggtacatatt    4140
ttttaaattg aattctacta tttatgtgat ccttttggag tcagacagat gtggttgcat    4200
cctaactcca tgtctctgag cattagattt ctcatttgcc aataataata cctcccttag    4260
aagtttgttg tgaggattaa ataatgtaaa taaagaacta gcataac                  4307
```

<210> SEQ ID NO 122
<211> LENGTH: 1423
<212> TYPE: DNA
<213> ORGANISM: Homo sapiens
<220> FEATURE:
<221> NAME/KEY: misc_feature
<223> OTHER INFORMATION: U94320

<400> SEQUENCE: 122

```
gaaaggctat cggtaacaac tgacctgcca caaagttaga agaaaggatt gattcaagaa      60
agactataat atggatttag agctcgacga gtattataac aagacacttg ccacagagaa     120
taatactgct gccactcgga attctgattt cccagtctgg gatgactata aaagcagtgt     180
agatgactta cagtatttc tgattgggct ctatacattt gtaagtcttc ttggctttat      240
ggggaatcta cttattttaa tggctctcat gaaaaagcgt aatcagaaga ctacggtaaa     300
cttcctcata ggcaatctgg ccttttctga tatcttggtt gtgctgtttt gctcacccttt    360 cacactgacg tctgtcttgc tggatcagtg gatgtttggc aaagtcatgt gccatattat     420
gccttttctt caatgtgtgt cagttttggt ttcaacttta attttaatat caattgccat     480
```

```
tgtcaggtat catatgataa aacatcccat atctaataat ttaacagcaa accatggcta      540
ctttctgata gctactgtct ggacactagg ttttgccatc tgttctcccc ttccagtgtt      600
tcacagtctt gtggaacttc aagaaacatt tggttcagca ttgctgagca gcaggtattt      660
atgtgttgag tcatggccat ctgattcata cagaattgcc tttactatct ctttattgct      720
agttcagtat attctgccct tagtttgtct tactgtaagt catacaagtg tctgcagaag      780
tataagctgt ggattgtcca acaaagaaaa cagacttgaa gaaaatgaga tgatcaactt      840
aactcttcat ccatccaaaa agagtgggcc tcaggtgaaa ctctctggca gccataaatg      900
gagttattca ttcatcaaaa aacacagaag aagatatagc aagaagacag catgtgtgtt      960
acctgctcca gaaagacctt ctcaagagaa ccactccaga atacttccag aaaactttgg     1020
ctctgtaaga agtcagctct cttcatccag taagttcata ccaggggtcc ccacttgctt     1080
tgagataaaa cctgaagaaa attcagatgt tcatgaattg agagtaaaac gttctgttac     1140
aagaataaaa aagagatctc gaagtgtttt ctacagactg accatactga tattagtatt     1200
tgctgttagt tggatgccac tacacctttt ccatgtggta actgattta atgacaatct      1260 tatttcaaat aggcatttca agttggtgta ttgcatttgt catttgttgg gcatgatgtc     1320
ctgttgtctt aatccaattc tatatgggtt tcttaataat gggattaaag ctgatttagt     1380
gtcccttata cactgtcttc atatgtaata attctcactg ttt                       1423

<210> SEQ ID NO 123
<211> LENGTH: 5078
<212> TYPE: DNA
<213> ORGANISM: Homo sapiens
<220> FEATURE:
<221> NAME/KEY: misc_feature
<223> OTHER INFORMATION: NM_002410

<400> SEQUENCE: 123
taatactcct ttattccctg ttttaaaaat ttttttaaat ttgatacaat aattatacat        60
aataatggag taccatgtga gattcaatcc acatatacat tgtgaaatga tcaaattagg      120
atagttagca tgcacatcac ccccaaataa ttattacttt tgtggtgaga acacttaaaa      180
ttgtctcttt tagaaatata cgttattatt aaccatagtc acctcgctgt gcaatagaac      240
accagaactt attcctccta aatgtaactt tttacccatt gaccactccc tcctcacccc      300
cctctctcct ccccacccct ggtaaccact gttctgttat ctcctatgat agcaacttt       360 tagcttctgc atgtgagatt gtacggtagt tgcctttctg tgcctggatt atttcattta      420
gcataatgtc cttcgggtat atccctgttg ctgcaaaaga caggatttct ctctcttttt      480
ctggttgaat agtattccat tgtcagagaa tgttgtaaga ctaggaaagg aacactgcag      540
gctggagccc tggggaaatg gtctgaggca ggtggtggga ctagagctgg ggtctggcaa      600
acaggctggg tttgattgtc agcataatag agagcactca tgtgccagct gggtgggagg      660
agcagccgag tgaagaaggg gaagcctctc aggaagcatg tgcagggttt atggtaatga      720
gcagaccagc aggtacgtag tgggagaggg gtgtgatggg gcagaggaac ttacgttatg      780
atagtacaag acagaggttg agcctcattt taataggcat tgtggtgggt gttgaatagt      840
gatggaatgt atgggtctgg aatcaggctg cctggtcaag ggctctgaaa catgagtgtg      900
catcagaatc acctcgaggc ttgttaaagg ataggctgtg gaccacatct cctcagttgc      960
tgattcagtg ggtgtgggtg gggcctgaga attcacattt cccactggtg atgctgctgt     1020
tactgattgg gaccacattt ggggaacact ggtctagaat tgagaggttg gcaaaccttc     1080
```

```
tctgttaaga ggtagatagt aaatatttta ggccttctgg gctacaaaga gtatctgtta   1140
catatttttt attgcttttc atgacccatt aagcatatat atatcattct ctgccatata   1200
caaacaggct gttgggggag tgaggatgat gtagggaagg tggggcatgg tttaataacc   1260
cctgggccat gcctagatga tcagtcctct gccacatagc tggctgacct ttgccaagtt   1320
aatcaccttt tacctttatt ttctcatgtt tctaataaaa cagagacgat aatattcata   1380
cttcttacca tatagaactt ctgaggattc agtgagcaaa gccacaaaag atggtatgtc   1440
acaatatctg ggatatagct agaatttata atttattttt actctgttga taggcaatgg   1500
gaaaacagta agaggcagac caacagtgat ccagggctct gaaagctaat tgcttcaaga   1560
tcctgctacc attttctttt gggccgcttg caaagaagaa tcctttgact gaagcatgta   1620
tgtacactct gaagtacagc ctgggttagt ctcttataag ggatcggatc attgctcagc   1680
tctcccttga gtggcactta gaaaatggcg ctattcgtaa gctgactggt attgggccca   1740
ggactctggc tgaaggggtg ggcatgctgg taaccatttg caacctatgc tcaggtccta   1800
cttgttggga agccctgatt gagaagagtg gcctggtctg tgctggcatt agataggatc   1860
tggctgcatt aatattgaaa ctactctgcc ttttaatgtc tcattttgcc tcatggtggg   1920
agtgaaagtg agaaccacag aaaatctgcc tgccaggtgt tccacatttc ttgtgctaca   1980
gcatgcaagt gagcagtgag gtgtaccttt tcctcatgta gctgggaaag caataccccct   2040 gcttgtacct ctggcatatc ttctctgtgc tggtgcacct agagaggttg cctggtggcc   2100
ctgagagagc catctcatca ctaaacactg atggtgaaaa gctggccatg ctcaaataag   2160
atgtagcaat ctacctcttc tttgtctagt tacccccaag ggggcatcca cttcttgct   2220 cacctcacca gttgcatgtt ctagtccttg ccagaagcac ataataatga ctttgtaagc   2280
ttaagttaca ggcacacaaa agggcctgat ggtgatatga ctccaccctc cccgtttttg   2340
ctgacattcc gccaaatatc cttctgtctc ctccccacct tgcaaaacaa acttcctgtt   2400
ttgaatttgg tccaggctgg aacagcccca ccacacctgt aacacacgc agacgcacac    2460 ttcccccttc ataattgctt agcttcttgt tgcctagcca gatttcccct cagcttacag   2520
ttcctgaatc ataagatatt gaaccagcaa atttaagagt tgacatttta cttagaggta   2580
ttcaagtgaa aacatggctt ctggtttatt ttgctgtatt gtgccatgac cacttggcta   2640
attcttctcc tccttcacat cagaatggaa gtgaggaaag caaccagct gacacaggag    2700 ccagagtgag accagcagac tctcacactc aacctacacc atgaatttgt gtctatcttc   2760
tacgcgttaa gagccaagga caggtgaagt tgccagagag caatggctct cttcactccg   2820
tggaagttgt cctctcagaa gctgggcttt ttcctggtga cttttggctt catttggggt   2880
atgatgcttc tgcactttac catccagcag cgaactcagc ctgaaagcag ctccatgctg   2940
cgcgagcaga tcctggacct cagcaaaagg tacatcaagg cactggcaga agaaaacagg   3000
aatgtggtgg atgggccata cgctggagtc atgacagctt atgatctgaa gaaaccctt    3060 gctgtgttat tagataacat tttgcagcgc attggcaagt tggagtcgaa ggtggacaat   3120
cttgttgtca atggcaccgg aacaaactca accaactcca ctacagctgt tcccagcttg   3180
gttgcacttg agaaaattaa tgtggcagat atcattaacg gagctcaaga aaatgtgta    3240 ttgcctccta tggacggcta ccctcactgt gagggaaaga tcaagtggat gaaagacatg   3300
tggcgttcag atccctgcta cgcagactat ggagtggatg gatccacctg ctcttttttt   3360
atttacctca gtgaggttga aaattggtgt cctcatttac cttggagagc aaaaaatccc   3420
```

```
tacgaagaag ctgatcataa ttcattggcg gaaattcgta cagattttaa tattctctac    3480
agtatgatga aaaagcatga agaattccgg tggatgagac tacggatccg gcgaatggct    3540
gacgcatgga tccaagcaat caagtccctg gcagaaaagc agaaccttga aaagagaaag    3600
cggaagaaag tcctcgttca cctgggactc ctgaccaagg aatctggatt taagattgca    3660
gagacagctt tcagtggtgg ccctcttggt gaattagttc aatggagtga tttaattaca    3720
tctctgtact tactgggcca tgacattagg atttcagctt cactggctga gctcaaggaa    3780
atcatgaaga aggttgtagg aaaccgatct ggctgcccaa ctgtaggaga cagaattgtt    3840
gagctcattt acattgatat tgtaggactt gctcaattca agaaaactct tggaccatcc    3900
tgggttcatt accagtgcat gctccgagtc cttgattcat ttggtactga acccgaattt    3960
aatcatgcaa attatgccca atcgaaaggc cacaagaccc cttggggaaa atggaatctg    4020
aaccctcagc agttttatac catgttccct catacccccag acaacagctt tctggggttt    4080
gtggttgagc agcacctgaa ctccagtgat atccaccaca ttaatgaaat caaaaggcag    4140
aaccagtccc ttgtgtatgg caaagtggat agcttctgga agaataagaa gatctacttg    4200
gacattattc acacatacat ggaagtgcat gcaactgttt atggctccag cacaaagaat    4260
attcccagtt acgtgaaaaa ccatggtatc ctcagtggac gggacctgca gttccttctt    4320
cgagaaacca gttgtttgt tggacttggg ttcccttacg agggcccagc tcccctggaa    4380
gctatcgcaa atggatgtgc ttttctgaat cccaagttca acccacccaa aagcagcaaa    4440
aacacagact ttttcattgg caagccaact ctgagagagc tgacatccca gcatccttac    4500
gctgaagttt tcatcgggcg gccacatgtg tggactgttg acctcaacaa tcaggaggaa    4560
gtagaggatg cagtgaaagc aattttaaat cagaagattg agccatacat gccatatgaa    4620
tttacgtgcg aggggatgct acagagaatc aatgctttca ttgaaaaaca ggacttctgc    4680
catgggcaag tgatgtggcc acccctcagc gccctacagg tcaagcttgc tgagcccggg    4740
cagtcctgca gcaggtgtg ccaggagagc cagctcatct gcgagccttc tttcttccag    4800
cacctcaaca aggacaagga catgctgaag tacaaggtga cctgccaaag ctcagagctg    4860
gccaaggaca tcctggtgcc ctcctttgac cctaagaata gcactgtgt gtttcaaggt    4920 gacctcctgc tcttcagctg tgcaggcgcc caccccaggc accagagggt ctgcccctgc    4980
cgggacttca tcaagggcca ggtggctctc tgcaaagact gcctatagca gctacctgct    5040
cagccctgca ccatgctgct ggggaagaca gtggcccc                           5078

<210> SEQ ID NO 124
<211> LENGTH: 887
<212> TYPE: DNA
<213> ORGANISM: Homo sapiens
<220> FEATURE:
<221> NAME/KEY: misc_feature
<223> OTHER INFORMATION: X16863

<400> SEQUENCE: 124
tctttggtga cttgtccact ccagtgtggc atcatgtggc agctgctcct cccaactgct     60
ctgctacttc tagtttcagc tggcatgcgg actgaagatc tcccaaaggc tgtggtgttc    120
ctggagcctc aatggtacag cgtgcttgag aaggacagtg tgactctgaa gtgccagggga    180 gcctactccc ctgaggacaa ttccacacag tggtttcaca atgagagcct catctcaagc    240
caggcctcga gctacttcat tgacgctgcc acagtcaacg acagtggaga gtacaggtgc    300
cagacaaacc tctccaccct cagtgacccg gtgcagctag aagtccatat cggctggctg    360
```

```
ttgctccagg cccctcggtg ggtgttcaag gaggaagacc ctattcacct gaggtgtcac      420
agctggaaga acactgctct gcataaggtc acatatttac agaatggcaa agacaggaag      480
tattttcatc ataattctga cttccacatt ccaaaagcca cactcaaaga tagcggctcc      540
tacttctgca gggggcttgt tgggagtaaa aatgtgtctt cagagactgt gaacatcacc      600
atcactcaag gtttggcagt gtcaaccatc tcatcattct ctccacctgg gtaccaagtc      660
tctttctgct tggtgatggt actccttttt gcagtggaca caggactata tttctctgtg      720
aagacaaaca tttgaagctc aacaagagac tggaaggacc ataaacttaa atggagaaag      780
gaccctcaag acaaatgacc cccatcccat gggagtaata agagcagtgg cagcagcatc      840
tctgaacatt tctctggatt tgcaaccca tcatcctcag gcctctc                     887

<210> SEQ ID NO 125
<211> LENGTH: 1800
<212> TYPE: DNA
<213> ORGANISM: Homo sapiens
<220> FEATURE:
<221> NAME/KEY: misc_feature
<223> OTHER INFORMATION: XM_042961

<400> SEQUENCE: 125
cttctctgcc agaagatacc atttcaactt taacacagca tgatcgaaac atacaaccaa       60
acttctcccc gatctgcggc cactggactg cccatcagca tgaaaatttt tatgtattta      120
cttactgttt ttcttatcac ccagatgatt gggtcagcac ttttgctgt gtatcttcat       180 agaaggttgg acaagataga agatgaaagg aatcttcatg aagattttgt attcatgaaa      240
acgatacaga gatgcaacac aggagaaaga tccttatcct tactgaactg tgaggagatt      300
aaaagccagt ttgaaggctt tgtgaaggat ataatgttaa acaaagagga gacgaagaaa      360
gaaaacagct ttgaaatgca aaaaggtgat cagaatcctc aaattgcggc acatgtcata      420
agtgaggcca gcagtaaaac aacatctgtg ttacagtggg ctgaaaaagg atactacacc      480
atgagcaaca acttggtaac cctggaaaat gggaaacagc tgaccgttaa agacaaggga      540
ctctattata tctatgccca agtcaccttc tgttccaatc gggaagcttc gagtcaagct      600
ccatttatag ccagcctctg cctaaagtcc cccggtagat cgagagaat cttactcaga      660 gctgcaaata cccacagttc cgccaaacct tgcgggcaac aatccattca cttgggagga      720
gtatttgaat tgcaaccagg tgcttcggtg tttgtcaatg tgactgatcc aagccaagtg      780
agccatggca ctggcttcac gtcctttggc ttactcaaac tctgaacagt gtcaccttgc      840
aggctgtggt ggagctgacg ctgggagtct tcataataca gcacagcggt taagcccacc      900
ccctgttaac tgcctattta aaccctagg atcctcctta tggagaacta tttattatac      960
actccaaggc atgtagaact gtaataagtg aattacaggt cacatgaaac caaaacgggc     1020
cctgctccat aagagcttat atatctgaag cagcaacccc actgatgcag acatccagag     1080
agtcctatga aaagacaagg ccattatgca caggttgaat tctgagtaaa cagcagataa     1140
cttgccaagt tcagttttgt ttctttgcgt gcagtgtctt tccatggata atgcatttga     1200
tttatcagtg aagatgcaga agggaaatgg ggagcctcag ctcacattca gttatggttg     1260 actctggggtt cctatggcct tgttggaggg ggccaggctc tagaacgtct aacacagtgg     1320
agaaccgaaa ccccccccc ccccccgcca ccctctcgga cagttattca ttctctttca     1380
atctctctct ctccatctct ctctttcagt ctctctctct caacctcttt cttccaatct     1440
ctctttctca atctctctgt ttccctttgt cagtctcttc cctcccccag tctctcttct     1500
```

-continued

| | | |
|---|---|---|
| caatccccct tcctaacaca cacacacaca cacacacaca cacacacaca cacacacaca | 1560 | |
| cacacacaga gtcaggccgt tgctagtcag ttctcttctt tccaccctgt ccctatctct | 1620 | |
| accactatag atgagggtga ggagtaggga gtgcagccct gagcctgccc actcctcatt | 1680 | |
| acgaaatgac tgtatttaaa ggaaatctat tgtatctacc tgcagtctcc attgtttcca | 1740 | |
| gagtgaactt gtaattatct tgttatttat ttttttgaata ataaagacct cttaacatta | 1800 | |

<210> SEQ ID NO 126
<211> LENGTH: 1450
<212> TYPE: DNA
<213> ORGANISM: Homo sapiens
<220> FEATURE:
<221> NAME/KEY: misc_feature
<223> OTHER INFORMATION: J04101

<400> SEQUENCE: 126

| | | |
|---|---|---|
| ttgggaagaa agtcggattt cccccgtccc cttcccctg ttactaatcc tcattaaaaa | 60 | |
| gaaaaacaac aataactgca aacttgctac catcccgtac gtcccccact cctggcacca | 120 | |
| tgaaggcggc cgtcgatctc aagccgactc tcaccatcat caagacggaa aaagtcgatc | 180 | |
| tggagctttt cccctccccg gatatggaat gtgcagatgt cccactatta actccaagca | 240 | |
| gcaaagaaat gatgtctcaa gcattaaaag ctactttcag tggtttcact aaagaacagc | 300 | |
| aacgactggg gatcccaaaa gaccccggc agtggacaga aacccatgtt cgggactggg | 360 | |
| tgatgtgggc tgtgaatgaa ttcagcctga aggtgtaga cttccagaag ttctgtatga | 420 | |
| atggagcagc cctctgcgcc ctgggtaaag actgctttct cgagctggcc ccagactttg | 480 | |
| ttggggacat cttatgggaa catctagaga tcctgcagaa agaggatgtg aaaccatatc | 540 | |
| aagttaatgg agtcaaccca gcctatccag aatcccgcta tacctcggat tacttcatta | 600 | |
| gctatggtat tgagcatgcc cagtgtgttc caccatcgga gttctcagag cccagcttca | 660 | |
| tcacagagtc ctatcagacg ctccatccca tcagctcgga agagctcctc tccctcaagt | 720 | |
| atgagaatga ctaccccctcg gtcattctcc gagaccctct ccagacagac accttgcaga | 780 | |
| atgactactt tgctatcaaa caagaagtcg tcaccccaga caacatgtgc atggggagga | 840 | |
| ccagtcgtgg taaactcggg ggccaggact cttttgaaag catagagagc tacgatagtt | 900 | |
| gtgatcgcct caccccagtcc tggagcagcc agtcatcttt caacagcctg cagcgtgttc | 960 | |
| cctcctatga cagcttcgac tcagaggact atccggctgc cctgcccaac acaagcccca | 1020 | |
| agggcacctt caaggactat gtgcgggacc gtgctgacct caataaggac aagcctgtca | 1080 | |
| ttcctgctgc tgccctagct ggctacacag gcagtggacc aatccagcta tggcagtttc | 1140 | |
| ttctggaatt actcactgat aaatcctgtc agtctttat cagctggaca ggagatggct | 1200 | |
| gggaattcaa actttctgac ccagatgagg tggccaggag atggggaaag aggaaaaaca | 1260 | |
| aacctaagat gaattatgag aaactgagcc gtggcctacg ctactattac gacaaaaaca | 1320 | |
| tcatccacaa gacagcgggg aaacgctacg tgtaccgctt tgtgtgtgac ctgcagagcc | 1380 | |
| tgctggggta caccctgag gagctgcacg ccatgctgga cgtcaagcca gatgccgacg | 1440 | |
| agtgatggca | 1450 | |

<210> SEQ ID NO 127
<211> LENGTH: 6069
<212> TYPE: DNA
<213> ORGANISM: Homo sapiens
<220> FEATURE:
<221> NAME/KEY: misc_feature
<223> OTHER INFORMATION: XM_047802

<400> SEQUENCE: 127

```
gcagctgccg actggggatg acggcgggca ggaggagacc gcagccgaag ggacacagac    60
acgccgcttc accagctcgc ctcaggctgc ccccctgcat ttttgtttta attttt acgg   120
cttttt cccc tctctttctt ccctt cctcc tggtcccagc agagccaagg aaacccacaa  180
aataagaaag gaagtgggcc ccggagcttg aacctccac agccggcttg tccagcgcag     240
cgcggggcg ggaggctgcg cgcaccagtt gccagcccgg tgcgcggtac ctttccttac     300
ttttcttgaa acagcgatcg tgcctgcatt tggtggtttt ttggtttttg ttttttt cct   360
tttcccgtat ttgctgaatc tccactatcc gactttttt ttttaatctt ttctttcccc    420
cccccccac cccacctctt tctggagcac gaatccaaac attttcccaa gcaacaaaga    480
aaagttcgca cgctggcacc gcagcccgga caggctggcg ctgctgccgg gccccctcc    540
ctccgacact tgactcaatc ctgcaagcaa gtgtgtgtgt gtcccatcc cccgcccgt     600
taacttcata gcaaataaca aatacccata aagtcccagt cgcgcagccc ctcccgcgg    660
gcagcgcact atgctgctcg ggtgggcgtc cctgctgctg tgcgcgttcc gcctgcccct   720
ggccgcggtc ggccccgccg cgacaccctgc ccaggataaa gccgggcagc ctccgactgc  780
tgcagcagcc gcccagcccc gccggcggca gggggaggag gtgcaggagc gagccgagcc   840
tcccggccac ccgcacccc tggcgcagcg gcgcaggagc aagggctgg tgcagaacat     900
cgaccaactc tactccggcg gcggcaaggt gggctaccctc gtctacgcgg gcggccggag  960
gttcctcttg gacctggagc gagatggttc ggtgggcatt gctggcttcg tgcccgcagg  1020
aggcgggacg agtgcgccct ggcgccaccg gagccactgc ttctatcggg gcacagtgga  1080
cggtagtccc cgctctctgg ctgtctttga cctctgtggg ggtctcgacg gcttcttcgc  1140
ggtcaagcac gcgcgctaca ccctaaaagcc actgctgcgc ggaccctggg cggaggaaga  1200
aaagggcgc gtgtacgggg atgggtccgc acggatcctg cacgtctaca cccgcgaggg  1260
cttcagcttc gaggccctgc cgccgcgcgc cagctgcgaa accccgcgt ccacaccgga   1320
ggcccacgag catgctccgg cgcacagcaa cccgagcgga cgcgcagcac tggcctcgca  1380
gctcttggac cagtccgctc tctcgcccgc tgggggctca ggaccgcaga cgtggtggcg  1440
gcggcggcgc cgctccatct cccgggcccg ccaggtggag ctgcttctgg tggctgacgc  1500
gtccatggcg cggttgtatg gccggggcct gcagcattac ctgctgaccc tggcctccat  1560
cgccaatagg ctgtacagcc atgctagcat cgagaaccac atccgcctgg ccgtggtgaa  1620
ggtggtggtg ctaggcgaca aggacaagag cctggaagtg agcaagaacg ctgccaccac  1680
actcaagaac ttttgcaagt ggcagcacca acacaaccag ctgggagatg accatgagga  1740
gcactacgat gcagctatcc tgtttactcg ggaggattta tgtgggcatc attcatgtga  1800
cacctgggga atggcagacg ttgggaccat atgttctcca gagcgcagct gtgctgtgat  1860
tgaagacgat ggcctccacg cagccttcac tgtggctcac gaaatcggac atttacttgg  1920
cctctcccat gacgattcca aattctgtga agagaccttt ggttccacag aagataagcg  1980
cttaatgtct tccatcctta ccagcattga tgcatctaag ccctggtcca aatgcacttc  2040
agccaccatc acagaattcc tggatgatgg ccatggtaac tgtttgctgg acctaccacg  2100
aaagcagatc ctgggccccg aagaactccc aggacagacc tacgatgcca cccagcagtg  2160
caacctgaca ttcgggcctg agtactccgt tgtcccggc atggatgtct gtgctcgcct  2220
gtggtgtgct gtggtacgcc agggccagat ggtctgtctg accaagaagc tgcctgcggt  2280
```

```
ggaagggacg ccttgtggaa aggggagaat ctgcctgcag ggcaaatgtg tggacaaaac    2340
caagaaaaaa tattattcaa cgtcaagcca tggcaactgg ggatcttggg gatcctgggg    2400
ccagtgttct cgctcatgtg gaggaggagt gcagtttgcc tatcgtcact gtaataaccc    2460
tgctcccaga acaacggac gctactgcac agggaagagg gccatctacc gctcctgcag     2520
tctcatgccc tgcccaccca atggtaaatc atttcgtcat gaacagtgtg aggccaaaaa    2580
tggctatcag tctgatgcaa aaggagtcaa aacttttgtg gaatgggttc ccaaatatgc    2640
aggtgtcctg ccagcggatg tgtgcaagct gacctgcaga gccaagggca ctggctacta    2700
tgtggtattt tctccaaagg tgaccgatgg cactgaatgt aggctgtaca gtaattccgt    2760
ctgcgtccgg gggaagtgtg tgagaactgg ctgtgacggc atcattggct caaagctgca    2820
gtatgacaag tgcggagtat gtggaggaga caactccagc tgtacaaaga ttgttggaac    2880
ctttaataag aaaagtaagg gttacactga cgtggtgagg attcctgaag gggcaaccca    2940
cataaaagtt cgacagttca agccaaagaa ccagactaga ttcactgcct atttagccct    3000 gaaaagaaa aacggtgagt acttatcaa tggaaagtac atgatctcca cttcagagac      3060
tatcattgac atcaatggaa cagtcatgaa ctatagcggt tggagccaca gggatgactt    3120
cctgcatggc atgggctact ctgccacgaa ggaaattcta atagtgcaga ttcttgcaac    3180
agaccccact aaaccattag atgtccgtta tagcttttttt gttcccaaga agtccactcc   3240
aaaagtaaac tctgtcacta gtcatggcag caataaagtg ggatcacaca cttcgcagcc    3300
gcagtgggtc acgggcccat ggctcgcctg ctctaggacc tgtgacacag gttggcacac    3360
cagaacggtg cagtgccagg atggaaaccg gaagttagca aaaggatgtc ctctctccca    3420
aaggccttct gcgtttaagc aatgcttgtt gaagaaatgt tagcctgtgg ttatgatctt    3480
atgcacaaag ataactggag gattcagcac tgatgcagtc gtggtgaaca ggaggtctac    3540
ctaacgcaca gaaagtcatg cttcagtgac attgtcaaca ggagtccaat tatgggcaga    3600
atctgctctc tgtgaccaaa agaggatgtg cactgcttca cgtgacagtg gtgaccttgc    3660
aatatagaaa aacttgggag ttattgaaca tcccctgggc ttacaagaaa cactgatgaa    3720
tgtaaaatca ggggacattt gaagatggca gaactgtctc cccccttgtca cctacctctg   3780 atagaatgtc tttaatggta tcataatcat tttcacccat aatacacagt agcttcttct    3840
tactgtttgt aaatacattc tcccttggta tgtcactttta tatcccctgg ttctattaaa   3900
atatccatat atatttctat aaaaaaagtg tttgaccaaa gtaggtctgc agctatttca    3960
acttccttcc gtttccagaa agagctgtgg atattttact ggaaattaag aacttgctgc    4020
tgttttaata agatgtagta tattttctga ctacaggaga taaaatttca gtcaaaaaac    4080
cattttgaca gcaagtatct tctgagaaat tttgaaaagt aaatagatct cagtgtatct    4140
agtcacttaa atacatacac gggttcattt acttaaacct ttgactgcct gtatttttttt  4200 caggtagcta gccaaattaa tgcataattt cagatgtaga agtagggttt gcgtgtgtgt    4260
gtgtgatcat actcaagagt ctaaaaacta gtttccttgt gttggaaatt taaaaggaaa    4320
aaaatcgtat ttcactgtgt tttcaattta tattttcaca actactttct ctctccagag    4380
ctttcatctg atatctcaca atgtatgata tacgtacaaa acacacagca agttttctat    4440
catgtccaac acattcaaca ctggtatacc tcctaccagc aagcctttaa aatgcatttg    4500
tgtttgctta tttgttttgt tcaagggttc agtaagacct acaatgtttt gtatttcttg    4560
acttatttta ttagaaacat taaagatcac ttggtagtta gccacattga gaagtggtta    4620
tcattgttaa tgtggttaat gccaaaaagt ggttaatatt aataagactg tttccacacc    4680
```

```
ataggcaata atttcttaat ttaaaaaatc taagtatatt cctattgtac taaatatttt    4740
tcccaactgg aaagcacttg attgtacccg taagtgtttg agtgatgaca tgtgatgatt    4800
ttcagaaagt tgttgttttt gtttccatag cctgtttaag taggttgtaa gtttgaatag    4860
ttagacatgg aaattatttt ataagcacac acctaaagat atcttttag atgataaaat     4920 gtacaccccc ccatcaccaa cctcacaact tagaaaatct aagttgtttg atttctttgg    4980
gatttctttt gttgtgaaac actgcaaagc caattttttct ttataaaaat tcatagtaat   5040
cctgccaaat gtgcctattg ttaaagattt gcatgtgaag atcttaggga accactgttt    5100
gagttctaca agctcatgag agtttatttt tattataaga tgttttaat ataaaagaat     5160 tatgtaactg atcactatat tacatcattt cagtgggcca ggaaaataga tgtcttgctg    5220
ttttcagtat tttcttaaga aattgctttt aaaacaaata attgttttac aaaaccaata    5280
attatccttt gaattttcat agactgactt tgcttttgac gtagaaattt ttttctcaa     5340 taaattatca ctttgagaaa tgaggcctgt acaaggctga taacctatat gtgatggaga    5400
tcacccaatg ccaagggcag aaagcaaacc tagttaaata ggtgagaaaa aaataataa    5460 tcccagtgcc atttgtctgt gcaaagagaa ttaggagaga ggttaatgtt actttttcc    5520 attttggaaa taattttaat caagtaactc aaatgtgaca aaatttattt ttattttttg    5580
tggttatatt cccaacaaca ttaaaaaata ctcgaggcat aaatgtagtt gtctcctact    5640
ctgcttctct tactatactc atacattttt aatatggttt atcaatgatt catgtttccc    5700
tcaaatagtg atggtttaca cctgtcatgg aaacaatcct agagagctca gagcaattaa    5760
accactattc catgctttta agtagttttc tccacctttt tcttatgagt ctcactagat    5820
tgactgagga atgtatgtct aaattcctgg agaagatgat atggattgga aactgaaatt    5880
cagagaaatg gagtgttcaa tagataccac gaattgtgaa caagggaaa attctataca    5940 actcaatcta agtcagtcca ctttgacttc gtactgtctt tcacctttcc attgttgcat    6000
cttgaatttt ttaaaatgtc tagaattcag gatgctaggg gctacttctt taaaaaaaaa    6060
aaaaaaaaa                                                             6069
```

<210> SEQ ID NO 128
<211> LENGTH: 3318
<212> TYPE: DNA
<213> ORGANISM: Homo sapiens
<220> FEATURE:
<221> NAME/KEY: misc_feature
<223> OTHER INFORMATION: NM_002827

<400> SEQUENCE: 128

```
gtgatgcgta gttccggctg ccggttgaca tgaagaagca gcagcggcta gggcggcggt      60
agctgcaggg gtcggggatt gcagcgggcc tcggggctaa gagcgcgacg cggcctagag     120
cggcagacgg cgcagtgggc cgagaaggag gcgcagcagc cgccctggcc cgtcatggag     180
atggaaaagg agttcgagca gatcgacaag tccgggagct gggcggccat ttaccaggat     240
atccgacatg aagccagtga cttcccatgt agagtggcca agcttcctaa gaacaaaaac     300
cgaaataggt acagagacgt cagtcccttt gaccatagtc ggattaaact acatcaagaa    360
gataatgact atatcaacgc tagtttgata aaaatggaag aagcccaaag gagttacatt    420
cttacccagg gccctttgcc taacacatgc ggtcactttt gggagatggt gtgggagcag   480
aaaagcaggg gtgtcgtcat gctcaacaga gtgatggaga aaggtcgtt aaaatgcgca     540 caatactggc cacaaaaaga agaaaaagag atgatctttg aagacacaaa tttgaaatta   600
```

```
acattgatct ctgaagatat caagtcatat tatacagtgc gacagctaga attggaaaac    660
cttacaaccc aagaaactcg agagatctta catttccact ataccacatg gcctgacttt    720
ggagtccctg aatcaccagc ctcattcttg aactttcttt tcaaagtccg agagtcaggg    780
tcactcagcc cggagcacgg gcccgttgtg gtgcactgca gtgcaggcat cggcaggtct    840
ggaaccttct gtctggctga tacctgcctc ttgctgatgg acaagaggaa agacccttct    900
tccgttgata tcaagaaagt gctgttagaa atgaggaagt tcggatggg gctgatccag     960
acagccgacc agctgcgctt ctcctacctg gctgtgatcg aaggtgccaa attcatcatg   1020
ggggactctt ccgtgcagga tcagtggaag gagctttccc acgaggacct ggagccccca   1080
cccgagcata tcccccacc tccccggcca cccaaacgaa tcctggagcc acacaatggg    1140
aaatgcaggg agttcttccc aaatcaccag tgggtgaagg aagagaccca ggaggataaa   1200
gactgcccca tcaaggaaga aaaaggaagc cccttaaatg ccgcaccta cggcatcgaa    1260
agcatgagtc aagacactga agttagaagt cgggtcgtgg ggggaagtct tcgaggtgcc   1320
caggctgcct ccccagccaa aggggagccg tcactgcccg agaaggacga ggaccatgca   1380
ctgagttact ggaagccctt cctggtcaac atgtgcgtgg ctacggtcct cacggccggc   1440
gcttacctct gctacaggtt cctgttcaac agcaacacat agcctgaccc tcctccactc   1500
cacctccacc cactgtccgc ctctgcccgc agagcccacg cccgactagc aggcatgccg   1560
cggtaggtaa gggccgccgg accgcgtaga gagccgggcc ccggacggac gttggttctg   1620
cactaaaacc catcttcccc ggatgtgtgt ctcacccctc atccttttac tttttgcccc   1680
ttccactttg agtaccaaat ccacaagcca ttttttgagg agagtgaaag agagtaccat   1740
gctggcggcg cagagggaag gggcctacac ccgtcttggg gctcgcccca cccagggctc   1800
cctcctggag catcccaggc gggcggcacg ccaacagccc cccccttgaa tctgcaggga   1860
gcaactctcc actccatatt tatttaaaca atttttttccc caaaggcatc catagtgcac   1920
tagcattttc ttgaaccaat aatgtattaa aattttttga tgtcagcctt gcatcaaggg   1980
ctttatcaaa aagtcaaata ataaatcctc aggtagtact gggaatggaa ggctttgcca   2040
tgggcctgct gcgtcagacc agtactggga aggaggacgg ttgtaagcag ttgttatta    2100
gtgatattgt gggtaacgtg agaagataga acaatgctat aatatataat gaacacgtgg   2160
gtatttaata agaaacatga tgtgagatta ctttgtcccg cttattctcc tccctgttat   2220
ctgctagatc tagttctcaa tcactgctcc cccgtgtgta ttagaatgca tgtaaggtct   2280
tcttgtgtcc tgatgaaaaa tatgtgcttg aaatgagaaa ctttgatctc tgcttactaa   2340
tgtgccccat gtccaagtcc aacctgcctg tgcatgacct gatcattaca tggctgtggt   2400
tcctaagcct gttgctgaag tcattgtcgc tcagcaatag ggtgcagttt tccaggaata   2460
ggcatttgcc taattcctgg catgacactc tagtgacttc ctggtgaggc ccagcctgtc   2520
ctggtacagc agggtcttgc tgtaactcag acattccaag ggtatgggaa gccatattca   2580
cacctcacgc tctggacatg atttagggaa gcagggacac ccccgcccc ccacctttgg    2640
gatcagcctc cgccattcca agtcaacact cttcttgagc agaccgtgat ttggaagaga   2700
ggcacctgct ggaaaccaca cttcttgaaa cagcctgggt gacggtcctt taggcagcct   2760
gccgccgtct ctgtcccggt tcaccttgcc gagagaggcg cgtctgcccc accctcaaac   2820
cctgtggggc ctgatggtgc tcacgactct tcctgcaaag ggaactgaag acctccacat   2880
taagtggctt tttaacatga aaaacacggc agctgtagct cccgagctac tctcttgcca   2940
```

| | |
|---|---|
| gcattttcac attttgcctt tctcgtggta gaagccagta cagagaaatt ctgtggtggg | 3000 |
| aacattcgag gtgtcaccct gcagagctat ggtgaggtgt ggataaggct taggtgccag | 3060 |
| gctgtaagca ttctgagctg ggcttgttgt ttttaagtcc tgtatatgta tgtagtagtt | 3120 |
| tgggtgtgta tatatagtag catttcaaaa tggacgtact ggtttaacct cctatccttg | 3180 |
| gagagcagct ggctctccac cttgttacac attatgttag agaggtagcg agctgctctg | 3240 |
| ctatatgcct taagccaata tttactcatc aggtcattat ttttacaat ggccatggaa | 3300 |
| taaaccattt ttacaaaa | 3318 |

<210> SEQ ID NO 129
<211> LENGTH: 1973
<212> TYPE: DNA
<213> ORGANISM: Homo sapiens
<220> FEATURE:
<221> NAME/KEY: misc_feature
<223> OTHER INFORMATION: NM_002421

<400> SEQUENCE: 129

| | |
|---|---|
| gggatattgg agtagcaaga ggctgggaag ccatcactta ccttgcactg agaaagaaga | 60 |
| caaaggccag tatgcacagc tttcctccac tgctgctgct gctgttctgg ggtgtggtgt | 120 |
| ctcacagctt cccagcgact ctagaaacac aagagcaaga tgtggactta gtccagaaat | 180 |
| acctggaaaa atactacaac ctgaagaatg atggggaggca agttgaaaag cggagaaata | 240 |
| gtggcccagt ggttgaaaaa ttgaagcaaa tgcaggaatt ctttgggctg aaagtgactg | 300 |
| ggaaaccaga tgctgaaacc ctgaaggtga tgaagcagcc cagatgtgga gtgcctgatg | 360 |
| tggctcagtt tgtcctcact gaggggaacc ctcgctggga gcaaacacat ctgacctaca | 420 |
| ggattgaaaa ttacacgcca gatttgccaa gagcagatgt ggaccatgcc attgagaaag | 480 |
| ccttccaact ctggagtaat gtcacacctc tgacattcac caaggtctct gagggtcaag | 540 |
| cagacatcat gatatctttt gtcaggggag atcatcggga caactctcct tttgatggac | 600 |
| ctggaggaaa tcttgctcat gctttcaac caggcccagg tattggaggg gatgctcatt | 660 |
| ttgatgaaga tgaaaggtgg accaacaatt tcagagagta caacttacat cgtgttgcgg | 720 |
| ctcatgaact cggccattct cttggactct cccattctac tgatatcggg gctttgatgt | 780 |
| accctagcta caccttcagt ggtgatgttc agctagctca ggatgacatt gatggcatcc | 840 |
| aagccatata tggacgttcc caaaatcctg tccagcccat cggcccacaa accccaaaag | 900 |
| cgtgtgacag taagctaacc tttgatgcta taactacgat tcggggagaa gtgatgttct | 960 |
| ttaaagacag attctacatg cgcacaaatc ccttctaccc ggaagttgag ctcaatttca | 1020 |
| tttctgtttt ctggccacaa ctgccaaatg ggcttgaagc tgcttacgaa tttgccgaca | 1080 |
| gagatgaagt ccggttttc aaagggaata agtactgggc tgttcaggga cagaatgtgc | 1140 |
| tacacggata ccccaaggac atctacagct ccttttggctt ccctagaact gtgaagcata | 1200 |
| tcgatgctgc tctttctgag gaaaacactg gaaaaaccta cttctttgtt gctaacaaat | 1260 |
| actggaggta tgatgaatat aaacgatcta tggatccagg ttatccaaa atgatagcac | 1320 |
| atgacttccc tggaattggc cacaaagttg atgcagtttt catgaaagat ggattttct | 1380 |
| atttctttca tggaacaaga caatacaaat ttgatcctaa aacgaagaga attttgactc | 1440 |
| tccagaaagc taatagctgg ttcaactgca ggaaaaattg aacattacta atttgaatgg | 1500 |
| aaaacacatg gtgtgagtcc aaagaaggtg ttttcctgaa gaactgtcta ttttctcagt | 1560 |
| cattttaac tctagagtc actgatacac agaatataat cttatttata cctcagtttg | 1620 |

-continued

| | |
|---|---|
| catatttttt tactatttag aatgtagccc tttttgtact gatataattt agttccacaa | 1680 |
| atggtgggta caaaaagtca agtttgtggc ttatggattc atataggcca gagttgcaaa | 1740 |
| gatcttttcc agagtatgca actctgacgt tgatcccaga gagcagcttc agtgacaaac | 1800 |
| atatcctttc aagacagaaa gagacaggag acatgagtct ttgccggagg aaaagcagct | 1860 |
| caagaacaca tgtgcagtca ctggtgtcac cctggatagg caagggataa ctcttctaac | 1920 |
| acaaaataag tgttttatgt ttggaataaa gtcaaccttg tttctactgt ttt | 1973 |

<210> SEQ ID NO 130
<211> LENGTH: 2279
<212> TYPE: DNA
<213> ORGANISM: Homo sapiens
<220> FEATURE:
<221> NAME/KEY: misc_feature
<223> OTHER INFORMATION: NM_001752

<400> SEQUENCE: 130

| | |
|---|---|
| tgcctgctga gggtggagac ccacgagccg aggcctcctg cagtgttctg cacagcaaac | 60 |
| cgcacgctat ggctgacagc cgggatcccg ccagcgacca gatgcagcac tggaaggagc | 120 |
| agcgggccgc gcagaaagct gatgtcctga ccactggagc tggtaaccca gtaggagaca | 180 |
| aacttaatgt tattacagta gggccccgtg ggcccttct tgttcaggat gtggttttca | 240 |
| ctgatgaaat ggctcatttt gaccgagaga aattcctga gagagttgtg catgctaaag | 300 |
| gagcagggc cttggctac tttgaggtca cacatgacat taccaaatac tccaaggcaa | 360 |
| aggtatttga gcatattgga aagaagactc ccatcgcagt tcggttctcc actgttgctg | 420 |
| gagaatcggg ttcagctgac acagttcggg accctcgtgg gtttgcagtg aaattttaca | 480 |
| cagaagatgg taactgggat ctcgttggaa ataacacccc cattttcttc atcagggatc | 540 |
| ccatattgtt tccatctttt atccacagcc aaaagagaaa tcctcagaca catctgaagg | 600 |
| atccggacat ggtctgggac ttctggagcc tacgtcctga gtctctgcat caggtttctt | 660 |
| tcttgttcag tgatcggggg attccagatg acatcgcca catgaatgga tatggatcac | 720 |
| atactttcaa gctggttaat gcaaatgggg aggcagttta ttgcaaattc cattataaga | 780 |
| ctgaccaggg catcaaaaac cttttctgttg aagatgcggc gagactttcc caggaagatc | 840 |
| ctgactatgg catccgggat cttttttaacg ccattgccac aggaaagtac ccctcctgga | 900 |
| cttttttacat ccaggtcatg acatttaatc aggcagaaac ttttccattt aatccattcg | 960 |
| atctcaccaa ggtttggcct cacaaggact accctctcat cccagttggt aaactggtct | 1020 |
| taaaccggaa tccagttaat tactttgctg aggttgaaca gatagccttc gacccaagca | 1080 |
| acatgccacc tggcattgag gccagtcctg acaaaatgct tcagggccgc cttttttgcct | 1140 |
| atcctgacac tcaccgccat cgcctgggac ccaattatct tcatataacct gtgaactgtc | 1200 |
| cctaccgtgc tcgagtggcc aactaccagc gtgatggccc gatgtgcatg caggacaatc | 1260 |
| agggtggtgt tccaaattac taccccaaca gctttggtgc tccggaacaa cagccttctg | 1320 |
| ccctggagca cagcatccaa tattctggag aagtgcggag attcaacact gccaatgatg | 1380 |
| ataacgttac tcaggtgcgg gcattctatg tgaacgtgct gaatgaggaa cagaggaaac | 1440 |
| gtctgtgtga gaacattgcc ggccacctga aggatgcaca aatttttcatc cagaagaaag | 1500 |
| cggtcaagaa cttcactgag gtccaccctg actacgggag ccacatccag gctcttctgg | 1560 |
| acaagtacaa tgctgagaag cctaagaatg cgattcacac ctttgtgcag tccggatctc | 1620 |
| acttggcggc aagggagaag gcaaatctgt gaggccgggg ccctgcacct gtgcagcgaa | 1680 |

-continued

| | |
|---|---|
| gcttagcgtt catccgtgta acccgctcat cactggatga agattctcct gtgctagatg | 1740 |
| tgcaaatgca agctagtggc ttcaaaatag agaatcccac tttctatagc agattgtgta | 1800 |
| acaattttaa tgctatttcc ccaggggaaa atgaaggtta ggatttaaca gtcatttaaa | 1860 |
| aaaaaaattt gttttgacgg atgattggat tattcattta aaatgattag aaggcaagtt | 1920 |
| tctagctaga aatatgattt tatttgacaa aatttgttga aattatgtat gtttacatat | 1980 |
| cacctcatgg cctattatat taaaatatgg ctataaatat ataaaaagaa aagataaaga | 2040 |
| tgatctactc agaaattttt attttttctaa ggttctcata ggaaaagtac atttaataca | 2100 |
| gcagtgtcat cagaagataa cttgagcacc gtcatggctt aatgtttatt cctgataata | 2160 |
| attgatcaaa ttcattttt tcactggagt tacattaatg ttaattcagc actgatttca | 2220 |
| caacagatca atttgtaatt gcttacattt ttacaataaa taatctgtac gtaagaaca | 2279 |

<210> SEQ ID NO 131
<211> LENGTH: 2438
<212> TYPE: DNA
<213> ORGANISM: Homo sapiens
<220> FEATURE:
<221> NAME/KEY: misc_feature
<223> OTHER INFORMATION: NM_016155

<400> SEQUENCE: 131

| | |
|---|---|
| ccggcggggg cgccgcggag agcggagggc gccgggctgc ggaacgcgaa gcggagggcg | 60 |
| cgggaccctg cacgccgccc gcgggcccat gtgagcgcca tgcggcgccg cgcagcccgg | 120 |
| ggacccggcc cgccgccccc agggcccgga ctctcgcggt tgccgctgct gccgctgccg | 180 |
| ctgctgctgc tgctggcgct ggggacccgc ggggctgcg ccgcgcccgc acccgcgccg | 240 |
| cgcgccgagg acctcagcct gggagtggag tggctaagca ggttcggtta cctgcccccg | 300 |
| gctgacccca acagggca gctgcagacg caagaggagc tgtctaaggc catcacagcc | 360 |
| atgcagcagt ttggtggcct ggaggccacc ggcatcctgg acgaggccac cctggccctg | 420 |
| atgaaaaccc cacgctgctc cctgccagac ctccctgtcc tgacccaggc tcgcaggaga | 480 |
| cgccaggctc cagcccccac caagtggaac aagaggaacc tgtcgtggag ggtccggacg | 540 |
| ttcccacggg actcaccact ggggcacgac acggtgcgtg cactcatgta ctacgccctc | 600 |
| aaggtctgga gcgacattgc gcccctgaac ttccacgagg tggcgggcag caccgccgac | 660 |
| atccagatcg acttctccaa ggccgaccat aacgacggct accccttcga cggccccggc | 720 |
| ggcaccgtgg cccacgcctt cttccccggc caccaccaca ccgccgggga cacccacttt | 780 |
| gacgatgacg aggcctggac cttccgctcc tcggatgccc acgggatgga cctgtttgca | 840 |
| gtggctgtcc acgagtttgg ccacgccatt gggttaagcc atgtggccgc tgcacactcc | 900 |
| atcatgcggc cgtactacca gggccgtgt ggtgacccgc tgcgctacgg gctccctac | 960 |
| gaggacaagg tgcgcgtctg gcagctgtac ggtgtgcggg agtctgtgtc tcccacggcg | 1020 |
| cagcccgagg agcctcccct gctgccgagg ccccagaca accggtccag cgccccgccc | 1080 |
| aggaaggacg tgcccacag atgcagcact cactttgacg cggtggccca gatccgcggt | 1140 |
| gaagctttct tcttcaaagg caagtacttc tggcggctga gcgggaccg gcacctggtg | 1200 |
| tccctgcagc cggcacagat gcaccgcttc tggcggggcc tgccgctgca cctggacagc | 1260 |
| gtggacgccg tgtacgagcg caccagcgac cacaagatcg tcttctttaa aggagacagg | 1320 |
| tactgggtgt tcaaggacaa taacgtagag aaggatacc cgcgcccgt ctccgacttc | 1380 |
| agcctcccgc ctggcggcat cgacgctgcc ttctcctggg cccacaatga caggacttat | 1440 |

```
ttctttaagg accagctgta ctggcgctac gatgaccaca cgaggcacat ggaccccggc    1500
taccccgccc agagccccct gtggaggggt gtcccagca cgctggacga cgccatgcgc    1560
tggtccgacg gtgcctccta cttcttccgt ggccaggagt actggaaagt gctggatggc    1620
gagctggagg tggcacccgg gtacccacag tccacggccc gggactggct ggtgtgtgga    1680
gactcacagg ccgatggatc tgtggctgcg ggcgtggacg cggcagaggg gccccgcgcc    1740
cctccaggac aacatgacca gagccgctcg gaggacggtt acgaggtctg ctcatgcacc    1800
tctggggcat cctctccccc gggggcccca ggcccactgg tggctgccac catgctgctg    1860
ctgctgccgc cactgtcacc aggcgccctg tggacagcgg cccaggccct gacgctatga    1920
cacacagcgc gagcccatga aggacagag gcggtgggac agcctggcca cagagggcaa    1980
ggactgtgcc ggagtccctg ggggaggtgc tggcgcggga tgaggacggg ccaccctggc    2040
accggaaggc cagcagaggg cacggcccgc cagggctggg caggctcagg tggcaaggac    2100
ggagctgtcc cctagtgagg gactgtgttg actgacgagc cgaggggtgg ccgctccaga    2160
agggtgccca gtcaggccgc accgccgcca gcctcctccg ccctggagg gagcatctcg    2220 ggctggggc ccacccctct ctgtgccggc gccaccaacc ccacccacac tgctgcctgg    2280
tgctcccgcc ggcccacagg gcctccgtcc ccaggtcccc agtggggcag ccctccccac    2340
agacgagccc cccacatggt gccgcggcac gtcccccctg tgacgcgttc cagaccaaca    2400
tgacctctcc ctgctttgta aaaaaaaaaa aaaaaaaa                             2438

<210> SEQ ID NO 132
<211> LENGTH: 1356
<212> TYPE: DNA
<213> ORGANISM: Homo sapiens
<220> FEATURE:
<221> NAME/KEY: misc_feature
<223> OTHER INFORMATION: U94332

<400> SEQUENCE: 132
gtatatataa cgtgatgagc gtacgggtgc ggagacgcac cggagcgctc gcccagccgc      60
cgyctccaag cccctgaggt ttccggggac cacaatgaac aagttgctgt gctgcgcgct     120
cgtgtttctg gacatctcca ttaagtggac cacccaggaa acgtttcctc caaagtacct     180
tcattatgac gaagaaacct ctcatcagct gttgtgtgac aaatgtcctc tggtaccta      240 cctaaaacaa cactgtacag caaagtgaa gaccgtgtgc gccccttgcc ctgaccacta      300
ctacacagac agctggcaca ccagtgacga gtgtctatac tgcagccccg tgtgcaagga     360
gctgcagtac gtcaagcagg agtgcaatcg cacccacaac cgcgtgtgcg aatgcaagga     420
agggcgctac cttgagatag agttctgctt gaaacatagg agctgccctc ctggatttgg     480
agtggtgcaa gctggaaccc cagagcgaaa tacagtttgc aaaagatgtc cagatgggtt     540
cttctcaaat gagacgtcat ctaaagcacc ctgtagaaaa cacacaaatt gcagtgtctt     600
tggtctcctg ctaactcaga aaggaaatgc aacacacgac aacatatgtt ccggaaacag     660
tgaatcaact caaaaatgtg aatagatgt taccctgtgt gaggaggcat tcttcaggtt      720
tgctgttcct acaaagttta cgcctaactg gcttagtgtc ttggtagaca atttgcctgg     780
caccaaagta aacgcagaga gtgtagagag gataaaacgg caacacagct cacaagaaca     840
gactttccag ctgctgaagt tatggaaaca tcaaaacaaa gcccaagata tagtcaagaa     900
gatcatccaa gatattgacc tctgtgaaaa cagcgtgcag cggcacattg gacatgctaa     960
cctcaccttc gagcagcttc gtagcttgat ggaaagctta ccgggaaaga aagtgggagc    1020
```

```
agaagacatt gaaaaaacaa taaaggcatg caaacccagt gaccagatcc tgaagctgct      1080
cagtttgtgg cgaataaaaa atggcgacca agacaccttg aagggcctaa tgcacgcact      1140
aaagcactca aagacgtacc actttcccaa aactgtcact cagagtctaa agaagaccat      1200
caggttcctt cacagcttca caatgtacaa attgtatcag aagttatttt tagaaatgat      1260
aggtaaccag gtccaatcag taaaaataag ctgcttataa ctggaaatgg ccattgagct      1320
gtttcctcac aattggcgag atcccatgga tgataa                                1356
```